US011046934B2

(12) United States Patent
Kawaoka et al.

(10) Patent No.: US 11,046,934 B2
(45) Date of Patent: Jun. 29, 2021

(54) MUTATIONS THAT CONFER GENETIC STABILITY TO ADDITIONAL GENES IN INFLUENZA VIRUSES

(71) Applicant: Wisconsin Alumni Research Foundation (WARF), Madison, WI (US)

(72) Inventors: Yoshihiro Kawaoka, Middleton, WI (US); Satoshi Fukuyama, Kanagawa (JP); Shinji Watanabe, Tokyo (JP)

(73) Assignee: Wisconsin Alumni Research Foundation (WARF), Madison, WI (US)

( * ) Notice: Subject to any disclaimer, the term of this patent is extended or adjusted under 35 U.S.C. 154(b) by 274 days.

(21) Appl. No.: 15/966,092

(22) Filed: Apr. 30, 2018

(65) Prior Publication Data

US 2018/0245054 A1 Aug. 30, 2018

Related U.S. Application Data

(62) Division of application No. 14/745,236, filed on Jun. 19, 2015, now Pat. No. 10,053,671.

(60) Provisional application No. 62/015,074, filed on Jun. 20, 2014.

(51) Int. Cl.
| | | |
|---|---|---|
| *C12N 7/00* | (2006.01) | |
| *A61K 39/145* | (2006.01) | |
| *C07K 14/005* | (2006.01) | |
| *A61K 39/00* | (2006.01) | |

(52) U.S. Cl.
CPC ............ *C12N 7/00* (2013.01); *A61K 39/145* (2013.01); *A61K 2039/525* (2013.01); *C07K 14/005* (2013.01); *C07K 2319/60* (2013.01); *C12N 2760/16121* (2013.01); *C12N 2760/16122* (2013.01); *C12N 2760/16131* (2013.01); *C12N 2760/16171* (2013.01)

(58) Field of Classification Search
None
See application file for complete search history.

(56) References Cited

U.S. PATENT DOCUMENTS

| | | |
|---|---|---|
| 4,071,618 A | 1/1978 | Konobe et al. |
| 4,659,569 A | 4/1987 | Mitsuhashi et al. |
| 5,166,057 A | 11/1992 | Palese et al. |
| 5,716,821 A | 2/1998 | Wertz et al. |
| 5,789,229 A | 8/1998 | Wertz et al. |
| 5,820,871 A | 10/1998 | Palese et al. |
| 5,840,520 A | 11/1998 | Clarke et al. |
| 5,854,037 A | 12/1998 | Palese et al. |
| 5,948,410 A | 9/1999 | Van Scharrenburg et al. |
| 5,994,526 A | 11/1999 | Meulewaeter et al. |
| 6,033,886 A | 3/2000 | Conzelmann |
| 6,037,348 A | 3/2000 | Colacino et al. |
| 6,146,642 A | 11/2000 | Garcia-Sastre et al. |
| 6,169,175 B1 | 1/2001 | Frace et al. |
| 6,194,546 B1 | 2/2001 | Newton et al. |
| 6,455,298 B1 | 9/2002 | Groner et al. |
| 6,544,785 B1 | 4/2003 | Palese et al. |
| 6,656,720 B2 | 12/2003 | Groner et al. |
| 6,825,036 B2 | 11/2004 | Makizumi et al. |
| 6,872,395 B2 | 3/2005 | Kawaoka |
| 6,951,752 B2 | 10/2005 | Reiter et al. |
| 6,951,754 B2 | 10/2005 | Hoffmann |
| 6,974,695 B2 | 12/2005 | Vogels et al. |
| 7,037,707 B2 | 5/2006 | Webster et al. |
| 7,176,021 B2 | 2/2007 | Kawaoka |
| 7,226,774 B2 | 6/2007 | Kawaoka |
| 7,312,064 B2 | 12/2007 | Hoffmann |
| 7,507,411 B2 | 3/2009 | Zhou et al. |
| 7,566,458 B2 | 7/2009 | Yang et al. |
| 7,585,657 B2 | 9/2009 | Kawaoka |
| 7,588,769 B2 | 9/2009 | Kawaoka |
| 7,670,837 B2 | 3/2010 | Schwartz |
| 7,833,788 B2 | 11/2010 | Pau et al. |
| 7,883,844 B2 | 2/2011 | Nouchi et al. |
| 7,955,833 B2 | 6/2011 | Reiter et al. |
| 7,959,930 B2 | 6/2011 | De Wit et al. |
| 7,972,843 B2 | 7/2011 | Hoffmann |

(Continued)

FOREIGN PATENT DOCUMENTS

| | | |
|---|---|---|
| AU | 2012204138 B2 | 5/2014 |
| AU | 2014202470 | 11/2016 |

(Continued)

OTHER PUBLICATIONS

"U.S. Appl. No. 15/170,556, Final Office Action dated Jul. 30, 2019", 6 pgs.
"U.S. Appl. No. 15/436,245, Response filed Jul. 29, 2019 to Non-Final Office Action dated Apr. 19, 2019", 11 pgs.
"U.S. Appl. No. 16/046,250, Restriction Requirement dated Jul. 25, 2019", 7 pgs.
"European Application Serial No. 10777154.5, Response filed Jul. 29, 2019 to Communication Pursuant to Article 94(3) EPC dated Jun. 11, 2019", 57 pgs.
"European Application Serial No. 14745060.5, Communication Pursuant to Article 94(3) EPC dated Jul. 18, 2019", 5 pgs.

(Continued)

*Primary Examiner* — Agnieszka Boesen
(74) *Attorney, Agent, or Firm* — Schwegman Lundberg & Woessner, P.A.

(57) ABSTRACT

The disclosure provides for an isolated recombinant influenza virus having at least one of: a PA gene segment encoding PA with a residue at position 443 that is not arginine, a PB1 gene segment encoding PB1 with a residue at position 737 that is not lysine, a PB2 gene segment encoding PB2 with a residue at position 25 that is not valine or a residue at position 712 that is not glutamic acid, a NS gene segment encoding a NS1 with a residue at position 167 that is not proline, a HA gene segment encoding a HA with a residue at position 380 that is not threonine, or any combination thereof, and methods of making and using the virus.

10 Claims, 45 Drawing Sheets

Specification includes a Sequence Listing.

(56) References Cited

U.S. PATENT DOCUMENTS

| | | |
|---|---|---|
| 7,993,924 B2 | 8/2011 | Billeter et al. |
| 8,012,736 B2 | 9/2011 | Hoffman et al. |
| 8,048,430 B2 | 11/2011 | Yang et al. |
| 8,057,806 B2 | 11/2011 | Kawaoka et al. |
| 8,093,033 B2 | 1/2012 | Kemble et al. |
| 8,114,415 B2 | 2/2012 | Hoffmann et al. |
| 8,119,337 B2 | 2/2012 | Gregersen |
| 8,119,388 B2 | 2/2012 | Schwartz et al. |
| 8,309,099 B2 | 11/2012 | Hoffmann |
| 8,354,114 B2 | 1/2013 | Lu et al. |
| 8,357,376 B2 | 1/2013 | Liu et al. |
| 8,409,843 B2 | 4/2013 | Kemble et al. |
| 8,460,914 B2 | 6/2013 | Gregersen |
| 8,475,806 B2 * | 7/2013 | Kawaoka ............... C12N 15/86 424/206.1 |
| 8,524,497 B2 | 9/2013 | Reiter et al. |
| 8,546,123 B2 | 10/2013 | Lewis |
| 8,574,591 B2 | 11/2013 | Hoffmann et al. |
| 8,574,593 B2 | 11/2013 | Yang et al. |
| 8,580,277 B2 | 11/2013 | Yang et al. |
| 8,591,914 B2 | 11/2013 | Yang et al. |
| 9,109,013 B2 | 8/2015 | Kawaoka et al. |
| 9,254,318 B2 | 2/2016 | Kawaoka et al. |
| 9,474,798 B2 | 10/2016 | Watanabe et al. |
| 10,053,671 B2 | 8/2018 | Kawaoka et al. |
| 10,059,925 B2 | 8/2018 | Kawaoka et al. |
| 10,172,934 B2 | 1/2019 | Kawaoka et al. |
| 10,246,686 B2 | 4/2019 | Kawaoka et al. |
| 10,633,422 B2 | 4/2020 | Kawaoka et al. |
| 10,808,229 B2 | 10/2020 | Kawaoka et al. |
| 2002/0164770 A1 | 11/2002 | Hoffmann |
| 2002/0197705 A1 | 12/2002 | Kawaoka |
| 2003/0035814 A1 | 2/2003 | Kawaoka et al. |
| 2003/0044962 A1 | 3/2003 | Makizumi et al. |
| 2003/0073223 A1 | 4/2003 | Groner et al. |
| 2003/0119183 A1 | 6/2003 | Groner |
| 2003/0194694 A1 | 10/2003 | Kawaoka |
| 2004/0002061 A1 | 1/2004 | Kawaoka |
| 2004/0063141 A1 | 4/2004 | Lok |
| 2004/0077086 A1 | 4/2004 | Reiter et al. |
| 2004/0219170 A1 | 11/2004 | Kawaoka |
| 2005/0003349 A1 | 1/2005 | Kawaoka |
| 2005/0037487 A1 | 2/2005 | Kawaoka et al. |
| 2005/0118140 A1 | 6/2005 | Vorlop et al. |
| 2005/0158342 A1 | 7/2005 | Kemble et al. |
| 2005/0186563 A1 | 8/2005 | Hoffmann |
| 2005/0202553 A1 | 9/2005 | Groner et al. |
| 2005/0232950 A1 | 10/2005 | Kawaoka |
| 2005/0266026 A1 | 12/2005 | Hoffmann et al. |
| 2006/0057116 A1 | 3/2006 | Kawaoka et al. |
| 2006/0166321 A1 | 7/2006 | Kawaoka et al. |
| 2006/0188977 A1 | 8/2006 | Schwartz et al. |
| 2006/0246092 A1 | 11/2006 | Neirynck et al. |
| 2007/0231348 A1 | 10/2007 | Kawaoka et al. |
| 2008/0233560 A1 | 9/2008 | Hoffmann |
| 2008/0254067 A1 | 10/2008 | Trepanier et al. |
| 2008/0274141 A1 | 11/2008 | Groner et al. |
| 2008/0311148 A1 | 12/2008 | Hoffmann |
| 2008/0311149 A1 | 12/2008 | Hoffmann |
| 2009/0074812 A1 | 3/2009 | Watanabe et al. |
| 2009/0081252 A1 | 3/2009 | Gregersen |
| 2009/0181446 A1 | 7/2009 | Nouchi et al. |
| 2010/0112000 A1 | 5/2010 | Schwartz |
| 2010/0183671 A1 | 7/2010 | Gregersen et al. |
| 2010/0247572 A1 | 9/2010 | Kawaoka |
| 2011/0027314 A1 | 2/2011 | Broeker |
| 2011/0045022 A1 | 2/2011 | Tsai |
| 2011/0110978 A1 | 5/2011 | Kawaoka et al. |
| 2011/0236417 A1 | 9/2011 | Watanabe et al. |
| 2012/0020997 A1 | 1/2012 | Hoffman et al. |
| 2012/0034600 A1 | 2/2012 | Gregersen |
| 2012/0115206 A1 | 5/2012 | Schwartz et al. |
| 2012/0156241 A1 | 6/2012 | De Wit et al. |
| 2012/0207785 A1 | 8/2012 | Fabry et al. |
| 2013/0095135 A1 | 4/2013 | Collignon et al. |
| 2013/0183741 A1 | 7/2013 | Park et al. |
| 2013/0316434 A1 | 11/2013 | Reiter et al. |
| 2014/0227310 A1 | 8/2014 | Li et al. |
| 2015/0017205 A1 | 1/2015 | Kawaoka et al. |
| 2015/0368621 A1 | 12/2015 | Kawaoka et al. |
| 2016/0024479 A1 | 1/2016 | Kawaoka et al. |
| 2016/0208223 A1 | 7/2016 | Kawaoka et al. |
| 2016/0355790 A1 | 12/2016 | Kawaoka et al. |
| 2017/0067029 A1 | 3/2017 | Kawaoka et al. |
| 2017/0258888 A1 | 9/2017 | Kawaoka |
| 2017/0354730 A1 | 12/2017 | Kawaoka et al. |
| 2018/0340152 A1 | 11/2018 | Kawaoka et al. |
| 2019/0032023 A1 | 1/2019 | Kawaoka et al. |
| 2019/0048324 A1 | 2/2019 | Kawaoka et al. |
| 2020/0237899 A1 | 7/2020 | Kawaoka et al. |

FOREIGN PATENT DOCUMENTS

| | | |
|---|---|---|
| CN | 1826407 B | 9/2013 |
| CN | 109477074 A | 3/2019 |
| EP | 0702085 A1 | 3/1996 |
| EP | 1201760 A1 | 5/2002 |
| EP | 2010557 B1 | 2/2014 |
| EP | 1631663 B1 | 8/2016 |
| EP | 2493912 B1 | 7/2020 |
| IL | 171831 A | 5/2015 |
| JP | 2004500842 A | 1/2004 |
| JP | 2004-531232 A | 10/2004 |
| JP | 2005523698 A | 8/2005 |
| JP | 2005245302 A | 9/2005 |
| JP | 2005535288 A | 11/2005 |
| JP | 2007-518395 A | 7/2007 |
| JP | 2009532352 A | 9/2009 |
| JP | 2010-530248 A | 9/2010 |
| JP | 4927290 B2 | 2/2012 |
| JP | 4927290 | 5/2012 |
| JP | 2013-507990 A | 3/2013 |
| JP | 2014039551 A | 3/2014 |
| JP | 2014131516 A | 7/2014 |
| JP | 2016-521553 A | 7/2016 |
| JP | 2016144463 A | 8/2016 |
| JP | 2016524915 A | 8/2016 |
| JP | 2016169225 A | 9/2016 |
| JP | 6352974 | 6/2018 |
| JP | 6375329 B2 | 7/2018 |
| JP | 2019-510481 A | 4/2019 |
| JP | 2020-010711 A | 1/2020 |
| MX | 285206 | 3/2011 |
| WO | WO-9610631 A1 | 4/1996 |
| WO | WO-9610632 A1 | 4/1996 |
| WO | WO-9640955 A1 | 12/1996 |
| WO | WO-9737000 A1 | 10/1997 |
| WO | WO-9802530 A1 | 1/1998 |
| WO | WO-9853078 A1 | 11/1998 |
| WO | WO-9928445 A1 | 6/1999 |
| WO | WO-0053786 A1 | 9/2000 |
| WO | WO-0060050 A2 | 10/2000 |
| WO | WO-0060050 A3 | 1/2001 |
| WO | WO-0179273 A2 | 10/2001 |
| WO | WO-0183794 A2 | 11/2001 |
| WO | WO-02/064757 A2 | 8/2002 |
| WO | WO-03068923 A2 | 8/2003 |
| WO | WO-03076462 A1 | 9/2003 |
| WO | WO-03091401 A2 | 11/2003 |
| WO | WO-04094466 A2 | 11/2004 |
| WO | WO-04112831 A2 | 12/2004 |
| WO | WO-2004112831 A2 | 12/2004 |
| WO | WO-2004112831 A3 | 12/2004 |
| WO | WO-2005062820 A2 | 7/2005 |
| WO | WO-2007126810 A2 | 11/2007 |
| WO | WO-2007126810 A3 | 11/2007 |
| WO | WO-2008156778 A2 | 12/2008 |
| WO | WO-2008156778 A3 | 12/2008 |
| WO | WO-2008157583 A1 | 12/2008 |
| WO | WO-2008156778 A9 | 2/2009 |
| WO | WO-2011056591 A1 | 5/2011 |
| WO | WO-2012177924 A2 | 12/2012 |
| WO | WO-2013034069 A1 | 3/2013 |
| WO | WO-2014195920 A2 | 12/2014 |

(56) References Cited

FOREIGN PATENT DOCUMENTS

| WO | WO-2015009743 | A1 | 1/2015 |
|---|---|---|---|
| WO | WO-2015196150 | A2 | 12/2015 |
| WO | WO-2015196150 | A3 | 12/2015 |
| WO | WO-2017007839 | A1 | 1/2017 |
| WO | WO-2017143236 | A1 | 8/2017 |
| WO | WO-2020167432 | A2 | 8/2020 |
| WO | WO-2020167432 | A3 | 12/2020 |

OTHER PUBLICATIONS

"Canadian Application Serial No. 2,525,953, Response filed May 2, 2019 to Office Action dated Nov. 2, 2018", 31 pgs.

"European Application Serial 17709236.8, Response filed Apr. 26, 2019 to Communication Pursuant to Rules 161(1) and 162 EPC dated Oct. 19, 2018", 9 pgs.

"European Application Serial No. 10777154.5, Communication Pursuant to Article 94(3) EPC dated Jun. 11, 2019", 3 pgs.

"European Application Serial No. 10777154.5, Response filed May 13, 2019 to Summons to Attend Oral Proceedings dated Jan. 7, 2019", 35 pgs.

"European Application Serial No. 10777154.5, Response filed Jun. 4, 2019 to Summons to Attend Oral Proceedings mailed Jan. 7, 2019", 9 pgs.

"Japanese Application Serial No. 2016-527046, Examiners Decision of Final Refusal dated May 21, 2019", (w/ English Translation), 20 pgs.

"U.S. Appl. No. 15/170,556, Response filed Oct. 29, 2018 to Non Final Office Action dated Jul. 27, 2018", 9 pgs.

"U.S. Appl. No. 15/436,245, Restriction Requirement dated Oct. 11, 2018", 9 pgs.

"U.S. Appl. No. 15/593,039, PTO Response to Rule 312 Communication dated Oct. 9, 2018", 2 pgs.

"U.S. Appl. No. 15/593,039, PTO Response to Rule312 Communication dated Oct. 9, 2018".

"U.S. Appl. No. 15/865,364, Notice of Allowance dated Nov. 15, 2018", 7 pgs.

"U.S. Appl. No. 15/905,454, Preliminary Amendment filed Nov. 2, 2018", 5 pgs.

"Canadian Application Serial No. 2,525,953, Office Action dated Nov. 2, 2018", 6 pgs.

"European Application Serial No. 10777154.5, Response filed Sep. 7, 2018 to Communication Pursuant to Article 94(3) EPC dated Apr. 4, 2018", 18 pgs.

"European Application Serial No. 14745060.5, Communication Pursuant to Article 94(3) EPC dated Sep. 19, 2018", 4 pgs.

"International Application Serial No. PCT/US2017/018443, International Preliminary Report on Patentability dated Aug. 30, 2018", 11 pgs.

"Israeli Application Serial No. 238584, Office Action dated Aug. 23, 2018", (w/ English Translation), 6 pgs.

"Israeli Application Serial No. 238584, Response Filed Dec. 10, 2018 to Office Action dated Aug. 23, 2018", (w/ English Translation of Claims), 10 pgs.

"Japanese Application Serial No. 2016-527046, Reasons for Rejection dated Aug. 14, 2018", (w/ English Translation), 14 pgs.

Jiang, H, et al., "Influenza virus genome C4 promoter/origin attenuates its transcription and replication activity by the low polymerase recognition activity", *Virology*, 408(2), (2010), 190-196.

Neumann, G., et al., "Mutational analysis of influenza virus promoter elements in vivo", *Journal of General Virology*, 76, (1995), 1709-1717.

Ramanunninair, M., et al., "Molecular Signature of High Yield (Growth) Influenza A Virus Reassortants Prepared as Candidate Vaccine Seeds", *Plos One*, 8(6): e65955, (2013), 1-16.

"U.S. Appl. No. 15/170,556, Notice of Allowability dated Jan. 29, 2020", 4 pgs.

"U.S. Appl. No. 16/046,250, Non-Final Office Action dated Mar. 6, 2020", 10 pgs.

"Brazilian Application Serial No. PI 0410702-0, Response filed Feb. 6, 2020 to Office Action dated Nov. 1, 2019", (w/ English Translation of Claims), 93 pgs.

"Canadian Application Serial No. 2,525,953, Office Action dated Jan. 29, 2020", 4 pgs.

"European Application Serial No. 14745060.5, Response filed Jan. 28, 2020 to Communication Pursuant to Article 94(3) EPC dated Jul. 18, 2019", 9 pgs.

"U.S. Appl. No. 15/170,556. PTO Response to Rule 312 Communication dated Apr. 3, 2020", 2 pgs.

"Australian Application Serial No. 2014290203, Response filed Mar. 13, 2020 to First Examination Report dated Oct. 10, 2019", 16 pgs.

"Australian Application Serial No. 2014290203, Subsequent Examiners Report dated Mar. 23, 2020", 6 pgs.

"Brazilian Application Serial No. PI0410702-0, Office Action dated Apr. 1, 2020", (w/ English Summary), 6 pgs.

"Canadian Application Serial No. 3,014,435, Response filed Mar. 13, 2020 to Office Action dated Nov. 13, 2019", 18 pgs.

"European Application Serial No. 14745060.5, Communication Pursuant to Article 94(3) EPC dated Mar. 12, 2020", 4 pgs.

Von Wielink, R., et al., "Mutations in the M-Gene Segment can Substantially Increase Replication Efficiency of NS1 Deletion Influenza A Virus in MCK Cells", Journal of Virology. vol. 86, (2012), 12341-12350.

"U.S. Appl. No. 15/170,556, Non Final Office ACtion dated Feb. 8, 2019", 11 pgs.

"U.S. Appl. No. 15/905,454, Restriction Requirement dated Jan. 3, 2019", 6 pgs.

"European Application Serial No. 10777154.5, Summons to Attend Oral Proceedings mailed Jan. 7, 2019", 5 pgs.

"Gen Bank Accession AFP82914", matrix protein 1 [Influenza A virus (A/reassortant/IVR-148(Brisbane/59/2007 x Texas/1/1977)(H1N1))], (2012), 2 pgs.

"Gen Bank Accession JX414012", Influenza A virus (A/reassortant/IVR-148(Brisbane/59/2007 x Texas/1/1977)(H1 N1)) segment 7 matrix protein 2 (M2) and matrix protein 1 (M1) genes, complete cds, (2012), 2 pgs.

"Japanese Application Serial No. 2016-527046, Response Filed Dec. 4, 2018 to Reasons For Rejection dated Aug. 14, 2018", (w/ English Translation of Amended Claims), 18 pgs.

Biere, Barbara, et al., "Differentiation of Influenza B Virus Lineages Yamagata and Victoria by Real-Time PCR", *Journal of Clinical Microbiology*, vol. 48, No. 4, (2010), 1425-1427.

Govorkova, E A, et al., "Replication of Influenza A Viruses in a Green Monkey Kidney Continuous Cell Line (Vero)", *J. Infect. Dis.* 172(1), (1995), 250-253.

"U.S. Appl. No. 15/170,556, Response filed Nov. 18, 2019 to Final Office Action dated Jul. 30, 2019", 8 pgs.

"U.S. Appl. No. 15/436,245, Final Office Action dated Nov. 18, 2019", 9 pgs.

"U.S. Appl. No. 16/046,250, Response filed Oct. 25, 2019 to Restriction Requirement dated Jul. 25, 2019", 9 pgs.

"Australian Application Serial No. 2014290203, First Examination Report dated Oct. 10, 2019", 4 pgs.

"Brazilian Application Serial No. PI 0410702-0, Office Action dated Nov. 1, 2019", (w/ English Translation), 6 pgs.

"Canadian Application Serial No. 3,014,435, Office Action dated Nov. 13, 2019", 4 pgs.

"Chinese Application Serial No. 200480021259.9, Reexamination Decision dated Mar. 25, 2013", (w/ English Translation), 17 pgs.

"Israeli Application Serial No. 238584, Notification of Defects in Patent Application dated Jul. 21, 2019", (w/ English Translation), 5 pgs.

U.S. Appl. No. 10/855,875, U.S. Pat. No. 8,475,806, filed May 27, 2004, High Titer Recombinant Influenza Viruses for Vaccines and Gene Therapy.

U.S. Appl. No. 11/729,557, U.S. Pat. No. 9,254,318, filed Mar. 29, 2007, High Titer Recombinant Influenza Viruses for Vaccines.

U.S. Appl. No. 15/000,851, U.S. Pat. No. 9,926,535, filed Jan. 19, 2016, High Titer Recombinant Influenza Viruses for Vaccines.

U.S. Appl. No. 15/905,454, filed Feb. 26, 2018, High Titer Recombinant Influenza Viruses for Vaccines.

(56) References Cited

OTHER PUBLICATIONS

U.S. Appl. No. 12/912,411, U.S. Pat. No. 9,109,013, filed Oct. 26, 2010, High Titer Recombinant Influenza Viruses With Enhanced Replication in Vero Cells.
U.S. Appl. No. 16/046,250, filed Jul. 26, 2018, High Titer Recombinant Influenza Viruses With Enhanced Replication in Vero Cells.
U.S. Appl. No. 14/816,807, U.S. Pat. No. 10,059,925, filed Aug. 3, 2015, High Titer Recombinant Influenza Viruses With Enhanced Replication in Vero Cells.
U.S. Appl. No. 14/332,121, U.S. Pat. No. 9,950,057, filed Jul. 15, 2014, High Titer Recombinant Influenza Viruses With Enhanced Replication in MDCK or Vero Cells or Eggs.
U.S. Appl. No. 15/593,039, U.S. Pat. No. 10/172,934, filed May 11, 2017, High Titer Recombinant Influenza Viruses With Enhanced Replication in MDCK or Vero Cells or Eggs.
U.S. Appl. No. 14/745,236, U.S. Pat. No. 10,053,671, filed Jun. 19, 2015, Mutations That Confer Genetic Stability to Additional Genes in Influenza Viruses.
U.S. Appl. No. 15/170,556, filed Jun. 1, 2016, Influenza Virus Replication by Inhibiting Microrna LEC7C Binding to Influenza Viral CRNA and MRNA.
U.S. Appl. No. 15/203,581, U.S. Pat. No. 9,890,363, filed Jul. 6, 2016, Influenza Virus Replication for Vaccine Development.
U.S. Appl. No. 15/865,364, filed Jan. 9, 2018, Influenza Virus Replication for Vaccine Development.
U.S. Appl. No. 15/436,245, filed Feb. 17, 2017, Influenza B Virus Replication for Vaccine Development.
"U.S. Appl. No. 15/170,556, Response filed Apr. 15, 2019 to Non Final Office Action dated Feb. 8, 2019", 9 pgs.
"U.S. Appl. No. 15/436,245, Non Final Office Action dated Apr. 19, 2019", 9 pgs.
"European Application Serial No. 14745060.5, Response filed Mar. 27, 2019 to Communication Pursuant to Article 94(3) EPC dated Sep. 18, 2018", 13 pgs.
McCullers, Jonathan A., et al., "A single amino acid change in the C-terminal domain of the matrix protein M1 of influenza B virus confers mouse adaption and virulence", Virology, 336(2), (Jun. 5, 2005), 318-326.
"U.S. Appl. No. 15/170,556, Notice of Allowance dated Nov. 27, 2019", 8 pgs.
"Israeli Application Serial No. 238584, Response filed Nov. 21, 2019 to Notification of Defects in Patent Application dated Jul. 21, 2019", (w/ English Translation of Claims), 6 pgs.
"Japanese Application Serial No. 2018-543688, Notification of Reasons for Rejection dated Oct. 29, 2019", (w/ English Translation), 14 pgs.
Result 17, NCBI Blast nucleotide search of SEQ ID No. 2, database "nr", (Jul. 18, 2006), 3 pgs.
Result 1, NCBI Blast nucleotide search of SEQ ID No. 3, database "nr", Result 4, NCBI Blast nucleotide search of SEQ ID No. 4, database "nr", (Jul. 22, 2006), 11 pgs.
Result 2, NCBI Blast nucleotide search of SEQ ID No. 5, database "nr"; Result 4, NCBI Blast nucleotide search of SEQ ID No. 6, database "nr", (Jul. 22, 2006), 6 pgs.
Results 1, NCBI Blast nucleotide search of SEQ ID No. 7, database "nr"; Result 1, NCBI Blast nucleotide search of SEQ ID No. 8, database "nr", (Jul. 23, 2006), 8 pgs.
Result 7, NCBI Blast nucleotide search of SEQ ID: 1, database "nr", (Jul. 18, 2006), 3 pgs.
"U.S. Appl. No. 10/855,875 , Response filed May 17, 2012 to Non Final Office Action dated Mar. 15, 2012", 15 pgs.
"U.S. Appl. No. 10/855,875, Final Office Action dated Mar. 11, 2008", FOAR, 20 Pgs.
"U.S. Appl. No. 10/855,875, Final Office Action dated Dec. 10, 2010", 15 pgs.
"U.S. Appl. No. 10/855,875, Final Office Action dated Aug. 2, 2006", 34 pgs.
"U.S. Appl. No. 10/855,875, Non Final Office Action dated Mar. 15, 2012", 15 pgs.
"U.S. Appl. No. 10/855,875, Non-Final Office Action dated Feb. 19, 2010", 7 pgs.
"U.S. Appl. No. 10/855,875, Non-Final Office Action dated Aug. 7, 2009", 32 pgs.
"U.S. Appl. No. 10/855,875, Non-Final Office Action dated Nov. 6, 2008", 12 pgs.
"U.S. Appl. No. 10/855,875, Non-Final Office Action dated Nov. 30, 2005", 13 pgs.
"U.S. Appl. No. 10/855,875, Non-Final Office Action dated May 3, 2007", 13 pgs.
"U.S. Appl. No. 10/855,875, Notice of Allowance dated Mar. 4, 2013", 8 pgs.
"U.S. Appl. No. 10/855,875, Preliminary Amendment filed Feb. 2, 2007", 14 pgs.
"U.S. Appl. No. 10/855,875, Response filed Jan. 29, 2007 to Final Office Action dated Aug. 2, 2007", 14 pgs.
"U.S. Appl. No. 10/855,875, Response filed Mar. 18, 2011 to Final Office Action dated Dec. 10, 2010", 15 pgs.
"U.S. Appl. No. 10/855,875, Response filed Aug. 17, 2010 to Non Final Office Action dated FEb. 19, 2010", 20 pgs.
"U.S. Appl. No. 10/855,875, Response filed Dec. 7, 2009 to Non Final Office Action dated Aug. 7, 2009", 15 pgs.
"U.S. Appl. No. 10/855,875, Response filed Mar. 31, 2009 to Non Final Office Action dated Nov. 6, 2008", 14 pgs.
"U.S. Appl. No. 10/855,875, Response filed May 1, 2006 Non-Final Office Action dated Nov. 30, 2005", 13 pgs.
"U.S. Appl. No. 10/855,875, Response filed Aug. 18, 2008 to final Office Action dated Mar. 11, 2008", 15 pgs.
"U.S. Appl. No. 10/855,875, Response filed Sep. 20, 2005 to Restriction Requirement dated Jul. 26, 2005", 4 pgs.
"U.S. Appl. No. 10/855,875, Restriction Requirement dated Dec. 23, 2011", 9 pgs.
"U.S. Appl. No. 10/855,875, Restriction Requirement dated Jul. 26, 2005", 9 pgs.
"U.S. Appl. No. 10/855,875, Response filed Nov. 2, 2007 to Office Action dated May 3, 2007", 16 pgs.
"U.S. Appl. No. 11/729,557, Advisory Action dated May 9, 2011", 3 pgs.
"U.S. Appl. No. 11/729,557, Advisory Action dated Dec. 24, 2014", 3 pgs.
"U.S. Appl. No. 11/729,557, Final Office Action date Feb. 2, 2011", 14 pgs.
"U.S. Appl. No. 11/729,557, Final Office Action dated Aug. 20, 2009", 13 Pgs.
"U.S. Appl. No. 11/729,557, Final Office Action dated Sep. 12, 2014", 14 pgs.
"U.S. Appl. No. 11/729,557, Non Final Office Action dated Feb. 18, 2015", 13 pgs.
"U.S. Appl. No. 11/729,557, Non Final Office Action dated Feb. 26, 2014", 16 pgs.
"U.S. Appl. No. 11/729,557, Non-Final Office Action dated Jan. 30, 2009", 20 pgs.
"U.S. Appl. No. 11/729,557, Non-Final Office Action dated Feb. 22, 2010", 16 pgs.
"U.S. Appl. No. 11/729,557, Non-Final Office Action dated Aug. 23, 2010", 15 pgs.
"U.S. Appl. No. 11/729,557, Notice of Allowance dated Sep. 30, 2015", 11 pgs.
"U.S. Appl. No. 11/729,557, Respons filed Jun. 22, 2010 to Non Final Office Action dated Feb. 22, 2010", 33 pgs.
"U.S. Appl. No. 11/729,557, Response filed Apr. 27. 2011 to Final Office Action dated Feb. 2, 2011", 14 pgs.
"U.S. Appl. No. 11/729,557, Response filed Apr. 30, 2009 to Non Final Office Action dated Jan. 30, 2009", 18 pgs.
"U.S. Appl. No. 11/729,557, Response filed May 22, 2014 to Non Final Office Action dated Feb. 26, 2014", 13 pgs.
"U.S. Appl. No. 11/729,557, Response filed May 28, 2008 to Restriction Requirement dated Nov. 28, 2007", 13 pgs.
"U.S. Appl. No. 11/729,557, Response filed Jun. 22, 2010 to Non Final Office Action dated Feb. 22, 2010", 16 pgs.
"U.S. Appl. No. 11/729,557, Response filed Jun. 22, 2015 to non Final Office Action dated Feb. 18, 2015", 13 pgs.

(56) References Cited

OTHER PUBLICATIONS

"U.S. Appl. No. 11/729,557, Response filed Oct. 28, 2010 to Non Final Office Action dated Aug. 23, 2010", 13 pgs.
"U.S. Appl. No. 11/729,557, Response filed Dec. 1, 2009 to Final Office Action dated Aug. 26, 2009", 16 pgs.
"U.S. Appl. No. 11/729,557, Response filed Dec. 11, 2014 to Final Office Action date Sep. 12, 2014", 15 pgs.
"U.S. Appl. No. 11/729,557, Restriction Requirement dated Nov. 28, 2007", 9 pgs.
"U.S. Appl. No. 12/912,411, Advisory Action dated Feb. 5, 2014", 3 pgs.
"U.S. Appl. No. 12/912,411, Examiner Interview Summary dated Feb. 11, 2014", 2 pgs.
"U.S. Appl. No. 12/912,411, Final Office Action dated Jan. 14, 2015", 10 pgs.
"U.S. Appl. No. 12/912,411, Final Office Action dated Oct. 25, 2013", 11 pgs.
"U.S. Appl. No. 12/912,411, Non Final Office Action dated Jun. 7, 2013", 8 pgs.
"U.S. Appl. No. 12/912,411, Non Final Office Action dated Sep. 24, 2014", 11 pgs.
"U.S. Appl. No. 12/912,411, Notice of Allowability dated May 20, 2015", 7 pgs.
"U.S. Appl. No. 12/912,411, Notice of Allowance dated Apr. 8, 2015", 11 pgs.
"U.S. Appl. No. 12/912,411, Response filed Jan. 27, 2014 to Final Office Action dated Oct. 25, 2013", 11 pgs.
"U.S. Appl. No. 12/912,411, Response filed Feb. 18, 2013 to Restriction Requirement dated Oct. 17, 2012", 9 pgs.
"U.S. Appl. No. 12/912,411, Response filed Feb. 25, 2014 to Final Office Action dated Oct. 25, 2013", 11 pgs.
"U.S. Appl. No. 12/912,411, Response filed Mar. 16, 2015 to Final Office Action dated Jan. 14, 2015", 9 pgs.
"U.S. Appl. No. 12/912,411, Response filed Oct. 7, 2013 to Non Final Office Action dated Jun. 7, 2013", 10 pgs.
"U.S. Appl. No. 12/912,411, Response filed Dec. 31, 2014 to Non Final Office Action dated Sep. 24, 2014", 12 pgs.
"U.S. Appl. No. 12/912,411, Restriction Requirement dated Oct. 17, 2012", 9 pgs.
"U.S. Appl. No. 14/332,121, Non Final Office Action dated May 16, 2016", 9 pgs.
"U.S. Appl. No. 14/332,121, Notice of Allowance dated Feb. 15, 2017", 10 pgs.
"U.S. Appl. No. 14/332,121, Notice of Allowance dated Jun. 15, 2017", 8 pgs.
"U.S. Appl. No. 14/332,121, Notice of Allowance dated Oct. 11, 2017", 8 pgs.
"U.S. Appl. No. 14/332,121, Preliminary Amendment filed Sep. 30, 2014", 5 pgs.
"U.S. Appl. No. 14/332,121, Response filed Jan. 29, 2016 to Restriction Requirement dated Jul. 30, 2015", 9 pgs.
"U.S. Appl. No. 14/332,121, Response filed Sep. 7, 2017 to Notice of Allowability dated Jun. 15, 2017", 8 pgs.
"U.S. Appl. No. 14/332,121, Response filed Oct. 11, 2016 to Non Final Office Action dated May 16, 2016", 9 pgs.
"U.S. Appl. No. 14/332,121, Restriction Requirement dated Jul. 30, 2015", 9 pgs.
"U.S. Appl. No. 14/332,121, Supplemental Amendment filed Jan. 23, 2017", 10 pgs.
"U.S. Appl. No. 14/745,236, Advisory Action dated Nov. 15, 2017", 2 pgs.
"U.S. Appl. No. 14/745,236, Final Office Action dated Aug. 25, 2017", 16 pgs.
"U.S. Appl. No. 14/745,236, Non Final Office Action dated Feb. 2, 2017", 14 pgs.
"U.S. Appl. No. 14/745,236, Notice of Allowance dated Feb. 5, 2018", 9 pgs.
"U.S. Appl. No. 14/745,236, Response filed May 2, 2017 to Non Final Office Action dated Feb. 2, 2017", 10 pgs.

"U.S. Appl. No. 14/745,236, Response filed Nov. 6, 2017 to Final Office Action dated Aug. 25, 2017", 12 pgs.
"U.S. Appl. No. 14/745,236, Response filed Dec. 14, 2017 to Final Office Action dated Aug. 25, 2017", 12 pgs.
"U.S. Appl. No. 14/745,236, Response filed Dec. 23, 2016 to Restriction Requirement dated Sep. 23, 2016", 8 pgs.
"U.S. Appl. No. 14/745,236, Restriction Requirement dated Sep. 23, 2016", 8 pgs.
"U.S. Appl. No. 14/816,807, Non Final Office Action dated Oct. 3, 2017", 7 pgs.
"U.S. Appl. No. 14/816,807, Preliminary Amendment filed Aug. 11, 2015", 8 pgs.
"U.S. Appl. No. 14/816,807, Response flied Jan. 3, 2018 to Non Final Office Action dated Oct. 3, 2017", 8 pgs.
"U.S. Appl. No. 14/816,807, Response filed May 1, 2017 to Restriction Requirement dated Nov. 1, 2016", 9 pgs.
"U.S. Appl. No. 14/816,807, Restriction Requirement dated Nov. 1, 2016", 8 pgs.
"U.S. Appl. No. 15/000,851, Non Final Office Action dated Jan. 26, 2017", 15 pgs.
"U.S. Appl. No. 15/000,851, Notice of Allowance dated Nov. 8, 2017", 9 pgs.
"U.S. Appl. No. 15/000,851, Preliminary Amendment filed Feb. 3, 2016", 3 pgs.
"U.S. Appl. No. 15/000,851, Response filed Jul. 26, 2017 to Non Final Office Action dated Jan. 26, 2017", 16 pgs.
"U.S. Appl. No. 15/000,851, Response filed Oct. 12, 2016 to Restriction Requirement dated May 12, 2016", 11 pgs.
"U.S. Appl. No. 15/000,851, Restriction Requirement dated May 12, 2016", 6 pgs.
"U.S. Appl. No. 15/000,851, Supplemental Amendment filed Apr. 4, 2016", 10 pgs.
"U.S. Appl. No. 15/203,581, Examiners Interview Summary dated Sep. 11, 2017", 1 pg.
"U.S. Appl. No. 15/203,581, Notice of Allowance dated Sep. 11, 2017", 12 pgs.
"U.S. Appl. No. 15/203,581, PTO Response to Rule 312 Communication dated Dec. 27, 2017", 2 pgs.
"U.S. Appl. No. 15/203,581, Response filed Aug. 15, 2017 to Restriction Requirement dated Jun. 16, 2017", 8 pgs.
"U.S. Appl. No. 15/203,581, Restriction Requirement dated Jun. 16, 2017", 8 pgs.
"U.S. Appl. No. 15/436,245, Preliminary Amendment flied May 5, 2017", 3 pgs.
"U.S. Appl. No. 15/593,039, Preliminary Amendment filed Jul. 25, 2017", 7 pgs.
"U.S. Appl. No. 15/593,039, Response filed Dec. 18, 2017 to Restriction Requirement dated Oct. 18, 2017", 8 pgs.
"U.S. Appl. No. 15/593,039, Restriction Requirement dated Oct. 18, 2017", 6 pgs.
"U.S. Appl. No. 15/593,039, Supplemental Preliminary Amendment filed Jul. 26, 2017", 4 pgs.
"Application Serial No. 200480021259.9 Office Action dated Sep. 11, 2009", 7 pgs.
"Application Serial No. 200480021259.9 Office Action Response Filed Aug. 20, 2010", 26 pgs.
"Application Serial No. 2006-533439 Office Action dated Mar. 9, 2010", 20 pgs.
"Australian Application Serial No. 2004249133, First Examiner's Report dated May 5, 2008", 4 pgs.
"Australian Application Serial No. 2004249133, Response filed Mar. 30, 2009 to First Examiner's Report dated Mar. 5, 2008", 30 pgs.
"Australian Application Serial No. 2007245192, Office Action dated Aug. 25, 2011", 2 pgs.
"Australian Application Serial No. 2007245192, Response filed Feb. 28, 2012 to Office Action dated Aug. 25, 2011", 22 pgs.
"Australian Application Serial No. 2012204138, First Examiner Report dated Jul. 16, 2013", 4 pgs.
"Australian Application Serial No. 2012204138, Response filed Dec. 24, 2013 to First Examiner Report dated Jul. 16, 2013", 21 pgs.
"Australian Application Serial No. 2014202470, First Examiner Report dated Jul. 20, 2015", 2 pgs.

(56) References Cited

OTHER PUBLICATIONS

"Australian Application Serial No. 2014202470, Response filed Jul. 4, 2016 to Subsequent Examiners Report dated Feb. 1, 2016", 3 pgs.
"Australian Application Serial No. 2014202470, Response filed Jul. 20, 2016 to Subsequent Examiners Report dated Jul. 19, 2016", 15 pgs.
"Australian Application Serial No. 2014202470, Response filed Dec. 1, 2015 to First Examiner Report dated Jul. 20, 2015", 22 pgs.
"Australian Application Serial No. 2014202470, Subsequent Examiners Report dated Feb. 1, 2016", 2 pgs.
"Australian Application Serial No. 2014202470, Subsequent Examiners Report dated Jul. 19, 2016", 3 pgs.
"Brazilian Application Serial No. PI0410702-0, Office Action dated Feb. 23, 2012", (w/ English Translation), 4 pgs.
"Brazilian Application Serial No. PI0410702-0, Response filed May 7, 2012 to Office Action dated Feb. 23, 2012", (w/ English Translation of Claims), 11 pgs.
"Canadian Application Serial No. 2,525,953, Amendment and Response filed Feb. 1, 2017 to Office Action dated Aug. 1, 2016", 28 pgs.
"Canadian Application Serial No. 2,525,953, Office Action dated Jan. 21, 2016", 6 pgs.
"Canadian Application Serial No. 2,525,953, Office Action dated Jul. 31, 2012", 4 pgs.
"Canadian Application Serial No. 2,525,953, Office Action dated Aug. 1, 2016", 6 pgs.
"Canadian Application Serial No. 2,525,953, Office Action dated Aug. 16, 2013", 3 pgs.
"Canadian Application Serial No. 2,525,953, Office Action dated Oct. 3, 2017", 4 pgs.
"Canadian Application Serial No. 2,525,953, Office Action dated Nov. 6, 2014", 3 pgs.
"Canadian Application Serial No. 2,525,953, Office Action dated Jun. 22, 2011", 4 pgs.
"Canadian Application Appl. No. 2,525,953, Office Action received Jun. 22, 2011", 4 pgs.
"Canadian Application Serial No. 2,525,953, Response filed Jan. 31, 2013 to Office Action dated Jul. 31, 2012", 11 pgs.
"Canadian Application Serial No. 2,525,953, Response filed Feb. 1, 2017 to Office Action dated Aug. 1, 2016", 28 pgs.
"Canadian Application Serial No. 2,525,953, Response filed Feb. 14, 2014 to Office Action dated Aug. 16, 2013", 16 pgs.
"Canadian Application Serial No. 2,525,953, Response filed May 1, 2015 to Office Action dated Nov. 6, 2014", 23 pgs.
"Canadian Application Serial No. 2,525,953, Response filed Jul. 11, 2016 to Office Action dated Jan. 21, 2016", 21 pgs.
"Canadian Application Serial No. 2,525,953, Response filed Dec. 22, 2011 to Office Action dated Jun. 22, 2011", 17 pgs.
"Canadian Application Serial No. 2,647,985, Office Action dated May 15, 2013", 3 pgs.
"Canadian Application Serial No. 2,647,985, Response filed Sep. 30, 2013 to Office Action dated May 15, 2013", 20 pgs.
"Chinese Application Serial No. 200480021259.9, First Offiice Action dated Aug. 24, 2007", (w/ English Translation), 9 pgs.
"Chinese Application Serial No. 200480021259.9, Notice of Reexamination dated Jul. 3, 2012", (w/ English Translation), 10 pgs.
"Chinese Application Serial No. 200480021259.9, Office Action dated Jan. 11, 2011", (w/ English Translation), 15 pgs.
"Chinese Application Serial No. 200480021259.9, Office Action dated May 6, 2010", (w/ English Translation), 12 pgs.
"Chinese Application Serial No. 200480021259.9, Office Action dated Jul. 3, 2012", (w/ English Translation), 10 pgs.
"Chinese Application Serial No. 200480021259.9, Request for Reexamination filed Apr. 26, 2011", (w/ English Translation of Amended Claims), 23 pgs.
"Chinese Application Serial No. 200480021259.9, Response filed Mar. 7, 2008 to Offiice Action dated Aug. 24, 2007", (w/ English Translation of Claims), 13 pgs.
"Chinese Application Serial No. 200480021259.9, Response filed Oct. 16, 2012 to Office Action dated Jul. 3, 2012", (wl English Translation of Claims), 13 pgs.
"Chinese Application Serial No. 200780020095.1, Decision on Rejection dated Jul. 22, 2013", (w/ English Translation), 11 pgs.
"Chinese Application Serial No. 200780020095.1, First Office Action dated Jun. 24, 2011", (w/ English Translation), 13 pgs.
"Chinese Application Serial No. 200780020095.1, Office Action dated Jan. 29, 2013", (w/ English Translation), 10 pgs.
"Chinese Application Serial No. 200780020095.1, Office Action dated Mar. 5, 2015", (w/ English Translation), 12 pgs.
"Chinese Application Serial No. 200780020095.1, Office Action dated Apr. 26, 2016", (w/ English Summary), 4 pgs.
"Chinese Application Serial No. 200780020095.1, Office Action dated May 3, 2012", (w/ English Translation), 10 pgs.
"Chinese Application Serial No. 200780020095.1, Office Action dated Nov. 2, 2016", (w/ English Translation), 11 pgs.
"Chinese Application Serial No. 200780020095.1, Response filed Jan. 6, 2017 to Office Action dated Nov. 2, 2016", (w/ English Translation of Claims), 15 pgs.
"Chinese Application Serial No. 200780020095.1, Response filed Jun. 9, 2013 to Office Action dated Jan. 29, 2013", (w/ English Translation of Claims), 10 pgs.
"Chinese Application Serial No. 200780020095.1, Response filed Jun. 23, 2015 to Office Action dated Mar. 5, 2015", (w/ English Translation of Claims), 16 pgs.
"Chinese Application Serial No. 200780020095.1, Response filed Jun. 30, 2016 to Office Action dated Apr. 26, 2016", (w/ English Translation of Claims), 22 pgs.
"Chinese Application U.S. Appl. No. 200780020095.1, Response filed Sep. 17, 2012 to Office Action dated May 3, 2012", (w/ English Translation of Claims), 17 pgs.
"Chinese Application Serial No. 200780020095.1, Response filed Nov. 5, 2013 to to Decision on Rejection dated Jul. 22, 2013", (w/ English Translation of Claims), 12 pgs.
"Chinese Application Serial No. 200780020095.1, Response filed Nov. 8, 2011 to Office Action dated Jun. 24, 2011", (w/ English Translation of Amended Claims), 20 pgs.
"Chinese Application Serial No. 200480021259.9, Office Action dated May 8, 2009", (w/ English Translation), 6 pgs.
"Eurasian Application No. 200501890, Notice of Allowance dated Jun. 23, 2009", 1 pg.
"Eurasian Application Serial No. 200501890, Office Action dated Mar. 23, 2007", (w English Translation), 2 pgs.
"Eurasian Application Serial No. 200501890, Office Action dated Sep. 4, 2008", (English Translation), 1 pg.
"Eurasian Application Serial No. 200501890, Office Action dated Dec. 17, 2007", (w/ English Translation), 6 pgs.
"Eurasian Application Serial No. 200501890, Response filed Mar. 26, 2008 to Office Action dated Dec. 17, 2007", (w/ English Translation of Claims), 15 pgs.
"Eurasian Application Serial No. 200501890, Response filed Jun. 14, 2007 to Office Action dated Mar. 23, 2007", (w/ English Translation of Claims), 11 pgs.
"Eurasian Application Serial No. 200501890, Response filed Dec. 17, 2008 to Office Action", (w/ English Translation of Claims), 13 pgs.
"Eurasian Application Serial No. 200501890, Response filed Dec. 17, 2008 to Office Action dated Sep. 4, 2008", (w/ English Translation of Claims), 14 pgs.
"European Application Serial No. 04776133.3, Communication dated Mar. 30, 2006", 3 pgs.
"European Application Serial No. 04776133.3, Examination Notification Art, 94(3) dated Jul. 28, 2015", 4 pgs.
"European Application Serial No. 04776133.3, Examination Notification Art. 94(3) dated Nov. 25, 2013", 5 pgs.
"European Application U.S. Appl. No. 04776133.3, Office Action dated Jan. 5, 2010", 4 pgs.
"European Application Serial No. 04776133.3, Response filed Jan. 25, 2007 to Communication dated Mar. 30, 2006", 20 pgs.
"European Application Serial No. 04776133.3, Response filed Apr. 30, 2014 to Examination Notification Art. 94(3) dated Nov. 25, 2013", 12 pgs.
"European Application Serial No. 04776133.3, Response filed Jul. 15, 2010 to Office Action dated Jan. 5, 2010", 9 pgs.

(56) References Cited

OTHER PUBLICATIONS

"European Application Serial No. 04776133.3, Response filed Sep. 18, 2015 to Examination Notification Art. 94(3) dated Jul. 28, 2015", 47 pgs.
"European Application Serial No. 07754132.4, Office Action dated Apr. 28, 2009", 4 pgs.
"European Application Serial No. 07754132.4, Office Action dated Sep. 5, 2011", 5 pgs.
"European Application Serial No. 07754132.4, Office Action dated Nov. 2, 2012", 4 pgs.
"European Application Serial No. 07754132.4, Response filed Feb. 5, 2010 to Office Action dated Apr. 28, 2009", 15 pgs.
"European Application Serial No. 07754132.4, Response filed Mar. 15, 2012 to Office Action dated Sep. 5, 2011", 21 pgs.
"European Application Serial No. 07754132.4, Response filed May 10, 2013 to Office Action dated Nov. 2, 2012", 14 pgs.
"European Application Serial No. 07754132.4, Response filed Jun. 26, 2013", 8 pgs.
"European Application Serial No. 10777154.5, Communication Pursuant to Article 94(3) EPC dated Oct. 12, 2017", 7 pgs.
"European Application Serial No. 10777154.5, Examination Notification Art. 94(3) dated Oct. 6, 2014", 7 pgs.
"European Application Serial No. 10777154.5, Office Action dated May 2, 2014", 6 pgs.
"European Application Serial No. 10777154.5, Office Action dated Jul. 4, 2012", 2 pgs.
"European Application Serial No. 10777154.5, Response filed Jan. 14, 2013 to Office Action dated Jul. 4, 2012", 12 pgs.
"European Application Serial No. 10777154.5, Response filed Sep. 8, 2016 to Office Action dated May 2, 2016", 69 pgs.
"European Application Serial No. 14745060.5, Response filed Dec. 22, 2016 to Communication pursuant to Rules 161(1) and 162 EPC dated Feb. 23, 2016", 6 pgs.
"Hemagglutinin [Influenza A virus (A/swine/France/WVL13/1995(H1N1))]", GenBank Accession# AC025026, (May 22, 2009), 1 pg.
"Hemagglutinin [Influenza B virus (B/Hong Kong/330/2001)]", GenBank ABL77178.1, (2006), 1 pg.
"Indian Application Serial No. 1026/KOLNP/2009, First Examiner Report dated Mar. 13, 2014", 2 pgs.
"Indian Application Serail No. 2272/KOLNP/2005, First Examination Report dated Mar. 17, 2008", 10 pgs.
"Indian Application Serial No. 2272/KOLNP/2005, Response filed Mar. 16, 2009 to Subsequent Examination Report dated Mar. 6, 2009", 12 pgs.
"Indian Application Serial No. 2272/KOLNP/2005, Response filed Oct. 11, 2008 to First Examination Report dated Mar. 17, 2008", 27 pgs.
"Indian Application Serial No. 2272/KOLNP/2005, Subsequent Examination Report dated Mar. 6, 2009", 1 pg.
"International Application No. PCT/US2004/016680, International Search Report", (dated Feb. 2, 2005), 7 pgs.
"International Application Serial No. PCT/US2004/016680, International Preliminary Report on Patentability dated Dec. 15, 2005", 11 pgs.
"International Application Serial No. PCT/US2007/007562, International Preliminary Report on Patentability dated Oct. 9, 2008", 5 pgs.
"International Application Serial No. PCT/US2007/007562, International Search Report dated Jan. 14, 2008", 8 pgs.
"International Application Serial No. PCT/US2007/007562, Written Opinion dated Jan. 14, 2008", 9 pgs.
"International Application Serial No. PCT/US2010/054128, Preliminary Report on Patentability dated May 10, 2012", 10 pgs.
"International Application Serial No. PCT/US2010/054128, Search Report dated Feb. 23, 2011", 6 pgs.
"International Application Serial No. PCT/US2010/054128, Written Opinion dated Feb. 23, 2011", 8 pgs.

"International Application Serial No. PCT/US2014/046731, International Preliminary Reporton Patentability dated Jan. 28, 2016", 12 pgs.
"International Application Serial No. PCT/US2014/046731, International Search Report dated Nov. 25, 2014", 9 pgs.
"International Application Serial No. PCT/US2014/046731, Written Opinion dated Nov. 25, 2014", 10 pgs.
"International Application Serial No. PCT/US2015/036803, International Preliminary Report Patentability dated Dec. 29, 2016", 10 pgs.
"International Application Serial No. PCT/US2015/036803, International Search Report dated Dec. 11, 2015", 8 pgs.
"International Application Serial No. PCT/US2015/036803, Invitation to Pay Add'l Fees and Partial Search Rpt dated Oct. 2, 2015", 8 pgs.
"International Application Serial No. PCT/US2015/036803, Written Opinion dated Dec. 11, 2015", 8 pgs.
"International Application Serial No. PCT/US2016/041172, International Search Report dated Oct. 27, 2016", 6 pgs.
"International Application Serial No. PCT/US2016/041172, Written Opinion dated Oct. 27, 2016", 8 pgs.
"International Application Serial No. PCT/US2017/018443, International Search Report dated May 22, 2017", 9 pgs.
"International Application Serial No. PCT/US2017/018443, Written Opinion dated May 22, 2017", 9 pgs.
"Israel Application Serial No. 238584, Office Action dated Jul. 24, 2017", 2 pgs.
"Israel Application Serial No. 238584, Response filed Nov. 21, 2017 to Office Action dated Jul. 24, 2017", W/English Translation, 2 pgs.
"Israeli Application Serial No. 171831, Notification of Defects dated Nov. 10, 2008", (English Translation), 10 pgs.
"Israeli Application Serial No. 171831, Office Action dated Feb. 21, 2010", (English Translation), 2 pgs.
"Israeli Application Serial No. 171831, Office Action dated Apr. 18, 2012", (English Translation), 2 pgs.
"Israeli Application Serial No. 171831, Response filed Jan. 20, 2011 to Office Action dated Feb. 21, 2010", (English Translation), 18 pgs.
"Israeli Application Serial No. 171831, Response filed Jun. 24, 2009 to Notification of Defects dated Nov. 10, 2008", (w/ English Translation of Claims), 10 pgs.
"Israeli Application Serial No. 171831, Response filed Nov. 6, 2012 to Office Action dated Apr. 18, 2012", (w/ English Translation of Amended Claims), 54 pgs.
"Israeli Application Serial No. 238584, Office Action dated Apr. 14, 2016", (English Translation), 3 pgs.
"Israeli Application Serial No. 238584, Office Action dated Jul. 24, 2017", (Translation), 2 pgs.
"Israeli Application Serial No. 238584, Response filed Aug. 3, 2016 to Office Action dated Apr. 14, 2016", (English Translation of Claims), 19 pgs.
"Israeli Application Serial No. 238584, Response filed Nov. 21, 2017 to Office Action dated Jul. 24, 2017", (Translation), 2 pgs.
"Japanese Application Serial No. 2006-533439, Decision of Final Rejection dated Aug. 14, 2012", (w/ English Translation), 5 pgs.
"Japanese Application Serial No. 2006-533439, Office Action dated Mar. 27, 2012", w/ English Translation, 8 pgs.
"Japanese Application Serial No. 2006-533439, Response filed May 21, 2012 to Office Action dated Mar. 27, 2012", (w/ English Translation of Amended Claims), 19 pgs.
"Japanese Application Serial No. 2006-533439, Response filed Aug. 3, 2011 to Office Action dated Feb. 15, 2011", (w/ English Translation of Amended Claims), 18 pgs.
"Japanese Application Serial No. 2006-533439,Office Action dated Feb. 15, 2011", (w/ English Translation), 13 pgs.
"Japanese Application Serial No. 2006-533439; Office Action Response filed Jul. 9, 2010", (w/ English Translation of Claims), 25 pgs.
"Japanese Application Serial No. 2009-502945, Examiners Decision of Final Refusal dated Nov. 12, 2013", (w/ English Translation), 8 pgs.
"Japanese Application Serial No. 2009-502945, Office Action dated Oct. 23, 2012", (w/ English Translation), 16 pgs.

(56) References Cited

OTHER PUBLICATIONS

"Japanese Application Serial No. 2009-502945, Response filed Apr. 10, 2013 to Office Action dated Oct. 23, 2012", (w/ English Translation of Claims), 18 pgs.
"Japanese Application Serial No. 2012-273898, Office Action dated Jun. 10, 2014", (w/ English Translation), 7 pgs.
"Japanese Application Serial No. 2012-273898, Response filed Sep. 4, 2014 to Office Action dated Jun. 10, 2014", W/ English Claims, 9 pgs.
"Japanese Application Serial No. 2012-536963, Amendment and Argument filed Jun. 26, 2015 to Office Action dated Jan. 6, 2015", (w/ English Translation of Amended Claims), 12 pgs.
"Japanese Application Serial No. 2012-536963, Examiners Decision of Final Refusal dated Nov. 17, 2015", (w/ English Translation), 8 pgs.
"Japanese Application Serial No. 2012-536963, Office Action dated Jan. 6, 2015", (w/ English Translation), 14 pgs.
"Japanese Application Serial No. 2012-536963, Voluntary Amendment filed Jun. 27, 2012", (w/ English Translation of Amended Claims), 17 pgs.
"Japanese Application Serial No. 2014-049025 Response filed Sep. 4, 2015 to Office Action dated Jun. 16, 2015", (w/ Amended Claims), 12 pgs.
"Japanese Application Serial No. 2014-049025, Examiners Decision of Final Refusal dated Feb. 2, 2016", W/ English Translation, 5 pgs.
"Japanese Application Serial No. 2014-049025, Office Action dated Jun. 16, 2015", (w/ English Translation), 6 pgs.
"Japanese Application Serial No. 2016-053990, Office Action dated Jun. 6, 2017", (w/ English Translation), 4 pgs.
"Japanese Application Serial No. 2016-053990, Response filed Dec. 6, 2017 to Office Action dated Jun. 6, 2017", (w/ English Translation of Amended Claims), 14 pgs.
"Japanese Application Serial No. 2016-110879, Office Action dated May 30, 2017", (w/ English Translation), 7 pgs.
"Japanese Application Serial No. 2016-110879, Response filed Nov. 30, 2017 to Office Action dated May 30, 2017", (w/ English Translation of Claims), 25 pgs.
"Korean Application Serial No. 10-2005-7022564, Notice of Preliminary Rejection dated Jul. 25, 2007", W/ English Translation, 5 pgs.
"Korean Application Serial No. 10-2005-7022564, Office Action dated Aug. 6, 2008", W/ English Translation, 4 pgs.
"Korean Application Serial No. 10-2005-7022564, Response and Amendment filed Dec. 29, 2008 to Office Action dated Aug. 6, 2008", W/ English Translation, 16 pgs.
"Korean Application Serial No. 10-2005-7022564, Response filed Mar. 25, 2008 to Notice of Preliminary Rejection dated Jul. 25, 2007", (w/ English Translation of Claims), 35 pgs.
"Korean Application Serial No. 10-2005-7022564, Response filed Dec. 29, 2008 to Office Action dated Aug. 6, 2008", (w/ English Translation of Claims), 16 pgs.
"Mexican Application Serial No. MX/a/2009/006341, Office Action dated Mar. 29, 2012", (English Translation), 1 pg.
"Mexican Application Serial No. MX/a/2009/006341, Response filed Jun. 4, 2012 to Mar. 29, 2012", (w/ English Translation of Amended Claims), 16 pgs.
"Mexican Application Serial No. MX/a/2012/009249 Response filed Sep. 10, 2015 to Office Action dated May 19, 2015", (w/ English Translation of Claims), 21 pgs.
"Mexican Application Serial No. MX/a/2012/009249, Office Action dated May 19, 2015", (English Translation), 1 pg.
"Mexican Application Serial No. PA/a/2005/012712, Response filed Sep. 28, 2009 to Office Action dated Jul. 21, 2009", (w/ English Translation of Claims), 24 pgs.
"Mexican Application Serial No. PA/a/2005/012712, Office Action dated May 12, 2010", (w/ English Translation), 19 pgs.
"Mexican Application Serial No. PA/a/2005/012712, Office Action dated Nov. 30, 2009", (w/ English Translation), 14 pgs.
"Mexican Application Serial No. PA/a/2005/012712, Official Action dated Mar. 5, 2009", (English Translation), 2 pgs.
"Mexican Application Serial No. PA/a/2005/012712, Response filed Feb. 3, 2010 to Office Action dated Nov. 30, 2009", (w/ English Translation of Amended Claims), 22 pgs.
"Mexican Application Serial No. PA/a2005/012712, Response filed Sep. 27, 2010 to Office Action dated May 12, 2010", (w/ English Translation of Claims), 19 pgs.
"Mexico Application Serial No. PA/a/2005/012712, Response filed Jun. 12, 2009 to Official Action dated Mar. 5, 2009", (w/ English Translation of Claims), 11 pgs.
"Neuraminidase, partial [Influenza A virus (A/swine/France/WVL13/1995(H1N1))]", GenBank Accession# AC025028, (May 22, 2009), 2 pgs.
"New Zealand Application Serial No. 543446, Examination Report dated Feb. 29, 2008", 2 pgs.
"New Zealand Application Serial No. 543446, Examination Report dated May 12, 2008", 2 pgs.
"New Zealand Application Serial No. 543446, Response dated Mar. 20, 2008 to Examination Report dated Feb. 29, 2008", 2 pgs.
"Nonstructural protein 1 [influenza B virus (B/Hong Kong/330/2001)]", GenBank AAT69443.1, (2006), 1 pg.
"Norway Application Serial No. 20056074, Office Action dated Jan. 17, 2017", (English Translation), 5 pgs.
"Norway Application Serial No. 20056074, Office Action dated Apr. 25, 2017", (w English Translation), 3 pgs.
"Norway Application Serial No. 20056074, Office Action Response dated 04-1817", W/ English Claims, 27 Pgs.
"Norway Application Serial No. 20056074, Response filed Jul. 25, 2017 to Office Action dated Apr. 25, 2017", (w/ English Translation of Amended Claims), 111 pgs.
"Polymerase acidic [influenza A virus (A/swine/Shizuoka/120/97(H3N2))]", GenBank AAO15329.1, (2003), 1 pg.
"Polymerase PA [Influenza B virus (B/Hong Kong/330/2001)]", GenBank ABL7718 6 .1, (2006), 1 pg.
"Polymerase PB1 [Influenza B virus (B/Hong Kong/330/2001 )]", GenBank ABL77187, (2006), 1 pg.
"Polymerase PB2 [Influenza B virus (B/Hong Kong/330/2001)] GenBank ABL77188.1", (2006), 1 pg.
"RecName: Full=Polymerase acidic protein {ECO:0000256{RuleBase;RU361280, ECO: 0000256{SAAS-:SAAS00262764}", XP002744257, retrieved from EBI accession No. UNIPROT:A3R6C9 Database accession No. A3R6C9 the whole document, (Apr. 3, 2007), 1 pgs.
"RecName: Full=Polymerase acidic protein {ECO:0000256{RuleBase;RU361280, ECO: 0000256{SAAS-:SAAS00262764}", XP002744258, retrieved from EBI accession No. UNIPROT:U3S198 Database accession No. U3S198 the whole document, (Dec. 11, 2013), 1 pg.
"Singaporean Application Serial No. 200507468-7, Examination Report dated Mar. 19, 2008", 5 pgs.
"Singaporean Application Serial No. 200507468-7, Invitation to Respond to Written Opinion dated Jun. 12, 2007", 6 pgs.
"Singaporean Application Serial No. 200507468-7, Response filed Nov. 7, 2007 to Invitation to Respond to Written Opinion dated Jun. 12, 2007", 9 pgs.
"Ukrainese Application Serial No. 200512619, Response filed Jan. 21, 2010 to Office Action dated Jun. 17, 2009", W/ English Claims, 14 pgs.
"Ukrainian Application Serial No. 200512619, Office Action dated Feb. 27, 2009", (w/ English Translation), 21 pgs.
"Ukrainian Application Serial No. 200512619, Office Action dated Jun. 17, 2009", (w/ English Translation), 4 pgs.
"Ukrainian Application Serial No. 200512619, Response filed Apr. 8, 2009 to Office Action dated Feb. 27, 2009", (w/ English Translation of Claims), 9 pgs.
Avilov, Sergiy V., et al., "Influenza A virus progeny vRNP trafficking in live infected cells studied with the virus-encoded fluorescently tagged PB2 protein", Vaccine, 30, (2012), 7411-7417.
Avilov, Sergiy V., et al., "Replication-Competent Influenza A Virus That Encodes a Split-Green Fluorescent Protein-Tagged PB2 Polymerase Subunit Allows", Journal of Virology, 86, (2012), 1433-1448.

(56) References Cited

OTHER PUBLICATIONS

Baez, M., et al., "Complete nucleotide sequence of the influenza APR/8/34 virus NS gene and comparison with the NS genes of the A/Udorn/72 and A/FPV/Rostock/34 strains", Nucleic Acids Research, 23(8), (1980), 5845-5858.
Bancroft, C. T, et al., "Evidence for seament-nonspecific packaging of the influenza a virus genome", J Virol., 76(14), (Jul. 2002), 7133-9.
Banerjee, A. K., et al., "Gene Expression of Vesicular Stomatitis Virus Genome RNA.", Virology, 188(2), (1992), 417-428.
Beare, A. S., "Trials in Man With Live Recombinants Made From A/PR/8/34 (H0 N1) and Wild H3 N2 Influenza Viruses", The Lancet, 2(7938), (1975), 729-732.
Brown, E. G., et al., "Genetic analysis of mouse-adapted influenza A virus identifies roles for the NA, PB1, and PB2 genes in virulence", Virus Research, 61(1), (May 1999), 63-76.
Cao, S., et al., "Characterization of the Nucleocytoplasmic Shuttle of the Matrix Protein of Influenza B Virus", Journal of Virology., 88(13), (Jul. 2014), 7464-7473.
Chan, Winnie, et al., "The cold adapted and temperature sensitive influenza A/Ann Arbor/6/60 virus, the master donor virus for live attenuated influenza vaccines, has multiple defects in replication at the restrictive temperature", Virology, 380(2), (2008), 304-311.
Chen, H, et al., "Generation and evaluation of a high-growth reassortant H9N2 influenza A virus as a pandemic vaccine candidate", Vaccine, 21(17-18), (May 16, 2003), 1974-9.
Chevalie, Christophe, et al., "PB1-F2 Influenza A Virus Protein Adopts a B-Sheet Conformation and Forms Amyloid Fibers in Membrane Environments", The of Biological Chemistry, 285(17), (2010), 13233-13243.
De, B. P., et al., "Reverse Genetics of Negative Strand RNA Viruses", Indian Journal of Biochemistry & Biophysics, 31, (1994), 367-375.
Dos Santos Afonso, Emmanuel, et al., "The generation of recombinant influenza A viruses expressing a PB2 fusion protein requires the conservation of a packaging signal overlapping the coding and noncoding regions at the 5V end of the PB2 segment", Virology, 341, (2005), 34-46.
Dreher, T. W., et al., "Mutational Analysis of the Sequence and Structural Requirements in Brome Mosaic Virus RNA for Minus Strand Promoter Activity", Journal of Molecular Biology, 201(1), (1988), 31-40.
Dunham, Eleca J., et al., "Different Evolutionary Trajectories of European Avian-Like and Classical Swine H1N1 Influenza A Viruses", Journal of Virology, 83(11), (Jun. 2009), 5485-5494.
Elliott, R. M., et al., "Rescue of Infectious Bunyavirus Entirely From Cloned cDNA", 10th International Conference on Negative Strand Virus, (Abstract No. 96), (1997), 1 pg.
Fodor, E., et al., "Rescue of Influenza A Virus from Recombinant DNA", Journal of Virology, 73(11), XP002151487; ISSN:0022-538X, (Nov. 1999), 9679-9682.
Forbes, Nicole E, et al., "Multifunctional Adaptive NS1 Mutations Are Selected upon Human Influenza Virus Evolution in the Mouse", Plos One, vol. 7, No. 2, (Feb. 21. 2012).
Fujii, Ken, et al., "Importance of both the Coding and the Segment-Speci?c Noncoding Regions of the In?uenza A Virus NS Segment for Its Ef?cient", Journal of Virology, 79(6), (Mar. 2005), 3766-3774.
Gao, Qinshan, et al., "A Nine-Segment in?uenza A Virus Carrying Subtype Hi and H3 Hemagglutinins\"", Journal of Virology, 84(16), (Aug. 2010), 8062-8071.
Gao, Oinshan, et al., "The in?uenza A Virus PB2, PA, NP, and M Segments Play a Pivotal Role during Genome Packaging", Journal of Virology, 86(13), Chou, (Jul. 2011), 043-7051.
Gotea, V, et al., "The functional relevance of somatic synonymous mutations in melanoma and other cancers", Pigment Cell & Melanoma Research, 28 issue 6, (Nov. 1, 2015), 673-686.
Hickman, Danielle, et al,. "An avian live attenuated master backbone for potential use in epidemic and pandemic influenza vaccines", Journal of General Virology, 89(Part 11), 2682-2690.
Hoffmann, E., et al., "A DNA transfection system for generation of influenza A virus from eight plasmids", Proc Natl Acad Sci U S A., 97(11), (May 23, 2000), 6108-13.
Hoffmann, E., et al., "Ambisense Approach for the Generation of Influenza A Virus: vRNA and mRNA Synthesis from One Template", Virology, 267, (2000), 310-317.
Hoffmann, E., et al., "Eight-plasmid System for Rapid Generation of Influenza Virus Vaccines", Vaccine, Butterworth Scientific Guildford, 20(25-56), (Aug. 19, 2002), 3165-3170.
Hoffmann, E., et al., "Rescue of Influenza B Virus from Eight Plasmids", Proceedings of the National Academy of Sciences of USA, National Academy of Science, 99(17), (Aug. 20, 2002), 11411-11416.
Holmes, E. C, et al., "Whole-Genome Analysis of Human Influenza A Virus Reveals Multiple Persistent Lineages and Reassortment Among Recent H3N2 Viruses", PLoS Biology, 3(9), (2005), 1579-1589.
Honda, Ayae, et al., "Differential Roles of Viral RNA and cRNA in Functional Modulation of tile Influenza Virus RNA Polymerase", The Journal of Biological Chemistry, 276(33), (2001), 31179-31185.
Horimoto, "Designing Vaccines for Pandemic Influenza", Current Topics Microbiol Immunol. 333, (2009), 165-176.
Horimoto, T,, et al., "Enhanced growth of seed viruses for H5N1 influenza vaccines", Virology, 366(1), (Sep. 15, 2007), 23-27.
Hiromoto, T., "Generation of Influenza A Viruses with Chimeric (Type A/B) Hemagglutinins", Journal of Virology, 77(14), (2003), 8031-8038.
Horimoto, T., et al., "The Development and Characterization of H5 Influenza Virus Vaccines Derived from a 2003 Human Isolate", Vaccine, 24(17), (2006), 3669-3676.
Isakova-Sivak, Irina, et al., "Characterization of Reverse Genetics-Derived Cold-Adapted Master Donor Virus A/Leningrad/134/17/57 (H2N2) and Reassortants with H5N1 Surface Genes in a Mouse Model", Clinical and Vaccine immunology, 21(5), (May 2014), 722-731.
Jang, S.-W., et al., "Deoxygedunin, a Natural Product with Potent Neurotrophic Activity in Mice", PLoS ONE 5(7): e11528, (2010), 1-15.
Katinger, D., et al., "Attenuated Influenza Viruses as a Vector for Mucosal Immunization Against HIV-1", Vaccines, 97, Cold Spring Harbor, (1997), 315-319.
Kawaoka, Y., "Mutant Cells With Altered Sialic Acid", U.S. Appl. No. 11/644,179, filed Dec. 22, 2006, 51 pgs.
Kilbourne, E. D, et al., "Related studies of a recombinant influenza-virus vaccine. I. Derivation and characterization of virus and vaccine", J Infect Dis., 124(5), (Nov. 1971), 449-62.
Kim, H., et al., "Cold adaptation generates mutations associated with the growth of influenza B vaccine viruses", Vaccine, 33(43), (2015), 5786-5793.
Kiseleva, I., et al "Role of individual genes of the A-Lenngrad/134/17/57 (H2N2) cold-adapted donor strain in manifestation of the temperature-sensitive phenotype of reassortant influenza A viruses", International Congress Series, vol. 1263, (2004), 547-550.
Kiseleva, Irina V, et al., "PB2 and PA genes control the expression of the temperature-sensitive phenotype of cold-adapted B/USSR/60/69 influenza master donor virus", Journal of General Virology, 91(4), (2010), 931-937.
Kistner, Otfried, et al., "Cell culture (Vero) derived whole virus (H5N1) vaccine based on wild-type virus strain induces cross-protective immune responses", Vaccine, 25(32), (2007), 6028-6036.
Kittel, Christian, et al., "Generation of an In?uenza A Virus Vector Expressing Biologically Active Human Interleukin-2 from the NS Gene Segment", Journal of Virology, 79(16), (Aug. 2005), 10672-10677.
Kovacova, A., et al., "Sequence similarities and evolutionary relationships of influenza virus A hemagglutinins.", Virus Genes, 24(1), (2002), 57-63.
Kovacova, Andrea, et al., "Sequence Similarities and Evolutionary Relationships of Influenza Vrus A Hemagglutinins", Virus Genes, 24(1), (2002), 57-63.

(56) References Cited

OTHER PUBLICATIONS

Lamb, Robert A., et al., "Chapter 20—Paramyxoviridae: The Viruses and Their Replication", In: Fundamental Virology, Fields, B. N., et al., editors, Lippincott-Raven (2nd Edition), (1996), 577-647.

Lazarovits, Janette, et al., "Endocytosis of Chimeric Influenza Virus Hemaggulutinin Proteins That Lack a Cytoplasmic Recognition Feature for Coated Pits", The Journal of Cell vol. 134, No. 2, (1996), 339-348.

Lee, C. W, et al., "Generation of reassortant influenza vaccines by reverse genetics that allows utilization of a DIVA (Differentiating Infected from Vaccinated Animals) strategy for the control of avian influenza", Vaccine, vol. 22, (2004), 3175-3181.

Lee, Jong-Soo, et al., "The Highly Conserved HA2 Protein of the Influenza A Virus Induces a Cross Protective Immune Response", Journal of Virological Methods, 194(1-2), (2013), 280-288.

Lee, M. S, et al., "Genetic and pathogenic characterization of H6NI avian influenza viruses isolated in Taiwan between 1972 and 2005", Avian Diseases, 50(4), (Dec. 2006), 561-571.

Li, et al., "Genesis of a highly pathogenic and potentially pandemic H5N1 influenza virus in eastern Asia", (2004), 209-213 pgs.

Li, K. S, et al., "Genesis of a highly pathogenic and potentially pandemic H5NI influenza virus in eastern Asia", Nature, 430(6996), (Jul. 8, 2004), 209-213.

Lin, Y P, et al., "Adaptation of egg-grown and transfectant influenza viruses for growth in mammalian cells: selection of hemagglutinin mutants with elevated pH of membrane fusion", Virology, vol. 233, No. 2, (1997), 402-410.

Liu, Bo, et al., "[Comparison of three methods in construction fusion gene of influenza A virus Nucleoprotein].", (English Abstract), Zhonghua Shi Yan He Lin Chuang Bing Du Xue Za Zhi, 26(1), 70-74, (Februrary 2012), 1 pg.

Lugovtsev, V. Y., et al., "Genetic Composition and Mutational Pattern of Influenza B Viruses Adapted to Replication in Embryonated Eggs", GenBank: AAT69446.1, (2005), 1 pg.

Manicassamy, Balaji, et al., "Analysis of in vivo dynamics of influenza virus infection in mice using a GFP reporter virus", Proc Natl Acad Sci. USA, 107(25), (2010), 11531-11536.

Manz, Benjamin, et al., "Disruption of the Viral Polymerase Complex Assembly as a Novel Approach to Attenuate Influenza A Virus", The Journal of Biological Chemistry, 286(10), (2011), 8414-8424.

Matsuoka, et al., "Neuraminidase Stalk Length and Additional Glycosylation of the Hemagglutinin Influence the Virulence of Influenza H5N1 Viruses for Mice", Journal of Virology, vol. 83, No. 9,, (2009), pp. 4704-4708.

Murakami, Murakami, "Enhanced Growth of Influenza Vaccine Seed Viruses in Vero Cells Mediated by Broadening the Optimal pH Range for Virus Membrane Fusion", J Virol 86(3), (2012), 1405-1410.

Shin, et al., "Growth Determinants for H5N1 Influenza Vaccine Seed Viruses in MDCK Cells", Journal of Virology, vol. 82, No. 21, (Nov. 2008), 10502-10509.

Nara, P. L., et al., "Simple, Rapid, Quantitative, Syncytium-Forming Microassay for the Detection of Human Immunodeficiency Virus Neutralizing Antibody", Aids Research and Human Retroviruses, 3(3), (1987), 283-302.

Neumann, G., et al., "An Improved Reverse Genetics System for Influenza A Virus Generation and Its Implications for Vaccine Production", Proc. Natl. Acad. Sci. USA, 102(46), (2005), 16825-16829.

Neumann, G., et al., "Emergence and pandemic potential of swin-origin H1N1 influenza virus", Nature (London), 459(7249), (Jun. 2009), 931-939.

Neumann, G., et al., "Generation of influenza A virus from cloned cDNAs—historical perspective and outlook for the new millenium.", Rev Med Virol., 12(1), XP002314285, (Jan.-Feb. 2002), 13-30.

Neumann, G., et al., "Generation of influenza A viruses entirely from cloned cDNAs", Proc. Natl. Acad. Sci. USA., 96(16), (1999), 9345-9350.

Neumann, G., et al., "Plasmid-driven formation of influenza virus-like particles", J Virol., 74(1), [Online] Retrieved From Internet: <http://www.ncbi.nlm.nih.gov/pmc/articles/PMC111569/>, (Jan. 2000), 547-551.

Neumann, G., et al., "Reverse Genetics of Influenza Viruses—Application in Research and Vaccine Design", Monographs in Virology, 27, (2008), 118-133.

Noda, Takeshi, et al., "Three-dimensional analysis of ribonucleoprotein complexes in influenza A virus", Nature Communications, 3, (2012), 1-6.

Odagiri, T., et al., "Nucleotide Sequence of the PA Gene of Influenza A/WSN/33 (H1N1)", Nucleic Acids Research, 18 (3), Department of Virology, (Jan. 9, 1990).

Orkin, S, H, et al., "Report and Recommendations of the Panel to Assess the NIH Investment in Research on Gene Therapy", http://www.nih.gov/news/panelrep.html, (Dec. 7, 1995), 37 pgs.

Ozaki, "Generation of High-Yielding Influenza A Viruses in African Green Monkey Kidney (Vero) Cells by Reverse Genetics", J Virol 78(4), (2004), 1851-1857.

Palese, P., "Negative-Strand RNA Viruses: Genetic Engineering and Applications", Proc. Natl. Acad. Sci. USA, 93(21), (1996), 11354-11358.

Perez, Jasmine T., et al., "Unit 15G.4—Insertion of a GFP Reporter Gene in Influenza Virus", Curr Protoc Microbiol., (2013), 20 pgs.

Ping, J, et al., "Development of high-yield influenza A virus vaccine viruses", Nature Communications, [online], Retrieved from the Internet: <http://www.nature.eom/article-assets/npg/ncomms/2015/150902/ncomms9148/extref/ncomms9148-sl.pdf>, (Sep. 2, 2015), 50 pgs.

Ping, J., et al., "Development of high-yield influenza B virus vaccine viruses", Proc. Natl. Acad, Sci. USA, 113(51), (2016), E8296-E8305, and 25 pgs. of Supplemental Material.

Plant, E P, et al., "Mutations to A/PuertoRico/8/34 PB1 gene improves seasonal reassortant influenza A virus growth kinetics", Vaccine, vol. 31, No. 1, (Dec. 1, 2012), 207-212 pgs.

Radecke, F., et al., "Reverse Genetics Meets the Nonsegmented Negative-Strand RNA Viruses", Reviews in Medical Virology, 7, (1997), 49-63.

Reed, M. L, et al., "Amino Acid Residues in the Fusion peptide Pocket Regulate the pH of Activation of the H5N1 Influenza Virus Hemagglutinin Protein", . J. Virol., 83(8), (2009), 3568-3580.

Romanova, J., et al., "Live cold-adapted influenza A vaccine produced in Vero cell line", Virus Research, 103, (2004), 187-193.

Schickli, J. H, et al., "Plasmid-only Rescue of Influenza A Virus Vaccine Candidates", Philosophical Transactions of the Royal Society of London. Series B, Biological Sciences, 356(1416), (Dec. 29, 2001), 1965-1973.

Schlesinger, S., "RNA Viruses as Vectors for the Expression of Heterologous Proteins", Molecular Biotechnology, 3(2), (1995), 155-165.

Shinya, Kyoko, et al., "Characterization of a Neuraminidase-Deficient Influenza A Virus as a Potential Gene Delivery Vector and a Live Vaccine", Journal of Virology, 78(6), (2004), 3083-3088.

Smeenk, et al., "Mutations in the Hemagglutinin and Matrix Genes of a Virulent Influenza Virus Variant, A/FM/1/47-MA, Control Different Stages in Pathogenesis", Virus Research 44, (1996), 79-95.

Subbarao, K., et al., "Evaluation of a Genetically Modified Reassortant H5N1 Influenza A Virus Vaccine Candidate Generated by Plasmid-based Reverse Genetics", Virology, vol. 305(1), (Jan. 5, 2003), 192-200.

Verma, I. M, et al., "Gene Therapy—Promises, Problems and Prospects", Nature, 389, 239-242.

Voeten, J. T, et al., "Characterization of high-growth reassortant influenza A viruses generated in MDCK cells cultured in serum-free medium", Vaccine, vol. 17, (1999), 1942-1950.

Wang, Wenlig, et al., "Robust Immunity and Heterologous Protection against Influenza in Mice Elicited by a Novel Recombinant NP-M2e Fusion Protein Expressed in *E. coli*", PLoS ONE 7(12): e52488, (Dec. 2012), 1-13.

(56) References Cited

OTHER PUBLICATIONS

Watanabe, Tokiko, et al., "Exploitation of Nucleic Acid Packaging Signals To Generate a Novel In?uenza Virus-Based Vector Stably Expressing Two Foreign Genes", Journal of Virology, 77(19), (Oct. 2003), 10575-10583.
Wei, Hung-Ju, et al., "Fabrication of influenza virus-like particles using M2 fusion proteins imaging single viruses and designing vaccines", Vaccine. 29, (2011), 7163-7172.
Winter, G., et al., "The use of synthetic oligodeoxynucleotide primers in cloning and sequencing segment 8 of influenza virus (A/PR18/34)", Nucleic Acids Res., 9(2), (1981), 237-245.
Wu, Rui, et al., "A live bivalent influenza vaccine based on a H9N2 virus strain", Vaccine, 28, (2010), 673-680.
Xu, X., et al., "Reassortment and evolution of current human influenza A and B viruses", Virus Research, 103, (2004), 55-60.
Yannarell, Dean A., et al., "Factors affecting the yield of cold-adapted influenza virus vaccine", Journal of Virological Methods, vol. 64,161-169, (1997), 1 pg.
Yi, Pu Lin, et al., "Adaptation of Egg-Grown and Transfectant Influenza Viruses for Growth in Mammalian Cells: Selection of Hemagglutinin Mutants with Elevated pH of Membrane Fusion", Virology, 233(2), (Jul. 7, 1997), 402-410.
Zobel, A., et al., "RNA Polymerase I Catalysed Transcription of Insert Viral cDNA", Nucleic Acids Research, 21(16), (1993), 3607-3614.
"U.S. Appl. No. 14/745,236, Notice of Allowability dated Jul. 5, 2018", 4 pgs.
"U.S. Appl. No. 14/745,236, PTO Response to Rule 312 Communication dated Jul. 10, 2018", 2 pgs.
"U.S. Appl. No. 14/816,807, PTO Response to Rule 312 Communication dated Jul. 6, 2018", 2 pgs.
"U.S. Appl. No. 15/170,556, Non Final Office Action dated Jul. 27, 2018", 10 pgs.
"U.S. Appl. No. 15/170,556, Preliminary Amendment filed Aug. 22, 2016", 9 pgs.
"U.S. Appl. No. 15/170,556, Response filed Apr. 5, 2018 to Restriction Requirement dated Feb. 16, 2018", 8 pgs.
"U.S. Appl. No. 15/170,556, Restriction Requirement date Feb. 16, 2018", 7 pgs.
"U.S. Appl. No. 15/593,039, Notice of Allowance dated Jul. 11, 2018", 5 pgs.
"U.S. Appl. No. 15/593,039, Response filed Apr. 30, 2018 to Non Final Office Action dated Feb. 4, 2018", 8 pgs.
"European Application Serial No. 14745060.5, Response filed Jun. 15, 2018 to Communication Pursuant to Article 94(3) EPC dated Feb. 6, 2018", 14 pgs.
Elhefnawi, M, et al., "Identification of novel conserved functional motifs across most Influenza A viral strains", Virol J. Jan. 27, 2011;8:44. doi: 10.1186/1743-422X-8-44, (2011), 2 pgs.
Gorman, O T, "Evolution of influenza A virus PB2 genes: implications for evolution of the ribonucleoprotein complex and origin of human influenza A virus", Department of Virology and Molecular Biology, St. Jude Children's Research Hospital, Memphis Tennessee 38101-0318 J. Virol. Oct. 1990; 64(10):4893-902, (1990), 2 pgs.
Ma, et al., "Cellular micro RNA let-7c inhibits M1 protein expression of the H1N1 influenza A virus in infected human lung epithelial cells", 2012, J. Cell. Mol. Med., vol. 16, No. 10, (2012), 2539-2546.
Matsuzaki, et al., "Epitope Mapping of the Hemagglutinin Molecule of A/(H1N1)pdm09 Influenza Virus by Using Monoclonal Antibody Escape Mutants", 2014, Journal of Virology, vol. 88, No, 21, (2014), 12364-12373.
"U.S. Appl. No. 15/436,245, Non Final Office Action dated Sep. 4, 2020", 9 pgs.
"U.S. Appl. No. 15/436,245, Response filed Apr. 27, 2020 to Final Office Action dated Nov. 18, 2019", 10 pgs.

"U.S. Appl. No. 16/046,250, Notice of Allowance dated Jun. 15, 2020", 9 pgs.
"U.S. Appl. No. 16/046,250, Response filed Jun. 3, 2020 to Non Final Office Action dated Mar. 6, 2020", 10 pgs.
"Australian Application Serial No. 2014290203, Response filed Jun. 24, 2020 to Subsequent Examiners Report dated Mar. 23, 2020", 16 pgs.
"Australian Application Serial No. 2014290203, Response filed Sep. 29, 2020 to Subsequent Examiners Report dated Jul. 21, 2020", 25 pgs.
"Australian Application Serial No. 2014290203, Subsequent Examiners Report dated Jul. 21, 2020", 5 pgs.
"Australian Application Serial No. 2014290203, Subsequent Examiners Report dated Oct. 6, 2020", 4 pgs.
"Australian Application Serial No. 2017221444, First Examination Report dated Jul. 8, 2020", 6 pgs.
"Brazilian Application Serial No. PI0410702-0, Response filed Aug. 28, 2020 to Office Action dated Apr. 1, 2020", w/ English Claims, 88 pgs.
"Canadian Application Serial No. 2,525,953, Response filed May 25, 2020 to Office Action dated Jan. 29, 2020", 35 pgs.
"European Application Serial No. 14745060.5, Response filed Jul. 17, 2020 to Communication Pursuant to Article 94(3) EPC dated Mar. 12, 2020", 52 pgs.
"Influenza B/Ann Arbor/1/66 (cold-adapted) nonstructural protein (seg 8) RNA, complete cds", GenBank Accession M20224, (Aug. 2, 1993).
"International Application Serial No. PCT/US2020/014659, Invitation to Pay Additional Fees dated Sep. 16, 2020", 11 pgs.
"Japanese Application Serial No. 2018-543688, Office Action dated Jun. 30, 2020", w/ English translation, 11 pgs.
"Japanese Application Serial No. 2018-543688, Response filed Apr. 28, 2020 to Notification of Reasons for Rejection dated Oct. 29, 2019", w/ English Claims, 12 pgs.
"RecName: Full=Non-structural protein 1; Short=NS1; AltName: Full=NS1 B", GenPept Accesion P08013, (Dec. 9, 2015).
"U.S. Appl. No. 15/436,245, Response filed Dec. 4, 2020 to Non Final Office Action dated Sep. 4, 2020", 12 pgs.
"Australian Application Serial No. 2014290203, Response filed Dec. 9, 2020 to Subsequent Examiners Report dated Oct. 6, 2020", 14 pgs.
"Australian Application Serial No. 2017221444, Response filed Nov. 13, 2020 to First Examination Report dated Jul. 8, 2020", 13 pgs.
"Australian Application Serial No. 2017221444, Subsequent Examiners Report dated Nov. 27, 2020", 4 pgs.
"Brazilian Application Serial No. PI 0410702-0, Office Action dated Oct. 6, 2020", (w/ English Translation), 9 pgs.
"Brazilian Application Serial No. PI 0410702.-0, Response filed Dec. 14, 2020 to Office Action dated Oct. 6, 2020", (w/ English Translation of Claims), 43 pgs.
"Canadian Application Serial No. 3,014,435, Office Action dated Nov. 6, 2020", 5 pgs.
"European Application Serial No. 14745060.5, Communication Pursuant to Article 94(3) EPC dated Nov. 9, 2020", 4 pgs
"International Application Serial No. PCT/US2020/014659, International Search Report dated Nov. 6, 2020", 7 pgs.
"International Application Serial No. PCT/US2020/014659, Written Opinion dated Nov. 6, 2020", 10 pgs.
"Japanese Application Serial No. 2019-171818, Notification of Reasons for Rejection dated Nov. 10, 2020", (w/ /English Translation), 11 pgs.
U.S. Appl. No. 16/178,323, filed Nov. 1, 2018, High Titer Recombinant Influenza Viruses With Enhanced Replication in MDCK or Vero Cells or Eggs.
U.S. Appl. No. 16/284,020, filed Feb. 25, 2019, Influenza Virus Replication for Vaccine Development.

* cited by examiner

| Virus | Genotype | | | | | | | | MLD$_{50}$(PFU) |
|---|---|---|---|---|---|---|---|---|---|
| | PB2 | PB1 | PA | HA | NP | NA | M | NS | |
| WT-Venus-H5N1 | | | | | | | | | $10^{3.0}$ |
| MA-Venus-H5N1 | | | | | | | | | 3.2 |
| RG-MA | | | | | | | | | 4.7 |
| WT+MA-PB2 | | | | | | | | | $10^{2.3}$ |
| WT+MA-PB1 | | | | | | | | | $10^{3.0}$ |
| WT+MA-PA | | | | | | | | | $10^{2.7}$ |
| WT+MA-NA | | | | | | | | | $10^{3.0}$ |
| WT+MA-M | | | | | | | | | $10^{2.7}$ |
| WT+MA-NS | | | | | | | | | $10^{3.5}$ |
| MA+WT-PB2 | | | | | | | | | $10^{2.3}$ |
| MA+WT-PA | | | | | | | | | $10^{2.3}$ |
| MA+WT-M | | | | | | | | | 4.7 |
| WT+MA-(PB2+PA) | | | | | | | | | 3.2 |
| MA+WT-(PB2+PA) | | | | | | | | | $10^{3.0}$ |

AGCGAAAGCA GGTACTGATC CAAAATGGAA GATTTTGTGC GACAATGCTT
CAATCCGATG ATTGTCGAGC TTGCGGAAAA AACAATGAAA GAGTATGGGG
AGGACCTGAA AATCGAAACA AACAAATTTG CAGCAATATG CACTCACTTG
GAAGTATGCT TCATGTATTC AGATTTTCAC TTCATCAATG AGCAAGGCGA
GTCAATAATC GTAGAACTTG GTGATCCAAA TGCACTTTTG AAGCACAGAT
TTGAAATAAT CGAGGGAAGA GATCGCACAA TGGCCTGGAC AGTAGTAAAC
AGTATTTGCA ACACTACAGG GGCTGAGAAA CCAAAGTTTC TACCAGATTT
GTATGATTAC AAGGAGAATA GATTCATCGA AATTGGAGTA ACAAGGAGAG
AAGTTCACAT ATACTATCTG GAAAAGGCCA ATAAAATTAA ATCTGAGAAA
ACACACATCC ACATTTTCTC GTTCACTGGG AAGAAATGG CCACAAAGGC
AGACTACACT CTCGATGAAG AAAGCAGGGC TAGGATCAAA ACCAGACTAT
TCACCATAAG ACAAGAAATG CCAGCAGAG GCCTCTGGGA TTCCTTTCGT
CAGTCCGAGA GAGGAGAAGA GACAATTGAA GAAAGGTTTG AAATCACAGG
AACAATGCGC AAGCTTGCCG ACCAAAGTCT CCCGCCGAAC TTCTCCAGCC
TTGAAAATTT TAGAGCCTAT GTGGATGGAT TCGAACCGAA CGGCTACATT
GAGGGCAAGC TGTCTCAAAT GTCCAAAGAA GTAAATGCTA GAATTGAACC
TTTTTTGAAA ACAACACCAC GACCACTTAG ACTTCCGAAT GGGCCTCCCT
GTTCTCAGCG GTCCAAATTC CTGCTGATGG ATGCCTTAAA ATTAAGCATT
GAGGACCCAA GTCATGAAGG AGAGGGAATA CCGCTATATG ATGCAATCAA
ATGCATGAGA ACATTCTTTG GATGGAAGGA ACCCAATGTT GTTAAACCAC
ACGAAAAGGG AATAAATCCA AATTATCTTC TGTCATGGAA GCAAGTACTG
GCAGAACTGC AGGACATTGA GAATGAGGAG AAAATTCCAA AGACTAAAAA
TATGAAGAAA ACAAGTCAGC TAAAGTGGGC ACTTGGTGAG AACATGGCAC
CAGAAAAGGT AGACTTTGAC GACTGTAAAG ATGTAGGTGA TTTGAAGCAA
TATGATAGTG ATGAACCAGA ATTGAGGTCG CTTGCAAGTT GGATTCAGAA
TGAGTTTAAC AAGGCATGCG AACTGACAGA TTCAAGCTGG ATAGAGCTCG
ATGAGATTGG AGAAGATGTG GCTCCAATTG AACACATTGC AAGCATGAGA
AGGAATTATT TCACATCAGA GGTGTCTCAC TGCAGAGCCA CAGAATACAT
AATGAAGGGA GTGTACATCA ATACTGCCTT GCTTAATGCA TCTTGTGCAG
CAATGGATGA TTTCCAATTA ATTCCAATGA TAAGCAAGTG TAGAACTAAG
GAGGGAAGGC GAAAGACCAA CTTGTATGGT TTCATCATAA AGGAAGATC
CCACTTAAGG AATGACACCG ACGTGGTAAA CTTTGTGAGC ATGGAGTTTT
CTCTCACTGA CCCAAGACTT GAACCACATA AATGGGAGAA GTACTGTGTT
CTTGAGATAG GAGATATGCT TATAAGAAGT GCCATAGGCC AGGTTTCAAG
GCCCATGTTC TTGTATGTGA GAACAAATGG AACCTCAAAA ATTAAAATGA
AATGGGGAAT GGAGATGAGG CGTTGCCTCC TCCAGTCACT TCAACAAATT
GAGAGTATGA TTGAAGCTGA GTCCTCTGTC AAAGAGAAAG ACATGACCAA
AGAGTTCTTT GAGAACAAAT CAGAAACATG GCCCATTGGA GAGTCCCCCA
AAGGAGTGGA GGAAAGTTCC ATTGGGAAGG TCTGCAGGAC TTTATTAGCA
AAGTCGGTAT TCAACAGCTT GTATGCATCT CCACAACTAG AAGGATTTTC

FIG. 25

AGCTGAATCA AGAAAACTGC TTCTTATCGT TCAGGCTCTT AGGGACAACC
TGGAACCTGG GACCTTTGAT CTTGGGGGGC TATATGAAGC AATTGAGGAG
TGCCTGATTA ATGATCCCTG GGTTTTGCTT AATGCTTCTT GGTTCAACTC
CTTCCTTACA CATGCATTGA GTTAGTTGTG GCAGTGCTAC TATTTGCTAT
CCATACTGTC CAAAAAAGTA CCTTGTTTCT ACT
(SEQ ID NO:1)

PB1

AGCGAAAGCA GGCAAACCAT TTGAATGGAT GTCAATCCGA
CCTTACTTTT CTTAAAAGTG CCAGCACAAA ATGCTATAAG CACAACTTTC
CCTTATACTG GAGACCCTCC TTACAGCCAT GGGACAGGAA CAGGATACAC
CATGGATACT GTCAACAGGA CACATCAGTA CTCAGAAAAG GGAAGATGGA
CAACAAACAC CGAAACTGGA GCACCGCAAC TCAACCCGAT TGATGGGCCA
CTGCCAGAAG ACAATGAACC AAGTGGTTAT GCCCAAACAG ATTGTGTATT
GGAGGCGATG GCTTTCCTTG AGGAATCCCA TCCTGGTATT TTTGAAAACT
CGTGTATTGA AACGATGGAG GTTGTTCAGC AAACACGAGT AGACAAGCTG
ACACAAGGCC GACAGACCTA TGACTGGACT CTAAATAGAA ACCAACCTGC
TGCAACAGCA TTGGCCAACA CAATAGAAGT GTTCAGATCA AATGGCCTCA
CGGCCAATGA GTCTGGAAGG CTCATAGACT TCCTTAAGGA TGTAATGGAG
TCAATGAACA AAGAAGAAAT GGGGATCACA ACTCATTTTC AGAGAAAGAG
ACGGGTGAGA GACAATATGA CTAAGAAAAT GATAACACAG AGAACAATGG
GTAAAAAGAA GCAGAGATTG AACAAAAGGA GTTATCTAAT TAGAGCATTG
ACCCTGAACA CAATGACCAA AGATGCTGAG AGAGGGAAGC TAAAACGGAG
AGCAATTGCA ACCCCAGGGA TGCAAATAAG GGGGTTTGTA TACTTTGTTG
AGACACTGGC AAGGAGTATA TGTGAGAAAC TTGAACAATC AGGGTTGCCA
GTTGGAGGCA ATGAGAAGAA AGCAAAGTTG GCAAATGTTG TAAGGAAGAT
GATGACCAAT TCTCAGGACA CCGAACTTTC TTTCACCATC ACTGGAGATA
ACACCAAATG GAACGAAAAT CAGAATCCTC GGATGTTTTT GGCCATGATC
ACATATATGA CCAGAAATCA GCCCGAATGG TTCAGAAATG TTCTAAGTAT
TGCTCCAATA ATGTTCTCAA ACAAAATGGC GAGACTGGGA AAAGGGTATA
TGTTTGAGAG CAAGAGTATG AAACTTAGAA CTCAAATACC TGCAGAAATG
CTAGCAAGCA TCGATTTGAA ATATTTCAAT GATTCAACAA GAAAGAAGAT
TGAAAAAATC CGACCGCTCT TAATAGAGGG GACTGCATCA TTGAGCCCTG
GAATGATGAT GGGCATGTTC AATATGTTAA GCACTGTATT AGGCGTCTCC
ATCCTGAATC TTGGACAAAA GAGATACACC AAGACTACTT ACTGGTGGGA
TGGTCTTCAA TCCTCTGACG ATTTTGCTCT GATTGTGAAT GCACCCAATC
ATGAAGGGAT TCAAGCCGGA GTCGACAGGT TTTATCGAAC CTGTAAGCTA
CTTGGAATCA ATATGAGCAA GAAAAGTCT TACATAAACA GAACAGGTAC
ATTTGAATTC ACAAGTTTTT TCTATCGTTA TGGGTTTGTT GCCAATTTCA
GCATGGAGCT TCCCAGTTTT GGGGTGTCTG GATCAACGA GTCAGCGGAC
ATGAGTATTG GAGTTACTGT CATCAAAAAC AATATGATAA ACAATGATCT
TGGTCCAGCA ACAGCTCAAA TGGCCCTTCA GTTGTTCATC AAAGATTACA
GGTACACGTA CCGATGCCAT ATAGGTGACA CACAAATACA AACCCGAAGA

FIG. 25 (Cont.)

TCATTTGAAA TAAAGAAACT GTGGGAGCAA ACCCGTTCCA AAGCTGGACT
GCTGGTCTCC GACGGAGGCC CAAATTTATA CAACATTAGA AATCTCCACA
TTCCTGAAGT CTGCCTAAAA TGGGAATTGA TGGATGAGGA TTACCAGGGG
CGTTTATGCA ACCCACTGAA CCCATTTGTC AGCCATAAAG AAATTGAATC
AATGAACAAT GCAGTGATGA TGCCAGCACA TGGTCCAGCC AAAAACATGG
AGTATGATGC TGTTGCAACA ACACACTCCT GGATCCCCAA AGAAATCGA
TCCATCTTGA ATACAAGTCA AAGAGGAGTA CTTGAGGATG AACAAATGTA
CCAAAGGTGC TGCAATTTAT TTGAAAAATT CTTCCCCAGC AGTTCATACA
GAAGACCAGT CGGGATATCC AGTATGGTGG AGGCTATGGT TTCCAGAGCC
CGAATTGATG CACGGATTGA TTTCGAATCT GGAAGGATAA AGAAAGAAGA
GTTCACTGAG ATCATGAAGA TCTGTTCCAC CATTGAAGAG CTCAGACGGC
AAAAATAGTG AATTTAGCTT GTCCTTCATG AAAAAATGCC TTGTTTCTAC
T
(SEQ ID NO:2)

PB2

AGCGAAAGCA GGTCAATTAT ATTCAATATG GAAAGAATAA AAGAACTACG
AAATCTAATG TCGCAGTCTC GCACCCGCGA GATACTCACA AAAACCACCG
TGGACCATAT GGCCATAATC AAGAAGTACA CATCAGGAAG ACAGGAGAAG
AACCCAGCAC TTAGGATGAA ATGGATGATG CAATGAAAT ATCCAATTAC
AGCAGACAAG AGGATAACGG AAATGATTCC TGAGAGAAAT GAGCAAGGAC
AAACTTTATG GAGTAAAATG AATGATGCCG GATCAGACCG AGTGATGGTA
TCACCTCTGG CTGTGACATG GTGGAATAGG AATGGACCAA TAACAAATAC
AGTTCATTAT CCAAAAATCT ACAAAACTTA TTTTGAAAGA GTCGAAAGGC
TAAAGCATGG AACCTTTGGC CCTGTCCATT TTAGAAACCA AGTCAAAATA
CGTCGGAGAG TTGACATAAA TCCTGGTCAT GCAGATCTCA GTGCCAAGGA
GGCACAGGAT GTAATCATGG AAGTTGTTTT CCCTAACGAA GTGGGAGCCA
GGATACTAAC ATCGGAATCG CAACTAACGA TAACCAAAGA GAAGAAAGAA
GAACTCCAGG ATTGCAAAAT TTCTCCTTTG ATGGTTGCAT ACATGTTGGA
GAGAGAACTG GTCCGCAAAA CGAGATTCCT CCCAGTGGCT GGTGGAACAA
GCAGTGTGTA CATTGAAGTG TTGCATTTGA CTCAAGGAAC ATGCTGGGAA
CAGATGTATA CTCCAGGAGG GGAAGTGAGG AATGATGATG TTGATCAAAG
CTTGATTATT GCTGCTAGGA ACATAGTGAG AAGAGCTGCA GTATCAGCAG
ATCCACTAGC ATCTTTATTG GAGATGTGCC ACAGCACACA GATTGGTGGA
ATTAGGATGG TAGACATCCT TAGGCAGAAC CCAACAGAAG AGCAAGCCGT
GGATATATGC AAGGCTGCAA TGGGACTGAG AATTAGCTCA TCCTTCAGTT
TTGGTGGATT CACATTTAAG AGAACAAGCG GATCATCAGT CAAGAGAGAG
GAAGAGGTGC TTACGGGCAA TCTTCAAACA TTGAAGATAA GAGTGCATGA
GGGATATGAA GAGTTCACAA TGGTTGGGAG AAGAGCAACA GCCATACTCA
GAAAAGCAAC CAGGAGATTG ATTCAGCTGA TAGTGAGTGG GAGAGACGAA
CAGTCGATTG CCGAAGCAAT AATTGTGGCC ATGGTATTTT CACAAGAGGA
TTGTATGATA AAAGCAGTCA GAGGTGATCT GAATTTCGTC AATAGGGCGA
ATCAACGATT GAATCCTATG CATCAACTTT AAGACATTT TCAGAAGGAT

GCGAAAGTGC TTTTTCAAAA TTGGGGAGTT GAACCTATCG ACAATGTGAT
GGGAATGATT GGGATATTGC CCGACATGAC TCCAAGCATC GAGATGTCAA
TGAGAGGAGT GAGAATCAGC AAAATGGGTG TAGATGAGTA CTCCAGCACG
GAGAGGGTAG TGGTGAGCAT TGACCGTTTT TTGAGAATCC GGGACCAACG
AGGAAATGTA CTACTGTCTC CCGAGGAGGT CAGTGAAACA CAGGGAACAG
AGAAACTGAC AATAACTTAC TCATCGTCAA TGATGTGGGA GATTAATGGT
CCTGAATCAG TGTTGGTCAA TACCTATCAA TGGATCATCA GAAACTGGGA
AACTGTTAAA ATTCAGTGGT CCCAGAACCC TACAATGCTA TACAATAAAA
TGGAATTTGA ACCATTTCAG TCTTTAGTAC CTAAGGCCAT TAGAGGCCAA
TACAGTGGGT TTGTAAGAAC TCTGTTCCAA CAAATGAGGG ATGTGCTTGG
GACATTTGAT ACCGCACAGA TAATAAAACT TCTTCCCTTC GCAGCCGCTC
CACCAAAGCA AGTAGAATG CAGTTCTCCT CATTTACTGT GAATGTGAGG
GGATCAGGAA TGAGAATACT TGTAAGGGGC AATTCTCCTG TATTCAACTA
TAACAAGGCC ACGAAGAGAC TCACAGTTCT CGGAAAGGAT GCTGGCACTT
TAACTGAAGA CCCAGATGAA GGCACAGCTG GAGTGGAGTC CGCTGTTCTG
AGGGGATTCC TCATTCTGGG CAAAGAAGAC AAGAGATATG GGCCAGCACT
AAGCATCAAT GAACTGAGCA ACCTTGCGAA AGGAGAGAAG GCTAATGTGC
TAATTGGGCA AGGAGACGTG GTGTTGGTAA TGAAACGGAA ACGGGACTCT
AGCATACTTA CTGACAGCCA GACAGCGACC AAAAGAATTC GGATGGCCAT
CAATTAGTGT CGAATAGTTT AAAAACGACC TTGTTTCTAC T (SEQ ID NO:3)

NP

AGCAAAAGCA GGGTAGATAA TCACTCACTG AGTGACATCA
AAATCATGGC GTCTCAAGGC ACCAAACGAT CTTACGAACA GATGGAGACT
GATGGAGAAC GCCAGAATGC CACTGAAATC AGAGCATCCG TCGGAAAAAT
GATTGGTGGA ATTGGACGAT TCTACATCCA AATGTGCACC GAACTCAAAC
TCAGTGATTA TGAGGGACGG TTGATCCAAA ACAGCTTAAC AATAGAGAGA
ATGGTGCTCT CTGCTTTTGA CGAAAGGAGA AATAAATACC TTGAAGAACA
TCCCAGTGCG GGGAAAGATC CTAAGAAAAC TGGAGGACCT ATATACAGGA
GAGTAAACGG AAAGTGGATG AGAGAACTCA TCCTTTATGA CAAAGAAGAA
ATAAGGCGAA TCTGGCGCCA AGCTAATAAT GGTGACGATG CAACGGCTGG
TCTGACTCAC ATGATGATCT GGCATTCCAA TTTGAATGAT GCAACTTATC
AGAGGACAAG AGCTCTTGTT CGCACCGGAA TGGATCCCAG GATGTGCTCT
CTGATGCAAG GTTCAACTCT CCCTAGGAGG TCTGGAGCCG CAGGTGCTGC
AGTCAAAGGA GTTGGAACAA TGGTGATGGA ATTGGTCAGA ATGATCAAAC
GTGGGATCAA TGATCGGAAC TTCTGGAGGG GTGAGAATGG ACGAAAAACA
AGAATTGCTT ATGAAAGAAT GTGCAACATT CTCAAAGGGA AATTTCAAAC
TGCTGCACAA AAAGCAATGA TGGATCAAGT GAGAGAGAGC CGGAACCCAG
GGAATGCTGA GTTCGAAGAT CTCACTTTTC TAGCACGGTC TGCACTCATA
TTGAGAGGGT CGGTTGCTCA CAAGTCCTGC CTGCCTGCCT GTGTGTATGG
ACCTGCCGTA GCCAGTGGGT ACGACTTTGA AAGGGAGGGA TACTCTCTAG
TCGGAATAGA CCCTTTCAGA CTGCTTCAAA ACAGCCAAGT GTACAGCCTA
ATCAGACCAA ATGAGAATCC AGCACACAAG AGTCAACTGG TGTGGATGGC
ATGCCATTCT GCCGCATTTG AAGATCTAAG AGTATTAAGC TTCATCAAAG

GGACGAAGGT GCTCCCAAGA GGGAAGCTTT CCACTAGAGG AGTTCAAATT
GCTTCCAATG AAAATATGGA GACTATGGAA TCAAGTACAC TTGAACTGAG
AAGCAGGTAC TGGGCCATAA GGACCAGAAG TGGAGGAAAC ACCAATCAAC
AGAGGGCATC TGCGGGCCAA ATCAGCATAC AACCTACGTT CTCAGTACAG
AGAAATCTCC CTTTTGACAG AACAACCATT ATGGCAGCAT TCAATGGGAA
TACAGAGGGG AGAACATCTG ACATGAGGAC CGAAATCATA AGGATGATGG
AAAGTGCAAG ACCAGAAGAT GTGTCTTTCC AGGGGCGGGG AGTCTTCGAG
CTCTCGGACG AAAAGGCAGC GAGCCCGATC GTGCCTTCCT TGACATGAG
TAATGAAGGA TCTTATTTCT TCGGAGACAA TGCAGAGGAG TACGACAATT
AAAGAAAAAT ACCCTTGTTT CTACT
(SEQ ID NO:4)

M

AGCAAAAGCA GGTAGATATT GAAAGATGAG TCTTCTAACC GAGGTCGAAA
CGTACGTACT CTCTATCATC CCGTCAGGCC CCTCAAAGC CGAGATCGCA
CAGAGACTTG AAGATGTCTT TGCAGGGAAG AACACCGATC TTGAGGTTCT
CATGGAATGG CTAAAGACAA GACCAATCCT GTCACCTCTG ACTAAGGGGA
TTTTAGGATT TGTGTTCACG CTCACCGTGC CAGTGAGCG AGGACTGCAG
CGTAGACGCT TGTCCAAAA TGCCCTTAAT GGGAACGGGG ATCCAAATAA
CATGGACAAA GCAGTTAAAC TGTATAGGAA GCTCAAGAGG GAGATAACAT
TCCATGGGGC CAAAGAAATC TCACTCAGTT ATTCTGCTGG TGCACTTGCC
AGTTGTATGG GCCTCATATA CAACAGGATG GGGGCTGTGA CCACTGAAGT
GGCATTTGGC CTGGTATGTG CAACCTGTGA ACAGATTGCT GACTCCCAGC
ATCGGTCTCA TAGGCAAATG GTGACAACAA CCAATCCACT AATCAGACAT
GAGAACAGAA TGGTTTTAGC CAGCACTACA GCTAAGGCTA TGGAGCAAAT
GGCTGGATCG AGTGAGCAAG CAGCAGAGGC CATGGAGGTT GCTAGTCAGG
CTAGACAAAT GGTGCAAGCG ATGAGAACCA TTGGGACTCA TCCTAGCTCC
AGTGCTGGTC TGAAAAATGA TCTTCTTGAA AATTTGCAGG CCTATCAGAA
ACGAATGGGG GTGCAGATGC AACGGTTCAA GTGATCCTCT CACTATTGCC
GCAAATATCA TTGGGATCTT GCACTTGACA TTGTGGATTC TTGATCGTCT
TTTTTTCAAA TGCATTTACC GTCGCTTTAA ATACGGACTG AAAGGAGGGC
CTTCTACGGA AGGAGTGCCA AAGTCTATGA GGGAAGAATA TCGAAAGGAA
CAGCAGAGTG CTGTGGATGC TGACGATGGT CATTTTGTCA GCATAGAGCT
GGAGTAAAAA ACTACCTTGT TTCTACT (SEQ ID NO:5)

NS

AGCAAAAGCA GGGTGACAAA AACATAATGG ATCCAAACAC TGTGTCAAGC
TTTCAGGTAG ATTGCTTTCT TTGGCATGTC CGCAAACGAG TTGCAGACCA
AGAACTAGGC GATGCCCCAT TCCTTGATCG GCTTCGCCGA GATCAGAAAT
CCCTAAGAGG AAGGGGCAGT ACTCTCGGTC TGGACATCAA GACAGCCACA
CGTGCTGGAA AGCAGATAGT GGAGCGGATT CTGAAAGAAG AATCCGATGA
GGCACTTAAA ATGACCATGG CCTCTGTACC TGCGTCGCGT TACCTAACTG

ACATGACTCT TGAGGAAATG TCAAGGGACT GGTCCATGCT CATACCCAAG
CAGAAAGTGG CAGGCCCTCT TTGTATCAGA ATGGACCAGG CGATCATGGA
TAAGAACATC ATACTGAAAG CGAACTTCAG TGTGATTTTT GACCGGCTGG
AGACTCTAAT ATTGCTAAGG GCTTTCACCG AAGAGGGAGC AATTGTTGGC
GAAATTTCAC CATTGCCTTC TCTTCCAGGA CATACTGCTG AGGATGTCAA
AAATGCAGTT GGAGTCCTCA TCGGAGGACT TGAATGGAAT GATAACACAG
TTCGAGTCTC TGAAACTCTA CAGAGATTCG CTTGGAGAAG CAGTAATGAG
AATGGGAGAC CTCCACTCAC TCCAAAACAG AAACGAGAAA TGGCGGGAAC
AATTAGGTCA GAAGTTTGAA GAAATAAGAT GGTTGATTGA AGAAGTGAGA
CACAAACTGA AGATAACAGA GAATAGTTTT GAGCAAATAA CATTTATGCA
AGCCTTACAT CTATTGCTTG AAGTGGAGCA AGAGATAAGA ACTTTCTCGT
TTCAGCTTAT TTAGTACTAA AAAACACCCT TGTTTCTACT
(SEQ ID NO:6)

HA

AGCAAAAGCAGGGGAAAATAAAAACAACCAAAATGAAGGCAAACCTACTGGTCCT
GTTATGTGCACTTGCAGCTGCAGAT
GCAGACACAATATGTATAGGCTACCATGCGAACAATTCAACCGACACTGTTGACAC
AGTACTCGAGAAGAATGTGACAGT
GACACACTCTGTTAACCTGCTCGAAGACAGCCACAACGGAAAACTATGTAGATTAA
AAGGAATAGCCCCACTACAATTGG
GGAAATGTAACATCGCCGGATGGCTCTTGGGAAACCCAGAATGCGACCCACTGCTT
CCAGTGAGATCATGGTCCTACATT
GTAGAAACACCAAACTCTGAGAATGGAATATGTTATCCAGGAGATTTCATCGACTAT
GAGGAGCTGAGGGAGCAATTGAG
CTCAGTGTCATCATTCGAAAGATTCGAAATATTTCCCAAAGAAAGCTCATGGCCCAA
CCACAACACAAACGGAGTAACGG
CAGCATGCTCCCATGAGGGGAAAAGCAGTTTTTACAGAAATTTGCTATGGCTGACGG
AGAAGGAGGGCTCATACCCAAAG
CTGAAAAATTCTTATGTGAACAAAAAGGGAAAGAAGTCCTTGTACTGTGGGGTAT
TCATCACCCGCCTAACAGTAAGGA
ACAACAGAATCTCTATCAGAATGAAAATGCTTATGTCTCTGTAGTGACTTCAAATTA
TAACAGGAGATTTACCCCGGAAA
TAGCAGAAAGACCCAAAGTAAGAGATCAAGCTGGGAGGATGAACTATTACTGGACC
TTGCTAAAACCCGGAGACACAATA
ATATTTGAGGCAAATGGAAATCTAATAGCACCAATGTATGCTTTCGCACTGAGTAGA
GGCTTTGGGTCCGGCATCATCAC
CTCAAACGCATCAATGCATGAGTGTAACACGAAGTGTCAAACACCCCTGGGAGCTA
TAAACAGCAGTCTCCCTTACCAGA
ATATACACCCAGTCACAATAGGAGAGTGCCCAAAATACGTCAGGAGTGCCAAATTG
AGGATGGTTACAGGACTAAGGAAC
ATTCCGTCCATTCAATCCAGAGGTCTATTTGGAGCCATTGCCGGTTTTATTGAAGGG
GGATGGACTGGAATGATAGATGG

FIG. 25 (Cont.)

ATGGTATGGTTATCATCATCAGAATGAACAGGGATCAGGCTATGCAGCGGATCAAA
AAAGCACACAAAATGCCATTAACG
GGATTACAAACAAGGTGAACACTGTTATCGAGAAAATGAACATTCAATTCACAGCT
GTGGGTAAAGAATTCAACAAATTA
GAAAAAAGGATGGAAAATTTAAATAAAAAAGTTGATGATGGATTTCTGGACATTTG
GACATATAATGCAGAATTGTTAGT
TCTACTGGAAAATGAAAGGACTCTGGATTTCCATGACTCAAATGTGAAGAATCTGTA
TGAGAAAGTAAAAAGCCAATTAA
AGAATAATGCCAAAGAAATCGGAAATGGATGTTTTGAGTTCTACCACAAGTGTGAC
AATGAATGCATGGAAAGTGTAAGA
AATGGGACTTATGATTATCCCAAATATTCAGAAGAGTCAAAGTTGAACAGGGAAAA
GGTAGATGGAGTGAAATTGGAATC
AATGGGGATCTATCAGATTCTGGCGATCTACTCAACTGTCGCCAGTTCACTGGTGCT
TTTGGTCTCCCTGGGGGCAATCA
GTTTCTGGATGTGTTCTAATGGATCTTTGCAGTGCAGAATATGCATCTGAGATTAGA
ATTTCAGAGATATGAGGAAAAAC
ACCCTTGTTTCTACT (SEQ ID NO:7)

NA
AGCAAAAGCAGGGGTTTAAAATGAATCCAAATCAGAAAATAATAACCATTGGATCA
ATCTGTCTGGTAGTCGGACTAATT
AGCCTAATATTGCAAATAGGGAATATAATCTCAATATGGATTAGCCATTCAATTCAA
ACTGGAAGTCAAAACCATACTGG
AATATGCAACCAAAACATCATTACCTATAAAAATAGCACCTGGGTAAAGGACACAA
CTTCAGTGATATTAACCGGCAATT
CATCTCTTTGTCCCATCCGTGGGTGGGCTATATACAGCAAAGACAATAGCATAAGAA
TTGGTTCCAAAGGAGACGTTTTT
GTCATAAGAGAGCCCTTTATTTCATGTTCTCACTTGGAATGCAGGACCTTTTTTCTGA
CCCAAGGTGCCTTACTGAATGA
CAAGCATTCAAGTGGGACTGTTAAGGACAGAAGCCCTTATAGGGCCTTAATGAGCT
GCCCTGTCGGTGAAGCTCCGTCCC
CGTACAATTCAAGATTTGAATCGGTTGCTTGGTCAGCAAGTGCATGTCATGATGGCA
TGGGCTGGCTAACAATCGGAATT
TCAGGTCCAGATAATGGAGCAGTGGCTGTATTAAAATACAACGGCATAATAACTGA
AACCATAAAAAGTTGGAGGAAGAA
AATATTGAGGACACAAGAGTCTGAATGTGCCTGTGTAAATGGTTCATGTTTTACTAT
AATGACTGATGGCCCGAGTGATG
GGCTGGCCTCGTACAAAATTTTCAAGATCGAAAAGGGGAAGGTTACTAAATCAATA
GAGTTGAATGCACCTAATTCTCAC
TATGAGGAATGTTCCTGTTACCCTGATACCGGCAAAGTGATGTGTGTGTGCAGAGAC
AATTGGCATGGTTCGAACCGGCC
ATGGGTGTCTTTCGATCAAAACCTGGATTATCAAATAGGATACATCTGCAGTGGGGT
TTTCGGTGACAACCCGCGTCCCG
AAGATGGAACAGGCAGCTGTGGTCCAGTGTATGTTGATGGAGCAAACGGAGTAAAG
GGATTTTCATATAGGTATGGTAAT

FIG. 25 (Cont.)

GGTGTTTGGATAGGAAGGACCAAAAGTCACAGTTCCAGACATGGGTTTGAGATGAT
TTGGGATCCTAATGGATGGACAGA
GACTGATAGTAAGTTCTCTGTGAGGCAAGATGTTGTGGCAATGACTGATTGGTCAGG
GTATAGCGGAAGTTTCGTTCAAC
ATCCTGAGCTGACAGGGCTAGACTGTATGAGGCCGTGCTTCTGGGTTGAATTAATCA
GGGGACGACCTAAAGAAAAAACA
ATCTGGACTAGTGCGAGCAGCATTTCTTTTTGTGGCGTGAATAGTGATACTGTAGAT
TGGTCTTGGCCAGACGGTGCTGA
GTTGCCATTCAGCATTGACAAGTAGTCTGTTCAAAAAACTCCTTGTTTCTACT (SEQ
ID NO:8)

Cambridge

```
agcgaaagca ggtcaattat attcaatatg gaaagaataa aagaactaag aaatctaatg
tcgcagtctc gcaccgcga gatactcaca aaaaccaccg tggaccatat ggccataatc
aagaagtaca catcaggaag acaggagaag aaccagcac ttaggatgaa atggatgatg
gcaatgasat atcaattac agcagacaag aggataacgg aaatgattcc tgagagaat
gagcaggac aaactttatg gagtaaaatg aatgatgccg gatcagaccg agtgatgta
tcacctctgg ctgtgacatg gtggaatagg aatggaccaa tgacaaatac agttcattat
ccaaaaatct acaaaactta ttttgaaaga gtcgaaaggc taaagcatgg aaccttggc
cctgtccatt ttagaaacca agtcaaaata ctcggagag ttgacataaa tctggtcat
gcagatctca gtgccagga ggcacaggat gtaatcatgg aagttgtttt ccctaacgaa
gtgggagcca ggatactaac atcggaatcg caactaacga taaccaagaa gaagaagaa
gaactccagg attgcaaaat ttctcctttg atggttgcat acatgttgga gagagaactg
gtccgcaaaa cgagattcct cccagtggct ggtggaacaa gcagtgtgta cattgaagtg
ttgcatttga ctcaaggaac atgctggaa cagatgtata ctccaggag ggaagtgaag
aatgatgatg ttgatcaaag cttgattatt gctgctagga acatagtgaa ggagctgca
gtatcagcag accactagc atctttattg gagatgtgcc acagcacaca gattggtgga
attaggatgg tagacatcct taagcagaac ccaacagaag agcaagccgt ggatatatgc
aaggctgcaa tgggactgag aattagctca tccttcagtt ttggtggatt cacatttaag
agaacaagcg gatcatcagt caagagagag gaagaggtgc ttacgggcaa tcttcaaaca
ttgaagataa gagtgcatga gggatctgaa gagttcacaa tggttggag aagagtaaca
gccatactca gaaaagcaac caggagattg attcagctga tagtgagtgg gagagacgaa
cagtcgattg ccgaagcaat aattgtggcc atggtatttt cacaagagga ttgtatgata
aaagcagtta gaggtgatct gaatttcgtc aatagggcga atcagcgact gaatcctatg
catcaacttt taagacattt tcagaaggat gcgaaagtgc tttttcaaaa ttggggagtt
gaacctatcg acaatgtgat gggaatgatt gggatattgc ccgacatgac tccaagcatc
gagatgtcaa tgagaggagt gagaatcagc aaatggggtg tagatgagta ctccagcacg
gagagggtag tggtgagcat tgaccggttc ttgagagtca gggaccaacg aggaaatgta
ctactgtctc ccgaggaggt cagtgaaaca cagggaacag agaaactgac aataacttac
tcatcgtcaa tgatgtggga gattaatggt cctgaatcag tgttggtcaa taactatcaa
tggatcatca gaaactggga aactgttaaa attcagtggt cccagaaccc tacaatgcta
tacaataaaa tggaatttga accatttcag tctttagtac ctaaggcat tagaggccaa
tacagtgggt ttgtaagaac tctgttccaa caaatgaggg atgtgcttgg gacatttgat
acgcacagaa taataaaact tcttccttc gcagccgctc caccaaagca aagtagaatg
cagttctcct cattactgt gaatgtgagg ggatcaggaa tgagaatact tgtaaggggc
aattctctg tattcaacta caacaaggcc acgaagagac tcacagttct cggaaaggat
gctggcactt taacgaaga ccagatgaa ggcacagctg gagtggagtc cgctgttctg
agggattcc tcattctggg caaagaagac aggagatatg ggccagcatt aagcatcaat
gaactgagca accttgcgaa aggagagaag gctaatgtgc taattgggca aggagacgtg
gtgttggtaa tgaaacgaaa acgggactct agcatactta ctgacagcca gacagcgacc
aaaagaattc ggatggccat caattagtgt cgaatagttt aaaaacgacc ttgtttctac
```

FIG. 26 (Cont.)

t (SEQ ID NO:10)

MERIKELRNLMSQSRTREILTKTTVDHMAIIKKYTSGR
QEKNPALRMKWMMAMKYPITADKRITEMIPERNEQGQ
TLWSKMNDAGSDRVMVSPLAVTWWNRNGPMTNTVHY
PKIYKTYFERVERLKHGTFGPVHFRNQVKIRRRVDINPG
HADLSAKEAQDVIMEVVFPNEVGARILTSESQLTITKEK
KEELQDCKISPLMVAYMLERELVRKTRFLPVAGGTSSV
YIEVLHLTQGTCWEQMYTPGGEVKNDDVDQSLIIAARN
IVRRAAVSADPLASLLEMCHSTQIGGIRMVDILKQNPTE
EQAVDICKAAMGLRISSSFSFGGFTFKRTSGSSVKREEE
VLTGNLQTLKIRVHEGSEEFTMVGRRATAILRKATRRLI
QLIVSGRDEQSIAEAIIVAMVFSQEDCMIKAVRGDLNFV
NRANQRLNPMHQLLRHFQKDAKVLFQNWGVEPIDNVM
GMIGILPDMTPSIEMSMRGVRISKMGVDEYSSTERVVV
SIDRFLRVRDQRGNVLLSPEEVSETQGTEKLTITYSSSM
MWEINGPESVLVNTYQWIIRNWETVKIQWSQNPTMLY
NKMEFEPFQSLVPKAIRGQYSGFVRTLFQQMRDVLGTF
DTAQIIKLLPFAAAPPKQSRMQFSSFTVNVRGSGMRILV
RGNSPVFNYNKATKRLTVLGKDAGTLTEDPDEGTAGV
ESAVLRGFLILGKEDRRYGPALSINELSNLAKGEKANVL
IGQGDVVLVMKRKRDSSILTDSQTATKRIRMAIN

```
agcgaaagca ggcaaaccat ttgaatggat gtcaatccga ccttactttt cttaaaagtg
ccagcacaaa atgctataag cacaacttt cc ttatacg gagaccctcc ttacagccat
gggacaggaa caggatacac catggatact gtcaacagga cacatcagta ctcagaaaag
ggaagatgca caacaaacac cgaaactgga gcaccgaaac tcaaccgat tgatgggcca
ctgccagaag acaatgaacc aagtggttat gccaaacag attgtgtatt ggaagcaatg
gctttccttg aggaatccca tcctggtatt tttgaaaact cgtgtattga aacgatggag
gttgttcagc aaacacgagt agacaagctg acacaaggcc gacagaccta tgactggact
ttaaatagaa accagcctgc tgcaacagca ttggccaaca caatagaagt gttcagatca
aatgcctca cggccaatga gtcaggaagg ctcatagact tccttaagga tgtaatggag
tcaatgaaca aagaagaaat ggggatcaca actcattttc agagaaagag acggtgaga
gacaatatga ctaagaaaat gataacacag agascaatag gtaaaggaa acagagattg
aacaaagcg gttatctaat tagagcattg acctgaaca caatgaccaa agatgctgag
agaggaagc taaaacggag agcaattgca acccaggga tgcaaataag ggggtttgta
tactttgttg agacactggc aaggagtata tgtgagaac ttgaacaatc agggttgcca
gttggaggca atgagaagaa agcaaagttg goaaatgttg taaggaagat gatgaccaat
tctcaggaca ccgaacttc tttcaccatc actggagata acaccaaatg gaacgaaaat
cagaatcctc ggatgttttt ggccatgatc acatatatga ccagaaatca gccgaatgg
ttcagaaatg ttctaagtat tgctccaata atgttctcaa acaaaatggc gagactggga
aaagggtata tgtttgagag caagagtatg aaacttagaa ctcaaatacc tgcagaaatg
ctagcaagca ttgatttgaa atatttcaat gattcaacaa gaagaagat tgaaaaaatc
cgaccgctct taatagaggg gactgcatca ttgagccctg gaatgatgat gggcatgttc
aatatgttaa gactgtatt aggcgtctcc atcctgaatc ttggacaaaa gagatacacc
aagactactt actggtggga tggtcttcaa tcctctgacg attttgctct gattgtgaat
gcacccaatc atgaagggat tcaagccgga gtggacaggt tttatcgaac ctgtaagcta
```

FIG. 25 (Cont.)

```
cttggaatca atatgagcaa gaaaaagtct tacataaaca gaacaggtac atttgaattc
acaagttttt tctatcgtta tgggtttgtt gccaatttca gcatggagct tcccagtttt
ggggtgtctg ggatcaaega gtcagcggac atgagtattg gagttactgt catcaaaaac
aatatgataa acaatgatct tggtccagca acagctcaaa tggccttca gttgttcatc
aaagattaca ggtacacgta ccgatgccat agaggtgaca cacaaataca aaccgaaga
tcatttgaaa taaagaaact gtgggagcaa acccgttcca aagctggact gctggtctcc
gacggaggcc caaatttata caacattaga aatctccaca ttcctgaagt ctgcctaaaa
tgggaattga tcgatgagga ttaccagggg cgtttatgca acccactgaa cccatttgtc
agccataaag aaattgaatc aatgaacaat gcagtgatga tgccagcaca tggtccagcc
aaaaacatgg agtatgatgc tgttgcaaca acacactctt ggatccccaa aagaaatcga
tccatcttga atacaagtca aagaggagta cttgaagatg aacaaatgta ccaaagytgc
tgcaatttat ttgaaaaatt cttccccagc agttcataca gaagaccagt ccggatatcc
agtatggtgg aggctatggt ttccagagcc cgaattgatg cacggattga tttcgaatct
ggaaggataa agaagaaga gttcactgag atcatgaaga tctgttccac cattgaagag
ctcagacggc aaaaatagtg aatttagctt gtccttcatg aaaaaatgcc ttgtttctac
t (SEQ ID NO:11)
```

MDVNPTLLFLKVPAQNAISTTFPYTGDPPYSHGTGTGY
TMDTVNRTHQYSEKGRWTTNTETGAPQLNPIDGPLPED
NEPSGYAQTDCVLEAMAFLEESHPGIFENSCIETMEVV
QQTRVDKLTQGRQTYDWTLNRNQPAATALANTIEVFR
SNGLTANESGRLIDFLKDVMESMKKEEMGITTHFQRKR
RVRDNMTKKMITQRTIGKRKQRLNKRGYLIRALTLNT
MTKDAERGKLKRRAIATPGMQIRGFVYFVETLARSICE
KLEQSGLPVGGNEKKAKLANVVRKMMTNSQDTELSFT
ITGDNTKWNENQPRMFLAMITYMTRNQPEWFRNVLS
IAPIMFSNKMARLGKGYMFESKSMKLRTQIPAEMLASI
DLKYFNDSTRKKIEKIRPLLIEGTASLSPGMMMGMFNM
LSTVLGVSILNLGQKRYTKTTYWWDGLQSSDDFALIVN
APNHEGIQAGVDRFYRTCKLLGINMSKKKSYINRTGTF
EFTSFFYRYGFVANFSMELPSFGVSGINESADMSIGVTV
IKNNMINNDLGPATAQMALQLFIKDYRYTYRCHRGDT
QIQTRRSFEIKKLWEQTRSKAGLLVSDGGPNLYNIRNLH
IPEVCLKWELMDEDYQGRLCNPLNPFVSHKEIESMNNA
VMMPAHGPAKNMEYDAVATTHSWIPKRNRSILNTSQR
GVLEDEQMYQRCCNLFEKFPSSSYRRPVGISSMVEAM
VSRARIDARIDFESGRIKKEEFTEIMKICSTIEELRRQK

```
agcgaaagca ggtactgatt caaaatggaa gattttgtgc gacaatgctt caatccgatg
attgtcgagc ttgcggaaaa aacaatgaaa gagtatgggg aggacctgaa aatcgaaaca
aacaaatttg cagcaatatg cactcacttg gaagtatgct tcatgtattc agatttccac
ttcatcaatg agcaaggcga gtcaataatc gtagaacttg gtgatcctaa tgcactttg
aagcacagat ttgaaataat cgagggaaga gatcgcacaa tggctggac agtagtaaac
agtatttgca acactacagg ggctgagaaa ccaaagtttc taccagattt gtatgattac
aagggaaata gattcatcga aattggagta acaaggagag aagttcacat atactatctg
gaaaaggcca ataaaattaa atctgagaaa acacacatcc acatttctc gttcactggg
gaagaaatgg ccacaagggc cgactacact ctcgatgaag aaagcagggc taggatcaaa
```

```
accaggctat tcaccataag acaagaaatg gccagcagag gcctctggga ttcctttcgt
cagtccgaga gaggagaaga gacaattgaa gaaaggtttg aaatcacagg aacaatgcgc
aagcttgccg accaaagtct cccgccgaac ttctccagcc ttgaaaattt tagagcctat
gtggatggat tcgaaccgaa cggctacatt gagggcaagc tgtctcaaat gtccaaagaa
gtaaatgcta gaattgaacc ttttttgaaa acaacaccac gaccacttag acttccgaat
gggcctccct gttctcagcg gtccaaattc ctgctgatgg atgccttaaa attaagcatt
gaggacccaa gtcatgaagg agagggaata ccgctatatg atgcaatcaa atgcatgaga
acattctttg gatggaagga acccaatgtt gttaaaccac acgaaaaggg aataaatcca
aattatcttc tgtcatggaa gcaagtactc gcagaactgc aggacattga gaatgaggag
aaaattccaa agactaaaaa tatgaaaaaa acaagtcagc taaagtgggc acttggtgag
aacatggcac cagaaaaggt agactttgac gactgtaaag atgtaggtga tttgaagcaa
tatgatagtg atgaaccaga attgaggtcg cttgcaagtt ggattcagaa tgagttcaac
aaggcatgcg aactgacaga ttcaagctgg atagagcttg atgagattgg agaagatgtg
gctccaattg aacacattgc aagcatgaga aggaattatt tcacatcaga ggtgtctcac
tgcagagcca cagaatacat aatgaagggg gtgtacatca atactgcctt acttaatgca
tcttgtgcag caatggatga tttccaatta attccaatga taagcaagtg tagaactaag
gagggaaggc gaaagaccaa cttgtatggt ttcatcatca aaggaagatc ccacttaagg
aatgacacgg acgtggtaaa ctttgtgagc atggagtttt ctctcactga cccaagactt
gaaccacaca aatgggagaa gtactgtgtt cttgagatag gagatatgct tctaagaagt
gccataggcc aggtttcaag gcccatgttc ttgtatgtga ggacaaatgg aacctcaaaa
attaaaatga aatggggaat ggagatgagg cgttgtctcc tccagtcact tcaacaaatt
gagagtatga ttgaagctga gtcctctgtc aaagagaaag acatgaccaa agagttcttt
gagaacaaat cagaaacatg gcccattgga gagtctccca aaggagtgga ggaaagttcc
attgggaagg tctgcaggac tttattagca aagtcggtat ttaacagctt gtatgcatct
ccacaactag aaggattttc agctgaatca agaaaactgc ttcttatcgt tcaggctctt
agggacaatc tggaacctgg gacctttgat cttgggggc tatatgaagc aattgaggag
tgcctaatta atgatccctg ggttttgctt aatgcttctt ggttcaactc cttccttacg
catgcattga gttagttgtg gcagtgctac tatttgctat ccatactgtc caaaaagta
ccttgtttct act (SEQ ID NO:12)
```

MEDFVRQCFNPMIVELAEKTMKEYGEDLKIETNKFAAI
CTHLEVCFMYSDFHPINEQGESIIVELGDPNALLKHRFE
IIEGRDRTMAWTVVNSICNTTGAEKPKFLPDLYDYKEN
RFIEIGVTRREVHIYYLEKANKIKSEKTHIHIFSFTGEEM
ATRADYTLDEESRARIKTRLFTIRQEMASRGLWDSFRQ
SERGEETIEERFEITGTMRKLADQSLPPNFSSLENFRAY
VDGFEPNGYIEGKLSQMSKEVNARIEPFLKTTPRPLRLP
NGPPCSQRSKFLLMDALKLSIEDPSHEGEGIPLYDAIKC
MRTFFGWKEPNVVKPHEKGINPNYLLSWKQVLAELQDI
ENEEKIPKTKNMKKTSQLKWALGENMAPEKVDFDDCK
DVGDLKQYDSDEPELRSLASWIQNEFNACELTDSSWI
ELDEIGEDVAPIEHIASMRRNYFTSEVSHCRATEYIMKG
VYINTALLNASCAAMDDFQLIPMISKCRTKEGRRKTNL
YGFIIKGRSHLRNDTDVVNFVSMEFSLTDPRLEPHKWE
KYCVLEIGDMLLRSAIGQVSRPMFLYVRTNGTSKIKMK
WGMEMRRCLLQSLQQIESMIEAESSVKEKDMTKEFFEN
KSETWPIGESPKGVEESSIGKVCRTLLAKSVFNSLYASP

FIG. 25 (Cont.)

QLEGFSAESRKLLLIVQALRDNLEPGTFDLGGLYEAIEE
CLINDPWVLLNASWFNSFLTHALS Stop

```
agcaaaagca gggtagataa tcactcactg agtgacatca aaatcatggc gtcccaaggc
accaaacggt cttacgaaca gatggagact gatggagaac gtcagaatgc cactgaaatc
agagcatccg tcggaaaaat gattggtgga attggacgat tctacatcca aatgtgcaca
gaacttaaac tcagtgatta tgagggacgg ttgatccaaa acagcttaac aatagagaga
atggtgctct ctgcttttga cgaaagqaga aataaatacc tggaagaaca tcccagtgcg
gggaaagatc ctaagaaaac tggaggacct atatacagaa gagtaaacgg aaagtggatg
agagaactca tcctttatga caaagaagaa ataaggcgaa tctggcgcca agctaataat
ggtgacgatg caacggctgg tctgactcac atgatgatct ggcattccaa tttgaatgat
gcaacttatc agaggacaag ggctcttgtt cgcaccggaa tggatcccag gatgtgctct
ctgatgcaag gttcaactct ccctaggagg tctgagccg caggtgctga agtcaaagga
gttggaacaa tggtgatgga attggtcagg atgatcaaac gtgggatcaa tgatcggaac
ttctggaggg gtgagaatgg acgaaaaaca agaattgctt atgaaagaat gtgcaacatt
ctcaaaggga aatttcaaac tgctgcacaa aaagcaatga tggatcaagt gagagagagc
cggaacccag ggaatgctga gttcgaagat ctcactttc tagcacggtc tgcactcata
ttgagagggt cggttgctca caagtcctgc ctgcctgcct gtgtgtatgg acctgccgta
gccagtgggt acgactttga aagagaggga tactctctag tcggaataga cccttcaga
ctgcttcaaa acagccaagt gtacagccta atcagaccaa atgagaatcc agcacacaag
agtcaactgg tgtggatggc atgccattct gccgcatttg aagatctaag agtattgagc
ttcatcaaag ggacgaaggt ggtcccaaga gggaagcttt ccactagagg agttcaaatt
gcttccaatg aaaatatgga gactatggaa tcaagtacac ttgaactgag aagcaggtac
tgggccataa ggaccagaag tggaggaaac accaatcaac agaggcatc tgcgggccaa
atcagcatac aacctacgtt ctcagtacag agaaatctcc cttttgacag aacaaccgtt
atggcagcat tcactgggaa tacagagggg agaacatctg acatgaggac cgaaatcata
aggatgatgg aaagtgcaag accagaagat gtgtcttttc agggcgggg agtcttcgag
ctctcggacg aaaaggcagc gagcccgatc gtgccttcct ttgacatgag taatgaagga
tcttatttct tcggagacaa tgcagaggag tacgacaatt aaagaaaaat acccttgttt
ctact    (SEQ ID NO:13)
```

MASQGTKRSYEQMETDGERQNATEIRASVGKMIGGIG
RFYIQMCTELKLSDYEGRLIQNSLTIERMVLSAFDERRN
KYLEEHPSAGKDPKKTGGPIYRRVNGKWMRELILYDKE
EIRRIWRQANNGDDATAGLTHMMIWHSNLNDATYQRT
RALVRTGMDPRMCSLMQGSTLPRRSGAAGAAVKGVGT
MVMELVRMIKRGINDRNFWRGENGRKTRIAYERMCNI
LKGKFQTAAQKAMMDQVRESRNPGNAEFEDLTFLARS
ALILRGSVAHKSCLPACVYGPAVASGYDFEREGYSLVG
IDPFRLLQNSQVYSLIRPNENPAHKSQLVWMACHSAAF
EDLRVLSFIKGTKVVPRGKLSTRGVQIASNENMETMES
STLELRSRYWAIRTRSGGNTNQQRASAGQISIQPTFSVQ
RNLPFDRTTVMAAFTGNTEGRTSDMRTEIIRMMESARP
EDVSFQGRGVFELSDEKAASPIVPSFDMSNEGSYFFGD
NAEEYDN Sto

```
agcaaaagca ggtagatatt gaaagatgag tcttctaacc gaggtcgaaa cgtacgttct
ctctatcatc ccgtcaggcc ccctcaaagc cgagatcgca cagagacttg aagatgtctt
tgcagggaag aacacggatc ttgaggttct catggaatgg ctaaagacaa gaccaatcct
```

FIG. 25 (Cont.)

```
gtcacctctg actaagggga ttttaggatt tgtgttcacg ctcacggtgc ccagtgagcg
aggactgcag cgtagacgct ttgtccaaaa tgccttaat gggaacgggg atccaaataa
catggacaaa gcagttaaac tgtataggaa gctcaagagg gagataacat tccatggggc
caaagaaatc tcactcagtt attctgctgg tgcacttgcc agttgtatgg gcctcatata
cacaggatg ggggctgtga ccactgaagt ggcatttggc ctgtatgtg caacctgtga
acagattgct gactccagc atcggtctca taggcaaatg gtgacaacaa ccacccact
aatcagacat gagaacagaa tggttttagc cagcactaca gctaaggcta tggagcaaat
ggctggatcg agtgagcaag cagcagaggc catggaggtt gctagtcagg ctaggcaaat
ggtgcaagcg atgagaacca ttgggactca tcctagctcc agtgctggtc tgaaaaatga
tcttcttgaa aatttgcagg cctatcagaa acgaatgggg gtgcagatgc aacggttcaa
gtgatcctct cgctattgcc gcaaatatca ttgggatctt gcacttgata ttgtggattc
ttgatcgtct ttttttcaaa tgcatttacc gtcgtttaa atacggactg aaaggagggc
cttctacgga aggagtgcca aagtctatga gggaagaata tcgaaaggaa cagcagagtg
ctgtggatgc tgacgatggt cattttgtca gcatagagct ggagtaaaaa actaccttgt
ttctact   (SEQ ID NO:14)
```

MSLLTEVETYVLSIIPSGPLKAEIAQRLEDVFAGKNTDL
EVLMEWLKTRPILSPLTKGILGFVFTLTVPSERGLQRRR
FVQNALNGNGDPNNMDKAVKLYRKLKREITFHGAKEI
SLSYSAGALASCMGLIYNRMGAVTTEVAFGLVCATCE
QIADSQHRSHRQMVTTTNPLIRHENRMVLASTTAKAM
EQMAGSSEQAAEAMEVASQARQMVQAMRTIGTHPSSS
AGLKNDLLENLQAYQKRMGVQMQRFK Stop

```
agcaaaagca gggtgacaaa gacataatgg atccaaacac tgtgtcaagc tttcaggtag    60
attgctttct ttggcatgtc cgcaaacgag ttgcagacca agaactaggt gatgccccat   120
tccttgatcg gcttcgccga gatcagaaat ccctaagagg aagggggcagc actcttggtc   180
tggacatcga gacagccaca cgtgctggaa agcagatagt ggagcggatt ctgaaagaag   240
aatccgatga ggcacttaaa atgaccatgg cctctgtacc tcgtcgcgt tacctaaccg    300
acatgactct tgaggaaatg tcaaggaat ggtccatgct catacccaag cagaaagtgg    360
caggccctct ttgtatcaga atggaaccagg cgatcatgga taaaaacatc atactgaaag    420
cgaacttcag tgtgatttt gacggtgg agactctaat attgctaagg gctttcaccg    480
aagagggagc aattgttggc gaaatttcac cattgccttc tcttccaggga catactgctg    540
aggatgtcaa aaatgcagtt ggagtcctca tcggaggact tgaatggaat gataacacag    600
ttcgagtctc tgaaactcta cagagattcg cttgagaag cagtaatgag aatgggagac    660
ctccactcac tccaaacag aaacgagaaa tggcgggaac aattaggtca gaagtttgaa    720
gaaataagat ggttgattga agaagtgaga cacaaactga aggtaacaga gaatagtttt    780
gagcaaaatca cattatgca agccttacat ctattgcttg aagtggagca agagatagga    840
actttctcat ttcagcttat
ttaataataa aaaacaccct
tgctttctact
890 (SEQ ID NO 15)
```

FIG. 25 (Cont.)

SEQUENCE LISTING

```
<160> NUMBER OF SEQ ID NOS: 27

<210> SEQ ID NO 1
<211> LENGTH: 2233
<212> TYPE: DNA
<213> ORGANISM: Influenza virus

<400> SEQUENCE: 1
agcgaaagca ggtactgatc caaaatggaa gattttgtgc gacaatgctt caatccgatg      60
attgtcgagc ttgcggaaaa aacaatgaaa gagtatgggg aggacctgaa aatcgaaaca     120
aacaaatttg cagcaatatg cactcacttg gaagtatgct tcatgtattc agattttcac     180
ttcatcaatg agcaaggcga gtcaataatc gtagaacttg gtgatccaaa tgcacttttg     240
aagcacagat ttgaaataat cgagggaaga gatcgcacaa tggcctggac agtagtaaac     300
agtatttgca acactacagg ggctgagaaa ccaaagtttc taccagattt gtatgattac     360
aaggagaata gattcatcga aattggagta acaaggagag aagttcacat atactatctg     420
gaaaaggcca ataaaattaa atctgagaaa acacacatcc acattttctc gttcactggg     480
gaagaaatgg ccacaaaggc agactacact ctcgatgaag aaagcagggc taggatcaaa     540
```

-continued

```
accagactat tcaccataag acaagaaatg gccagcagag gcctctggga ttcctttcgt    600
cagtccgaga gaggagaaga gacaattgaa gaaaggtttg aaatcacagg aacaatgcgc    660
aagcttgccg accaaagtct cccgccgaac ttctccagcc ttgaaaattt tagagcctat    720
gtggatggat tcgaaccgaa cggctacatt gagggcaagc tgtctcaaat gtccaaagaa    780
gtaaatgcta gaattgaacc ttttttgaaa acaacaccac gaccacttag acttccgaat    840
gggcctccct gttctcagcg gtccaaattc ctgctgatgg atgccttaaa attaagcatt    900
gaggacccaa gtcatgaagg agagggaata ccgctatatg atgcaatcaa atgcatgaga    960
acattctttg gatggaagga acccaatgtt gttaaaccac acgaaagggg aataaatcca   1020
aattatcttc tgtcatggaa gcaagtactg gcagaactgc aggacattga gaatgaggag   1080
aaaattccaa agactaaaaa tatgaagaaa acaagtcagc taaagtgggc acttggtgag   1140
aacatggcac cagaaaaggt agactttgac gactgtaaag atgtaggtga tttgaagcaa   1200
tatgatagtg atgaaccaga attgaggtcg cttgcaagtt ggattcagaa tgagtttaac   1260
aaggcatgcg aactgacaga ttcaagctgg atagagctcg atgagattgg agaagatgtg   1320
gctccaattg aacacattgc aagcatgaga aggaattatt tcacatcaga ggtgtctcac   1380
tgcagagcca cagaatacat aatgaaggga gtgtacatca atactgcctt gcttaatgca   1440
tcttgtgcag caatggatga tttccaatta attccaatga taagcaagtg tagaactaag   1500
gagggaaggc gaaagaccaa cttgtatggt ttcatcataa aaggaagatc ccacttaagg   1560
aatgacaccg acgtggtaaa ctttgtgagc atggagtttt ctctcactga cccaagactt   1620
gaaccacata aatgggagaa gtactgtgtt cttgagatag agatatgct tataagaagt   1680 gccataggcc aggtttcaag gcccatgttc tgtatgtga aacaaatgg aacctcaaaa   1740 attaaaatga atggggaat ggagatgagg cgttgcctcc tccagtcact tcaacaaatt   1800
gagagtatga ttgaagctga gtcctctgtc aaagagaaag acatgaccaa agagttcttt   1860
gagaacaaat cagaaacatg gcccattgga gagtccccca aggagtggga ggaaagttcc   1920
attgggaagg tctgcaggac tttattagca aagtcggtat caacagctt gtatgcatct   1980 ccacaactag aaggattttc agctgaatca agaaaactgc ttcttatcgt tcaggctctt   2040
agggacaacc tggaacctgg gacctttgat cttggggggc tatatgaagc aattgaggag   2100
tgcctgatta atgatcctg ggttttgctt aatgcttctt ggttcaactc cttccttaca   2160
catgcattga gttagttgtg gcagtgctac tatttgctat ccatactgtc caaaaagta   2220 ccttgtttct act                                                     2233
```

<210> SEQ ID NO 2
<211> LENGTH: 2341
<212> TYPE: DNA
<213> ORGANISM: Influenza virus

<400> SEQUENCE: 2

```
agcgaaagca ggcaaaccat ttgaatggat gtcaatccga ccttactttt cttaaaagtg     60
ccagcacaaa atgctataag cacaactttc ccttatactg gagaccctcc ttacagccat    120
gggacaggaa caggatacac catggatact gtcaacagga cacatcagta tcagaaaaag    180
ggaagatgga caacaaacac cgaaactgga gcaccgcaac tcaacccgat tgatgggcca    240
ctgccagaag acaatgaacc aagtggttat gcccaaacag attgtgtatt ggaggcgatg    300
gctttccttg aggaatccca tcctggtatt tttgaaaact cgtgtattga aacgatggag    360
```

| | |
|---|---|
| gttgttcagc aaacacgagt agacaagctg acacaaggcc gacagaccta tgactggact | 420 |
| ctaaatagaa accaacctgc tgcaacagca ttggccaaca caatagaagt gttcagatca | 480 |
| aatggcctca cggccaatga gtctggaagg ctcatagact tccttaagga tgtaatggag | 540 |
| tcaatgaaca aagaagaaat ggggatcaca actcattttc agagaaagag acgggtgaga | 600 |
| gacaatatga ctaagaaaat gataacacag agaacaatgg gtaaaagaa gcagagattg | 660 |
| aacaaaagga gttatctaat tagagcattg accctgaaca caatgaccaa agatgctgag | 720 |
| agagggaagc taaaacggag agcaattgca accccaggga tgcaaataag ggggtttgta | 780 |
| tactttgttg agacactggc aaggagtata tgtgagaaac ttgaacaatc agggttgcca | 840 |
| gttggaggca atgagaagaa agcaaagttg gcaaatgttg taaggaagat gatgaccaat | 900 |
| tctcaggaca ccgaactttc tttcaccatc actggagata caccaaatg gaacgaaaat | 960 |
| cagaatcctc ggatgttttt ggccatgatc acatatatga ccagaaatca gcccgaatgg | 1020 |
| ttcagaaatg ttctaagtat tgctccaata atgttctcaa acaaaatggc gagactggga | 1080 |
| aaagggtata tgtttgagag caagagtatg aaacttagaa ctcaaatacc tgcagaaatg | 1140 |
| ctagcaagca tcgatttgaa atatttcaat gattcaacaa gaagaagat tgaaaaatc | 1200 |
| cgaccgctct aatagaggg gactgcatca ttgagccctg aatgatgat gggcatgttc | 1260 |
| aatatgttaa gcactgtatt aggcgtctcc atcctgaatc ttggacaaaa gagatacacc | 1320 |
| aagactactc actggtggga tggtcttcaa tcctctgacg atttttgctct gattgtgaat | 1380 |
| gcacccaatc atgaagggat tcaagccgga gtcgacaggt tttatcgaac ctgtaagcta | 1440 |
| cttggaatca atatgagcaa gaaaaagtct tacataaaca gaacaggtac atttgaattc | 1500 |
| acaagttttt tctatcgtta tgggtttgtt gccaatttca gcatggagct tcccagtttt | 1560 |
| ggggtgtctg ggatcaacga gtcagcggac atgagtattg gagttactgt catcaaaaac | 1620 |
| aatatgataa acaatgatct tggtccagca acagctcaaa tggcccttca gttgttcatc | 1680 |
| aaagattaca ggtacacgta ccgatgccat ataggtgaca cacaaataca aacccgaaga | 1740 |
| tcatttgaaa taaagaaact gtgggagcaa acccgttcca agctggact gctggtctcc | 1800 |
| gacggaggcc caaatttata caacattaga aatctccaca ttcctgaagt ctgcctaaaa | 1860 |
| tgggaattga tggatgagga ttaccagggg cgtttatgca cccactgaa cccatttgtc | 1920 |
| agccataaag aaattgaatc aatgaacaat gcagtgatga tgccagcaca tggtccagcc | 1980 |
| aaaaacatgg agtatgatgc tgttgcaaca acacactcct ggatcccaa agaaatcga | 2040 |
| tccatcttga atacaagtca agaggagta cttgaggatg aacaaatgta ccaaaggtgc | 2100 |
| tgcaatttat ttgaaaaatt cttccccagc agttcataca agaaccagt cgggatatcc | 2160 |
| agtatggtgg aggctatggt ttccagagcc cgaattgatg cacggattga tttcgaatct | 2220 |
| ggaaggataa agaagaaga gttcactgag atcatgaaga tctgttccac cattgaagag | 2280 |
| ctcagacggc aaaaatagtg aatttagctt gtccttcatg aaaaaatgcc ttgtttctac | 2340 |
| t | 2341 |

<210> SEQ ID NO 3
<211> LENGTH: 2341
<212> TYPE: DNA
<213> ORGANISM: Influenza virus

<400> SEQUENCE: 3

| | |
|---|---|
| agcgaaagca ggtcaattat attcaatatg gaaagaataa agaactacg aaatctaatg | 60 |
| tcgcagtctc gcacccgcga gatactcaca aaaaccaccg tggaccatat ggccataatc | 120 |

```
aagaagtaca catcaggaag acaggagaag aacccagcac ttaggatgaa atggatgatg      180
gcaatgaaat atccaattac agcagacaag aggataacgg aaatgattcc tgagagaaat      240
gagcaaggac aaactttatg gagtaaaatg aatgatgccg gatcagaccg agtgatggta      300
tcacctctgg ctgtgacatg gtggaatagg aatggaccaa taacaaatac agttcattat      360
ccaaaaatct acaaaactta ttttgaaaga gtcgaaaggc taaagcatgg aacctttggc      420
cctgtccatt ttagaaacca agtcaaaata cgtcggagag ttgacataaa tcctggtcat      480
gcagatctca gtgccaagga ggcacaggat gtaatcatgg aagttgtttt ccctaacgaa      540
gtgggagcca ggatactaac atcggaatcg caactaacga taaccaaaga gaagaaagaa      600
gaactccagg attgcaaaat ttctcctttg atggttgcat acatgttgga gagagaactg      660
gtccgcaaaa cgagattcct cccagtggct ggtggaacaa gcagtgtgta cattgaagtg      720
ttgcatttga ctcaaggaac atgctgggaa cagatgtata ctccaggagg ggaagtgagg      780
aatgatgatg ttgatcaaag cttgattatt gctgctagga acatagtgag aagagctgca      840
gtatcagcag atccactagc atctttattg gagatgtgcc acagcacaca gattggtgga      900
attaggatgt tagacatcct taggcagaac ccaacagaag agcaagccgt ggatatatgc      960
aaggctgcaa tgggactgag aattagctca tccttcagtt ttggtggatt cacatttaag     1020
agaacaagcg gatcatcagt caagagagag gaagaggtgc ttacgggcaa tcttcaaaca     1080
ttgaagataa gagtgcatga gggatatgaa gagttcacaa tggttgggag aagagcaaca     1140
gccatactca gaaaagcaac caggagattg attcagctga tagtgagtgg gagagacgaa     1200
cagtcgattg ccgaagcaat aattgtggcc atggtatttt cacaagagga ttgtatgata     1260
aaagcagtca gaggtgatct gaatttcgtc aatagggcga atcaacgatt gaatcctatg     1320
catcaacttt taagacattt tcagaaggat gcgaaagtgc tttttcaaaa ttggggagtt     1380
gaacctatcg acaatgtgat gggaatgatt gggatattgc ccgacatgac tccaagcatc     1440
gagatgtcaa tgagaggagt gagaatcagc aaaatgggtg tagatgagta ctccagcacg     1500
gagagggtag tggtgagcat tgaccgtttt ttgagaatcc gggaccaacg aggaaatgta     1560
ctactgtctc ccgaggaggt cagtgaaaca cagggaacag agaaactgac aataacttac     1620
tcatcgtcaa tgatgtggga gattaatggt cctgaatcag tgttggtcaa tacctatcaa     1680
tggatcatca gaaactggga aactgttaaa attcagtggt cccagaaccc tacaatgcta     1740
tacaataaaa tggaatttga accatttcag tctttagtac taaggccat tagaggccaa     1800 tacagtgggt ttgtaagaac tctgttccaa caaatgaggg atgtgcttgg gacatttgat     1860
accgcacaga taataaaact tcttcccttc gcagccgctc caccaaagca agtagaatg      1920 cagttctcct catttactgt gaatgtgagg ggatcaggaa tgagaatact tgtaaggggc     1980
aattctcctg tattcaacta taacaaggcc acgaagagac tcacagttct cggaaaggat     2040
gctggcactt taactgaaga cccagatgaa ggcacagctg gagtggagtc cgctgttctg     2100
aggggattcc tcattctggg caaagaagac aagagatatg gccagcact aagcatcaat     2160 gaactgagca accttgcgaa aggagagaag gctaatgtgc taattgggca aggagacgtg     2220
gtgttggtaa tgaaacggaa acgggactct agcatactta ctgacagcca gacagcgacc     2280
aaaagaattc ggatggccat caattagtgt cgaatagttt aaaaacgacc ttgtttctac     2340
t                                                                    2341

<210> SEQ ID NO 4
```

<211> LENGTH: 1565
<212> TYPE: DNA
<213> ORGANISM: Influenza virus

<400> SEQUENCE: 4

```
agcaaaagca gggtagataa tcactcactg agtgacatca aaatcatggc gtctcaaggc    60
accaaacgat cttacgaaca gatggagact gatggagaac gccagaatgc cactgaaatc   120
agagcatccg tcggaaaaat gattggtgga attggacgat tctacatcca aatgtgcacc   180
gaactcaaac tcagtgatta tgagggacgg ttgatccaaa acagcttaac aatagagaga   240
atggtgctct ctgcttttga cgaaaggaga aataaatacc ttgaagaaca tcccagtgcg   300
gggaaagatc ctaagaaaac tggaggacct atatacagga gagtaaacgg aaagtggatg   360
agagaactca tcctttatga caaagaagaa ataaggcgaa tctggcgcca agctaataat   420
ggtgacgatg caacggctgg tctgactcac atgatgatct ggcattccaa tttgaatgat   480
gcaacttatc agaggacaag agctcttgtt cgcaccggaa tggatcccag atgtgctct   540
ctgatgcaag gttcaactct ccctaggagg tctggagccg caggtgctgc agtcaaagga   600
gttggaacaa tggtgatgga attggtcaga atgatcaaac gtgggatcaa tgatcggaac   660
ttctggaggg gtgagaatgg acgaaaaaca agaattgctt atgaaagaat gtgcaacatt   720
ctcaaaggga aatttcaaac tgctgcacaa aaagcaatga tggatcaagt gagagagagc   780
cggaacccag gaatgctga gttcgaagat ctcactttc tagcacggtc tgcactcata   840
ttgagagggt cggttgctca caagtcctgc ctgcctgcct gtgtgtatgg acctgccgta   900
gccagtgggt acgactttga aagggaggga tactctctag tcggaataga ccctttcaga   960
ctgcttcaaa acagccaagt gtacagccta atcagaccaa atgagaatcc agcacacaag  1020
agtcaactgg tgtggatggc atgccattct gccgcatttg aagatctaag agtattaagc  1080
ttcatcaaag gacgaaggt gctcccaaga gggaagcttt ccactagagg agttcaaatt  1140
gcttccaatg aaaatatgga gactatgaa tcaagtacac ttgaactgag aagcaggtac  1200
tgggccataa ggaccagaag tggaggaaac accaatcaac agagggcatc tgcgggccaa  1260
atcagcatac aacctacgtt ctcagtacag agaaatctcc ctttgacag aacaaccatt  1320
atggcagcat tcaatgggaa tacagagggg agaacatctg acatgaggac cgaaatcata  1380
aggatgatgg aaagtgcaag accagaagat gtgtctttcc aggggcgggg agtcttcgag  1440
ctctcggacg aaaaggcagc gagcccgatc gtgccttcct ttgacatgag taatgaagga  1500
tcttatttct tcggagacaa tgcagaggag tacgacaatt aaagaaaaat acccttgttt  1560
ctact                                                              1565
```

<210> SEQ ID NO 5
<211> LENGTH: 1027
<212> TYPE: DNA
<213> ORGANISM: Influenza virus

<400> SEQUENCE: 5

```
agcaaaagca ggtagatatt gaaagatgag tcttctaacc gaggtcgaaa cgtacgtact    60
ctctatcatc ccgtcaggcc ccctcaaagc cgagatcgca cagagacttg aagatgtctt   120
tgcagggaag aacaccgatc ttgaggttct catggaatgg ctaaagacaa gaccaatcct   180
gtcacctctg actaagggga ttttaggatt tgtgttcacg ctcaccgtgc ccagtgagcg   240
aggactgcag cgtagacgct ttgtccaaaa tgcccttaat gggaacgggg atccaaataa   300
catggacaaa gcagttaaac tgtataggaa gctcaagagg gagataacat tccatgggc   360
```

```
caaagaaatc tcactcagtt attctgctgg tgcacttgcc agttgtatgg gcctcatata    420
caacaggatg ggggctgtga ccactgaagt ggcatttggc ctggtatgtg caacctgtga    480
acagattgct gactcccagc atcggtctca taggcaaatg gtgacaacaa ccaatccact    540
aatcagacat gagaacagaa tggttttagc cagcactaca gctaaggcta tggagcaaat    600
ggctggatcg agtgagcaag cagcagaggc catggaggtt gctagtcagg ctagacaaat    660
ggtgcaagcg atgagaacca tgggactca tcctagctcc agtgctggtc tgaaaaatga    720
tcttcttgaa aatttgcagg cctatcagaa acgaatgggg gtgcagatgc aacggttcaa    780
gtgatcctct cactattgcc gcaaatatca ttgggatctt gcacttgaca ttgtggattc    840
ttgatcgtct tttttcaaa tgcatttacc gtcgctttaa atacggactg aaaggagggc    900
cttctacgga aggagtgcca aagtctatga gggaagaata tcgaaaggaa cagcagagtg    960
ctgtggatgc tgacgatggt cattttgtca gcatagagct ggagtaaaaa actaccttgt   1020
ttctact                                                             1027

<210> SEQ ID NO 6
<211> LENGTH: 890
<212> TYPE: DNA
<213> ORGANISM: Influenza virus

<400> SEQUENCE: 6
agcaaaagca gggtgacaaa aacataatgg atccaaacac tgtgtcaagc tttcaggtag     60
attgctttct ttggcatgtc cgcaaacgag ttgcagacca agaactaggc gatgccccat    120
tccttgatcg gcttcgccga gatcagaaat ccctaagagg aaggggcagt actctcggtc    180
tggacatcaa gacagccaca cgtgctggaa agcagatagt ggagcggatt ctgaaagaag    240
aatccgatga ggcacttaaa atgaccatgg cctctgtacc tgcgtcgcgt tacctaactg    300
acatgactct tgaggaaatg tcaagggact ggtccatgct catacccaag cagaaagtgg    360
caggccctct ttgtatcaga atggaccagg cgatcatgga taagaacatc atactgaaag    420
cgaacttcag tgtgattttt gaccggctgg agactctaat attgctaagg ctttcaccg    480
aagagggagc aattgttggc gaaatttcac cattgccttc tcttccagga catactgctg    540
aggatgtcaa aaatgcagtt ggagtcctca tcggaggact tgaatggaat gataacacag    600
ttcgagtctc tgaaactcta cagagattcg cttggagaag cagtaatgag aatgggagac    660
ctccactcac tccaaaacag aaacgagaaa tggcgggaac aattaggtca gaagtttgaa    720
gaaataagat ggttgattga agaagtgaga cacaaactga gataacaga aatagttttt    780
gagcaaataa catttatgca agccttacat ctattgcttg aagtggagca agagataaga    840
actttctcgt ttcagcttat ttagtactaa aaaacaccct tgtttctact                890

<210> SEQ ID NO 7
<211> LENGTH: 1775
<212> TYPE: DNA
<213> ORGANISM: Influenza virus

<400> SEQUENCE: 7
agcaaaagca ggggaaaata aaacaacca aatgaaggc aaacctactg gtcctgttat     60
gtgcacttgc agctgcagat gcagacacaa tatgtatagg ctaccatgcg aacaattcaa    120
ccgacactgt tgacacagta ctcgagaaga atgtgacagt gacacactct gttaacctgc    180
tcgaagacag ccacaacgga aaactatgta gattaaaagg aatagcccca ctacaattgg    240
```

| | |
|---|---|
| ggaaatgtaa catcgccgga tggctcttgg gaaacccaga atgcgaccca ctgcttccag | 300 |
| tgagatcatg gtcctacatt gtagaaacac caaactctga aatggaaata tgttatccag | 360 |
| gagatttcat cgactatgag gagctgaggg agcaattgag ctcagtgtca tcattcgaaa | 420 |
| gattcgaaat atttcccaaa gaaagctcat ggcccaacca caacacaaac ggagtaacgg | 480 |
| cagcatgctc ccatgagggg aaaagcagtt tttacagaaa tttgctatgg ctgacggaga | 540 |
| aggagggctc atacccaaag ctgaaaaatt cttatgtgaa caaaaagggg aaagaagtcc | 600 |
| ttgtactgtg gggtattcat cacccgccta acagtaagga acaacagaat ctctatcaga | 660 |
| atgaaaatgc ttatgtctct gtagtgactt caaattataa caggagattt accccggaaa | 720 |
| tagcagaaag acccaaagta agagatcaag ctggggaggat gaactattac tggaccttgc | 780 |
| taaaacccgg agacacaata atatttgagg caaatggaaa tctaatagca ccaatgtatg | 840 |
| ctttcgcact gagtagaggc tttgggtccg gcatcatcac ctcaaacgca tcaatgcatg | 900 |
| agtgtaacac gaagtgtcaa acaccccctgg gagctataaa cagcagtctc ccttaccaga | 960 |
| atatacaccc agtcacaata ggagagtgcc caaaatacgt caggagtgcc aaattgagga | 1020 |
| tggttacagg actaaggaac attccgtcca ttcaatccag aggtctattt ggagccattg | 1080 |
| ccggtttttat tgaaggggga tggactgaaa tgatagatgg atggtatggt tatcatcatc | 1140 |
| agaatgaaca gggatcaggc tatgcagcgg atcaaaaaag cacacaaaat gccattaacg | 1200 |
| ggattacaaa caaggtgaac actgttatcg agaaaatgaa cattcaattc acagctgtgg | 1260 |
| gtaaagaatt caacaaatta gaaaaaagga tggaaaattt aaataaaaaa gttgatgatg | 1320 |
| gatttctgga catttggaca tataatgcag aattgttagt tctactggaa aatgaaagga | 1380 |
| ctctggattt ccatgactca aatgtgaaga atctgtatga aaagtaaaa agccaattaa | 1440 |
| agaataatgc caaagaaatc ggaaatggat gttttgagtt ctaccacaag tgtgacaatg | 1500 |
| aatgcatgga aagtgtaaga aatgggactt atgattatcc caaatattca gaagagtcaa | 1560 |
| agttgaacag ggaaaaggta gatggagtga aattggaatc aatggggatc tatcagattc | 1620 |
| tggcgatcta ctcaactgtc gccagttcac tggtgctttt ggtctccctg ggggcaatca | 1680 |
| gtttctggat gtgttctaat ggatctttgc agtgcagaat atgcatctga gattagaatt | 1740 |
| tcagagatat gaggaaaaac acccttgttt ctact | 1775 |

<210> SEQ ID NO 8
<211> LENGTH: 1413
<212> TYPE: DNA
<213> ORGANISM: Influenza virus

<400> SEQUENCE: 8

| | |
|---|---|
| agcaaaagca ggggtttaaa atgaatccaa atcagaaaat aataaccatt ggatcaatct | 60 |
| gtctggtagt cggactaatt agcctaatat tgcaaatagg aatataatc tcaatatgga | 120 |
| ttagccattc aattcaaact ggaagtcaaa accatactgg aatatgcaac caaaacatca | 180 |
| ttacctataa aaatagcacc tgggtaaagg acacaacttc agtgatatta accggcaatt | 240 |
| catctctttg tcccatccgt gggtgggcta tatacagcaa agacaatagc ataagaattg | 300 |
| gttccaaagg agacgttttt gtcataagag agccctttat ttcatgttct cacttggaat | 360 |
| gcaggacctt ttttctgacc caaggtgcct tactgaatga caagcattca agtgggactg | 420 |
| ttaaggacag aagcccttat agggccttaa tgagctgccc tgtcggtgaa gctccgtccc | 480 |
| cgtacaattc aagatttgaa tcggttgctt ggtcagcaag tgcatgtcat gatggcatgg | 540 |
| gctggctaac aatcggaatt tcaggtccag ataatggagc agtggctgta ttaaaataca | 600 |

```
acggcataat aactgaaacc ataaaaagtt ggaggaagaa atattgagg acacaagagt      660 ctgaatgtgc ctgtgtaaat ggttcatgtt ttactataat gactgatggc ccgagtgatg    720
ggctggcctc gtacaaaatt ttcaagatcg aaaaggggaa ggttactaaa tcaatagagt    780
tgaatgcacc taattctcac tatgaggaat gttcctgtta ccctgatacc ggcaaagtga    840
tgtgtgtgtg cagagacaat tggcatggtt cgaaccggcc atgggtgtct ttcgatcaaa    900
acctggatta tcaaatagga tacatctgca gtggggtttt cggtgacaac ccgcgtcccg    960
aagatggaac aggcagctgt ggtccagtgt atgttgatgg agcaaacgga gtaaagggat   1020
tttcatatag gtatggtaat ggtgtttgga taggaaggac caaaagtcac agttccagac   1080
atgggtttga tgatttggga tcctaatg gatggacaga gactgatagt aagttctctg     1140
tgaggcaaga tgttgtggca atgactgatt ggtcagggta tagcggaagt ttcgttcaac   1200
atcctgagct gacagggcta gactgtatga ggccgtgctt ctgggttgaa ttaatcaggg   1260
gacgacctaa agaaaaaaca atctggacta gtgcgagcag catttctttt tgtggcgtga   1320
atagtgatac tgtagattgg tcttggccag acggtgctga gttgccattc agcattgaca   1380
agtagtctgt tcaaaaaact ccttgtttct act                                1413
```

<210> SEQ ID NO 9
<211> LENGTH: 759
<212> TYPE: PRT
<213> ORGANISM: Influenza virus

<400> SEQUENCE: 9

```
Met Glu Arg Ile Lys Glu Leu Arg Asn Leu Met Ser Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ala Leu Arg Met Lys
        35                  40                  45

Trp Met Met Ala Met Lys Tyr Pro Ile Thr Ala Asp Lys Arg Ile Thr
    50                  55                  60

Glu Met Ile Pro Glu Arg Asn Glu Gln Gly Gln Thr Leu Trp Ser Lys
65                  70                  75                  80

Met Asn Asp Ala Gly Ser Asp Arg Val Met Val Ser Pro Leu Ala Val
                85                  90                  95

Thr Trp Trp Asn Arg Asn Gly Pro Met Thr Asn Thr Val His Tyr Pro
            100                 105                 110

Lys Ile Tyr Lys Thr Tyr Phe Glu Arg Val Glu Arg Leu Lys His Gly
        115                 120                 125

Thr Phe Gly Pro Val His Phe Arg Asn Gln Val Lys Ile Arg Arg Arg
    130                 135                 140

Val Asp Ile Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Gln Asp Cys Lys Ile Ser Pro Leu Met Val Ala Tyr Met Leu Glu
        195                 200                 205

Arg Glu Leu Val Arg Lys Thr Arg Phe Leu Pro Val Ala Gly Gly Thr
    210                 215                 220
```

```
Ser Ser Val Tyr Ile Glu Val Leu His Leu Thr Gln Gly Thr Cys Trp
225                 230                 235                 240
Glu Gln Met Tyr Thr Pro Gly Gly Glu Val Lys Asn Asp Asp Val Asp
            245                 250                 255
Gln Ser Leu Ile Ile Ala Ala Arg Asn Ile Val Arg Arg Ala Ala Val
            260                 265                 270
Ser Ala Asp Pro Leu Ala Ser Leu Leu Glu Met Cys His Ser Thr Gln
            275                 280                 285
Ile Gly Gly Ile Arg Met Val Asp Ile Leu Lys Gln Asn Pro Thr Glu
            290                 295                 300
Glu Gln Ala Val Asp Ile Cys Lys Ala Ala Met Gly Leu Arg Ile Ser
305                 310                 315                 320
Ser Ser Phe Ser Phe Gly Gly Phe Thr Phe Lys Arg Thr Ser Gly Ser
            325                 330                 335
Ser Val Lys Arg Glu Glu Val Leu Thr Gly Asn Leu Gln Thr Leu
            340                 345                 350
Lys Ile Arg Val His Glu Gly Ser Glu Glu Phe Thr Met Val Gly Arg
            355                 360                 365
Arg Ala Thr Ala Ile Leu Arg Lys Ala Thr Arg Arg Leu Ile Gln Leu
370                 375                 380
Ile Val Ser Gly Arg Asp Glu Gln Ser Ile Ala Glu Ala Ile Ile Val
385                 390                 395                 400
Ala Met Val Phe Ser Gln Glu Asp Cys Met Ile Lys Ala Val Arg Gly
            405                 410                 415
Asp Leu Asn Phe Val Asn Arg Ala Asn Gln Arg Leu Asn Pro Met His
            420                 425                 430
Gln Leu Leu Arg His Phe Gln Lys Asp Ala Lys Val Leu Phe Gln Asn
            435                 440                 445
Trp Gly Val Glu Pro Ile Asp Asn Val Met Gly Met Ile Gly Ile Leu
            450                 455                 460
Pro Asp Met Thr Pro Ser Ile Glu Met Ser Met Arg Gly Val Arg Ile
465                 470                 475                 480
Ser Lys Met Gly Val Asp Glu Tyr Ser Ser Thr Glu Arg Val Val Val
            485                 490                 495
Ser Ile Asp Arg Phe Leu Arg Val Arg Asp Gln Arg Gly Asn Val Leu
            500                 505                 510
Leu Ser Pro Glu Glu Val Ser Glu Thr Gln Gly Thr Glu Lys Leu Thr
            515                 520                 525
Ile Thr Tyr Ser Ser Ser Met Met Trp Glu Ile Asn Gly Pro Glu Ser
530                 535                 540
Val Leu Val Asn Thr Tyr Gln Trp Ile Ile Arg Asn Trp Glu Thr Val
545                 550                 555                 560
Lys Ile Gln Trp Ser Gln Asn Pro Thr Met Leu Tyr Asn Lys Met Glu
            565                 570                 575
Phe Glu Pro Phe Gln Ser Leu Val Pro Lys Ala Ile Arg Gly Gln Tyr
            580                 585                 590
Ser Gly Phe Val Arg Thr Leu Phe Gln Gln Met Arg Asp Val Leu Gly
            595                 600                 605
Thr Phe Asp Thr Ala Gln Ile Ile Lys Leu Leu Pro Phe Ala Ala Ala
            610                 615                 620
Pro Pro Lys Gln Ser Arg Met Gln Phe Ser Ser Phe Thr Val Asn Val
625                 630                 635                 640
Arg Gly Ser Gly Met Arg Ile Leu Val Arg Gly Asn Ser Pro Val Phe
```

```
                      645                 650                 655
Asn Tyr Asn Lys Ala Thr Lys Arg Leu Thr Val Leu Gly Lys Asp Ala
                660                 665                 670

Gly Thr Leu Thr Glu Asp Pro Asp Glu Gly Thr Ala Gly Val Glu Ser
            675                 680                 685

Ala Val Leu Arg Gly Phe Leu Ile Leu Gly Lys Glu Asp Arg Arg Tyr
        690                 695                 700

Gly Pro Ala Leu Ser Ile Asn Glu Leu Ser Asn Leu Ala Lys Gly Glu
705                 710                 715                 720

Lys Ala Asn Val Leu Ile Gly Gln Gly Asp Val Val Leu Val Met Lys
                725                 730                 735

Arg Lys Arg Asp Ser Ser Ile Leu Thr Asp Ser Gln Thr Ala Thr Lys
            740                 745                 750

Arg Ile Arg Met Ala Ile Asn
        755

<210> SEQ ID NO 10
<211> LENGTH: 2341
<212> TYPE: DNA
<213> ORGANISM: Influenza virus

<400> SEQUENCE: 10
agcgaaagca ggtcaattat attcaatatg gaaagaataa agaactaag aaatctaatg      60 tcgcagtctc gcacccgcga gatactcaca aaaaccaccg tggaccatat ggccataatc    120
aagaagtaca catcaggaag acaggagaag aacccagcac ttaggatgaa atggatgatg    180
gcaatgaaat atccaattac agcagacaag aggataacgg aaatgattcc tgagagaaat    240
gagcaaggac aaactttatg gagtaaaatg aatgatgccg gatcagaccg agtgatggta    300
tcacctctgg ctgtgacatg gtggaatagg aatggaccaa tgacaaatac agttcattat    360
ccaaaaatct acaaaactta ttttgaaaga gtcgaaaggc taaagcatgg aacctttggc    420
cctgtccatt ttagaaacca gtcaaaata cgtcggagag ttgacataaa tcctggtcat    480
gcagatctca gtgccaagga ggcacaggat gtaatcatgg aagttgtttt ccctaacgaa    540
gtgggagcca ggatactaac atcggaatcg caactaacga taaccaaaga gaagaaagaa    600
gaactccagg attgcaaaat ttctcctttg atggttgcat acatgttgga gagagaactg    660
gtccgcaaaa cgagattcct cccagtggct ggtggaacaa gcagtgtgta cattgaagtg    720
ttgcatttga ctcaaggaac atgctgggaa cagatgtata ctccaggagg ggaagtgaag    780
aatgatgatg ttgatcaaag cttgattatt gctgctagga caatagtgag aagagctgca    840
gtatcagcag cccactagc atctttattg gagatgtgcc acagcacaca gattggtgga    900
attaggatgg tagacatcct taagcagaac caaacagaag agcaagccgt ggatatatgc    960
aaggctgcaa tgggactgag aattagctca tccttcagtt ttggtggatt cacatttaag   1020
agaacaagcg gatcatcagt caagagagag gaagaggtgc ttacgggcaa tcttcaaaca   1080
ttgaagataa gagtgcatga gggatctgaa gagttcacaa tggttgggag aagagcaaca   1140
gccatactca gaaaagcaac caggagattg attcagctga tagtgagtgg gagagacgaa   1200
cagtcgattg ccgaagcaat aattgtggcc atggtatttt cacaagagga ttgtatgata   1260
aaagcagtta gaggtgatct gaatttcgtc aatagggcga atcagcgact gaatcctatg   1320
catcaacttt taagacattt tcagaaggat gcgaaagtgc tttttcaaaa ttggggagtt   1380
gaacctatcg acaatgtgat gggaatgatt gggatattgc ccgacatgac tccaagcatc   1440
```

```
gagatgtcaa tgagaggagt gagaatcagc aaaatgggtg tagatgagta ctccagcacg    1500
gagagggtag tggtgagcat tgaccggttc ttgagagtca gggaccaacg aggaaatgta    1560
ctactgtctc ccgaggaggt cagtgaaaca cagggaacag agaaactgac aataacttac    1620
tcatcgtcaa tgatgtggga gattaatggt cctgaatcag tgttggtcaa tacctatcaa    1680
tggatcatca gaaactggga aactgttaaa attcagtggt cccagaaccc tacaatgcta    1740
tacaataaaa tggaatttga accatttcag tctttagtac ctaaggccat tagaggccaa    1800
tacagtgggt ttgtaagaac tctgttccaa caaatgaggg atgtgcttgg gacatttgat    1860
accgcacaga taataaaact tcttcccttc gcagccgctc caccaaagca agtagaatg     1920 cagttctcct catttactgt gaatgtgagg ggatcaggaa tgagaatact tgtaaggggc    1980
aattctcctg tattcaacta caacaaggcc acgaagagac tcacagttct cggaaaggat    2040
gctggcactt taaccgaaga cccagatgaa ggcacagctg gagtggagtc cgctgttctg    2100
aggggattcc tcattctggg caaagaagac aggagatatg gccagcatt aagcatcaat    2160 gaactgagca accttgcgaa aggagagaag gctaatgtgc taattgggca aggagacgtg    2220
gtgttggtaa tgaaacgaaa acgggactct agcatactta ctgacagcca gacagcgacc    2280
aaaagaattc ggatggccat caattagtgt cgaatagttt aaaaacgacc ttgtttctac    2340
t                                                                     2341

<210> SEQ ID NO 11
<211> LENGTH: 2341
<212> TYPE: DNA
<213> ORGANISM: Influenza virus

<400> SEQUENCE: 11
agcgaaagca ggcaaaccat ttgaatggat gtcaatccga ccttactttt cttaaaagtg      60
ccagcacaaa atgctataag cacaactttc ccttataccg gagaccctcc ttacagccat     120
gggacaggaa caggatacac catggatact gtcaacagga cacatcagta ctcagaaaag     180
ggaagatgga caacaaacac cgaaactgga gcaccgcaac tcaacccgat tgatgggcca     240
ctgccagaag acaatgaacc aagtggttat gcccaaacag attgtgtatt ggaagcaatg     300
gctttccttg aggaatccca tcctggtatt tttgaaaact cgtgtattga acgatggag     360 gttgttcagc aaaacacgag tagacaagctg acacaaggcc gacagaccta tgactggact     420
ttaaatagaa accagcctgc tgcaacagca ttggccaaca caatagaagt gttcagatca     480
aatggcctca cggccaatga gtcaggaagg ctcatagact tccttaagga tgtaatggag     540
tcaatgaaaa agaagaaat ggggatcaca actcattttc agagaaagag acgggtgaga     600
gacaatatga ctaagaaaat gataacacag agaacaatag gtaaaggaa acagagattg     660 aacaaagggg ttatctaat tagagcattg accctgaaca caatgaccaa agatgctgag     720
agagggaagc taaacggag agcaattgca accccaggga tgcaaataag ggggtttgta     780
tactttgttg agacactggc aaggagtata tgtgagaaac ttgaacaatc agggttgcca     840
gttggaggca atgagaagaa agcaaagttg gcaaatgttg taaggaagat gatgaccaat     900
tctcaggaca ccgaacttc tttcaccatc actggagata acaccaaatg gaacgaaaat     960
cagaatcctc ggatgttttt ggccatgatc acatatatga ccagaaatca gcccgaatgg    1020
ttcagaaatg ttctaagtat tgctccaata atgttctcaa acaaaatggc gagactggga    1080 aagggtata tgtttgagag caagagtatg aaacttagaa ctcaaatacc tgcagaaatg    1140
ctagcaagca ttgatttgaa atatttcaat gattcaacaa gaagaagat tgaaaaaatc    1200
```

```
cgaccgctct taatagaggg gactgcatca ttgagccctg gaatgatgat gggcatgttc    1260
aatatgttaa gcactgtatt aggcgtctcc atcctgaatc ttggacaaaa gagatacacc    1320
aagactactt actggtggga tggtcttcaa tcctctgacg attttgctct gattgtgaat    1380
gcacccaatc atgaagggat tcaagccgga gtcgacaggt tttatcgaac ctgtaagcta    1440
cttggaatca atatgagcaa gaaaaagtct tacataaaca gaacaggtac atttgaattc    1500
acaagttttt tctatcgtta tgggtttgtt gccaatttca gcatggagct tcccagtttt    1560
ggggtgtctg ggatcaacga gtcagcggac atgagtattg gagttactgt catcaaaaac    1620
aatatgataa acaatgatct tggtccagca acagctcaaa tggcccttca gttgttcatc    1680
aaagattaca ggtacacgta ccgatgccat agaggtgaca cacaaataca aacccgaaga    1740
tcatttgaaa taaagaaact gtgggagcaa acccgttcca aagctggact gctggtctcc    1800
gacggaggcc caaatttata caacattaga aatctccaca ttcctgaagt ctgcctaaaa    1860
tgggaattga tggatgagga ttaccagggg cgtttatgca acccactgaa cccatttgtc    1920
agccataaag aaattgaatc aatgaacaat gcagtgatga tgccagcaca tggtccagcc    1980
aaaaacatgg agtatgatgc tgttgcaaca acacactcct ggatccccaa agaaatcga    2040 tccatcttga atacaagtca agaggagta cttgaagatg aacaaatgta ccaaaggtgc    2100 tgcaattat ttgaaaaatt cttccccagc agttcataca aagaccagt cgggatatcc    2160 agtatggtgg aggctatggt ttccagagcc cgaattgatg cacggattga tttcgaatct    2220
ggaaggataa agaagaaga gttcactgag atcatgaaga tctgttccac cattgaagag    2280
ctcagacggc aaaaatagtg aatttagctt gtccttcatg aaaaaatgcc ttgtttctac    2340
t                                                                   2341

<210> SEQ ID NO 12
<211> LENGTH: 2233
<212> TYPE: DNA
<213> ORGANISM: Influenza virus

<400> SEQUENCE: 12
agcgaaagca ggtactgatt caaaatggaa gattttgtgc gacaatgctt caatccgatg     60
attgtcgagc ttgcggaaaa aacaatgaaa gagtatgggg aggacctgaa atcgaaaca    120 aacaaatttg cagcaatatg cactcacttg gaagtatgct tcatgtattc agatttccac    180
ttcatcaatg agcaaggcga gtcaataatc gtagaacttg gtgatcctaa tgcacttttg    240
aagcacagat ttgaaataat cgagggaaga gatcgcacaa tggcctggac agtagtaaac    300
agtatttgca acactacagg ggctgagaaa ccaaagtttc taccagattt gtatgattac    360
aaggaaaata gattcatcga aattggagta acaaggagag aagttcacat atactatctg    420
gaaaaggcca ataaaattaa atctgagaaa acacacatcc acattttctc gttcactggg    480
gaagaaatgg ccacaagggc cgactacact ctcgatgaag aaagcagggc taggatcaaa    540
accaggctat tcaccataag acaagaaatg gccagcagag gcctctggga ttcctttcgt    600
cagtccgaga gaggagaaga gacaattgaa gaaggtttg aaatcacagg aacaatgcgc    660
aagcttgccg accaaagtct cccgccgaac ttctccagcc ttgaaaattt tagagcctat    720
gtggatggat tcgaaccgaa cggctacatt gagggcaagc tgtctcaaat gtccaaagaa    780
gtaaatgcta gaattgaacc ttttttgaaa acaacaccac gaccacttag acttccgaat    840
gggcctccct gttctcagcg gtccaaattc ctgctgatgg atgccttaaa attaagcatt    900
```

-continued

```
gaggacccaa gtcatgaagg agagggaata ccgctatatg atgcaatcaa atgcatgaga    960
acattctttg gatggaagga acccaatgtt gttaaaccac acgaaaaggg aataaatcca   1020
aattatcttc tgtcatggaa gcaagtactg gcagaactgc aggacattga gaatgaggag   1080
aaaattccaa agactaaaaa tatgaaaaaa acaagtcagc taaagtgggc acttggtgag   1140
aacatggcac cagaaaaggt agactttgac gactgtaaag atgtaggtga tttgaagcaa   1200
tatgatagtg atgaaccaga attgaggtcg cttgcaagtt ggattcagaa tgagttcaac   1260
aaggcatgcg aactgacaga ttcaagctgg atagagcttg atgagattgg agaagatgtg   1320
gctccaattg aacacattgc aagcatgaga aggaattatt tcacatcaga ggtgtctcac   1380
tgcagagcca cagaatacat aatgaagggg gtgtacatca atactgcctt acttaatgca   1440
tcttgtgcag caatggatga tttccaatta attccaatga taagcaagtg tagaactaag   1500
gagggaaggc gaaagaccaa cttgtatggt ttcatcataa aaggaagatc ccacttaagg   1560
aatgacaccg acgtggtaaa ctttgtgagc atggagtttt ctctcactga cccaagactt   1620
gaaccacaca aatgggagaa gtactgtgtt cttgagatag gagatatgct tctaagaagt   1680
gccataggcc aggtttcaag gcccatgttc ttgtatgtga ggacaaatgg aacctcaaaa   1740
attaaaatga aatggggaat ggagatgagg cgttgtctcc tccagtcact tcaacaaatt   1800
gagagtatga ttgaagctga gtcctctgtc aaagagaaag acatgaccaa agagttcttt   1860
gagaacaaat cagaaacatg gcccattgga gagtctccca aaggagtgga ggaaagttcc   1920
attgggaagg tctgcaggac tttattagca aagtcggtat ttaacagctt gtatgcatct   1980
ccacaactag aaggattttc agctgaatca agaaaactgc ttcttatcgt tcaggctctt   2040
agggacaatc tggaacctgg gacctttgat cttggggggc tatatgaagc aattgaggag   2100
tgcctaatta atgatccctg ggttttgctt aatgcttctt ggttcaactc cttccttaca   2160
catgcattga gttagttgtg gcagtgctac tatttgctat ccatactgtc caaaaaagta   2220
ccttgtttct act                                                      2233
```

<210> SEQ ID NO 13
<211> LENGTH: 1565
<212> TYPE: DNA
<213> ORGANISM: Influenza virus

<400> SEQUENCE: 13

```
agcaaaagca gggtagataa tcactcactg agtgacatca aaatcatggc gtcccaaggc     60
accaaacggt cttacgaaca gatggagact gatggagaac gccagaatgc cactgaaatc    120
agagcatccg tcggaaaaat gattggtgga attggacgat tctacatcca aatgtgcaca    180
gaacttaaac tcagtgatta tgagggacgg ttgatccaaa acagcttaac aatagagaga    240
atggtgctct ctgcttttga cgaaaggaga aataaatacc tggaagaaca tcccagtgcg    300
gggaaagatc ctaagaaaac tggaggacct atatacagaa gagtaaacgg aaagtggatg    360
agagaactca tcctttatga caaagaagaa ataaggcgaa tctggcgcca agctaataat    420
ggtgacgatg caacggctgg tctgactcac atgatgatct ggcattccaa tttgaatgat    480
gcaacttatc agaggacaag ggctcttgtt cgcaccggaa tggatcccag gatgtgctct    540
ctgatgcaag gttcaactct ccctaggagg tctggagccg caggtgctgc agtcaaagga    600
gttggaacaa tggtgatgga attggtcagg atgatcaaac gtgggatcaa tgatcggaac    660
ttctggaggg gtgagaatgg acgaaaaaca agaattgctt atgaaagaat gtgcaacatt    720
ctcaaaggga aatttcaaac tgctgcacaa aaagcaatga tggatcaagt gagagagagc    780
```

```
cggaacccag ggaatgctga gttcgaagat ctcactttc tagcacggtc tgcactcata      840
ttgagagggt cggttgctca caagtcctgc ctgcctgcct gtgtgtatgg acctgccgta      900
gccagtgggt acgactttga aagagaggga tactctctag tcggaataga ccctttcaga      960
ctgcttcaaa acagccaagt gtacagccta atcagaccaa atgagaatcc agcacacaag     1020
agtcaactgg tgtggatggc atgccattct gccgcatttg aagatctaag agtattgagc     1080
ttcatcaaag ggacgaaggt ggtcccaaga gggaagcttt ccactagagg agttcaaatt     1140
gcttccaatg aaaatatgga gactatggaa tcaagtacac ttgaactgag aagcaggtac     1200
tgggccataa ggaccagaag tggaggaaac accaatcaac agagggcatc tgcgggccaa     1260
atcagcatac aacctacgtt ctcagtacag agaaatctcc cttttgacag aacaaccgtt     1320
atggcagcat tcactgggaa tacagagggg agaaacatctg acatgaggac cgaaatcata     1380
aggatgatgg aaagtgcaag accagaagat gtgtctttcc aggggcgggg agtcttcgag     1440
ctctcggacg aaaaggcagc gagcccgatc gtgccttcct ttgacatgag taatgaagga     1500
tcttatttct tcggagacaa tgcagaggag tacgacaatt aaagaaaaat acccttgttt     1560
ctact                                                                 1565

<210> SEQ ID NO 14
<211> LENGTH: 1027
<212> TYPE: DNA
<213> ORGANISM: Influenza virus

<400> SEQUENCE: 14
agcaaaagca ggtagatatt gaaagatgag tcttctaacc gaggtcgaaa cgtacgttct       60
ctctatcatc ccgtcaggcc ccctcaaagc cgagatcgca cagagacttg aagatgtctt      120
tgcagggaag aacaccgatc ttgaggttct catggaatgg ctaaagacaa gaccaatcct      180
gtcacctctg actaagggga ttttaggatt tgtgttcacg ctcaccgtgc ccagtgagcg      240
aggactgcag cgtagacgct ttgtccaaaa tgcccttaat gggaacgggg atccaaataa      300
catggacaaa gcagttaaac tgtataggaa gctcaagagg gagataacat tccatggggc      360
caaagaaatc tcactcagtt attctgctgg tgcacttgcc agttgtatgg gcctcatata      420
caacaggatg ggggctgtga ccactgaagt ggcatttggc ctggtatgtg caacctgtga      480
acagattgct gactcccagc atcggtctca taggcaaatg gtgacaacaa ccaacccact      540
aatcagacat gagaacagaa tggttttagc cagcactaca gctaaggcta tggagcaaat      600
ggctggatcg agtgagcaag cagcagaggc catggaggtt gctagtcagg ctaggcaaat      660
ggtgcaagcg atgagaacca ttgggactca tcctagctcc agtgctggtc tgaaaaatga      720
tcttcttgaa aatttgcagg cctatcagaa acgaatgggg gtgcagatgc aacggttcaa      780
gtgatcctct cgctattgcc gcaaatatca ttgggatctt gcacttgata ttgtggattc      840
ttgatcgtct ttttttcaaa tgcatttacc gtcgctttaa atacggactg aaaggagggc      900
cttctacgga aggagtgcca aagtctatga gggaagaata tcgaaggaa cagcagagtg      960
ctgtggatgc tgacgatggt cattttgtca gcatagagct ggagtaaaaa actaccttgt     1020
ttctact                                                               1027

<210> SEQ ID NO 15
<211> LENGTH: 890
<212> TYPE: DNA
<213> ORGANISM: Influenza virus
```

<400> SEQUENCE: 15

```
agcaaaagca gggtgacaaa gacataatgg atccaaacac tgtgtcaagc tttcaggtag      60
attgctttct ttggcatgtc cgcaaacgag ttgcagacca agaactaggt gatgccccat     120
tccttgatcg gcttcgccga gatcagaaat ccctaagagg aagggcagc actcttggtc      180
tggacatcga gacagccaca cgtgctggaa agcagatagt ggagcggatt ctgaaagaag     240
aatccgatga ggcacttaaa atgaccatgg cctctgtacc tgcgtcgcgt tacctaaccg     300
acatgactct tgaggaaatg tcaagggaat ggtccatgct catacccaag cagaaagtgg     360
caggccctct ttgtatcaga atggaccagg cgatcatgga taaaaacatc atactgaaag     420
cgaacttcag tgtgattttt gaccggctgg agactctaat attgctaagg ctttcaccg      480
aagagggagc aattgttggc gaaatttcac cattgccttc tcttccagga catactgctg     540
aggatgtcaa aaatgcagtt ggagtcctca tcggaggact tgaatggaat gataacacag     600
ttcgagtctc tgaaactcta cagagattcg cttggagaag cagtaatgag aatgggagac     660
ctccactcac tccaaaacag aaacgagaaa tggcgggaac aattaggtca gaagtttgaa     720
gaaataagat ggttgattga agaagtgaga cacaaactga aggtaacaga aatagttttt     780
gagcaaataa catttatgca agccttacat ctattgcttg aagtggagca agagataaga     840
actttctcat ttcagcttat ttaataataa aaaacacccct tgtttctact               890
```

<210> SEQ ID NO 16
<211> LENGTH: 757
<212> TYPE: PRT
<213> ORGANISM: Influenza virus

<400> SEQUENCE: 16

```
Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Lys Gly Arg Trp Thr Thr Asn Thr Glu Thr Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Ile Glu Thr Met Glu
            100                 105                 110

Val Val Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Lys Lys
                165                 170                 175

Glu Glu Met Gly Ile Thr Thr His Phe Gln Arg Lys Arg Arg Val Arg
            180                 185                 190

Asp Asn Met Thr Lys Lys Met Ile Thr Gln Arg Thr Ile Gly Lys Arg
        195                 200                 205
```

-continued

Lys Gln Arg Leu Asn Lys Arg Gly Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
                260                 265                 270

Val Gly Gly Asn Glu Lys Lys Ala Lys Leu Ala Asn Val Val Arg Lys
                275                 280                 285

Met Met Thr Asn Ser Gln Asp Thr Glu Leu Ser Phe Thr Ile Thr Gly
    290                 295                 300

Asp Asn Thr Lys Trp Asn Glu Asn Gln Asn Pro Arg Met Phe Leu Ala
305                 310                 315                 320

Met Ile Thr Tyr Met Thr Arg Asn Gln Pro Glu Trp Phe Arg Asn Val
                325                 330                 335

Leu Ser Ile Ala Pro Ile Met Phe Ser Asn Lys Met Ala Arg Leu Gly
                340                 345                 350

Lys Gly Tyr Met Phe Glu Ser Lys Ser Met Lys Leu Arg Thr Gln Ile
                355                 360                 365

Pro Ala Glu Met Leu Ala Ser Ile Asp Leu Lys Tyr Phe Asn Asp Ser
                370                 375                 380

Thr Arg Lys Lys Ile Glu Lys Ile Arg Pro Leu Leu Ile Glu Gly Thr
385                 390                 395                 400

Ala Ser Leu Ser Pro Gly Met Met Met Gly Met Phe Asn Met Leu Ser
                405                 410                 415

Thr Val Leu Gly Val Ser Ile Leu Asn Leu Gly Gln Lys Arg Tyr Thr
                420                 425                 430

Lys Thr Thr Tyr Trp Trp Asp Gly Leu Gln Ser Ser Asp Asp Phe Ala
                435                 440                 445

Leu Ile Val Asn Ala Pro Asn His Glu Gly Ile Gln Ala Gly Val Asp
    450                 455                 460

Arg Phe Tyr Arg Thr Cys Lys Leu Leu Gly Ile Asn Met Ser Lys Lys
465                 470                 475                 480

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
                500                 505                 510

Gly Val Ser Gly Ile Asn Glu Ser Ala Asp Met Ser Ile Gly Val Thr
                515                 520                 525

Val Ile Lys Asn Asn Met Ile Asn Asn Asp Leu Gly Pro Ala Thr Ala
    530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Ile
                565                 570                 575

Lys Lys Leu Trp Glu Gln Thr Arg Ser Lys Ala Gly Leu Leu Val Ser
                580                 585                 590

Asp Gly Gly Pro Asn Leu Tyr Asn Ile Arg Asn Leu His Ile Pro Glu
                595                 600                 605

Val Cys Leu Lys Trp Glu Leu Met Asp Glu Asp Tyr Gln Gly Arg Leu
    610                 615                 620

Cys Asn Pro Leu Asn Pro Phe Val Ser His Lys Glu Ile Glu Ser Met

```
                625                 630                 635                 640
Asn Asn Ala Val Met Met Pro Ala His Gly Pro Ala Lys Asn Met Glu
                        645                 650                 655
Tyr Asp Ala Val Ala Thr Thr His Ser Trp Ile Pro Lys Arg Asn Arg
                        660                 665                 670
Ser Ile Leu Asn Thr Ser Gln Arg Gly Val Leu Glu Asp Glu Gln Met
                        675                 680                 685
Tyr Gln Arg Cys Cys Asn Leu Phe Glu Lys Phe Phe Pro Ser Ser Ser
                        690                 695                 700
Tyr Arg Arg Pro Val Gly Ile Ser Ser Met Val Glu Ala Met Val Ser
705                 710                 715                 720
Arg Ala Arg Ile Asp Ala Arg Ile Asp Phe Glu Ser Gly Arg Ile Lys
                        725                 730                 735
Lys Glu Glu Phe Thr Glu Ile Met Lys Ile Cys Ser Thr Ile Glu Glu
                        740                 745                 750
Leu Arg Arg Gln Lys
                755

<210> SEQ ID NO 17
<211> LENGTH: 716
<212> TYPE: PRT
<213> ORGANISM: Influenza virus

<400> SEQUENCE: 17

Met Glu Asp Phe Val Arg Gln Cys Phe Asn Pro Met Ile Val Glu Leu
1               5                   10                  15
Ala Glu Lys Thr Met Lys Glu Tyr Gly Glu Asp Leu Lys Ile Glu Thr
                20                  25                  30
Asn Lys Phe Ala Ala Ile Cys Thr His Leu Glu Val Cys Phe Met Tyr
                35                  40                  45
Ser Asp Phe His Phe Ile Asn Glu Gln Gly Glu Ser Ile Ile Val Glu
            50                  55                  60
Leu Gly Asp Pro Asn Ala Leu Leu Lys His Arg Phe Glu Ile Ile Glu
65                  70                  75                  80
Gly Arg Asp Arg Thr Met Ala Trp Thr Val Val Asn Ser Ile Cys Asn
                        85                  90                  95
Thr Thr Gly Ala Glu Lys Pro Lys Phe Leu Pro Asp Leu Tyr Asp Tyr
                100                 105                 110
Lys Glu Asn Arg Phe Ile Glu Ile Gly Val Thr Arg Arg Glu Val His
                115                 120                 125
Ile Tyr Tyr Leu Glu Lys Ala Asn Lys Ile Lys Ser Glu Lys Thr His
            130                 135                 140
Ile His Ile Phe Ser Phe Thr Gly Glu Glu Met Ala Thr Arg Ala Asp
145                 150                 155                 160
Tyr Thr Leu Asp Glu Glu Ser Arg Ala Arg Ile Lys Thr Arg Leu Phe
                165                 170                 175
Thr Ile Arg Gln Glu Met Ala Ser Arg Gly Leu Trp Asp Ser Phe Arg
                180                 185                 190
Gln Ser Glu Arg Gly Glu Glu Thr Ile Glu Glu Arg Phe Glu Ile Thr
                195                 200                 205
Gly Thr Met Arg Lys Leu Ala Asp Gln Ser Leu Pro Pro Asn Phe Ser
            210                 215                 220
Ser Leu Glu Asn Phe Arg Ala Tyr Val Asp Gly Phe Glu Pro Asn Gly
225                 230                 235                 240
```

```
Tyr Ile Glu Gly Lys Leu Ser Gln Met Ser Lys Glu Val Asn Ala Arg
            245                 250                 255

Ile Glu Pro Phe Leu Lys Thr Thr Pro Arg Pro Leu Arg Leu Pro Asn
        260                 265                 270

Gly Pro Pro Cys Ser Gln Arg Ser Lys Phe Leu Leu Met Asp Ala Leu
    275                 280                 285

Lys Leu Ser Ile Glu Asp Pro Ser His Glu Gly Gly Ile Pro Leu
290                 295                 300

Tyr Asp Ala Ile Lys Cys Met Arg Thr Phe Phe Gly Trp Lys Glu Pro
305                 310                 315                 320

Asn Val Val Lys Pro His Glu Lys Gly Ile Asn Pro Asn Tyr Leu Leu
                325                 330                 335

Ser Trp Lys Gln Val Leu Ala Glu Leu Gln Asp Ile Glu Asn Glu Glu
            340                 345                 350

Lys Ile Pro Lys Thr Lys Asn Met Lys Lys Thr Ser Gln Leu Lys Trp
        355                 360                 365

Ala Leu Gly Glu Asn Met Ala Pro Glu Lys Val Asp Phe Asp Asp Cys
    370                 375                 380

Lys Asp Val Gly Asp Leu Lys Gln Tyr Asp Ser Asp Glu Pro Glu Leu
385                 390                 395                 400

Arg Ser Leu Ala Ser Trp Ile Gln Asn Glu Phe Asn Lys Ala Cys Glu
                405                 410                 415

Leu Thr Asp Ser Ser Trp Ile Glu Leu Asp Glu Ile Gly Glu Asp Val
            420                 425                 430

Ala Pro Ile Glu His Ile Ala Ser Met Arg Arg Asn Tyr Phe Thr Ser
        435                 440                 445

Glu Val Ser His Cys Arg Ala Thr Glu Tyr Ile Met Lys Gly Val Tyr
    450                 455                 460

Ile Asn Thr Ala Leu Leu Asn Ala Ser Cys Ala Ala Met Asp Asp Phe
465                 470                 475                 480

Gln Leu Ile Pro Met Ile Ser Lys Cys Arg Thr Lys Glu Gly Arg Arg
                485                 490                 495

Lys Thr Asn Leu Tyr Gly Phe Ile Ile Lys Gly Arg Ser His Leu Arg
            500                 505                 510

Asn Asp Thr Asp Val Val Asn Phe Val Ser Met Glu Phe Ser Leu Thr
        515                 520                 525

Asp Pro Arg Leu Glu Pro His Lys Trp Glu Lys Tyr Cys Val Leu Glu
    530                 535                 540

Ile Gly Asp Met Leu Leu Arg Ser Ala Ile Gly Gln Val Ser Arg Pro
545                 550                 555                 560

Met Phe Leu Tyr Val Arg Thr Asn Gly Thr Ser Lys Ile Lys Met Lys
                565                 570                 575

Trp Gly Met Glu Met Arg Arg Cys Leu Leu Gln Ser Leu Gln Gln Ile
            580                 585                 590

Glu Ser Met Ile Glu Ala Glu Ser Ser Val Lys Glu Lys Asp Met Thr
        595                 600                 605

Lys Glu Phe Phe Glu Asn Lys Ser Glu Thr Trp Pro Ile Gly Glu Ser
    610                 615                 620

Pro Lys Gly Val Glu Ser Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Ile Val Gln Ala Leu
```

```
                    660                 665                 670
Arg Asp Asn Leu Glu Pro Gly Thr Phe Asp Leu Gly Gly Leu Tyr Glu
                675                 680                 685

Ala Ile Glu Glu Cys Leu Ile Asn Asp Pro Trp Val Leu Leu Asn Ala
            690                 695                 700

Ser Trp Phe Asn Ser Phe Leu Thr His Ala Leu Ser
705                 710                 715

<210> SEQ ID NO 18
<211> LENGTH: 498
<212> TYPE: PRT
<213> ORGANISM: Influenza virus

<400> SEQUENCE: 18

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
                20                  25                  30

Ile Gly Gly Ile Gly Arg Phe Tyr Ile Gln Met Cys Thr Glu Leu Lys
            35                  40                  45

Leu Ser Asp Tyr Glu Gly Arg Leu Ile Gln Asn Ser Leu Thr Ile Glu
        50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asn Gly Lys Trp Met Arg Glu Leu Ile Leu Tyr Asp
                100                 105                 110

Lys Glu Glu Ile Arg Arg Ile Trp Arg Gln Ala Asn Asn Gly Asp Asp
            115                 120                 125

Ala Thr Ala Gly Leu Thr His Met Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
                180                 185                 190

Leu Val Arg Met Ile Lys Arg Gly Ile Asn Asp Arg Asn Phe Trp Arg
            195                 200                 205

Gly Glu Asn Gly Arg Lys Thr Arg Ile Ala Tyr Glu Arg Met Cys Asn
    210                 215                 220

Ile Leu Lys Gly Lys Phe Gln Thr Ala Ala Gln Lys Ala Met Met Asp
225                 230                 235                 240

Gln Val Arg Glu Ser Arg Asn Pro Gly Asn Ala Glu Phe Glu Asp Leu
                245                 250                 255

Thr Phe Leu Ala Arg Ser Ala Leu Ile Leu Arg Gly Ser Val Ala His
                260                 265                 270

Lys Ser Cys Leu Pro Ala Cys Val Tyr Gly Pro Ala Val Ala Ser Gly
            275                 280                 285

Tyr Asp Phe Glu Arg Glu Gly Tyr Ser Leu Val Gly Ile Asp Pro Phe
        290                 295                 300

Arg Leu Leu Gln Asn Ser Gln Val Tyr Ser Leu Ile Arg Pro Asn Glu
305                 310                 315                 320
```

```
Asn Pro Ala His Lys Ser Gln Leu Val Trp Met Ala Cys His Ser Ala
                325                 330                 335

Ala Phe Glu Asp Leu Arg Val Leu Ser Phe Ile Lys Gly Thr Lys Val
            340                 345                 350

Val Pro Arg Gly Lys Leu Ser Thr Arg Gly Val Gln Ile Ala Ser Asn
        355                 360                 365

Glu Asn Met Glu Thr Met Glu Ser Ser Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Ile Gln Pro Thr Phe Ser Val Gln Arg
                405                 410                 415

Asn Leu Pro Phe Asp Arg Thr Thr Val Met Ala Ala Phe Thr Gly Asn
            420                 425                 430

Thr Glu Gly Arg Thr Ser Asp Met Arg Thr Glu Ile Ile Arg Met Met
        435                 440                 445

Glu Ser Ala Arg Pro Glu Asp Val Ser Phe Gln Gly Arg Gly Val Phe
    450                 455                 460

Glu Leu Ser Asp Glu Lys Ala Ala Ser Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn

<210> SEQ ID NO 19
<211> LENGTH: 252
<212> TYPE: PRT
<213> ORGANISM: Influenza virus

<400> SEQUENCE: 19

Met Ser Leu Leu Thr Glu Val Glu Thr Tyr Val Leu Ser Ile Ile Pro
1               5                   10                  15

Ser Gly Pro Leu Lys Ala Glu Ile Ala Gln Arg Leu Glu Asp Val Phe
                20                  25                  30

Ala Gly Lys Asn Thr Asp Leu Glu Val Leu Met Glu Trp Leu Lys Thr
            35                  40                  45

Arg Pro Ile Leu Ser Pro Leu Thr Lys Gly Ile Leu Gly Phe Val Phe
        50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Lys Ala
                85                  90                  95

Val Lys Leu Tyr Arg Lys Leu Lys Arg Glu Ile Thr Phe His Gly Ala
                100                 105                 110

Lys Glu Ile Ser Leu Ser Tyr Ser Ala Gly Ala Leu Ala Ser Cys Met
            115                 120                 125

Gly Leu Ile Tyr Asn Arg Met Gly Ala Val Thr Thr Glu Val Ala Phe
        130                 135                 140

Gly Leu Val Cys Ala Thr Cys Glu Gln Ile Ala Asp Ser Gln His Arg
145                 150                 155                 160

Ser His Arg Gln Met Val Thr Thr Thr Asn Pro Leu Ile Arg His Glu
                165                 170                 175

Asn Arg Met Val Leu Ala Ser Thr Thr Ala Lys Ala Met Glu Gln Met
            180                 185                 190
```

```
Ala Gly Ser Ser Glu Gln Ala Ala Glu Ala Met Glu Val Ala Ser Gln
            195                 200                 205

Ala Arg Gln Met Val Gln Ala Met Arg Thr Ile Gly Thr His Pro Ser
    210                 215                 220

Ser Ser Ala Gly Leu Lys Asn Asp Leu Leu Glu Asn Leu Gln Ala Tyr
225                 230                 235                 240

Gln Lys Arg Met Gly Val Gln Met Gln Arg Phe Lys
                245                 250
```

<210> SEQ ID NO 20
<211> LENGTH: 40
<212> TYPE: DNA
<213> ORGANISM: Artificial Sequence
<220> FEATURE:
<223> OTHER INFORMATION: A synthetic oligonucleotide

<400> SEQUENCE: 20
cccatcgata ccatggagag gataaaagaa ttacgagatc    40

<210> SEQ ID NO 21
<211> LENGTH: 40
<212> TYPE: DNA
<213> ORGANISM: Artificial Sequence
<220> FEATURE:
<223> OTHER INFORMATION: A synthetic oligonucleotide

<400> SEQUENCE: 21
ctagctagcc tactaattga tggccatccg aattcttttg    40

<210> SEQ ID NO 22
<211> LENGTH: 38
<212> TYPE: DNA
<213> ORGANISM: Artificial Sequence
<220> FEATURE:
<223> OTHER INFORMATION: A synthetic oligonucleotide

<400> SEQUENCE: 22
tacgagctca ccatggatgt caatccgact ttactttt    38

<210> SEQ ID NO 23
<211> LENGTH: 40
<212> TYPE: DNA
<213> ORGANISM: Artificial Sequence
<220> FEATURE:
<223> OTHER INFORMATION: A synthetic oligonucleotide

<400> SEQUENCE: 23
ctagctagcc tactattttt gccgtctgag ttcttcaatg    40

<210> SEQ ID NO 24
<211> LENGTH: 36
<212> TYPE: DNA
<213> ORGANISM: Artificial Sequence
<220> FEATURE:
<223> OTHER INFORMATION: A synthetic oligonucleotide

<400> SEQUENCE: 24
cccatcgata ccatggaaga ctttgtgcga caatgc    36

<210> SEQ ID NO 25
<211> LENGTH: 39
<212> TYPE: DNA
<213> ORGANISM: Artificial Sequence
<220> FEATURE:
<223> OTHER INFORMATION: A synthetic oligonucleotide

```
<400> SEQUENCE: 25
ctagctagcc tactatttca gtgcatgtgc gaggaagga                              39

<210> SEQ ID NO 26
<211> LENGTH: 34
<212> TYPE: DNA
<213> ORGANISM: Artificial Sequence
<220> FEATURE:
<223> OTHER INFORMATION: A synthetic oligonucleotide

<400> SEQUENCE: 26
ttcatcgata ccatggcgtc tcaaggcacc aaac                                   34

<210> SEQ ID NO 27
<211> LENGTH: 40
<212> TYPE: DNA
<213> ORGANISM: Artificial Sequence
<220> FEATURE:
<223> OTHER INFORMATION: A synthetic oligonucleotide

<400> SEQUENCE: 27
cgcgctagcc tattaattgt catactcctc tgcattgtct                             40
```

MUTATIONS THAT CONFER GENETIC STABILITY TO ADDITIONAL GENES IN INFLUENZA VIRUSES

CROSS-REFERENCE TO RELATED APPLICATIONS

This application is a divisional of U.S. application Ser. No. 14/745,236, filed Jun. 19, 2015, which claims the benefit of the filing date of U.S. application Ser. No. 62/015,074, filed on Jun. 20, 2014, the disclosures of which are incorporated by reference herein.

STATEMENT OF GOVERNMENT RIGHTS

This invention was made with government support under HHSN266200700010C awarded by the National Institutes of Health. The government has certain rights in the invention.

BACKGROUND

Influenza A virus is a respiratory pathogen that causes annual epidemics and sporadic pandemics (Wright et al., 2013). Moreover, highly pathogenic avian H5N1 and the recently emerged H7N9 influenza viruses have caused an appreciable number of human infections with high mortality rates (Watanabe et al., 2013; Zhang et al., 2013). Influenza viruses infect respiratory epithelial cells and alveolar macrophages in mammalian hosts (Yu et al., 2010). The host immune system recognizes the RNA genome of influenza viruses via cytosolic sensors (Diebold et al., 2004; Pichlmair et al., 2006), which trigger innate immune responses that lead to the production of type I interferons (IFNs) and proinflammatory cytokines and chemokines (Honda and Taniguchi, 2006). Type I IFNs upregulate the production of antiviral proteins including myxovirus resistance (Mx), oligoadenylate synthetase (OAS), and interferon-stimulated gene 15 (ISG15) (Garcia-Sastre et al., 2011). Dysregulation of the innate immune responses to influenza virus infection causes lung pathology mediated by infiltrating immune cells, including macrophages and neutrophils (Heron et al., 2008; Perrone et al., 2008). Although several studies have addressed host responses to influenza virus infections (Fakuyama and Kawaoka, 2011), the mechanisms of influenza virus-induced pathology are still not fully understood.

To analyze the immune responses to influenza virus infection in vivo, viruses have been generated that expressed a fluorescent reporter protein (Kittel et al., 2004; Shinya et al., 2004). However, these viruses were significantly attenuated (Kittel et al., 2004; Shinya et al., 2004) and may not accurately reflect natural infections. For example, Manicassamy et al. (2010) generated a GFP-expressing influenza virus, which they used to assess the route of antigen presentation upon influenza virus infection (Helft et al., 2012). However, the GFP gene was not stably maintained during replication in mouse lung or cultured cells (Manicassamy et al., 2010).

Highly pathogenic avian influenza viruses (HPAI) of the H5N1 subtype continue to evolve in nature, threatening animal and public health. These viruses were first identified in Guangdong province in China in 1996 (Li et al., 2006), and have since been found in over 63 countries in multiple avian species, repeatedly infecting mammals such as pigs and humans (Li et al., 2010; Neumann et al., 2010). By December 2013, 648 human cases of H5N1 virus infection had been confirmed by the World health organization (WHO), of which 384 were fatal, yielding a mortality rate of almost 60% (http://www.who.int). In addition, novel subtypes of influenza viruses, such as H7N9 and H10N8 virus, have spontaneously appeared and sporadically infected humans causing fatal outcomes (Chen et al., 2014; Li et al., 2013) (http://www.who.int). Thus, the current threat from influenza viruses reminds us of the urgent need to gain a thorough understanding of their pathogenic mechanism in order to develop more effective strategies for control, including dynamic processes of influenza virus infection and virus-target cells in vivo remain unclear.

SUMMARY OF THE INVENTION

The present invention relates to mutations in influenza virus gene segment(s) that increase genetic stability, for instance, of an additional, non-influenza viral gene, such as a "heterologous" gene sequence that is inserted into one of the viral gene segments, e.g., fused to an intact or modified (for example, truncated or internally deleted) viral protein coding region, or that is present on an additional gene segment. In one embodiment, one or more of the mutations may be employed to enhance the stability of influenza viruses that are not augmented with heterologous gene sequences. In one embodiment, the heterologous gene sequence is a marker gene, e.g., a fluorescent protein gene such as one for GFP, BFP, RFP, or YFP, a luciferase gene, a beta-glucuronidase gene, or beta-lactamase gene. In one embodiment, the heterologous sequence is for a prophylactic gene product. In one embodiment, the heterologous sequence encodes a therapeutic gene product.

As disclosed herein, influenza viruses expressing fluorescent proteins of different colors (Color-flu viruses) were generated. Viruses containing the foreign matter gene were passaged. Upon adaptation to mice, stable expression of the fluorescent proteins in infected animals allowed their detection by different types of microscopy and by flow cytometry. The use of fluorescent influenza viruses, each of which stably expresses one of four different fluorescent proteins, allows for simultaneous monitoring and live imaging. Using these viruses, several studies were performed to demonstrate the versatility of these viruses. For example, this system was used to analyze the progression of viral spread in mouse lungs, for live imaging of virus-infected cells, and for differential gene expression studies in virus antigen-positive and -negative live cells in the lungs of Color-flu-infected mice. Thus, Color-flu viruses are powerful tools to analyze virus infections at the cellular level in vivo to better understand influenza pathogenesis. Moreover, different stabilizing mutations in the resulting viruses were identified. These mutations include the T380A in HA protein (numbering is that for H1) and E712D in PB2 protein of A/PR/8/34 (H1N1) virus, and V25A, R443K, K737R and P167S amino acid replacements in the PB2, PA, PB1 and NS1 proteins of A/Vietnam/1203/2004 (H5N1) virus, respectively. The individual mutations in the H5 virus alone resulted in the virus containing a foreign gene more stable in vitro, and the combination of all of them provided even greater stability in vivo. These mutations are useful for any HA/NA combination.

In one embodiment, a recombinant virus has one or more stabilizing mutations, e.g., one or more substitutions in one or more influenza virus proteins that enhance the stability or replication (for instance, enhance the titer) of the recombinant virus with the one or more substitutions relative to a corresponding virus without the one or more substitutions (a parental virus) and/or one or more substitutions in one or more influenza virus proteins that enhance the stability or replication of a heterologous gene sequence present on one of the gene segments in the recombinant virus relative to a corresponding virus without the one or more substitutions that has the heterologous gene sequence in the respective gene segment and/or one or more substitutions in one or more influenza virus proteins that enhance the stability or replication of a heterologous gene sequence that is present on an additional gene segment in the recombinant virus relative to a corresponding virus without the one or more substitution and that has the additional gene segment with the heterologous gene sequence. The one or more substitutions include but are not limited to substitutions in any of influenza PA, PA-X, PB1, PB1-F2, PB2, NP, NS1, NS2, M1, M2, NA, and/or HA (e.g., a HA of influenza A virus), substitutions encoded in the corresponding gene segments therefor (PA, PB1, PB2, NP, NS, M, NA, and/or HA), or a combination of substitutions in any one of those influenza virus proteins or genes, or a combination of one or more substitutions in two or more of those proteins or genes. In one embodiment, the one or more substitutions that enhance the stability or replication of an influenza virus are in the PA protein, e.g., a substitution for arginine at position 443 in PA (which is located on the protein surface) that enhances, for example, RNA replication, PA proteolytic activity and/or interaction with one or more viral or cellular proteins. In one embodiment, the substitution for arginine at position 443 in PA is a conservative substitution. In one embodiment, the substitution for arginine at position 443 in PA is a non-conservative substitution. In one embodiment, the one or more substitutions that enhance the stability or replication of an influenza virus are in the PB2 protein, e.g., a substitution for valine at position 25 and/or for glutamic acid at position 712 in PB2 that, for example, enhances polymerase activity, interaction with MAVS (for position 25) and/or protein folding or stability (for position 712). In one embodiment, the substitution for valine at position 25 in PB2 is a conservative substitution. In one embodiment, the substitution for valine at position 25 in PB2 is a non-conservative substitution. In one embodiment, the substitution for glutamic acid at position 712 in PB2 is a conservative substitution. In one embodiment, the substitution for glutamic acid at position 712 in PB2 is a non-conservative substitution. In one embodiment, the one or more substitutions that enhance the stability or replication of an influenza virus are in the PB1 protein, e.g., a substitution for lysine at position 737 in PB1 (which is located on the protein surface) that, for instance, alter polymerase or endonuclease activity. In one embodiment, the substitution for lysine at position 737 in PB1 is a conservative substitution. In one embodiment, the substitution for lysine at position 737 in PB1 is a non-conservative substitution. In one embodiment, the one or more substitutions that enhance the stability or replication, e.g., by altering the interferon interfering activity or transcription regulatory activity of NS1 of an influenza virus, are in the NS1 protein, e.g., a substitution for proline at position 167 in NS1 which may alter interaction with cellular proteins. In one embodiment, the substitution for proline at position 167 in NS1 is a conservative substitution. In one embodiment, the substitution for proline at position 167 in NS1 is a non-conservative substitution. In one embodiment, the one or more substitutions that enhance the stability or replication of an influenza virus are in the HA protein, e.g., a substitution for threonine at position 380 in HA (which is in an alpha helix of HA-2). In one embodiment, the substitution for threonine at position 380 in HA is a conservative substitution. In one embodiment, the substitution for threo-nine at position 380 in HA is a non-conservative substitution. In one embodiment, the residue at position 443 in PA is K or H. In one embodiment, the residue at position 737 in PB1 is H or R. In one embodiment, the residue at position 25 in PB2 is A, L, T, I, or G. In one embodiment, the residue at position 712 in PB2 is D. In one embodiment, the residue at position 167 in NS1 is C, M, A, L, I, G or T.

The vectors comprise influenza cDNA, e.g., influenza A (e.g., any influenza A gene including any of the 17 HA or 10 NA subtypes), B or C DNA (see Fields *Virology* (Fields et al. (eds.), Lippincott, Williams and Wickens (2006), which is specifically incorporated by reference herein).

In one embodiment, PB1, PB2, PA, NP, M, and NS encode proteins having at least 80%, e.g., 90%, 92%, 95%, 97%, 98%, or 99%, including any integer between 80 and 99, contiguous amino acid sequence identity to, a polypeptide encoded by one of SEQ ID NOs:1-6 or 10-15, although the disclosed positions and substitutions in viral proteins may be made in a gene segment from any influenza virus isolate or may be used to select gene segments with specified residues at the one or more disclosed positions. In one embodiment, PB1, PB2, PA, NP, M, and NS encode proteins that are having at least 80%, e.g., 90%, 92%, 95%, 97%, 98%, or 99%, including any integer between 80 and 99, contiguous amino acid sequence identity to, a polypeptide encoded by one of SEQ ID NOs:1-6 or 10-15. In one embodiment, the influenza virus polypeptide has one or more, for instance, 2, 5, 10, 15, 20 or more, conservative amino acids substitutions, e.g., conservative substitutions of up to 10% or 20% of 2, 5, 10, 15, 20 or more, of a combination of conservative and non-conservative amino acids substitutions, e.g., conservative substitutions of up to 10% or 20% of the residues, or relative to a polypeptide encoded by one of SEQ IS NOs:1-6 or 10-15, and has a characteristic residue as described herein that provides for stability.

A recombinant influenza virus of the invention may be prepared by selecting gene segments for inclusion in a recombinant virus, such as a reassortant virus, having one or more stabilizing mutations in one or more influenza virus proteins. For example, a HA gene segment encoding a HA with a residue at position 380 that is not threonine may be selected; a PA gene segment encoding a PA with a residue at position 443 that is not arginine may be selected; a PB1 gene segment encoding a PB1 with a residue at position 737 that is not lysine may be selected; a PB2 gene segment encoding a PB2 with a residue at position 25 that is not valine or a residue at position 712 that is not glutamic acid may be selected; a NS gene segment encoding a NS1 with a residue at position 167 that is not proline may be selected; or any combination thereof. In one embodiment, the residue at position 443 in PA is K or H. In one embodiment, the residue at position 737 in PB1 is H or R. In one embodiment, the residue at position 25 in PB2 is A, L, T, I, or G. In one embodiment, the residue at position 712 in PB2 is D. In one embodiment, the residue at position 167 in NS1 is S, C, M, A, L, I, G or T. In one embodiment, the residue at position 380 in HA is A, I, V, L or G.

In one embodiment, the influenza virus of the invention is a recombinant influenza virus having two or more of selected amino acid residues at specified positions in one or more of PA, PB1, PB2, HA, and/or NS1. In one embodiment, the recombinant reassortant influenza virus has a lysine or histidine at position 443 in PA, a histidine or arginine at position 737 in PB1, a leucine, isoleucine, threonine, alanine or glycine at position 25 in PB2 and/or an aspartic acid, histidine, arginine, lysine or asparagine at position 712 in PB2; a leucine, alanine, valine, isoleucine, or glycine at position 380 in HA, or serine, cysteine, methionine, alanine, valine, glycine, isoleucine or leucine at position 167 in NS1.

A recombinant influenza virus of the invention having an extra gene segment with a heterologous gene sequence (a "9 segment" virus) which virus has enhanced stability and/or replication may be prepared by selecting gene segments for inclusion in the recombinant virus having one or more of the stabilizing mutations in an influenza virus protein. For example, a HA gene segment encoding a HA with a residue at position 380 that is not threonine may be selected; a PA gene segment encoding a PA with a residue at position 443 that is not arginine may be selected; a PB1 gene segment encoding a PB1 with a residue at position 737 that is not lysine may be selected; a PB2 gene segment encoding a PB2 with a residue at position 25 that is not valine or a residue at position 712 that is not glutamic acid may be selected; a NS gene segment enclosing a NS1 with a residue at position 167 that is not proline may be selected; or any combination thereof. The extra gene segment may be derived from any of the naturally occurring gene segments. In one embodiment, the residue at position 443 in PA is K or H. In one embodiment, the residue at position 737 in PB1 is H or R. In one embodiment, the residue at position 25 in PB2 is A, L, T, I, or G. In one embodiment, the residue at position 712 in PB2 is D. In one embodiment, the residue at position 167 in NS1 is C, M, A, L, I, G or T. The heterologous gene sequence may be of length that results in the gene segment with that heterologous gene sequence having a length that is up to 4 kb, 4.2 kb, 4.5 kb, 4.7 kb, 5 kb, 5.2 kb, 5.5 kb, 5.7 kb or 6 kb in length. In one embodiment, the heterologous gene in the extra gene segment replaces influenza virus protein coding sequences (e.g., there is a deletion of influenza virus coding sequences without deleting encapsidation (incorporation) sequences in coding sequences that are linked to encapsidation sequences in non-coding sequences at one or both ends of the gene segment). In one embodiment, the heterologous gene sequence in the extra gene segment is in genomic orientation. In one embodiment, the heterologous gene sequence in the extra gene segment is fused in frame to N-terminal influenza virus protein coding sequences. In one embodiment, the heterologous gene sequence in the extra gene segment is fused in frame to C-terminal influenza virus protein coding sequences. The heterologous gene may encode a RNA, e.g., a microRNA, or a protein, e.g., a gene product that is prophylactic or therapeutic. In one embodiment, the gene product is an antigen from a different influenza virus isolate, or an antigen from a bacteria, a virus other than influenza virus, a parasite, or a fungus.

A recombinant influenza virus of the invention having a heterologous gene sequence in one of the eight gene segments (an "8 segment" virus) with enhanced stability and/or replication may be prepared by selecting gene segments for inclusion in the recombinant virus having one or more of the stabilizing mutations in an influenza virus protein. For example, a HA gene segment encoding a HA with a residue at position 380 that is not threonine may be selected; a PA gene segment encoding a PA with a residue at position 443 that is not arginine may be selected; a PB1 gene segment encoding a PB1 with a residue at position 737 that is not lysine may be selected; a PB2 gene segment encoding a PB2 with a residue at position 25 that is not valine or a residue at position 712 that is not glutamic acid may be selected; a NS gene segment enclosing a NS1 with a residue at position 167 that is not proline may be selected; or any combination thereof. In one embodiment, the residue at position 443 in PA is K or H. In one embodiment, the residue at position 737 in PB1 is H or R. In one embodiment, the residue at position 25 in PB2 is A, L, T, I, or G. In one embodiment, the residue at position 712 in PB2 is D. In one embodiment, the residue at position 167 in NS1 is C, M, A, L, I, G or T.

A recombinant influenza virus of the invention having a heterologous gene sequence in one of the influenza virus gene segments that also lacks a gene segment (a "7 segment" virus), which virus has enhanced stability and/or replication, may be prepared by selecting gene segments for inclusion in the recombinant virus having one or more of the stabilizing mutations in an influenza virus protein. For example, a HA gene segment encoding a HA with a residue at position 380 that is not threonine may be selected; a PA gene segment encoding a PA with a residue at position 443 that is not arginine may be selected; a PB1 gene segment encoding a PB1 with a residue at position 737 that is not lysine may be selected; a PB2 gene segment encoding a PB2 with a residue at position 25 that is not valine or a residue at position 712 that is not glutamic acid may be selected; a NS gene segment enclosing a NS1 with a residue at position 167 that is not proline may be selected; or any combination thereof. The gene segment that is omitted may be any one of the naturally occurring gene segments and optionally the encoded protein is provided in trans. In one embodiment, the 7 segment virus includes a PA gene segment, or the PA protein is provided in trans, and the residue at position 443 in PA is K or H. In one embodiment, the 7 segment virus includes a PB1 gene segment, or the PB1 protein is provided in trans, and the residue at position 737 in PB1 is H or R. In one embodiment, the 7 segment virus includes a PB2 gene segment, or the PB2 protein is provided in trans, and the residue at position 25 in PB2 is A, L, T, I, or G. In one embodiment, the 7 segment virus includes a PB2 gene segment, or the PB2 protein is provided in trans, and the residue at position 712 in PB2 is D. In one embodiment, the 7 segment virus includes a NS gene segment, or the NS1 protein is provided in trans, and the residue at position 167 in NS1 is C, M, A, L, I, G or T. The heterologous gene sequence may be of length that results in the gene segment with that heterologous gene sequence having a length that is up to 4 kb, 4.2 kb, 4.5 kb, 4.7 kb, 5 kb, 5.2 kb, 5.5 kb, 5.7 kb or 6 kb in length. In one embodiment, the heterologous gene replaces influenza virus protein coding sequences (e.g., there is a deletion of influenza virus coding sequences without deleting encapsidation (incorporation) sequences in coding sequences that are linked to encapsidation sequences in non-coding sequences at one or both ends of the gene segment). In one embodiment, the heterologous gene sequence in the extra gene segment is in genomic orientation. In one embodiment, the heterologous gene sequence is fused in frame to N-terminal influenza virus protein coding sequences. In one embodiment, the heterologous gene sequence in the extra gene segment is fused in frame to C-terminal influenza virus protein coding sequences. The heterologous gene may encode a RNA, e.g., a microRNA, or a protein, e.g., a gene product that is prophylactic or therapeutic. In one embodiment, the gene product is an antigen from a different influenza virus isolate, or an antigen from a bacteria, a virus other than influenza virus, a parasite, or a fungus.

The heterologous gene sequence may be inserted into any gene segment. The heterologous gene sequence may be of length that results in the gene segment with that heterologous gene sequence having a length that is up to 4 kb, 4.2 kb, 4.5 kb, 4.7 kb, 5 kb, 5.2 kb, 5.5 kb, 5.7 kb or 6 kb in length. In one embodiment, the heterologous gene replaces internal influenza virus sequences in the gene segment. In one embodiment, the insertion of a heterologous gene sequence may result in a "knock-out" of the respective influenza virus gene product and to prepare such a virus, influenza virus protein(s) may be provided in trans to complement that type of mutation. In one embodiment, the heterologous gene sequences are in addition to influenza virus coding sequences in the gene segment. In one embodiment, the heterologous gene sequence is fused in frame to N-terminal influenza virus protein coding sequences. In one embodiment, the heterologous gene in is fused in frame to C-terminal influenza virus protein coding sequences. The heterologous gene may encode a RNA or a protein, e.g., a gene product that is prophylactic or therapeutic. In one embodiment, the gene product is an antigen from a different influenza virus isolate, an antigen from a bacteria, a virus other than influenza virus, a parasite, or a fungus. In one embodiment, the heterologous gene sequence is in the NA gene segment. In one embodiment, the heterologous gene sequence is in the HA gene segment. In one embodiment, the heterologous gene sequence is in the M gene segment. In one embodiment, the heterologous gene sequence is in the NS gene segment. In one embodiment, the heterologous gene sequence is in the NP gene segment, e.g., see Liu et al., 2012; Wang et al. 2010; Arilor et al., 2010; Dos Santos Afonso et al., 2005). In one embodiment, the heterologous gene sequence is in the PA gene segment. In one embodiment, the heterologous gene sequence is in the PB1 gene segment. In one embodiment, the heterologous gene sequence is in the PB2 gene segment. In one embodiment, the heterologous gene sequence is 5' or 3' to, replaces at least some of or is inserted into, the PA coding sequence in the PA gene segment. In one embodiment, the heterologous gene sequence is 5' or 3' to, replaces at least some of or is inserted into, the PB1 coding sequence in the PB1 gene segment. In one embodiment, the heterologous gene sequence is 5' or 3' to, replaces at least some of or is inserted into, the PB2 coding sequence in the PB2 gene segment (see, e.g., Avilov et al. 2012). In one embodiment, the heterologous gene sequence is 5' or 3' to, replaces at least some of or is inserted into, the NS coding sequence in the NS gene segment (Manicassamy et al. 2010). In one embodiment, the heterologous gene sequence is 5' or 3' to, replaces at least some of or is inserted into, the NS1 coding sequence in the NS gene segment. In one embodiment, the heterologous gene sequence is 5' or 3' to, replaces at least some of or is inserted into, the NS2 coding sequence in the NS gene segment. In one embodiment, the heterologous gene sequence is 5' or 3' to, replaces at least some of or is inserted into, the HA coding sequence in the HA gene segment. In one embodiment, the heterologous gene sequence is 5' or 3' to, replaces at least some of or is inserted into, the NA coding sequence in the NA gene segment (see, e.g., Perez et al. 2004). In one embodiment, the heterologous gene sequence is 5' or 3' to, replaces at least some of or is inserted into, the M1 coding sequence in the M gene segment. In one embodiment, the heterologous gene sequence is 5' or 3' to, replaces at least some of or is inserted into, the M2 coding sequence in the M gene segment (see, e.g., Wei et al. 2011).

Further provided is a vaccine comprising the recombinant virus of the invention, e.g., a live attenuated vaccine or where the recombinant virus is cold adapted, one or more vectors comprising one or more gene segments with one or more of the disclosed substitutions, as well as methods of making and using the recombinant virus. In one embodiment, the vector for vRNA production comprises a promoter such as a RNA polymerase I promoter, a RNA polymerase II promoter, a RNA polymerase III promoter, a T3 promoter or a T7 promoter.

Also provided is a method to generate influenza viruses with an altered property, e.g., enhanced replication or stability, in a selected avian or mammalian host. The method includes serially passaging an isolate of an influenza virus in an individual host organism, and identifying individual viruses with the altered property and optionally molecularly characterizing the individual viruses.

Further provided is a set of recombinant influenza viruses, each member of the set encoding a distinct optically detectable marker, e.g., the open reading frame of which is fused to the open reading frame of an influenza virus protein, the open reading frame of which is on a ninth gene segment for influenza A or B viruses, or the open reading frame of which replaces at least a portion of one of the viral protein coding regions. For example, one of the members includes a luminescent protein gene, e.g., a luciferase gene, a fluorescent protein gene, for instance, green fluorescent protein gene, yellow fluorescent protein gene, or red fluorescent protein gene, photoprotein genes such as Aequorin photoprotein gene or obelin photoprotein gene, chloramphenical acetyltransferase gene, a phosphatase gene such as alkaline phosphatase gene, a peroxidase gene such as horseradish peroxidase gene, beta-galactosidase gene, beta-lactamase gene or beta-glucuronidase gene.

BRIEF DESCRIPTION OF THE FIGURES

FIGS. 3A-K. Analysis of macrophage infiltration. Lung tissues were harvested from PBS-inoculated mice (mock) or mice infected with $10^5$ PFU of MA-Venus-PR8 at day 2 p.i., and tissues were fixed and processed for histological analysis. Sections were incubated with PE-anti-Mac3 antibody to detect macrophages (red) and counterstained with Hoechst dye (blue) to visualize nuclei (A,B). The fluorescent signal of the Venus protein is shown in green. The scale bar represents 200 µm. (C,D) Kinetics of the interaction between virus infected cells and lung macrophages. Images of eGFP positive cells (green) and CD11b+ macrophage (red) in lung tissue from naïve B6 mice and B6 mice on day 3 p.i. with $10^5$ PFU MA-eGFP-PR8 were obtained by using two-photon microscope. Sequential images (E,H) show an enlarged view of the box in the upper right panel. Arrowheads indicate the blebbing of eGFP positive cells. Scale bar, 40 µm. (I) Infection of macrophages by influenza viruses. Single cell suspensions were obtained from lungs of PBS-inoculated (mock) mice or mice infected with $10^5$ PFU of MA-Venus-PR8 at day 3 p.i., stained with antibodies against CD45, CD11b, and F4/80, and analyzed by flow cytometry. The panel shows Venus expression versus the CD11b staining profile from cells gated on F4/80 and CD45 expression levels. (J,K) Gene expression analysis. Total RNA was isolated from sorted macrophages of PBS-inoculated (naive) mice, and from sorted Venus-positive (Venus(+)) and Venus-negative (Venus(−)) macrophages of mice inoculated with $10^5$ PFU of MA-Venus-PR8 at day 3 p.i. (9 mice per treatment), and microarray analysis was performed. (J) Differentially expressed (DE) transcripts were identified by comparing gene expression levels in naive macrophages with those in Venus(+) macrophages from infected mice. Likewise, gene expression levels were compared for naive macrophages and Venus(−) macrophages obtained from infected mice. DE transcripts were organized by hierarchical clustering and each cluster was analyzed for enriched biological functions. A heat map of the clustered transcripts for each condition is displayed (a color key is shown at the top of the panel), and the different clusters are illustrated by the color bar on the left of the heat map. Enriched annotations for each cluster are listed to the left of each cluster, with the enrichment score for each annotation in parentheses. The blue line in the heat map illustrates fold changes of DE transcripts when comparing Venus(+) with Venus(−) macrophages. A shift of the blue line to the left indicates that the DE transcript is more highly expressed in Venus(+) macrophages, whereas a shift to the right indicates that the DE transcript is more highly expressed in Venus(−) macrophages. (K) This panel shows a heat map comparing expression levels of type I interferons (IFNs) between Venus(+) and Venus(−) macrophages. A color key is shown at the bottom of the panel. NS denotes comparisons that were not statistically significant between Venus(−) cells from infected animals and naive macrophages from uninfected animals.

FIG. 4. Characterization of MA-Venus-HPAI virus. (A) Four B6 mice per group were intranasally inoculated with MA-Venus-HPAI virus. Mouse body weight and survival were monitored for 14 days. (B) Lungs, spleens, kidneys, and brains were harvested from B6 mice at day 3 p.i. with $10^5$ PFU of MA-Venus-HPAI virus. Virus titers of tissue homogenates were determined by use of plaque assays in MDCK cells. Each data point represents mean±s.d. (n=3) (C, D) Lung tissues were harvested from B6 mice at day 1 and day 2 p.i. with $10^5$ PFU of MA-Venus-HPAI virus and PR8. Images of transparent lung tissues (bronchus, red; alveolar, green) were obtained by a two-photon microscope. Each data point represents mean±s.d. (n=3). Statistical significance was calculated using the Student's t-test. (D) The distribution of Venus-positive cells was evaluated via volume analysis of the Venus-positive bronchus and alveolar area using 3D images of the transparent lung tissues. (E,F) Cells were collected from lungs of B6 mice at days 1, 2, 3, and 4 p.i. with $10^5$ PFU of MA-Venus-PR8 or MA-Venus-HPAI virus, and stained for CD45, CD11b, and F4/80. Venus expression in CD45-negative cells, and the Venus versus F4/80 staining profile gated on CD45-positive cells were analyzed by flow cytometry. A representative data plot form day 2 p.i. is shown with the percentage of Venus-positive cells.

FIG. 5. Virus yield of various viruses.

FIG. 6. Virulence of WT-Venus-H5N1 virus and RG-MA virus in mice. Groups of four mice were intranasally infected with WT-Venus-H5N1 virus at doses of $10^1$ to $10^5$ PFU or with RG-MA virus at doses of $10^0$ to $10^5$ PFU, and their body weight changes (A-C) and survival (B-D) were monitored for two weeks.

FIG. 7. Venus expression of various H5N1 viruses in MDCK cells. MDCK cells were infected with Venus-H5N1-related viruses, and at 24 hpi the Venus expression of each virus plaque was observed by using fluorescent microscopy (Axio Observer.Z1, Zeiss). A representative image of each virus is shown.

FIG. 8. Venus expression of various H5N1 viruses in mouse lung. Groups of three mice were intranasally infected with $10^5$ PFU (50 µl) of virus. The mice were euthanized on day 2 p.i., and their lungs were collected and fixed in 4% PFA and then embedded in O.C.T Compound. The frozen tissues were cut into 5-µm slices and then stained with Hoechst 33342. Venus signal was detected by using the Nikon confocal microscope system A1+. Blue represents nuclei stained by Hoechst 33342; green represents Venus expression.

FIG. 9. Genotypes of Venus-H5N1-related reassortants and their virulence in mice. The colors indicate the origins of the gene segments: blue, WT-Venus-H5N1 virus; red, MA-Venus-H5N1 virus. $MLD_{50}$ values were determined by inoculating groups of four mice with 10-fold serial dilutions contain $10^0$ to $10^5$ PFU of virus in a 50-µL volume and were calculated by using the method of Reed and Muench (30).

FIG. 10. Growth kinetics of reassortants in MDCK cells. MDCK cells were infected with virus at an MOI of 0.0001, and culture supernatants were collected at the indicated times and then titrated in MDCK cells. The reported values are means±standard deviations (SD) from two independent experiments. **, P<0.01 compared with that of WT-Venus-H5N1 virus-infected cells.

FIG. 12B. Schematic of deleted viruses.

FIG. 14. Comparison of the growth capabilities of mutant viruses in MDCK cells. MDCK cells were infected at a MOI of 0.001 with PR8, NS1-Venus PR8 WT, NS1-Venus PR8 MA, and mutant NS1-Venus PR8 viruses that possess amino acid substitutions found in NS1-Venus PR8 MA virus. Virus titers were determined every 12 hours by means of plaque assays. Results are expressed as the mean titer ($\log_{10}$ [PFU/ml])±standard deviation.

FIG. 15. Body weight changes and survival rates for mice infected with viruses carrying Venus. Four mice per group were intranasally infected with $10^3$, $10^4$ and $10^5$ PFU of each NS1-Venus PR8 virus. Body weights were measured and survival rates were monitored for 14 days after infection.

FIGS. 18A-G. Comparison of Venus expression in cells infected with each NS1-Venus PR8 virus. (A)-(B) Venus protein expression in cells infected with each NS1-Venus PR8 virus was detected by means of western blotting. MDCK cells were infected with each virus at an MOI of 1. Twelve hours after infection, virus-infected cells were lysed and western blotting was performed. An anti-GFP antibody was used to detect Venus protein, and M1 protein was detected as a control. The bands appeared at approximately 27 kDa were shown in M1 panel. Representative results of two independent experiments are shown. (C)-(F) Observation of Venus expression by use of confocal microscopy. MDCK cells were infected with each virus at an MOI of 1. Twelve hours after infection, cells were fixed, and Venus expression was observed. Representative results of two independent experiments are shown. Indicated viruses were used to infect MDCK cells (MOI of 1) and confocal microscopy was performed 12 hours later. (G) HEK293 cells were infected with viral protein expression plasmids for NP, PA, PB1 and PB2 or PB-2-E712D, together with a plasmid expressing a vRNA encoding firefly luciferase.

FIG. 25. Exemplary parental sequences for PR8HG and the Cambridge strain of PR8 (SEQ ID Nos: 1-19).

DETAILED DESCRIPTION

Definitions

Figure 1A:
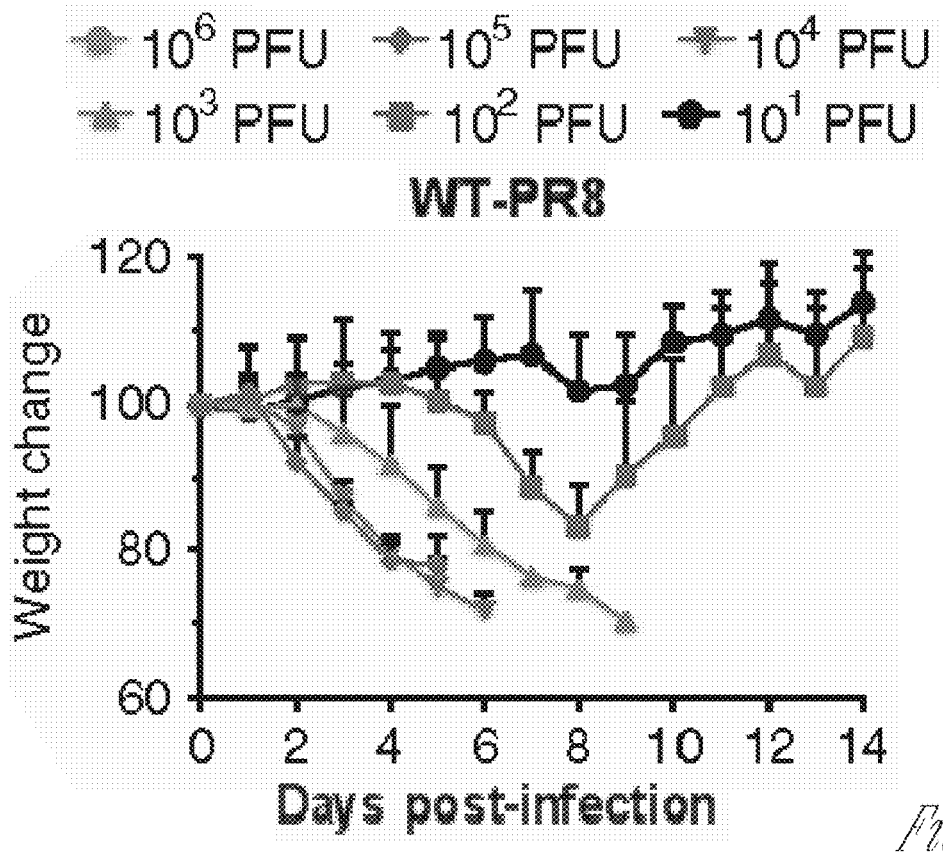
FIGS. 1A-G. Characteristics of mouse-adapted Venus-PR8 in mice. (A)-(F) Four B6 mice per group were intranasally inoculated with WT-PR8, WT-Venus-PR8, or MA-Venus-PR8. Body weight and survival of mice were monitored for 14 days. (G) Lungs of animals infected with $10^4$ PFU of PR8 or MA-Venus PR8 (three mice per group) were harvested at days 3, 5, and 7 p.i. Virus titers were analyzed by use of a plaque assay in MDCK cells.

As used herein, the term "isolated" refers to in vitro preparation and/or isolation of a nucleic acid molecule, e.g., vector or plasmid, peptide or polypeptide (protein), or virus of the invention, so that it is not associated with in vivo substances, or is substantially purified from in vitro substances. An isolated virus preparation is generally obtained by in vitro culture and propagation, and/or via passage in eggs, and is substantially free from other infectious agents.

As used herein, "substantially purified" means the object species is the predominant species, e.g., on a molar basis it is more abundant than any other individual species in a composition, and preferably is at least about 80% of the species present, and optionally 90% or greater, e.g., 95%, 98%, 99% or more, of the species present in the composition.

As used herein, "substantially free" means below the level of detection for a particular infectious agent using standard detection methods for that agent.

A "recombinant" virus is one which has been manipulated in vitro, e.g., using recombinant DNA techniques, to introduce changes to the viral genome. Reassortant viruses can be prepared by recombinant or nonrecombinant techniques.

As used herein, the term "recombinant nucleic acid" or "recombinant DNA sequence or segment" refers to a nucleic acid, e.g., to DNA, that has been derived or isolated from a source, that may be subsequently chemically altered in vitro, so that its sequence is not naturally occurring, or corresponds to naturally occurring sequences that are not positioned as they would be positioned in the native genome. An example of DNA "derived" from a source, would be a DNA sequence that is identified as a useful fragment, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

As used herein, a "heterologous" influenza virus gene or gene segment is from an influenza virus source that is different than a majority of the other influenza viral genes or gene segments in a recombinant, e.g., reassortant, influenza virus.

The terms "isolated polypeptide", "isolated peptide" or "isolated protein" include a polypeptide, peptide or protein encoded by cDNA or recombinant RNA including one of synthetic origin, or some combination thereof.

The term "recombinant protein" or "recombinant polypeptide" as used herein refers to a protein molecule expressed from a recombinant DNA molecule. In contrast, the term "native protein" is used herein to indicate a protein isolated from a naturally occurring (i.e., a nonrecombinant) source. Molecular biological techniques may be used to produce a recombinant form of a protein with identical properties as compared to the native form of the protein.

Methods of alignment of sequences for comparison are well known in the art. Thus, the determination of percent identity between any two sequences can be accomplished using a mathematical algorithm.

Computer implementations of these mathematical algorithms can be utilized for comparison of sequences to determine sequence identity. Alignments using these programs can be performed using the default parameters. Software for performing BLAST analyses is publicly available through the National Center for Biotechnology Information (http://www.ncbi.nlm.nih.gov/). The algorithm may involve first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm may also perform a statistical analysis of the similarity between two sequences. One measure of similarity provided by the BLAST algorithm may be the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

The BLASTN program (for nucleotide sequences) may use as defaults a wordlength (W) of 11, an expectation (E) of 10, a cutoff of 100, M=5, N=−4, and a comparison of both strands. For amino acid sequences, the BLASTP program may use as defaults a wordlength (W) of 3, an expectation (E) of 10, and the BLOSUM62 scoring matrix. See http/www.ncbi.nlm.nih.gov. Alignment may also be performed manually by inspection.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

"Conservative" amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine and tryptophan; a group of amino acids having basic side chains is lysine, arginine and histidine; and a group of amino acids having sulfur-containing side chain is cysteine and methionine. In one embodiment, conservative amino acid substitution groups are: threonine-valine-leucine-isoleucine-alanine; phenylalanine-tyrosine; lysine-arginine; alanine-valine; glutamic-aspartic; and asparagine-glutamine.

Encapsidation Sequences

The gene segment for incorporation of heterologous gene sequences into a recombinant influenza virus includes at each end non-coding sequences that provide for encapsidation (incorporation or packaging) into virions. The gene segments also include adjacent coding sequences, from one or both ends, that contribute to encapsidation, e.g., enhance encapsidation relative to gene segments that lack the adjacent coding sequences but have with the heterologous gene sequence. The vectors with the gene segment having the heterologous gene sequence thus include encapsidation sequences that at the 3' end of vRNA that may include adjacent 5' coding sequences, at the 5' end of vRNA that may include 3' coding sequences, or at the 3' end of vRNA that may include adjacent 5' coding sequences and at the 5' end of vRNA that may include 3' coding sequences. For example, HA encapsidation sequences include sequences at the 3' end of HA vRNA including 33-nt of non-coding sequences and at least 3, 6, 9, or 15 or up to about 216 nt of HA coding sequence and/or at the 5' end of HA vRNA including about 45 nt of non-coding sequence and up to about 75, 80, 268 or 291 of HA coding sequence (Watanabe et al. 2003). HS encapsidation sequences include sequences at the 3' end of NS vRNA including at least 30, 60, 90 or 150 nt of coding sequence and at the 5' end of NS vRNA including at least 30, 60, 90 or 100 nt of coding sequence (Fujii et al. 2005).

In one embodiment, the 3' NA incorporation sequences correspond to nucleotides 1 to 183, nucleotides 1 to 90, nucleotides 1 to 45, nucleotides 1 to 21, nucleotides 1 to 19 or any integer between 19 and 183, of the N-terminal NA coding region, and may include a mutation at the NA initiation codon. In another embodiment, the 5' NA incorporation sequences correspond to sequences in the C-terminal coding region of NA, sequences corresponding to the 3' most 39, 78, or 157, or any integer between 1 and 157, nucleotides for C-terminal NA coding region.

In one embodiment, the 5' HA incorporation sequences correspond to sequences in the C-terminal coding region of HA, sequences corresponding to the 3' most 75, 80, 268, 291, or 518, or any integer between 1 and 518, nucleotides of the C-terminal HA coding region. The 3' HA incorporation sequences correspond to nucleotides 1 to 3, 1 to 6, 1 to 9, 1 to 15, 1 to 216, 1 to 468, or any integer between 1 and 468, of the N-terminal HA coding region.

In one embodiment, the 3' PB1 or PB2 incorporation sequences correspond to nucleotides 1 to 250, nucleotides 1 to 200, nucleotides 1 to 150, nucleotides 1 to 160 or 1 to 130 or any integer between 1 and 250, of the N-terminal PB1 or PB2 coding region. In one embodiment, the 5' PB1 or PB2 incorporation sequences correspond to the 3' most nucleotides, e.g., the 3' 1 to 250 nucleotides, 1 to 200 nucleotides, nucleotides 1 to 150, nucleotides 1 to 160, 1 to 170 or 1 to 190, or any integer between 1 and 250, of the C-terminal PB1 or PB2 coding region.

In one embodiment, the 3' PA incorporation sequences correspond to nucleotides 1 to 250, nucleotides 1 to 200, nucleotides 1 to 150, or any integer between 1 and 250, of the N-terminal PA coding region. In one embodiment, the 5' PA incorporation sequences correspond to the 3' most nucleotides, e.g., the 3' 1 to 250 nucleotides, 1 to 200 nucleotides, nucleotides 1 to 150, nucleotides 1 to 160, 1 to 170 or 1 to 190, or any integer between 1 and 250, of the C-terminal PA coding region.

In one embodiment, the 3' M incorporation sequences correspond to nucleotides 1 to 250, nucleotides 1 to 242, nucleotides 1 to 240 or any integer between 1 and 250, of the N-terminal M coding region, and may include a mutation at the M initiation codon. In another embodiment, the 5' M incorporation sequences correspond to sequences in the C-terminal coding region of M, sequences corresponding to the 3' most 50, 100, or 220, or any integer between 1 and 250, nucleotides for C-terminal M coding region.

In one embodiment, the 3' NS or NP incorporation sequences correspond to nucleotides 1 to 250, nucleotides 1 to 200, nucleotides 1 to 150, nucleotides 1 to 30, or any integer between 1 and 250, e.g., 1 to 60, 1 to 70, 1 to 80 or 1 to 90 of the N-terminal NS or NP coding region, and may include a mutation at the NS or NP initiation codon. In another embodiment, the 5' NS or NP incorporation sequences correspond to sequences in the C-terminal coding region of NS or NP, sequences corresponding to the 3' most 10, 30, 150, 200 or 250, or any integer between 1 and 250, nucleotides for the C-terminal NS or NP coding region, e.g., nucleotides 1 to 250, nucleotides 1 to 200, nucleotides 1 to 150, nucleotides 1 to 30, or any integer between 1 and 250, e.g., 1 to 60, 1 to 70, 1 to 80 or 1 to 90 of the C-terminal NS or NP codon region.

Accordingly, the invention provides influenza virus vectors which include sequences corresponding to the 3' and 5' noncoding regions of a particular vRNA, incorporation sequences of the corresponding vRNA, and a heterologous nucleic acid segment. Thus, in one embodiment, the vector includes the 3' noncoding region of NA vRNA, 3' or 5' NA vRNA incorporation sequences, and optionally both 3' and 5' NA incorporation sequences, a heterologous nucleic acid segment, and the 5' noncoding region of NA vRNA. In another embodiment, the vector includes the 3' noncoding region of HA vRNA, 5' or 3' HA vRNA incorporation sequences or both 5' and 3' HA incorporation sequences, a heterologous nucleic acid segment, and the 5' noncoding region of HA vRNA. In another embodiment, the vector includes the 3' noncoding region of NS vRNA, NS incorporation sequences, a heterologous nucleic acid segment, and the 5' noncoding region of NS vRNA. In another embodiment, the vector includes the 3' noncoding region of M vRNA, 5' or 3' M incorporation sequences or both 5' and 3' M incorporation sequences, a heterologous nucleic acid segment, and the 5' noncoding region of M vRNA. In yet another embodiment, the vector includes the 3' noncoding region of PB2 vRNA, a heterologous nucleic acid segment, PB2 incorporation sequences, and the 5' noncoding region of PB2 vRNA. When two incorporation sequences are employed in a vector, they preferably are separated by the heterologous nucleic acid segment. Each vector may be employed so as to prepare vRNA for introduction to a cell, or to express vRNA in a cell, in which other influenza virus vRNAs and proteins necessary for virus production, are present.

In another embodiment, the heterologous gene sequence comprises sequences corresponding to an open reading frame for a therapeutic gene. In yet a further embodiment, the heterologous gene sequence comprises sequences corresponding to an open reading frame for an immunogenic peptide or protein of a pathogen or a tumor cell, e.g., one useful to induce a protective immune response. For example, the heterologous nucleic acid segment may encode an immunogenic epitope useful in cancer therapy or a vaccine. The vector comprising the heterologous nucleic acid segment may be prepared such that transcription of vector vRNA results in mRNA encoding a fusion protein with an influenza protein such as NA. Thus, it is envisioned that the heterologous nucleic acid segment may be fused with viral incorporation sequences so as to encode a fusion protein, e.g., a fusion with the N-terminal 21 residues of NA. The fusion protein may comprise sequences from two different influenza virus proteins including sequences from two different NA or HA proteins. In another embodiment, the heterologous nucleic acid segment may comprise sequences corresponding to an IRES linked 5N to an open reading frame.

In one embodiment of the invention, the heterologous gene sequence may encode a heterologous protein (a non-influenza viral protein such as a glycoprotein or a cytosolic, nuclear or mitochondrial specific protein), which may confer a detectable phenotype. In one embodiment, the heterologous gene sequence may be fused to truncated portions of PB2 coding sequences, e.g., those corresponding to 5' or 3' PB2 coding incorporation sequences, optionally forming a chimeric protein. In one embodiment, the heterologous nucleotide sequence replaces or is introduced to sequences in the viral gene segment corresponding to the coding region for that segment, so as not to disrupt the incorporation sequences in the coding region of the gene segment. For instance, the heterologous nucleotide sequence may be flanked by about 3 to about 400 nucleotides of the 5' and/or 3' PB2 coding region adjacent to non-coding sequence. In one embodiment, the 3' PB2 incorporation sequences correspond to nucleotides 3 to 400, nucleotides 3 to 300, nucleotides 3 to 100, nucleotides 3 to 50, or any integer between 3 and 400, of the N-terminal and/or C-terminal PB2 coding region. In one embodiment, after infection of a host cell with the biologically contained PB2-KO virus, a heterologous protein is produced which is a fusion with the N-terminus and/or C-terminus of the remaining residues of the deleted PB2 protein.

The vRNA for the additional gene segment or a gene segment having the heterologous gene sequence may be incorporated into virions at an efficiency that is at least 1%, 5%, 10%, or 30%, or at least 50%, that of a corresponding wild-type vRNA.

Influenza Virus Structure and Propagation

Influenza A viruses possess a genome of eight single-stranded negative-sense viral RNAs (vRNAs) that encode at least ten proteins. The influenza virus life cycle begins with binding of the hemagglutinin (HA) to sialic acid-containing receptors on the surface of the host cell, followed by receptor-mediated endocytosis. The low pH in late endosomes triggers a conformational shift in the HA, thereby exposing the N-terminus of the HA2 subunit (the so-called fusion peptide). The fusion peptide initiates the fusion of the viral and endosomal membrane, and the matrix protein (M1) and RNP complexes are released into the cytoplasm. RNPs consist of the nucleoprotein (NP), which encapsidates vRNA, and the viral polymerase complex, which is formed by the PA, PB1, and PB2 proteins. RNPs are transported into the nucleus, where transcription and replication take place. The RNA polymerase complex catalyzes three different reactions: synthesis of an mRNA with a 5' cap and 3' polyA structure, of a full-length complementary RNA (cRNA), and of genomic vRNA using the cRNA as a template. Newly synthesized vRNAs, NP, and polymerase proteins are then assembled into RNPs, exported from the nucleus, and transported to the plasma membrane, where budding of progeny virus particles occurs. The neuraminidase (NA) protein plays a crucial role late in infection by removing sialic acid from sialyloligosaccharides, thus releasing newly assembled virions from the cell surface and preventing the self-aggregation of virus particles. Although virus assembly involves protein-protein and protein-vRNA interactions, the nature of these interactions is largely unknown.

Although influenza B and C viruses are structurally and functionally similar to influenza A virus, there are some differences. For example, influenza B virus does not have a M2 protein with ion channel activity but has BM2 and has a gene segment with both NA and NB sequences. Influenza C virus has only seven gene segments.

Cell Lines that can be Used in the Present Invention

Any cell, e.g., any avian or mammalian cell, such as a human, e.g., 293T or PER.C6® cells, or canine, e.g., MDCK, bovine, equine, feline, swine, ovine, rodent, for instance mink, e.g., MvLu1 cells, or hamster, e.g., CHO cells, or non-human primate, e.g., Vero cells, including mutant cells, which supports efficient replication of influenza virus can be employed to isolate and/or propagate influenza viruses. Isolated viruses can be used to prepare a reassortant virus. In one embodiment, host cells for vaccine production are continuous mammalian or avian cell lines or cell strains. A complete characterization of the cells to be used, may be conducted so that appropriate tests for purity of the final product can be included. Data that can be used for the characterization of a cell includes (a) information on its origin, derivation, and passage history; (b) information on its growth and morphological characteristics; (c) results of tests of adventitious agents; (d) distinguishing features, such as biochemical, immunological, and cytogenetic patterns which allow the cells to be clearly recognized among other cell lines; and (e) results of tests for tumorigenicity. In one embodiment, the passage level, or population doubling, of the host cell used is as low as possible.

In one embodiment, the cells are WHO certified, or certifiable, continuous cell lines. The requirements for certifying such cell lines include characterization with respect to at least one of genealogy, growth characteristics, immunological markers, virus susceptibility tumorigenicity and storage conditions, as well as by testing in animals, eggs, and cell culture. Such characterization is used to confirm that the cells are free from detectable adventitious agents. In some countries, karyology may also be required. In addition, tumorigenicity may be tested in cells that are at the same passage level as those used for vaccine production. The virus may be purified by a process that has been shown to give consistent results, before vaccine production (see, e.g., World Health Organization, 1982).

Virus produced by the host cell may be highly purified prior to vaccine or gene therapy formulation. Generally, the purification procedures result in extensive removal of cellular DNA and other cellular components, and adventitious agents. Procedures that extensively degrade or denature DNA may also be used.

Influenza Vaccines

A vaccine of the invention includes an isolated recombinant influenza virus of the invention, and optionally one or more other isolated viruses including other isolated influenza viruses, one or more immunogenic proteins or glycoproteins of one or more isolated influenza viruses or one or more other pathogens, e.g., an immunogenic protein from one or more bacteria, non-influenza viruses, yeast or fungi, or isolated nucleic acid encoding one or more viral proteins (e.g., DNA vaccines) including one or more immunogenic proteins of the isolated influenza virus of the invention. In one embodiment, the influenza viruses of the invention may be vaccine vectors for influenza virus or other pathogens.

A complete virion vaccine may be concentrated by ultrafiltration and then purified by zonal centrifugation or by chromatography. Viruses other than the virus of the invention, such as those included in a multivalent vaccine, may be inactivated before or after purification using formalin or beta-propiolactone, for instance.

A subunit vaccine comprises purified glycoproteins. Such a vaccine may be prepared as follows: using viral suspensions fragmented by treatment with detergent, the surface antigens are purified, by ultracentrifugation for example. The subunit vaccines thus contain mainly HA protein, and also NA. The detergent used may be cationic detergent for example, such as hexadecyl trimethyl ammonium bromide (Bachmeyer, 1975), an anionic detergent such as ammonium deoxycholate (Laver & Webster, 1976); or a nonionic detergent such as that commercialized under the name TRITON X100. The hemagglutinin may also be isolated after treatment of the virions with a protease such as bromelin, and then purified. The subunit vaccine may be combined with an attenuated virus of the invention in a multivalent vaccine.

A split vaccine comprises virions which have been subjected to treatment with agents that dissolve lipids. A split vaccine can be prepared as follows: an aqueous suspension of the purified virus obtained as above, inactivated or not, is treated, under stirring, by lipid solvents such as ethyl ether or chloroform, associated with detergents. The dissolution of the viral envelope lipids results in fragmentation of the viral particles. The aqueous phase is recuperated containing the split vaccine, constituted mainly of hemagglutinin and neuraminidase with their original lipid environment removed, and the core or its degradation products. Then the residual infectious particles are inactivated if this has not already been done. The split vaccine may be combined with an attenuated virus of the invention in a multivalent vaccine.

Inactivated Vaccines.

Inactivated influenza virus vaccines are provided by inactivating replicated virus using known methods, such as, but not limited to, formalin or β-propiolactone treatment. Inactivated vaccine types that can be used in the invention can include whole-virus (WV) vaccines or subvirion (SV) (split) vaccines. The WV vaccine contains intact, inactivated virus, while the SV vaccine contains purified virus disrupted with detergents that solubilize the lipid-containing viral envelope, followed by chemical inactivation of residual virus.

In addition, vaccines that can be used include those containing the isolated HA and NA surface proteins, which are referred to as surface antigen or subunit vaccines.

Live Attenuated Virus Vaccines.

Live, attenuated influenza virus vaccines, such as those including a recombinant virus of the invention can be used for preventing or treating influenza virus infection. Attenuation may be achieved in a single step by transfer of attenuated genes from an attenuated donor virus to a replicated isolate or reassorted virus according to known methods. Since resistance to influenza A virus is mediated primarily by the development of an immune response to the HA and/or NA glycoproteins, the genes coding for these surface antigens come from the reassorted viruses or clinical isolates. The attenuated genes are derived from an attenuated parent. In this approach, genes that confer attenuation generally do not code for the HA and NA glycoproteins.

Viruses (donor influenza viruses) are available that are capable of reproducibly attenuating influenza viruses, e.g., a cold adapted (ca) donor virus can be used for attenuated vaccine production. See, for example, Isakova-Sivall et al., 2014. Live, attenuated reassortant virus vaccines can be generated by mating the ca donor virus with a virulent replicated virus. Reassortant progeny are then selected at 25° C. (restrictive for replication of virulent virus), in the presence of an appropriate antiserum, which inhibits replication of the viruses bearing the surface antigens of the attenuated ca donor virus. Useful reassortants are: (a) infectious, (b) attenuated for seronegative non-adult mammals and immunologically primed adult mammals, (c) immunogenic and (d) genetically stable. The immunogenicity of the ca reassortants parallels their level of replication. Thus, the acquisition of the six transferable genes of the ca donor virus by new wild-type viruses has reproducibly attenuated these viruses for use in vaccinating susceptible mammals both adults and non-adult.

Other attenuating mutations can be introduced into influenza virus genes by site-directed mutagenesis to rescue infectious viruses bearing these mutant genes. Attenuating mutations can be introduced into non-coding regions of the genome, as well as into coding regions. Such attenuating mutations can also be introduced into genes other than the HA or NA, e.g., the PB2 polymerase gene. Thus, new donor viruses can also be generated bearing attenuating mutations introduced by site-directed mutagenesis, and such new donor viruses can be used in the production of live attenuated reassortants vaccine candidates in a manner analogous to that described above for the ca donor virus. Similarly, other known and suitable attenuated donor strains can be reassorted with influenza virus to obtain attenuated vaccines suitable for use in the vaccination of mammals.

In one embodiment, such attenuated viruses maintain the genes from the virus that encode antigenic determinants substantially similar to those of the original clinical isolates. This is because the purpose of the attenuated vaccine is to provide substantially the same antigenicity as the original clinical isolate of the virus, while at the same time lacking pathogenicity to the degree that the vaccine causes minimal chance of inducing a serious disease condition in the vaccinated mammal.

The viruses in a multivalent vaccine can thus be attenuated or inactivated, formulated and administered, according to known methods, as a vaccine to induce an immune response in an animal, e.g., a mammal. Methods are well-known in the art for determining whether such attenuated or inactivated vaccines have maintained similar antigenicity to that of the clinical isolate or high growth strain derived therefrom. Such known methods include the use of antisera or antibodies to eliminate viruses expressing antigenic determinants of the donor virus; chemical selection (e.g., amantadine or rimantidine); HA and NA activity and inhibition; and nucleic acid screening (such as probe hybridization or PCR) to confirm that donor genes encoding the antigenic determinants (e.g., HA or NA genes) are not present in the attenuated viruses.

Pharmaceutical Compositions

Pharmaceutical compositions of the present invention, suitable for inoculation, e.g., nasal, parenteral or oral administration, comprise one or more influenza virus isolates, e.g., one or more attenuated or inactivated influenza viruses, a subunit thereof, isolated protein(s) thereof, and/or isolated nucleic acid encoding one or more proteins thereof, optionally further comprising sterile aqueous or non-aqueous solutions, suspensions, and emulsions. The compositions can further comprise auxiliary agents or excipients, as known in the art. The composition of the invention is generally presented in the form of individual doses (unit doses).

Conventional vaccines generally contain about 0.1 to 200 µg, e.g., 30 to 100 µg, of HA from each of the strains entering into their composition. The vaccine forming the main constituent of the vaccine composition of the invention may comprise a single influenza virus, or a combination of influenza viruses, for example, at least two or three influenza viruses, including one or more reassortant(s).

Preparations for parenteral administration include sterile aqueous or non-aqueous solutions, suspensions, and/or emulsions, which may contain auxiliary agents or excipients known in the art. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents.

When a composition of the present invention is used for administration to an individual, it can further comprise salts, buffers, adjuvants, or other substances which are desirable for improving the efficacy of the composition. For vaccines, adjuvants, substances which can augment a specific immune response, can be used. Normally, the adjuvant and the composition are mixed prior to presentation to the immune system, or presented separately, but into the same site of the organism being immunized.

Heterogeneity in a vaccine may be provided by mixing replicated influenza viruses for at least two influenza virus strains, such as 2-20 strains or any range or value therein. Vaccines can be provided for variations in a single strain of an influenza virus, using techniques known in the art.

A pharmaceutical composition according to the present invention may further or additionally comprise at least one chemotherapeutic compound, for example, for gene therapy, immunosuppressants, anti-inflammatory agents or immune enhancers, and for vaccines, chemotherapeutics including, but not limited to, gamma globulin, amantadine, guanidine, hydroxybenzimidazole, interferon-α, interferon-β, interferon-γ, tumor necrosis factor-alpha, thiosemicarbarzones, methisazone, rifampin, ribavirin, a pyrimidine analog, a purine analog, foscarnet, phosphonoacetic acid, acyclovir, dideoxynucleosides, a protease inhibitor, or ganciclovir.

The composition can also contain variable but small quantities of endotoxin-free formaldehyde, and preservatives, which have been found safe and not contributing to undesirable effects in the organism to which the composition is administered.

Pharmaceutical Purposes

The administration of the composition (or the antisera that it elicits) may be for either a "prophylactic" or "therapeutic" purpose. When provided prophylactically, the compositions of the invention which are vaccines are provided before any symptom or clinical sign of a pathogen infection becomes manifest. The prophylactic administration of the composition serves to prevent or attenuate any subsequent infection. When provided prophylactically, the gene therapy compositions of the invention, are provided before any symptom or clinical sign of a disease becomes manifest. The prophylactic administration of the composition serves to prevent or attenuate one or more symptoms or clinical signs associated with the disease.

When provided therapeutically, a viral vaccine is provided upon the detection of a symptom or clinical sign of actual infection. The therapeutic administration of the compound(s) serves to attenuate any actual infection. When provided therapeutically, a gene therapy composition is provided upon the detection of a symptom or clinical sign of the disease. The therapeutic administration of the compound(s) serves to attenuate a symptom or clinical sign of that disease.

Thus, a vaccine composition of the present invention may be provided either before the onset of infection (so as to prevent or attenuate an anticipated infection) or after the initiation of an actual infection. Similarly, for gene therapy, the composition may be provided before any symptom or clinical sign of a disorder or disease is manifested or after one or more symptoms are detected.

A composition is said to be "pharmacologically acceptable" if its administration can be tolerated by a recipient mammal. Such an agent is said to be administered in a "therapeutically effective amount" if the amount administered is physiologically significant. A composition of the present invention is physiologically significant if its presence results in a detectable change in the physiology of a recipient patient, e.g., enhances at least one primary or secondary humoral or cellular immune response against at least one strain of an infectious influenza virus.

The "protection" provided need not be absolute, i.e., the influenza infection need not be totally prevented or eradicated, if there is a statistically significant improvement compared with a control population or set of mammals. Protection may be limited to mitigating the severity or rapidity of onset of symptoms or clinical signs of the influenza virus infection.

Pharmaceutical Administration

A composition of the present invention may confer resistance to one or more pathogens, e.g., one or more influenza virus strains, by either passive immunization or active immunization. In active immunization, an attenuated live vaccine composition is administered prophylactically to a host (e.g., a mammal), and the host's immune response to the administration protects against infection and/or disease. For passive immunization, the elicited antisera can be recovered and administered to a recipient suspected of having an infection caused by at least one influenza virus strain. A gene therapy composition of the present invention may yield prophylactic or therapeutic levels of the desired gene product by active immunization.

In one embodiment, the vaccine is provided to a mammalian female (at or prior to pregnancy or parturition), under conditions of time and amount sufficient to cause the production of an immune response which serves to protect both the female and the fetus or newborn (via passive incorporation of the antibodies across the placenta or in the mother's milk).

The present invention thus includes methods for preventing or attenuating a disorder or disease, e.g., an infection by at least one strain of pathogen. As used herein, a vaccine is said to prevent or attenuate a disease if its administration results either in the total or partial attenuation (i.e., suppression) of a clinical sign or condition of the disease, or in the total or partial immunity of the individual to the disease. As used herein, a gene therapy composition is said to prevent or attenuate a disease if its administration results either in the total or partial attenuation (i.e., suppression) of a clinical sign or condition of the disease, or in the total or partial immunity of the individual to the disease.

A composition having at least one influenza virus of the present invention, including one which is attenuated and one or more other isolated viruses, one or more isolated viral proteins thereof, one or more isolated nucleic acid molecules encoding one or more viral proteins thereof, or a combination thereof, may be administered by any means that achieve the intended purposes.

For example, administration of such a composition may be by various parenteral routes such as subcutaneous, intravenous, intradermal, intramuscular, intraperitoneal, intranasal, oral or transdermal routes. Parenteral administration can be accomplished by bolus injection or by gradual perfusion over time.

A typical regimen for preventing, suppressing, or treating an influenza virus related pathology, comprises administration of an effective amount of a vaccine composition as described herein, administered as a single treatment, or repeated as enhancing or booster dosages, over a period up to and including between one week and about 24 months, or any range or value therein.

According to the present invention, an "effective amount" of a composition is one that is sufficient to achieve a desired effect. It is understood that the effective dosage may be dependent upon the species, age, sex, health, and weight of the recipient, kind of concurrent treatment, if any, frequency of treatment, and the nature of the effect wanted. The ranges of effective doses provided below are not intended to limit the invention and represent dose ranges.

The dosage of a live, attenuated or killed virus vaccine for an animal such as a mammalian adult organism may be from about $10^2$-$10^{15}$, e.g., $10^3$-$10^{12}$, plaque forming units (PFU)/kg, or any range or value therein. The dose of inactivated vaccine may range from about 0.1 to 1000, e.g., 30 to 100 μg, of HA protein. However, the dosage should be a safe and effective amount as determined by conventional methods, using existing vaccines as a starting point.

The dosage of immunoreactive HA in each dose of replicated virus vaccine may be standardized to contain a suitable amount, e.g., 30 to 100 μg or any range or value therein, or the amount recommended by government agencies or recognized professional organizations. The quantity of NA can also be standardized, however, this glycoprotein may be labile during purification and storage.

The dosage of immunoreactive HA in each dose of replicated virus vaccine can be standardized to contain a suitable amount, e.g., 1-50 μg or any range or value therein, or the amount recommended by the U.S. Public Health Service (PHS), which is usually 15 μg, per component for older children ⌊3 years of age, and 7.5 μg per component for older children <3 years of age. The quantity of NA can also be standardized, however, this glycoprotein can be labile during the processor purification and storage (Kendal et al., 1980; Kerr et al., 1975). Each 0.5-ml dose of vaccine may contains approximately 1-50 billion virus particles, and preferably 10 billion particles.

The invention will be further described by the following non-limiting examples.

Example I

Methods

Generation of Color-Flu

The NS segments of PR8 fused with different fluorescent reporter genes including eCFP, eGFP, Venus, and mCherry were constructed by overlapping fusion PCR as described in Manicassamy et al. (2010). In brief, the open reading frame (ORF) of the NS1 gene without the stop codon was fused with the N-terminus of fluorescent reporter genes via a sequence encoding the amino acid linker GSGG. The fluorescent reporter ORFs were followed by a sequence encoding the GSG linker, a foot-and-mouth virus protease 2A autoproteolytic site with 57 nucleotides from porcine teschovirus-1 in Manicassamy et al. (2010), and by the ORF of nuclear export protein (NEP) (FIG. 5). In addition, silent mutations were introduced into the endogenous splice acceptor site of the NS1 gene to abrogate splicing (Basler et al., 2001). The constructed NS segments (designated eCFP-NS, eGFP-NS, Venus-NS, and mCherry-NS) were subsequently cloned into a pPolI vector for reverse genetics as described in Newmann et al. (1999). The plasmid encoding the Venus reporter protein was a kind gift from Dr. A. Miyawaki (Laboratory for Cell Function Dynamics, RIKEN Brain Science Institute, Wako, Japan) (Nagai et al., 2002). WT-Venus-PR8 was generated by using the reverse genetics system as described in Newmann et al. (1999). Since WT-Venus-PR8 pathogenicity and Venus expression levels were appreciably attenuated in mice, WT-Venus-PR8 was serially passaged in mice. After six passages, a variant (MA-Venus-PR8) was obtained with increased pathogenicity and strong Venus expression. A stock of MA-Venus-PR8 was generated in MDCK cells. Since serial passage in animals typically results in virus populations composed of genetic variants, MA-Venus-PR8 was recreated by using reverse genetics. Likewise, MA-eCFP-PR8, -eGFP-PR8, and -mCherry-PR8 were generated with the same genetic backbone as MA-Venus-PR8.

To generate a Venus-HPAI virus by reverse genetics, the NS segment of A/Vietnam/1203/2004 (H5N1; VN1203) was replaced with Venus-NS of PR8, and the virus was adapted to mice as described for MA-Venus-PR8. A stock of MA-Venus-HPAI virus was made in MDCK cells. The set of these influenza viruses carrying various fluorescent proteins was collectively termed "Color-flu".

Mouse Experiments Female, 6-week-old C57BL/6 ('B6') mice were purchased from Japan SLC, Inc. (Shizuoka, Japan). Mice were intranasally inoculated with Color-flu viruses, at the dosages indicated in the figure panels, in 50 µL of PBS under sevoflurane anesthesia, and body weights and survival were monitored for 14 days. Lungs were harvested from PBS-inoculated or Color-flu-infected mice for virus titration, flow cytometric analysis, and histological experiments at the times indicated in the figure panels. All animal experiments were performed in accordance with the regulations of the University of Tokyo Committee for Animal Care and Use and were approved by the Animal Experiment Committee of the Institute of Medical Science of the University of Tokyo.

Histology and Cytology

Lungs were fixed in 4% paraformaldehyde (PFA) phosphate buffer solution. Fixed tissues were embedded in OCT compound (Sakura Finetek, Tokyo, Japan), frozen by liquid $N_2$ and stored at −80° C. Cryostat 6-µm sections were treated for 30 minutes with PBS containing 1% BSA (PBS-BSA) to block nonspecific binding, and then incubated with phycoerythrin (PE)-Mac3 (M3/84, BD Biosciences, San Jose, Calif.). To examine the cytology of the MDCK cells, cells were infected with Color-flu virus and then fixed in 4% PFA phosphate buffer solution. Nuclei were stained with Hoechst33342 (Invitrogen, Carlsbad, Calif.). Sections and cells were visualized by using a confocal microscope (Nikon A1, Nikon, Tokyo, Japan), controlled by NIS-Elements software. For quantitative multi-color imaging analysis, the slides were visualized by use of an inverted fluorescence microscope (Nikon Eclipse TS100) with a Nuance FX multispectral imaging system with InForm software (PerkinElmer, Waltham, Mass.).

Whole-Mount Imaging of Lung Tissue

Mice were euthanized and intracardially perfused with PBS to remove blood cells from the lung. The lungs were isolated after intratracheal perfusion with 4% PFA phosphate buffer solution. The lung tissues were cleared with SCALEVIEW-A2 solution (Olympus, Tokyo, Japan) according to the manufacturer's instructions. Images were acquired by using a stereo fluorescence microscope (M205FA, Leica Microsystems, Wetzlar, Germany) equipped with a digital camera (DFC365FX, Leica Microsystems).

Two-Photon Laser Microscopy

A total of $10^5$ PFU of MA-eGFP-PR8 was intranasally inoculated into B6 mice. To label lung macrophages, 50 µL of PE-CD11b (M1/70, BioLegend, San Diego. Calif.) was injected intravenously to the mice at day 3 p.i. Thirty minutes after the antibody injection, the lungs of the mice were harvested. The kinetics of eGFP- and PE-positive cells in the lungs were imaged with a multi-photon microscope (LSM 710 NLO, Carl Zeiss, Oberkochen, Germany). During the analysis, the lungs were maintained in complete medium (RPMI 1640 with 10% fetal calf serum) in a humid chamber (37° C., 5% $CO_2$). The data were processed with LSM software Zen 2009 (Carl Zeiss). For three-dimensional imaging of HPAI virus-infected lung tissues, B6 mice were intranasally inoculated with $10^5$ PFU of MA-Venus-HPAI virus. The lung tissues were collected from the mice at day 2 p.i., and treated with SCALEVIEW-A2 solution (Olympus) to make tissues transparent as described above. Three-dimensional images of lung tissues were obtained from a multi-photon microscope (Nikon A1R MP).

Flow Cytometric Analysis and Cell Sorting

To obtain single-cell suspensions, lungs were dissociated with Collagenase D (Roche Diagnostics, Mannheim, Germany; final concentration: 2 µg/mL) and DNase I (Worthington Biochemical, Lakewood, N.J.; final concentration: 40 U/mL) for 30 minutes at 37° C. by grinding the tissue through nylon filters (BD Biosciences). Red blood cells (RBCs) were lysed by treatment with RBC lysing buffer (Sigma Aldrich, St. Louis, Mo.). To block nonspecific binding of antibodies, cells were incubated with purified anti-mouse CD16/32 (Fc Block, BD Biosciences, San Diego, Calif.). Cells were stained with appropriate combinations of fluorescent antibodies to analyze the population of each immune cell subset. The following antibodies were used: anti-CD45 (30-F11: eBioscience, San Diego, Calif.), anti-CD11b (M1/70: BioLegend), anti-F4/80 (BM8: eBioscience), and anti-CD11c (HL3: BD Biosciences). All samples were also incubated with 7-aminoactinomycin D (Via-Probe, BD Biosciences) for dead cell exclusion. Data from labeled cells were acquired on a FACSAria II (BD Biosciences) and analyzed with FlowJo software version 9.3.1 (Tree Star, San Carlos, Calif.). To isolate Venus-positive and -negative macrophages from lungs, stained cells were sorted using a FACSAria II (BD Biosciences).

Microarray Analysis

Total RNA of sorted macrophages was extracted using TRIzol reagent (Life Technologies, Carlsbad, Calif.) and precipitated with isopropanol. RNA amplification was performed using the Arcturus Riboamp Plus RNA Amplification Kit (Life technologies) in accordance with the manufacturer's instructions. RNA was labeled by using the Agilent Low Input Quick Amp Labeling kit, one color (Agilent Technologies, Santa Clara, Calif.) and hybridized to the SurePrint G3 Mouse GE 8X60K microarray (Agilent Technologies). Arrays were scanned with a DNA Microarray Scanner with SureScan High-Resolution Technology, (G2565CA; Agilent Technologies), and data were acquired using Agilent Feature Extraction software ver. 10.7.3.1. (Agilent Technologies). Probe annotations were provided by Agilent Technologies (AMADID 028005). Probe intensities were background corrected and normalized using the normal-exponential and quantile methods, respectively. The $log_2$ of the intensities were then fit to a linear model that compared the groups of interest[34]. All reported p values were adjusted for multiple hypothesis comparisons using the Benjamini-Hochberg method. Transcripts were considered differentially expressed if there was at least a 2-fold change in the mean probe intensity between contrasts with an adjusted p<0.01. Hierarchical clustering was performed in R. The resultant gene clusters were then analyzed with ToppCluster (Kaimal et al., 2010) to identify gene annotations that were enriched in each duster. The reported scores are the $-log_{10}$ of the Benjamini-Hochberg adjusted p-value.

Western Blot Analysis

Whole lysates of MDCK cells were electrophoresed through SDS-polyacrylamide gels (Bio-Rad Laboratories, Hercules, Calif.) and transferred to a PVDF membrane (Miilipore, Billerica, Mass.). The membrane was blocked with Blocking One (Nacalai Tesque, Kyoto, Japan) and incubated with a rabbit anti-GFP polyclonal antibody (MBL, Nagoyua, Japan), mouse anti-NS1 antibody (188/5), rabbit antiserum to A/WSN/33(H1N1)(R309) or mouse anti-actin antibody (A2228; Sigma-Aldrich), followed by HR-conjugated anti-mouse or anti-rabbit IgG antibody (GE Healthcare, Waukesha, Wis.). After the membrane was washed with PBS-Tween, specific proteins were detected using ECL Plus Western Blotting Dectection System (GE Healthcare. The specific protein bands were visualized by the use of the VersaDoc Imaging System (Bio-Rad).

Results

Figure 1B:
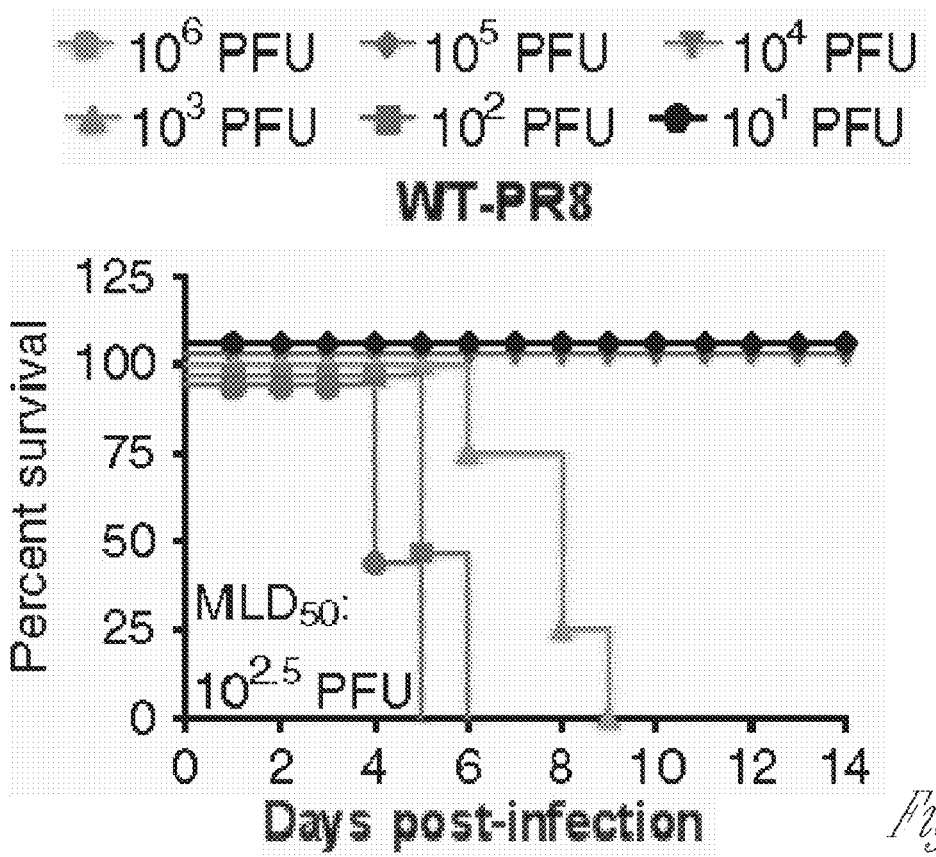
Figure 1C:
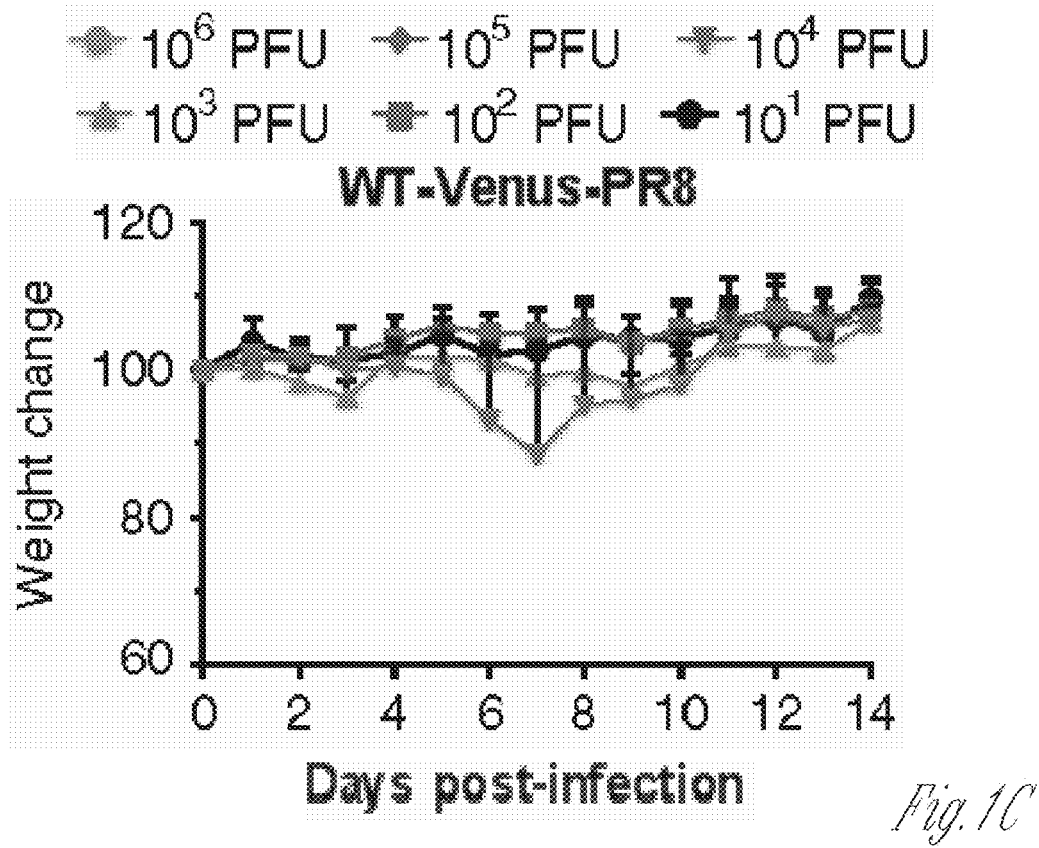
Figure 1D:
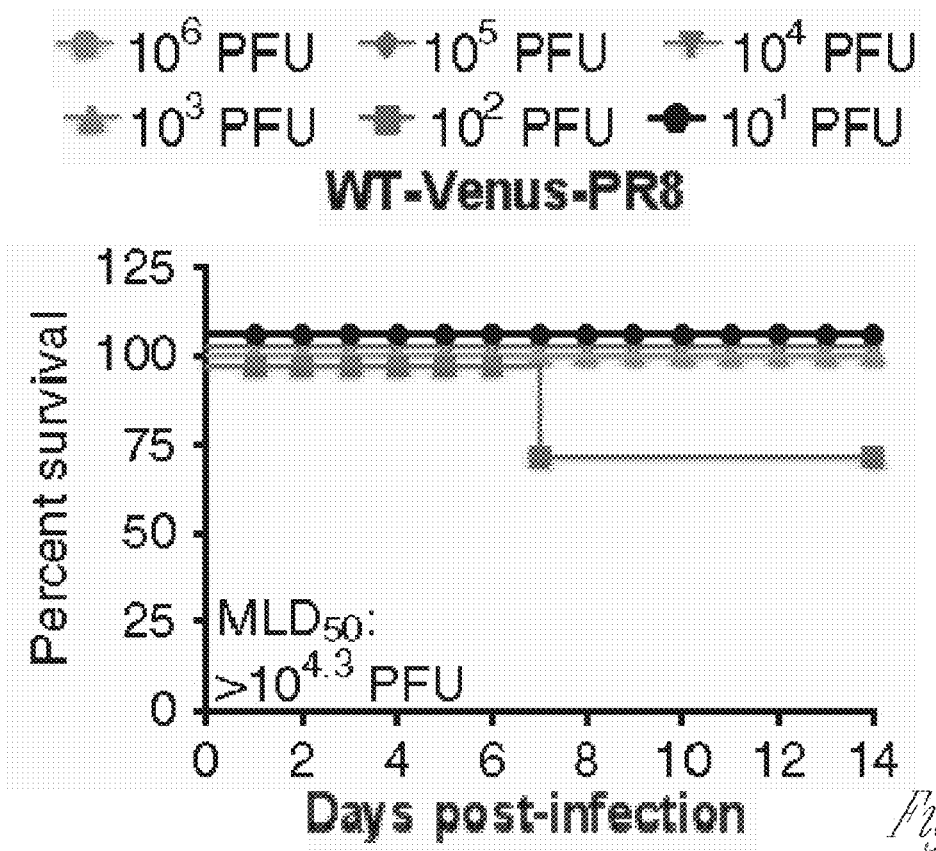
Figure 1E:
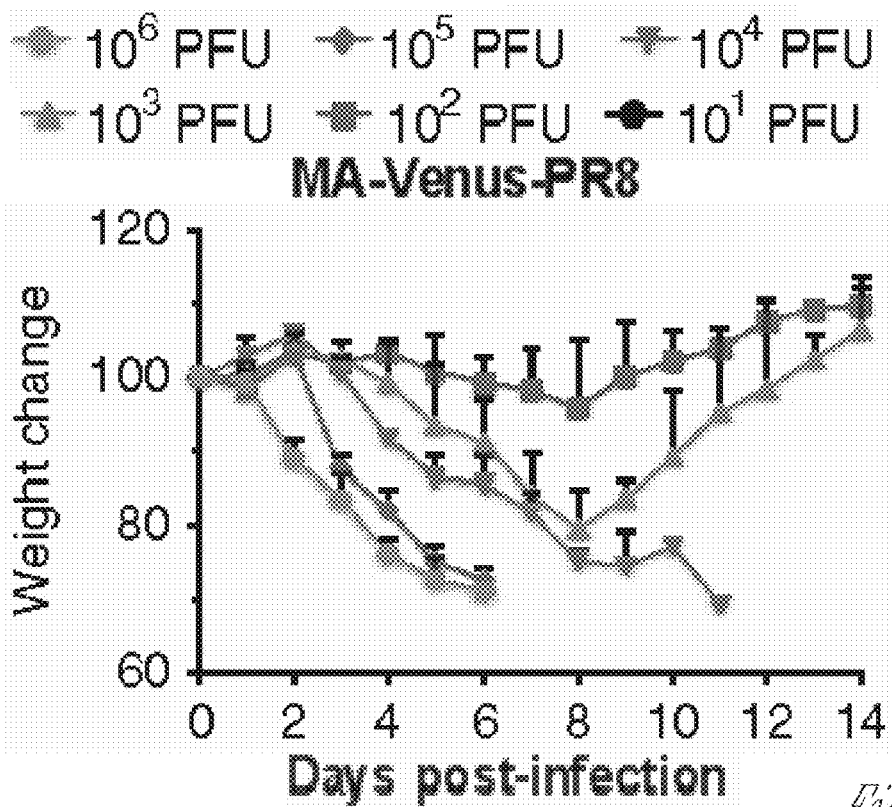
Figure 1F:
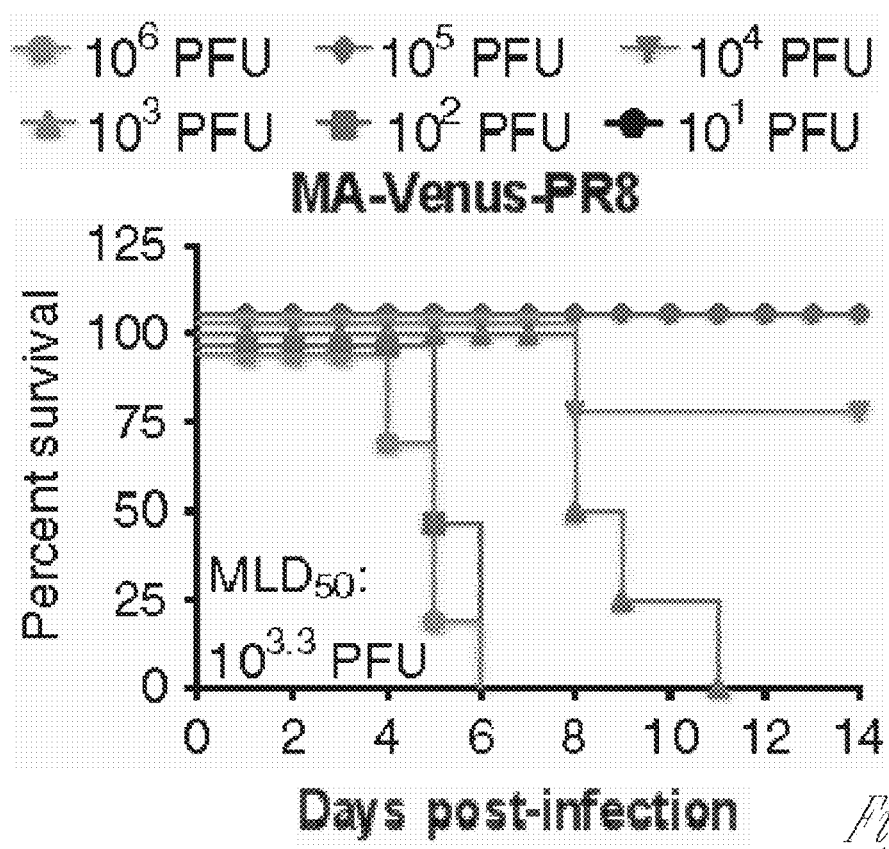
Figure 1G:
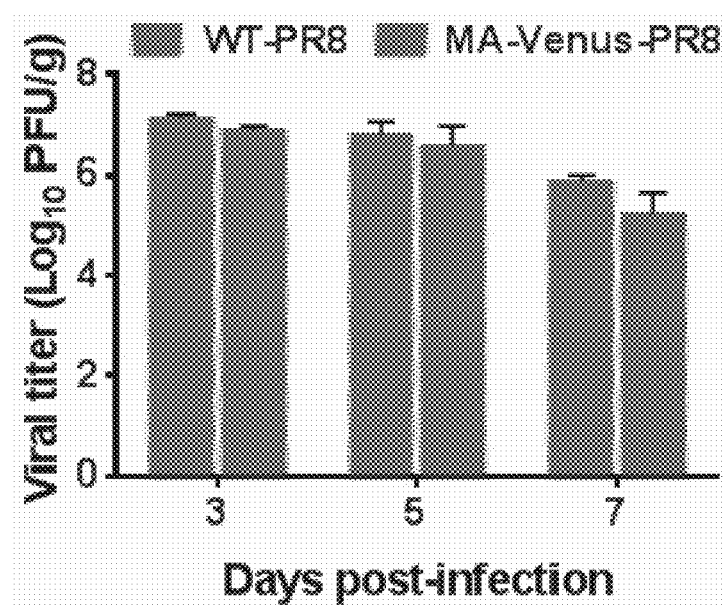

To generate a fluorescent influenza virus expressing a reporter protein fused to the NS1 open reading frame, Venus was chosen, a GFP variant with eight mutations including F46L, which improves chromophore formation and increases brightness compared with GFP (Wagai et al., 2002). As expected based on previous findings of attenuation for influenza viruses expressing reporter proteins (Kittel et al., 2004; Shinhya et al., 2004), the mouse pathogenicity of A/Puerto Rico/8/34 (PR8; H1N1) virus expressing Venus (WT-Venus-PR8) was substantially lower than that of wild-type PR8 (WT-PR8); the dose required to kill 50% of infected mice ($MLD_{50}$) was more than $10^{4.5}$ plaque-forming units (PFU) for WT-Venus-PR8 compared with $10^{2.5}$ PFU for WT-PR8. WT-Venus-PR8 was serially passaged in C57BL/6 (B6) mice. After six consecutive passages, a variant (designated MA-Venus-PR8; possessing a T-to-A mutation at position 380 of the hemagglutinin protein, and an E-to-D mutation at position 712 of the polymerase subunit PB2) was identified with appreciably higher pathogenicity ($MLD_{50}=10^{3.5}$ PFU) compared with WT-Venus-PR8, although it was still less pathogenic than the original PR8 virus (FIG. 1A). To assess the replicative ability of MA-Venus-PR8 in mouse lungs, B6 mice were intranasally infected with $10^4$ PFU of MA-Venus-PR8 or PR8 virus. At all time points tested, the lung virus titers were similar for MA-Venus-PR8- and PR8-infected mice (FIG. 1B). To test the stability of Venus expression, plaque assays were performed using lung homogenate from infected mice and found that only one of 150 plaques on each of days 3, 5, and 7 post-infection (p.i.) was Venus-negative, attesting to the high genetic stability of Venus expression in this recombinant virus. In contrast, only 70% of NS1-GFP virus expressed the reporter protein (Manicassamy et al., 2010). The robust virulence and genetic stability of MA-Venus-PR8 indicate that this virus represents a highly attractive reporter system to visualize influenza virus-infected cells in vivo.

To increase the versatility of fluorescent influenza viruses as imaging tools, additional MA-PR8 variants were generated that expressed different spectral GFP mutants, namely, eCFP (ex. 434 nm, em. 477 nm) and eGFP (ex. 489 nm, em. 508 nm) (Patterson, 2001). A mCherry variant (ex. 587 nm, em. 610 nm), which emits fluorescence at a longer wavelength than Venus (ex. 515 nm, em. 528 nm) (Nagai et al., 2002; Shaner et al., 2004), was also generated. These influenza viruses encoding the multi-spectral fluorescent reporter proteins were collectively named "Color-flu". To determine the pathogenicity of Color-flu viruses, the virus titres in mouse lung tissues and the $MLD_{50}$ values of MA-eCFP, eGFP and mCherry-PR8 were compared with those of MA-Venus-PR8 and MA-PR8. All of virus strains showed comparatively high replication in the lungs and the $MLD_{50}$ values were similar among the Color-flu viruses (Table 1). The stability of the fluorescent expression of the Color-flu viruses was tested in vivo and in vitro by plaque assay. When virus was collected from the lungs of mice on day 7 p.i., the percentages of fluorescent-positive plaques were 98.0% (MA-eCFP-PR8), 100.0% (MA-eGFP-PR8) and 96.4% (MA-mCherry-PR8). The percentages of fluorescent-positive plaques in the sample from the culture medium of MDCK cells after 72 hours p.i. was found to be 100.0% (MA-eCFP-PR8), 99.2% (MA-eGFP-PR8) and 98.2% (MA-mCherry-PR8). In addition, the stability of an NS1-fluorescent protein chimera in virus-infected cells was examined by infecting MDCK cells with MA-Venus-PR8 virus and detecting NS1-Venus chimeric protein by using anti-GFP and anti-NS1 antibodies. The NS1-Venus chimeric protein was not degraded until the time point examined (that is, 12 hours p.i.), indicating that the fluorescent signal is mainly emitted from the NS1-fluorescent protein chimera and not from degradation products in cells infected with Color-flu viruses. These findings indicate that the pathogenicity and stability of the Color-flu viruses were not affected by the different fluorescent reporter genes.

Figure 2:
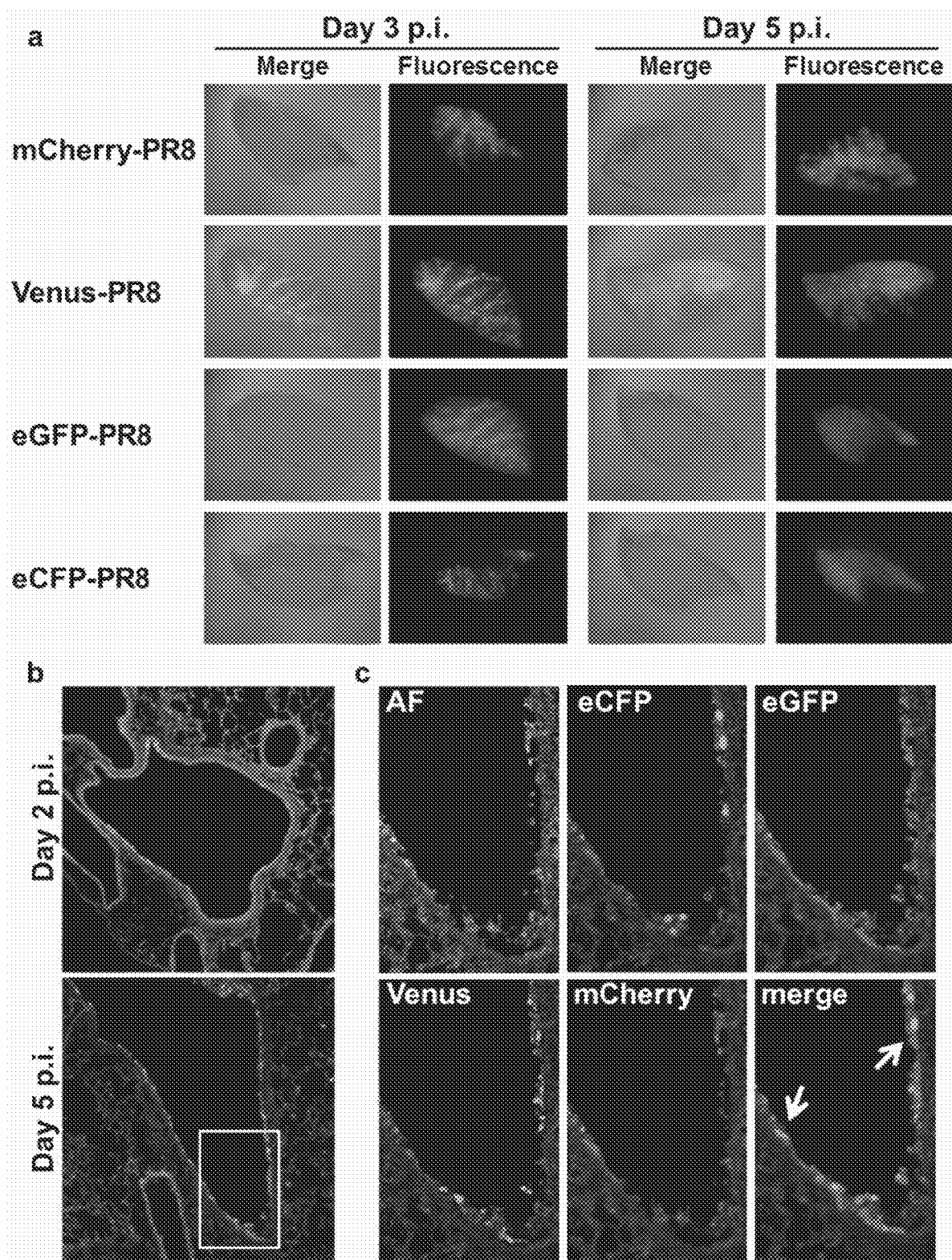
FIG. 2. Distribution of Color-flu viruses in lungs. (A) Lung tissues were harvested from B6 mice at days 3 and 5 p.i. with Color-flu viruses ($10^5$ PFU of MA-eCFP, eGFP, Venus, and mCherry-PR8). The open reading frame (ORF) of the NS1 gene without a stop codon was fused with the N-terminus of fluorescent reporter genes (Venus, eCFP, eGFP, and mCherry) via a sequence encoding the protein linker GSGG. The fluorescent genes are followed by a sequence encoding the GSG linker, a foot-and-mouth virus protease 2A autoproteolytic site with 57 nucleotides from porcine teschovirus-1, and by the ORF of NEP. In addition, silent mutations were introduced into the endogenous splice acceptor site of the NS1 ORF to prevent splicing. Whole-mount images of transparent lung tissues were obtained by using a fluorescent stereomicroscope. (B, C) B6 mice were intranasally inoculated with a mixture of MA-eCFP, eGFP, Venus, and mCherry-PR8 ($2.5\times10^4$ PFU per strain). Scale bar, 5 mm. (B) The sections of lungs at days 2 and 5 p.i. were analyzed by using an inverted fluorescence microscope with a Nuance FX multispectral imaging system with InForm software. Scale bar, 100 μm. (C) Enlarged images of the indicated area in (B) were unmixed and separated into autofluorescence (AF), eCFP, eGFP, Venus, and mCherry fluorescence. Arrows in the merged image indicate cells infected with different color variants of Color-flu viruses.

To assess the expression of Color-flu viruses in mouse lungs, we collected lungs from B6 mice infected with each of the Color-flu viruses and processed them for visualization as described in the Methods section. All four colors were clearly visible in whole transparent lung tissue when analyzed with a fluorescent stereomicroscope (FIG. 2A). Fluorescent signals were mainly seen in the bronchial epithelial layer at day 3 p.i. At day 5 p.i., fluorescent signals extended to the peripheral alveolar regions. These data indicated that all four Color-flu viruses are useful for analyzing the distribution of influenza virus-infected cells in mouse lungs. To assess the expression of Color-flu viruses in mouse lungs, lungs were collected from B6 mice infected with each of the Color-flu viruses and processed them for visualization as described in the Methods section. All four colors were clearly visible in whole transparent lung tissue when analyzed with a fluorescent stereomicroscope (FIG. 2A). Fluorescent signals were mainly seen in the bronchial epithelial layer at day 3 p.i. At day 5 p.i., fluorescent signals extended to the peripheral alveolar regions. These data indicate that all four Color-flu viruses are useful for analyzing the distribution of influenza virus-infected cells in mouse lungs.

Next, the Nuance™ spectral imaging system was employed to test whether the fluorescent signals of all four

TABLE 1

Replication and virulence of Color-flu in mice*.

| Virus | Mean virus titer (log10 PFU/g ± s.d.) in the mouse lung on the indicated day p.i. | | | $MLD_{50}$ |
|---|---|---|---|---|
| | Day 3 p.i. | Day 5 p.i. | Day 7 p.i. | (PFU) |
| MA-eCFP-PR8 | 8.1 ± 0.2** | 8.0 ± 0.1 | 6.3 ± 0.1 | $10^{3.0}$ |
| MA-eGFP-PR8 | 8.6 ± 0.1 | 8.3 ± 0.1 | 6.3 ± 0.1 | $10^{3.5}$ |
| MA-Venus-PR8 | 8.6 ± 0.2 | 8.4 ± 0.1 | 6.5 ± 0.3 | $10^{3.3}$ |
| MA-mCherry-PR8 | 7.7 ± 0.3** | 7.5 ± 0.7 | 6.1 ± 0.4 | $10^{2.7}$ |
| WT-Venus-PR8 | 5.6 ± 0.3** | 5.3 ± 0.3** | 5.2 ± 0.2** | $>10^{4.3}$ |
| WT-PR8 | 8.8 ± 0.1 | 8.2 ± 0.5 | 6.9 ± 0.2 | $10^{2.5}$ |
| MA-PR8 | 8.9 ± 0.1 | 9.0 ± 0.0 | 7.9 ± 0.2** | $10^{2.3}$ |

*B6 mice were inoculated intranasally with $10^4$ PFU of each virus in a 50 mL volume. Three mice from each group were killed on days 3, 5 and 7 p.i., and virus titres in the lungs were determined in MDCK cells.
**Statistical significance was calculated by using the Student's t-test; the P value was < 0.01 compared with the titres in the lungs of mice infected with WT-PR8 virus.

Color-flu viruses could be detected simultaneously. Lung tissues were collected from B6 mice intranasally inoculated with a mixture of the four strains ($2.5 \times 10^4$ PFU each in a total volume of 50 μL). Analysis of lung sections obtained at days 2 and 5 p.i. showed that the fluorescent signals of all four Color-flu viruses were distinguishable from each other (FIG. 2B). At day 2 p.i., clusters of the same fluorescent color were found in bronchial epithelial cells, suggesting local spread of the individual viruses. At this time point, a limited number of alveolar cells were infected. At day 5 p.i., we detected a duster of alveolar cells expressing a single fluorescent protein, indicative of the initiation of infection with a single virus and its local spread (FIG. 2B). Interestingly, epithelial cells simultaneously expressing two or three fluorescent proteins were detected, albeit at a low frequency, suggesting co-infection of these cells (FIG. 2C). The ability to visualize cells co-infected with different influenza viruses in vivo is a major advance in technology and will allow insights into influenza co-infection and reassortment processes.

Figure 3A:
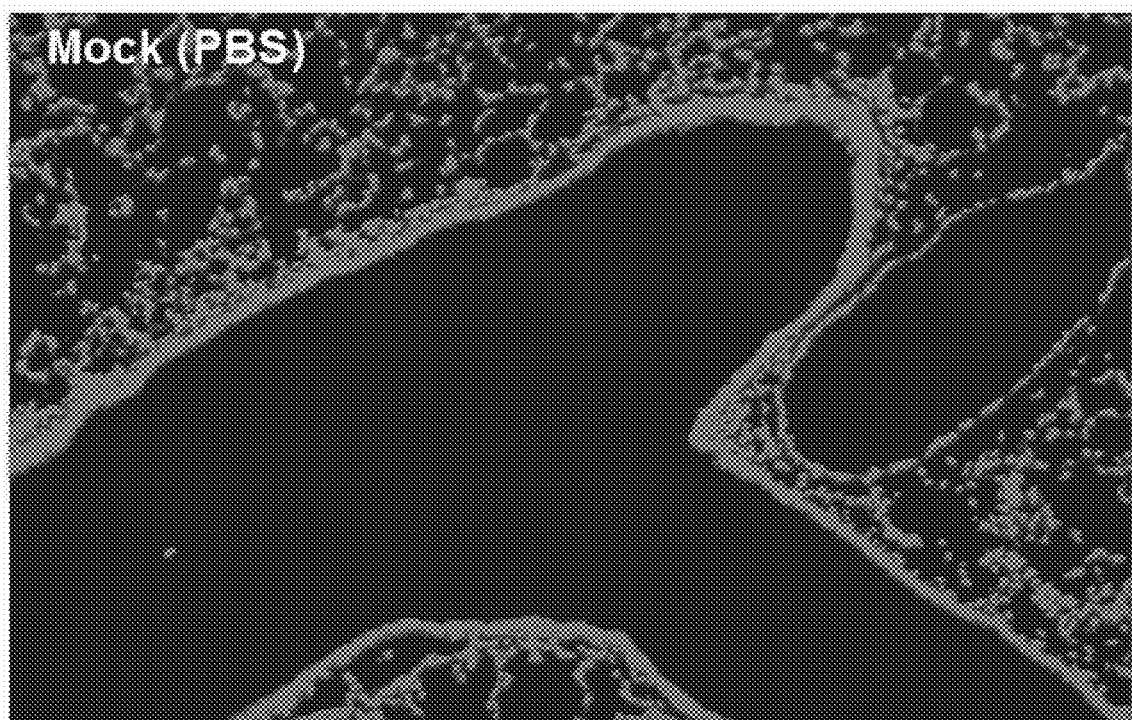

Next, the utility of Color-flu viruses was tested for the analysis of host responses to infection. Since macrophages are involved in innate immunity and acute inflammation in influenza virus-infected lungs, lung sections that were stained with an antibody to macrophages (PE-Mac3) were examined by using confocal microscopy. Macrophages infiltrated regions containing Venus-positive bronchial epithelial cells at day 2 p.i. of mice with MA-Venus-PR8 (FIG. 3A); by contrast, only a few Mac3-positive cells were detected in the alveoli of lungs from mock-infected animals. On the basis of this finding, live imaging was employed to further study the interaction between influenza virus-infected epithelial cells and macrophages in mouse lungs. In the lung tissue of naive B6 mice, CD11b+ alveolar macrophages were detected by use of a two-photon laser microscope. Most of these macrophages did not migrate (i.e., showed little movement) during the observation period (49 minutes; data not shown). In mice infected with MA-eGFP-PR8 virus, many CD11b+ macrophages appeared to be 'attached' to eGFP-positive epithelial cells (data not shown); moreover, some of these eGFP-positive epithelial cells exhibited blebbing similar to apoptotic cells. Interestingly, a number of CD11b+ macrophages quickly moved around the eGFP-positive epithelial cells, suggesting possible macrophage responses to inflammatory signals such as IFNs or chemokines. The present system can thus be used to monitor the in vivo interactions between virus-infected and immune cells.

Figure 3B:
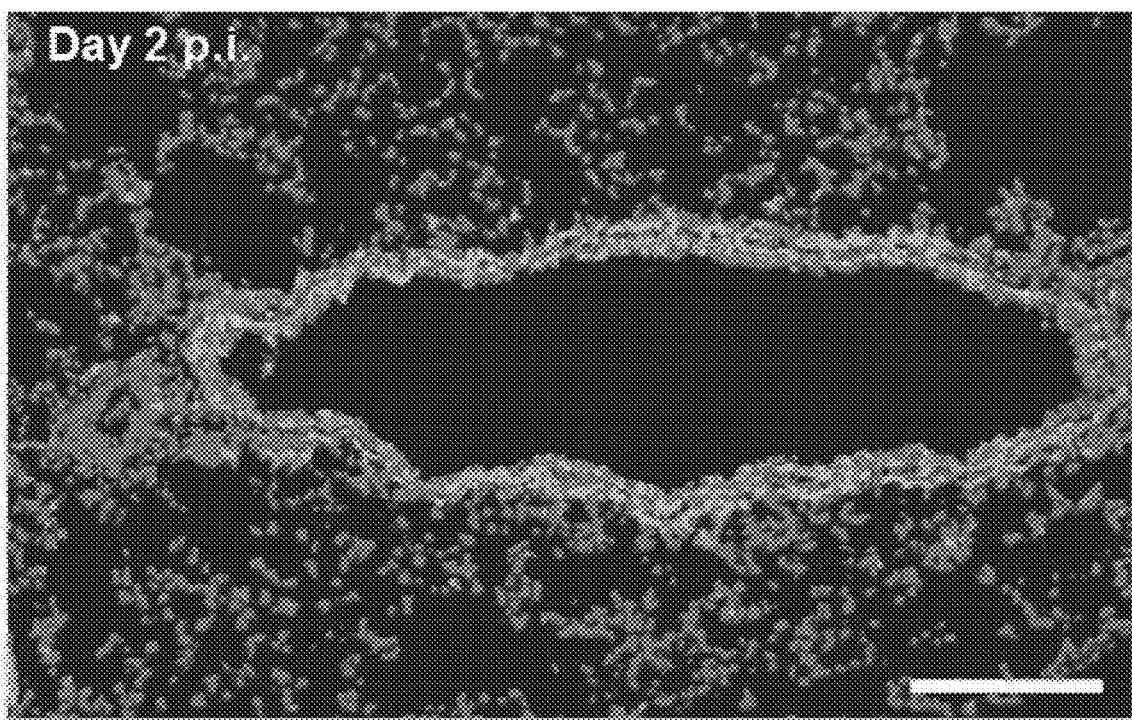
Figure 3C:
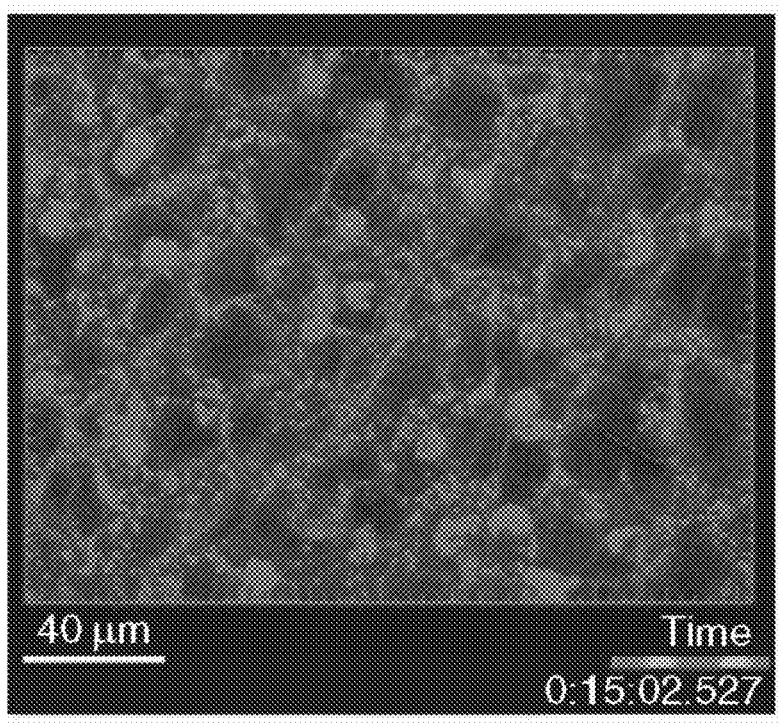
Figure 3D:
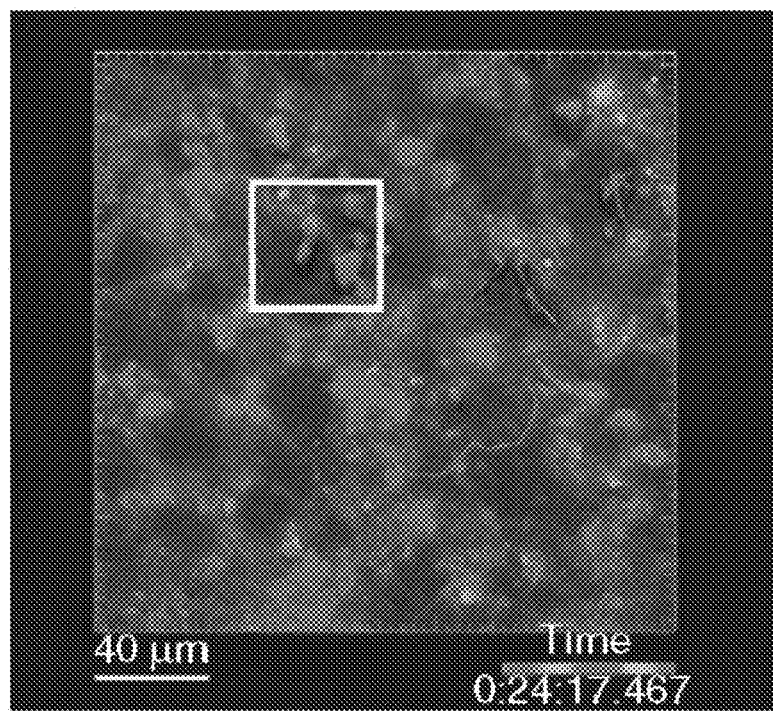
Figure 3I:
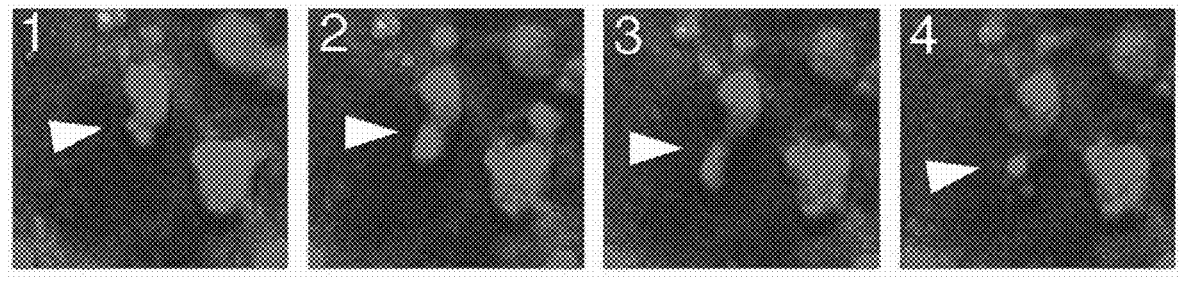
Figure 3I:
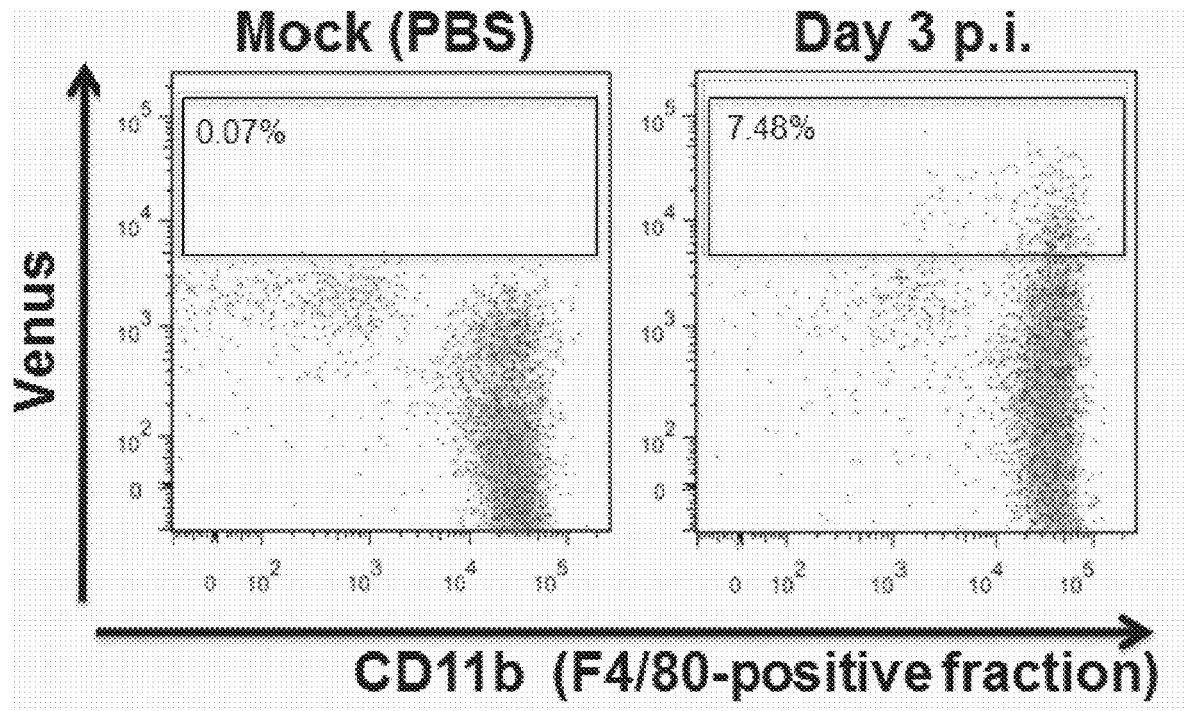
Figure 3J:
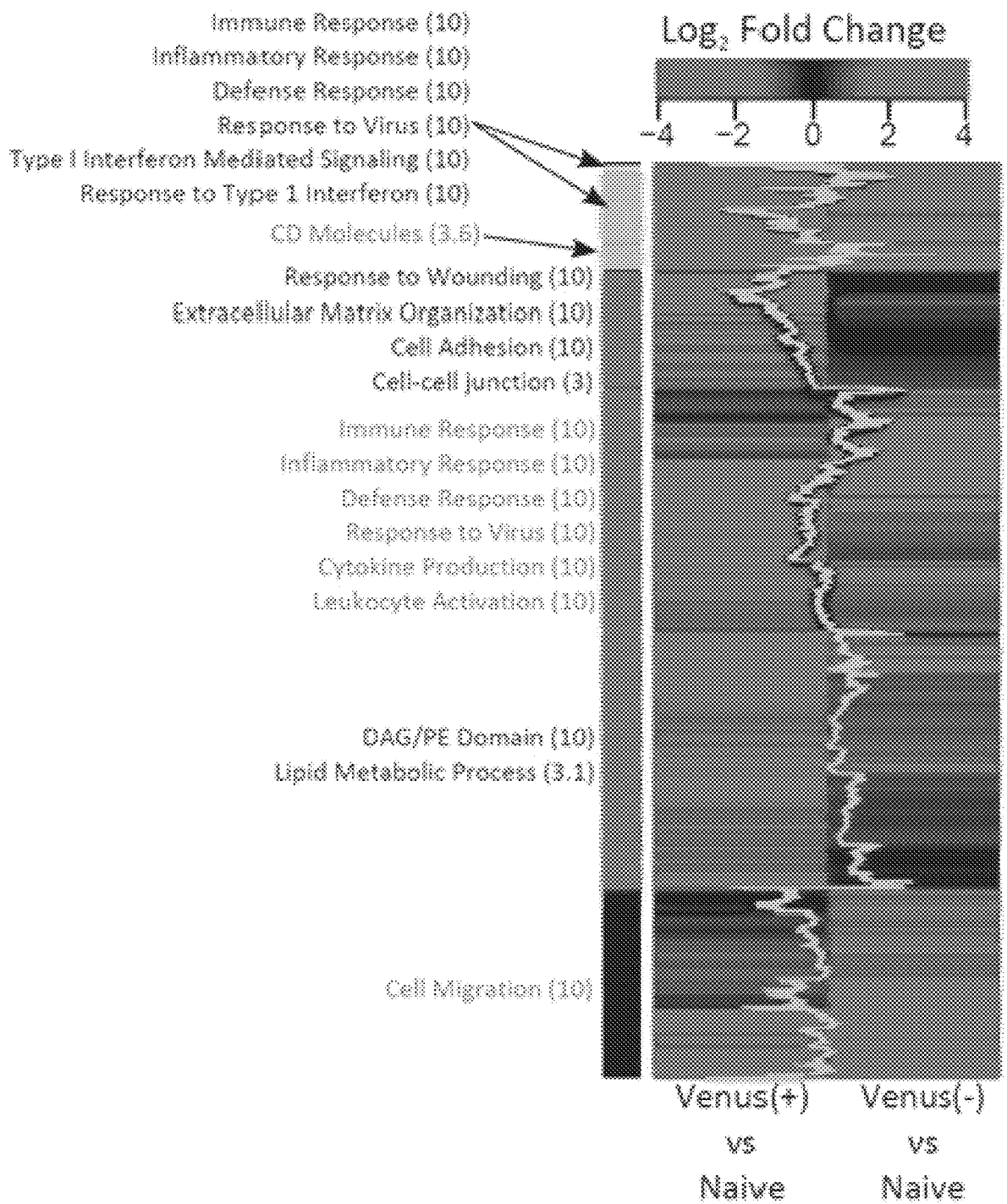
Figure 3K:
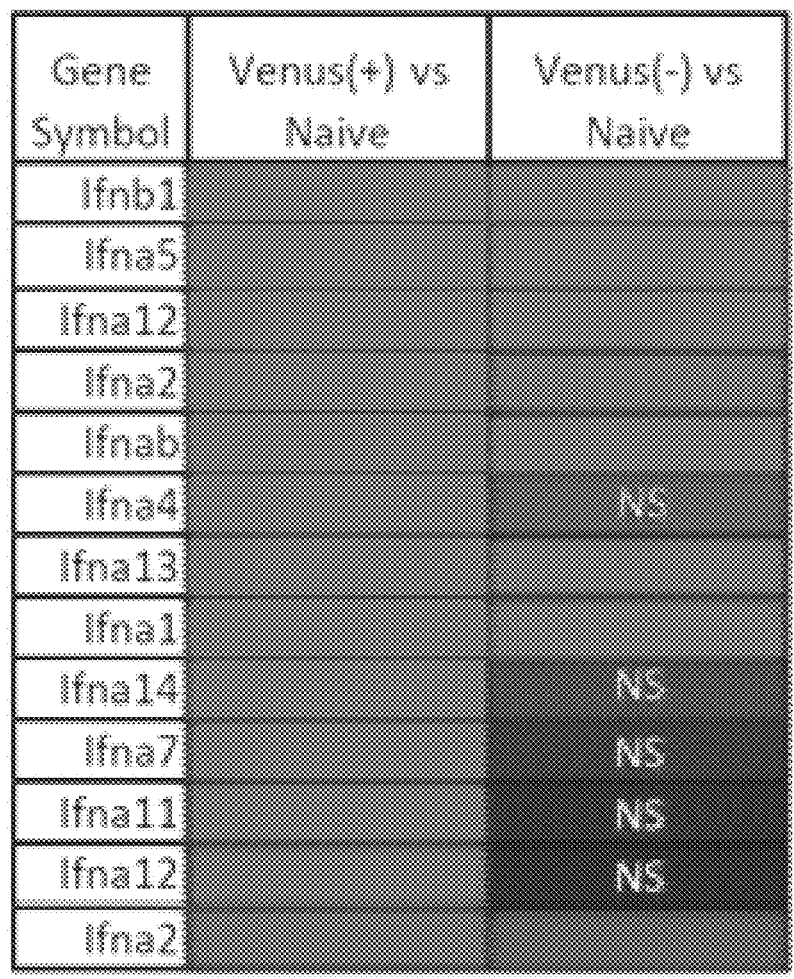
Figure 3K:
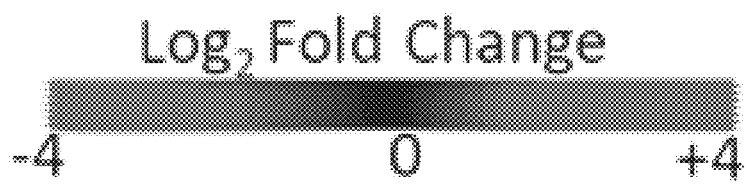

A number of studies have assessed the transcriptomics and proteomics profiles of influenza virus-infected mice (Go et al., 2012; Zhao et al., 2012). Since these studies used whole lung samples, the results are the sum of virus-infected and uninfected cells, leading to the dilution of host responses and not allowing one to distinguish the profiles of infected cells from those of uninfected, bystander cells. As a first step to overcome this shortcoming, macrophages (known to be infected by influenza viruses (FIG. 3B)) from the lungs of mice infected with MA-Venus-PR8 were sorted on the basis of their fluorescent protein expression and performed microarray analysis. Macrophages isolated from the lungs of mice inoculated with PBS (naive macrophages) served as controls. In fluorescent-positive macrophages, 6,199 transcripts were differently expressed relative to naive macrophages. By contrast, in fluorescent-negative macrophages obtained from infected mice, only 4,252 transcripts were differentially expressed relative to the naive macrophages. This difference likely reflects differences in gene transcription induced by active influenza virus infection. However, it should be noted that the fluorescent-negative cell populations obtained from infected animals may have included infected cells in which the fluorescent signal had not yet been detected as would be expected at an early stage of virus infection. In fact, confocal microscopy revealed that it took 9 hours to detect fluorescent protein expression in the majority of MDCK cells. Hierarchical clustering of differentially expressed transcripts, followed by functional enrichment analysis of each duster, indicated that both fluorescent-positive and fluorescent-negative macrophages obtained from infected animals exhibit activation of pathways associated with the immune response, cytokine production, and inflammation (FIG. 3D, green cluster). The upregulation of these pathways in the fluorescent-negative cells may have resulted from cell activation by IFN and cytokines released from infected cells, and/or from cells that were at an early stage of virus infection (as discussed earlier). Yet, a subset of enriched annotations, for example, type I IFN-mediated signaling (FIG. 3D, light blue cluster), included transcripts that were more highly expressed in fluorescent-positive macrophages. In addition, it was observed that type I IFN genes were among the most upregulated transcripts in the fluorescent-positive macrophages (FIG. 3E). Taken together, this enhanced type I IFN activity is consistent with the suggestion that the fluorescent-positive cells had been infected whereas the fluorescent-negative cells included both uninfected (but potentially 'stimulated') cells and cells at early stages of influenza virus infection. Indeed, it took at least 5 hours to detect fluorescent protein expression after infection with Color-flu viruses, although all of the fluorescent proteins (that is, eCFP, eGFP, Venus, and mCherry) were detectable in the majority of cells by 9 hours p.i. These findings open new avenues in infectious disease research to compare gene expression (or other types of expression) patterns of reporter protein-positive cells with those of reporter protein-negative cells (but potentially stimulated by released cytokines and/or are at an early stage of infection).

Figure 4:
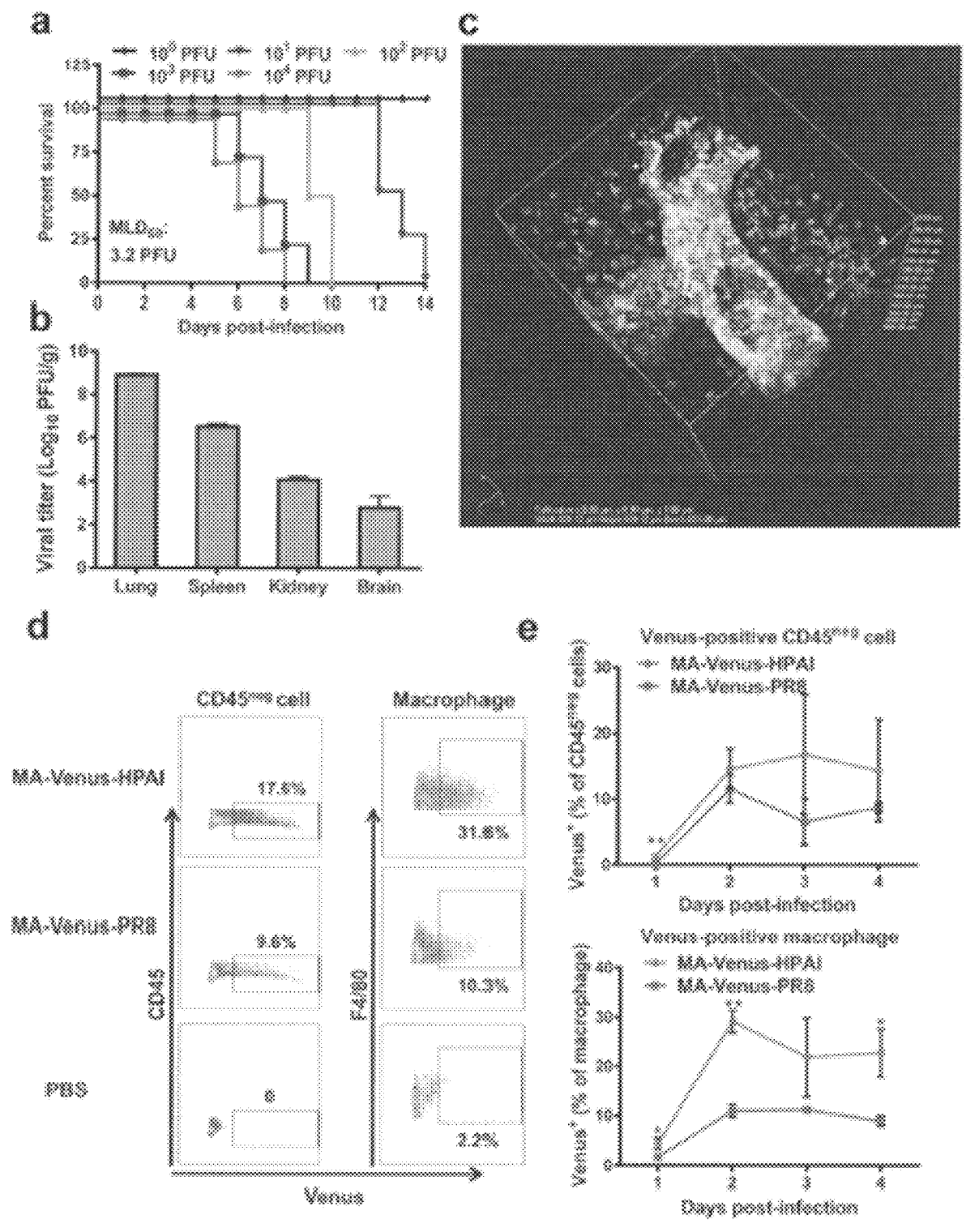

Finally, as discussed in more detail in Example II, it was tested whether the concept of mouse-adapted fluorescent influenza viruses could be applied to other influenza virus strains, such as highly pathogenic avian influenza A (H5N1) (HPAI) viruses, which are a research priority due to the threat they pose to humans. An MA-Venus-HPAI virus based on A/Vietnam/1203/2004 (VN1203; H5N1) was generated, employing the same strategy used to create MA-Venus-PR8; however, the PR8 NS gene was used to express NS1-Venus chimeric protein because Venus virus with the VN1203 NS gene did not contribute to pathogenicity in mice. The pathogenicity of MA-Venus-HPAI virus for B6 mice was comparable to that of VN1203, with $MLD_{50}$ values for both viruses being less than 5 PFU (FIG. 4A and Hatta et al., 2007). MA-Venus-HPAI virus also shared with other HPAI viruses the ability to spread systemically and replicate in various organs including spleen, kidney, and brain (FIG. 4B and Hatta et al., 2007). Moreover, taking advantage of the strong fluorescent signal emitted by MA-Venus-HPAI virus-infected cells, a three-dimensional image of an HPAI virus-infected bronchus deep inside the lung tissues was successfully constructed (FIG. 4C and data not shown). This type of three-dimensional imaging analysis will improve the understanding of the spatial distribution of influenza virus-infected bronchi. When the distribution of virus-infected cells was compared between HPAI virus and PR8-infected lungs, it was found that HPAI virus spreads from the bronchial epithelium to alveolar sites more quickly than did PR8 (FIGS. 4C and D). By using flow cytometric analysis, it was found that CD45-negative, non-hematopoietic cells and F4/80-positive macrophages more frequently expressed Venus in the lungs of mice infected with MA-Venus-HPAI virus than in the lungs of animals inoculated with MA-Venus-PR8 (FIGS. 4E and F), supporting findings that H5N1 HPAI viruses induce more severe inflammatory responses in the lung than does PR8, demonstrating the utility of Color-flu viruses for comparative studies of influenza pathogenesis.

Discussion

In this study, Color-flu viruses were generated to study influenza virus infections at the cellular level. Color-flu viruses combine several improvements over existing systems, including robust viral replication, virulence, stable fluorescent protein expression, and a set of four different colors that can be visualized simultaneously. Color-flu viruses are applicable to all influenza virus strains. These improvements allowed global transcriptomics analyses of infected and bystander cells and, for the first time, live-imaging of influenza virus-infected cells in the mouse lung.

Previous versions of fluorescent influenza viruses (Kittel et al., 2004; Shinya et al., 2004) including our original construct (i.e., WT-Venus-PR8) were appreciably attenuated in mice. These attenuated fluorescent viruses may still be useful for identifying initial target cells. However, the immune responses elicited by these highly attenuated, non-lethal viruses most likely differ considerably from those of the mouse-lethal parent virus, making their use for pathogenesis studies problematic. This problem was solved by passaging viruses in mice. This strategy proved to be successful for two different influenza virus strains, suggesting its broad applicability. A second drawback of previously tested fluorescent influenza viruses is the genetic instability of the added reporter protein (Manicassamy et al., 2010). However, almost 100% of virus plaques examined from mouse lung samples on day 7 post-infection expressed the reporter protein.

At present, Color-flu viruses cannot be monitored in live animals non-invasively because fluorescent reporter proteins must be within a "biological optical window (650-900 nm)" to be detected for imaging of tissues in live animals using fluorescent probes (Weisslander, 2001; Jobsis, 1977), and none of the fluorescent reporter proteins including mCherry, which has the longest emission among the reporter proteins of Color-flu, is inside this biological optical window. Heaton et al. (2013) generated a luciferase reporter-expressing influenza virus that can be used to monitor virus replication in live animals; however, this system needs systemic inoculation of substrate into the animals at every observation point. In addition, the resolution of their imaging system (based on the IVIS® system) is not adequate for the analysis of cellular immune mechanisms in vivo, which we are able to achieve with the present system.

Newer technologies for imaging analysis (Ghoznari et al., 2013) have enabled the development of a set of four different influenza color variants that can be distinguished from one another by using Nuance™, hence allowing their simultaneous detection. In fact, our pilot study identified lung epithelial cells expressing two or three different fluorescent proteins (FIG. 2C). This may be the first visualization of mouse lung cells infected with more than one influenza virus strain. In future studies, these color variants could be used to address long-standing questions in influenza virus research, such as the frequency of viral co-infections in vivo, which may be critical to better understand influenza virus reassortment and, hence, the generation of novel influenza viruses such as the pandemic viruses of 1957 (Schaltissek et al., 1978; Kanaoka et al., 1989), 1968 (Schaltissek et al., 1978; Kanaoka et al., 1989), and 2009 (Smith et al., 2009; Itoh et al., 2009).

By employing the described tool sets, influenza virus-infected cells were detected in whole lung tissues of mice, allowing the observation of the location and distribution of influenza viruses in the lung. Moreover, interactions of virus-infected epithelial cells with immune cells were observed. Such studies will allow direct monitoring influenza disease progression from acute bronchitis to severe viral pneumonia, which causes considerable morbidity and mortality in highly pathogenic influenza virus infections (Gambotto et al., 2008; Shieh et al., 2009).

In conclusion, Color-flu viruses in combination with advanced imaging technologies allow for detection at the cellular level in animals.

Example II

As disclosed in Example I, an H5N1 virus with the Venus (Nagai et al., 2002) (a variant of eGFP; ref) reporter gene (designated wild-type Venus-H5N1 virus, and abbreviated as WT-Venus-H5N1 virus) was prepared using reverse genetics; this virus showed moderate virulence and low Venus expression in mice. After six passages in mice a mouse-adapted Venus-H5N1 virus was acquired (abbreviated as MA-Venus-H5N1 virus) that stably expressed high levels of Venus in vivo and was lethal to mice; a dose required to kill 50% of infected mice ($MLD_{50}$) was 3.2 plaque-forming units (PFU), while that of its parent WT-Venus-H5N1 virus was $10^3$ PFU. However, the mechanism for this difference in virulence and Venus stability was unclear.

In this study, the molecular mechanism that determines the virulence and Venus stability of Venus-H5N1 virus in mice was explored. By using reverse genetics, various reassortants between WT-Venus-H5N1 and MA-Venus-H5N1 virus were rescued and their virulence in mice examined to identify determinants for pathogenicity. Further, the determinants for Venus expression and Venus stability in vitro and in vivo were investigated. The findings further the understanding of the pathogenicity of influenza virus in mammals and will benefit the development of influenza virus-related vaccines and therapy.

Materials and Methods

Cells.

Human embryonic kidney 293 and 293T cells were maintained in Dulbecco's modified Eagle's medium (DMEM) with 10% fetal calf serum, and Madin-Darby canine kidney (MDCK) cells were maintained in minimal essential medium (MEM) supplemented with 5% newborn calf serum. All the cells were incubated at 37° C. in 5% $CO_2$.

Construction of Plasmids.

Plasmids for virus rescue was constructed as described in Neumann et al. (1999). To measure viral polymerase activity, the open reading frames of the PB1, PB2, PA, and NP of influenza virus were amplified by PCR with gene-specific primers and cloned into the pCAGGS/MCS protein expression plasmid (Dias et al., 2009). The primer sequences are listed below:

TABLE 2

| Gene | | Primer sequence (5'-3') |
|---|---|---|
| VN1203-PB2 | Upper | CCCATCGATACCATGGAGAGGATAAAAGAATTAC GAGATC (SEQ ID NO: 20) |

TABLE 2-continued

| Gene | Primer | sequence (5'-3') |
|---|---|---|
| | Low | CTAGCTAGCCTACTAATTGATGGCCATCCGAATT CTTTTG (SEQ ID NO: 21) |
| VN1203-PB1 | Upper | TACGAGCTCACCATGGATGTCAATCCGACTTTAC TTTT (SEQ ID NO: 22) |
| | Low | CTAGCTAGCCTACTATTTTGCCGTCTGAGTTCT TCAATG (SEQ ID NO: 23) |
| VN1203-PA | Upper | CCCATCGATACCATGGAAGACTTTGTGCGACAAT GC (SEQ ID NO: 24) |
| | Low | CTAGCTAGCCTACTATTTCAGTGCATGTGCGAGG AAGGA (SEQ ID NO: 25) |
| VN1203-NP | Upper | TTCATCGATACCATGGCGTCTCAAGGCACCAAAC (SEQ ID NO: 26) |
| | Low | CGCGCTAGCCTATTAATTGTCATACTCCTCTGCA TTGTCT (SEQ ID NO: 27) |

All of the constructs were completely sequenced to ensure the absence of unwanted mutations.

Plasmid-Based Reverse Genetics.

Influenza A viruses were generated by using plasmid-based reverse genetics, as described previously (Murakami, 2008; Ozawa et al.; 2007). Viral titers of the rescued viruses were determined by use of plaque assays in MDCK cells. All rescued viruses were sequenced to confirm the absence of unwanted mutations.

Mouse Experiments.

Six-week-old female C57/BL6 (B6) mice (Japan SLC, Inc., Shizuoka, Japan) were used in this study. To measure viral replication in mice, six mice in each group were anesthetized with isoflurane and then intranasally inoculated with $10^5$ PFU (50 μL) of virus. On days 1 and 3 post-infection (p.i.) three mice were euthanized, and their organs including the lungs, kidneys, spleens, and brains were collected and titrated in MDCK cells. To determine the 50% mouse lethal dose ($MLD_{50}$) of the viruses, four mice from each group were inoculated intranasally with 10-fold serial dilutions containing $10^0$ to $10^5$ PFU (50 μL) of virus, respectively. Body weight and survival were monitored daily for 14 days. The $MLD_{50}$ was calculated by using the method of Reed and Muench (1938). All mouse experiments were performed in accordance with the University of Tokyo's Regulations for Animal Care and Use and were approved by the Animal Experiment Committee of the Institute of Medical Science, the University of Tokyo.

Virus Passage in Mice and MDCK Cells.

Mouse adaptation of virus was performed as described in Example I. For virus passages in MDCK cells, confluent MDCK cells were infected with virus at a multiplicity of infection (MOI) of 0.0001. At 48 hours post-infection (hpi) the supernatants were collected and titered in MDCK cells. The new, harvested viruses were used to infect MDCK cells for the next passage. This procedure was repeated five times.

Growth Kinetics Assays.

Each virus was inoculated into triplicate wells of subconfluent MDCK cells at an MOI of 0.0001. The cells were supplemented with MEM containing 0.3% bovine serum albumin (BSA) and 1 μg/mL tosylsulfonyl phenylalanyl chloromethyl ketone (TPCK) trypsin and incubated at 37° C. in 5% $CO_2$. Culture supernatants were harvested at the indicated hours post-infection. The viral titers of the supernatants at the different time-points were determined by use of plaque assays in MDCK cells.

Mini-Genome Luciferase Assay.

Polymerase activity was tested with a mini-genome assay by using the dual-luciferase system as previously described in Murakami (2008) and Ozawa et al. (2007). Briefly, 293 cells were transfected with viral protein expression plasmids for NP, PB1, PB2, and PA from the WT-Venus-H5N1 or MA-Venus-H5N1 virus (0.2 μg each), with a plasmid expressing a reporter vRNA encoding the firefly luciferase gene under the control of the human RNA polymerase I promoter (pPolI/NP(0)Fluc(0), 0.2 μg), and with pRL-null (Promega, 0.2 μg), which encodes the Renilla luciferase, as an internal transfection control. At 24 hours post-transfection, cell lysate was prepared with the Dual-Luciferase Reporter Assay System (Promega) and luciferase activity was measured by using the GloMax 96 microplate luminometer (Promega). The assay was standardized against Renilla luciferase activity. All experiments were performed in triplicate.

Laboratory Facility.

All studies with H5N1 viruses were performed in enhanced biosafety level 3 containment laboratories at the University of Tokyo (Tokyo, Japan), which are approved for such use by the Ministry of Agriculture, Forestry, and Fisheries, Japan.

Statistical Analysis.

The data were analyzed by using the R software (www.r-project.org), version 3.1. For comparisons of measurements from multiple groups collected at a single time point, we used one-way ANOVA followed by Tukey's Post hoc test. For comparisons of multiple groups with measurements collected independently at different time-points (i.e., viral growth curves from mice, collected in MDCK cells), we used two-way ANOVA followed by Tukey's Post hoc test. For comparisons of multiple groups with dependent measurements (i.e., viral growth 7 curves in cell culture for which aliquots were collected from the same culture at different time points), a linear mixed-effects model was fitted to the data using the R package NLME, and the time, the virus strain, and the interaction between these two factors were considered. Next, a contrast matrix was built to compare the strains in a pairwise fashion at the same time points (e.g., group_1 vs group_2 at 24 hours post-infection, group_1 vs group_3 at 24 hours post-infection, group_2 vs group_3 at 24 hours post-infection), using the R package PHIA. Because the comparisons were performed individually, the final p-values were adjusted by using Holm's method to account for multiple comparisons. In all cases, the results were considered statistically significant if we obtained In all cases, the results were considered statistically significant if we obtained p-values (or adjusted p-values) <0.05.

Sequence Analysis.

The PB2 and PA sequences from the NCBI Influenza Virus Database were aligned by using the MUSCLE program (Edgar, 2004), with the default parameters and a maximum of 100 iterations. The alignment was visualized by using Clustal X (Larkin et al., 2007), and the frequency of amino acid occurrences at specific positions was determined by using custom written Perl scripts.

Results

Comparison Between WT-Venus-H5N1 and MA-Venus-H5N1 Viruses.

Figure 6:
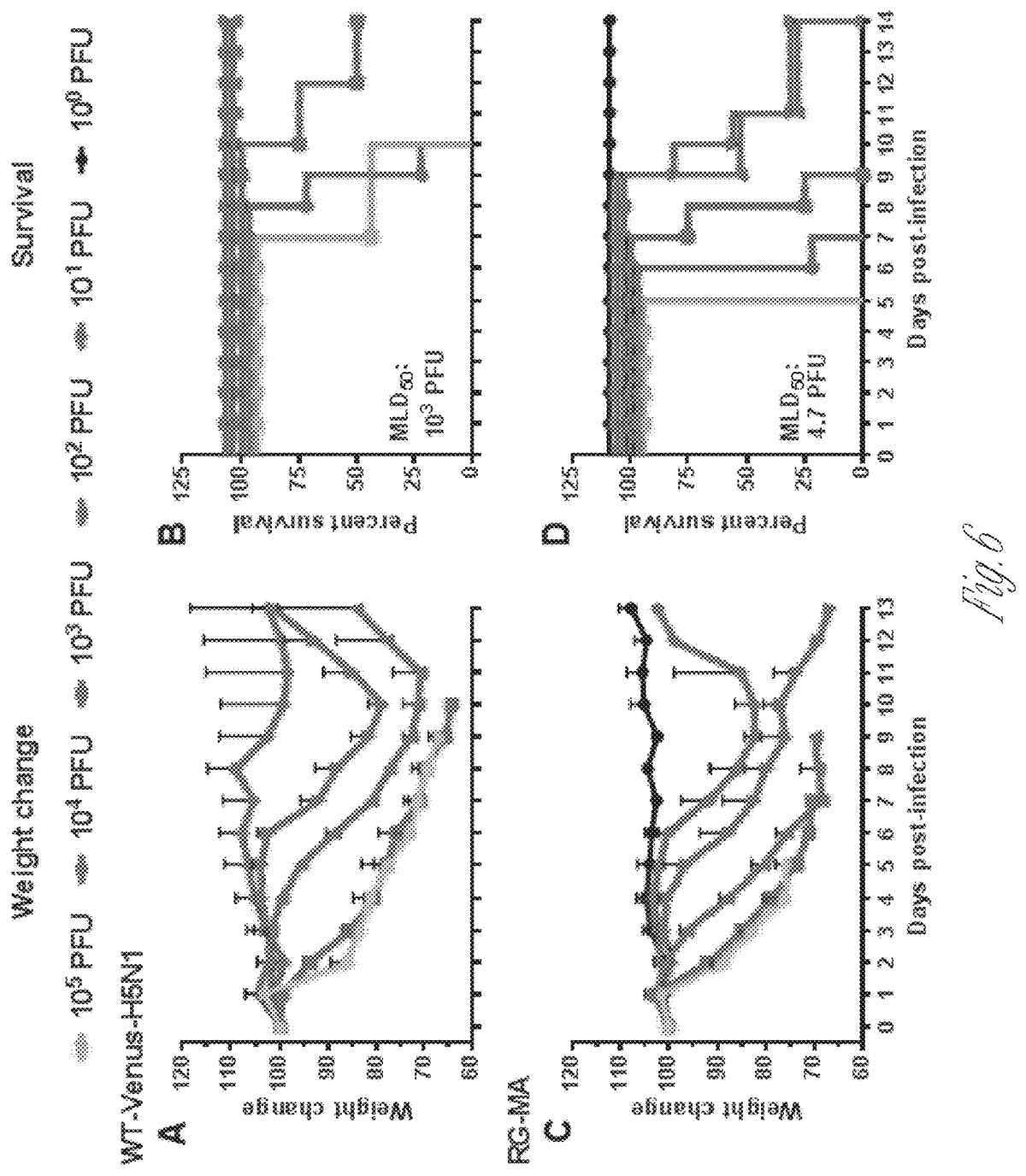

As in Example I, the NS segment of A/Viet Nam/1203/2004 (H5N1) (abbreviated as VN1203) was substituted with a Venus-fused NS segment of Venus-PR8 virus by using reverse genetics, and acquired an H5N1 virus that expressed the Venus fluorescent reporter gene (WT-Venus-H5N1 virus). A pathogenicity analysis in mice revealed that this virus exhibited attenuated virulence in mice compared with that of the parental VN1203 with an $MLD_{50}$ value of $10^3$ PFU (compared with 0.7 PFU for VN1203) (FIGS. 6A and 6B and Hatta et al. (2007)). Moreover, WT-Venus-H5N1 virus mainly replicated in respiratory organs (Table 3), and its Venus expression was very weak in both MDCK cells (FIG. 7) and in mice after virus infection (FIG. 8).

TABLE 3

Replication and virulence of H5N1 reassortants and mutants in mice[a]

| | Mean virus titer ($\log_{10}$ PFU/g ± SD) on the indicated day p.i. | | | | | | | |
|---|---|---|---|---|---|---|---|---|
| | Lung | | Spleen | | Kidney | | Brain | |
| Virus | Day 1 p.i. | Day 3 p.i. | Day 1 p.i. | Day 3 p.i | Day 1 p.i. | Day 3 p.i. | Day 1 p.i. | Day 3 p.i. |
| WT-Venus-H5N1 | 6.5 ± 0.2 | 6.3 ± 0.2 | —[b] | — | — | — | — | — |
| MA-Venus-H5N1 | 9.1 ± 0.1[c] | 8.9 ± 0.0[c] | 3.4 ± 0.2 | 6.5 ± 0.1 | 2.4 ± 0.1 | 4.1 ± 0.1 | — | 2.8 ± 0.6 |
| RG-MA | 9.1 ± 0.1[c] | 9.2 ± 0.1[c] | 2.8 ± 0.4 | 7.1 ± 0.0 | 2.3, —, — | 4.0 ± 0.1 | — | 2.3 ± 0.2 |
| WT + MA-PB2 | 7.7 ± 0.0[c] | 8.0 ± 0.1[c] | — | 4.1, 4.4, — | — | — | — | — |
| WT + MA-PA | 7.1 ± 0.1[c] | 6.8 ± 0.1[d] | — | — | — | — | — | — |
| WT + MA-(PB2 + PA) | 8.6 ± 0.3[c] | 8.7 ± 0.1[c] | 2.9 ± 0.4 | 6.8 ± 0.0 | 2.0, 1.7, — | 4.3 ± 0.7 | — | 2.7 ± 0.8 |

[a]Six-week-old SPF C57/BL6 mice were inoculated intranasally with $10^5$ PFU of each virus in a 50-μl volume. Three mice from each group were euthanized on days 1 and 3 p.i., and virus titers were determined in samples of lung, spleen, kidney, and brain in MDCK cells.
[b]—, no virus was isolated from the sample.
[c]P value was <0.01 compared with the titers in the lungs of mice infected with WT-Venus-H5N1 virus.
[d]P value was <0.05 compared with the titers in the lungs of mice infected with WT-Venus-H5N1 virus.

After six passages of WT-Venus-H5N1 virus in mice, MA-Venus-H5N1 virus was obtained. MA-Venus-H5N1 virus was lethal to mice with an $MLD_{50}$ of 3.2 PFU (Example I). This virus replicated systemically in mice; on day 1 p.i., high viral titers were detected in lungs, spleens, and kidneys, and on day 3 p.i. virus could be detected in brains (Table 3). Moreover we detected high Venus expression of MA-Venus-H5N1 virus in MDCK cells (FIG. 7) and in mice (FIG. 8). Therefore, compared with WT-Venus-H5N1, MA-Venus-H5N1 virus showed much higher pathogenicity in mice and a higher replicative ability. Moreover, this virus exhibited high Venus expression during its replication in vitro and in vivo.

To identify the genetic mutations that had occurred during mouse adaptation, the genome of MA-Venus-H5N1 virus was sequenced and compared to that of WT-Venus-H5N1 virus. At the amino acid level, a total of seven differences were found between the two viruses in their PB1, PB2, PA, NA, M2, and NS1 genes (Table 4). Thus single or multiple amino-acid changes among these seven different amino acids may contribute to the difference in virulence in mice and in Venus expression between these two viruses.

TABLE 4

Amino acid differences between WT-Venus-H5N1 and MA-Venus-H5N1 viruses.

| Gene segment | Amino acid position | Amino acid in: | |
|---|---|---|---|
| | | WT-Venus-H5N1 | MA-Venus-H5N1 |
| PB2 | 25 | Val (V) | Ala (A) |
| PB1 | 737 | Lys (K) | Arg (R) |

TABLE 4-continued

Amino acid differences between WT-Venus-H5N1 and MA-Venus-H5N1 viruses.

| Gene segment | Amino acid position | Amino acid in: | |
|---|---|---|---|
| | | WT-Venus-H5N1 | MA-Venus-H5N1 |
| PA | 443 | Arg (R) | Lys (K) |
| NA | 35 | Ser (S) | Arg (R) |
| | 284 | Val (V) | Leu (L) |

TABLE 4-continued

Amino acid differences between WT-Venus-H5N1 and MA-Venus-H5N1 viruses.

| Gene segment | Amino acid position | Amino acid in: | |
|---|---|---|---|
| | | WT-Venus-H5N1 | MA-Venus-H5N1 |
| M2 | 64 | Ala (A) | Asp (D) |
| NS1 | 167 | Pro (P) | Ser (S) |

V25A of PB2 and R443K of PA Determine the Pathogenicity and Venus Expression of Venus-H5N1 Virus in Mice.

To investigate the genetic basis for the difference in the virulence and Venus expression of Venus-H5N1 virus after mouse adaptation, a reverse genetics system was established for MA-Venus-H5N1 virus, which was named RG-MA virus. RG-MA virus exhibited similar viral titers in organs, $MLD_{50}$ value (FIGS. 6C and 6D and FIG. 9), and Venus expression in mice (FIG. 9) to those of its original virus (MA-Venus-H5N1 virus).

To identify the amino acids responsible for the difference in virulence and Venus expression between WT-Venus-H5N1 and MA-Venus-H5N1 virus, six single-gene recombinant viruses were generated, each bearing the PB2, PB1, PA, NA, M, or NS gene from MA-Venus-H5N1 virus and the other seven genes from WT-Venus-H5N1 virus. The recombinant viruses that contained the PB1, NA, or NS gene of MA-Venus-H5N1 virus (designated WT+MA-PB1, WT+MA-NA, or WT+MA-NS) displayed similar pathogenicity in mice to that of WT-Venus-H5N1 ($MLD_{50}$, $10^3$ PFU) (FIG. 9), whereas the reassortants with the PB2, PA, or M gene of MA-Venus-H5N1 (designated WT+MA-PB2, WT+MA-PA, or WT+MA-M) exhibited higher pathogenicity in mice than WT-Venus-H5N1 (FIG. 9). WT+MA-PB2 and WT+MA-PA replicated more efficiently in mouse lungs than did WT-Venus-H5N1; moreover virus was detected in the spleens of two of three mice infected with WT+MA-PB2.

The effect of the PB2, PA, or M genes derived from WT-Venus-H5N1 on the virulence of MA-Venus-H5N1 was also examined by generating three single-gene recombinant viruses, each containing the PB2, PA, or M gene from WT-Venus-H5N1 virus and the remaining segments from MA-Venus-H5N1 virus (designated MA+WT-PB2, MA+WT-PA, or MA+WT-M). The $MLD_{50}$ values of MA+WT-PB2 and MA+WT-PA were $10^{2.3}$ PFU, significantly higher than that of MA-Venus-H5N1 ($MLD_{50}$, 3.2 PFU), whereas the virulence of MA+WT-M in mice was similar with that of MA-Venus-H5N1 (FIG. 9). These data suggest that the PB2 and PA genes played an important role in the pathogenicity of MA-Venus-H5N1 virus in mice.

To assess the potential synergetic effects of the PB2 and PA genes on viral pathogenicity in mice, a reassortant carrying both the PB2 and PA genes of MA-Venus-H5N1 [MA-(PB2+PA)] on the WT-Venus-H5N1 virus backbone and a reciprocal reassortant on the MA-Venus-H5N1 virus backbone [designated WT+MA-(PB2+PA) and MA+WT-(PB2+PA)] were rescued, and assessed for virulence in mice. The substitution of the PB2 and PA genes from MA-Venus-H5N1 virus into WT-Venus-H5N1 virus significantly enhanced its virulence in mice, with an $MLD_{50}$ value of 3.2 PFU (FIG. 9), and also enhanced virus spread and replication in mice, similar to that of MA-Venus-H5N1 virus, and vice versa. Given that a single mutation is present in PB2 and in PA after mouse adaptation, these data indicate that V25A of PB2 and R443K of PA synergistically contribute to the virulence of MA-Venus-H5N1 virus in mice.

Figure 7:
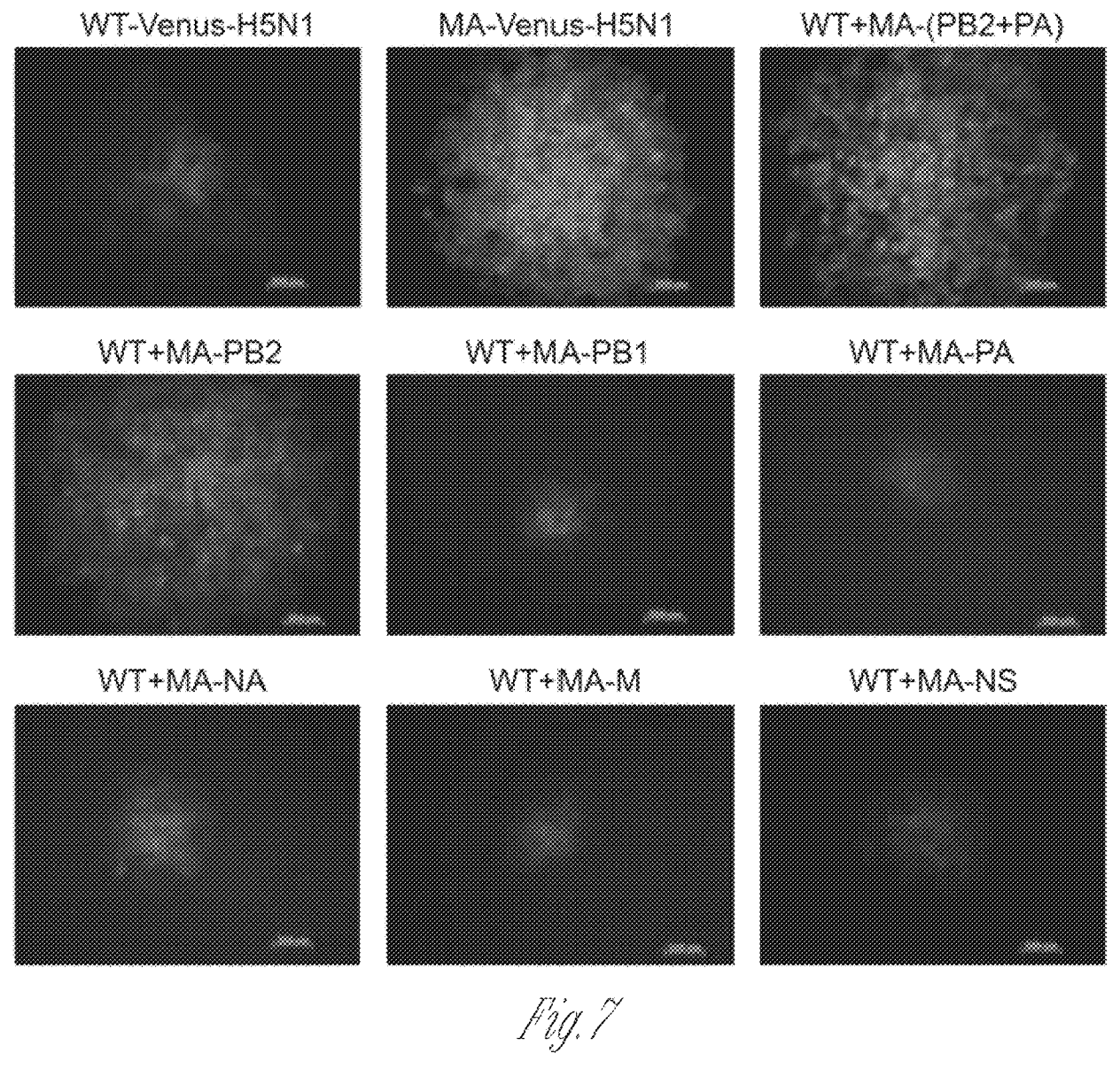
Figure 8:
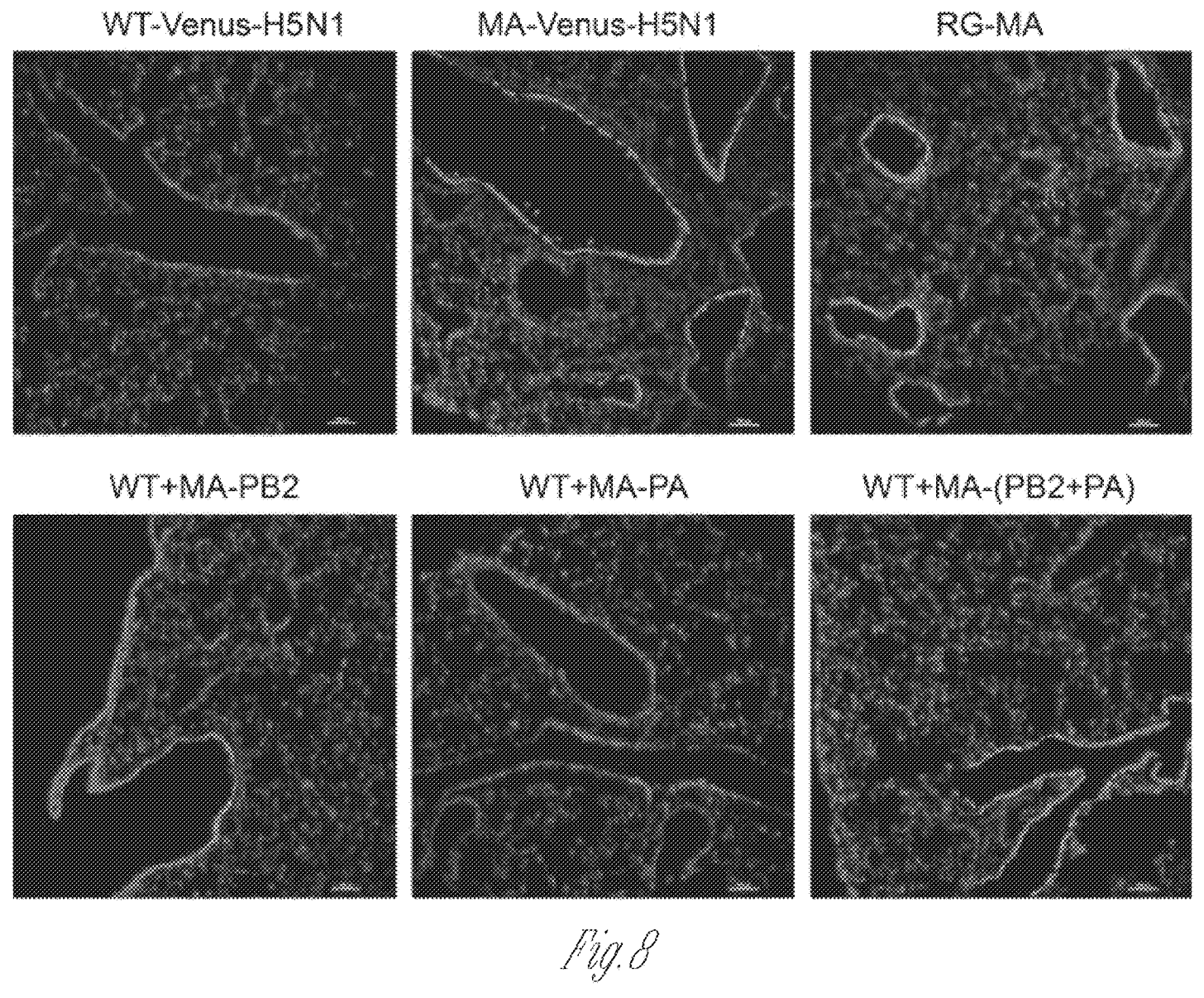

When checking the Venus expression of the above reassortants in MDCK cells, it was found that the MA-PB2 gene markedly increased Venus expression (FIG. 7). In addition, Venus expression of WT+MA-PB2 virus in the lungs was also appreciably enhanced (FIG. 8). The other single-gene substitutions including MA-PA did not affect Venus expression; however, the double substitution of MA-PB2 and MA-PA on the WT-Venus-H5N1 virus backbone increased Venus expression in MDCK cells and in mouse lung compared with those achieved by WT-Venus-H5N1 and WT+MA-PB2 virus (FIGS. 7 and 8). These data indicate that V25A of the PB2 protein plays a vital role in the Venus expression of MA-Venus-H5N1 virus in vitro and in vivo, and that R443K of the PA protein enhances the PB2 effect on Venus expression.

The Amino Acid at Position 25 in the PB2 Protein Significantly Enhances Viral Replication in Mammalian Cells.

Figure 10:
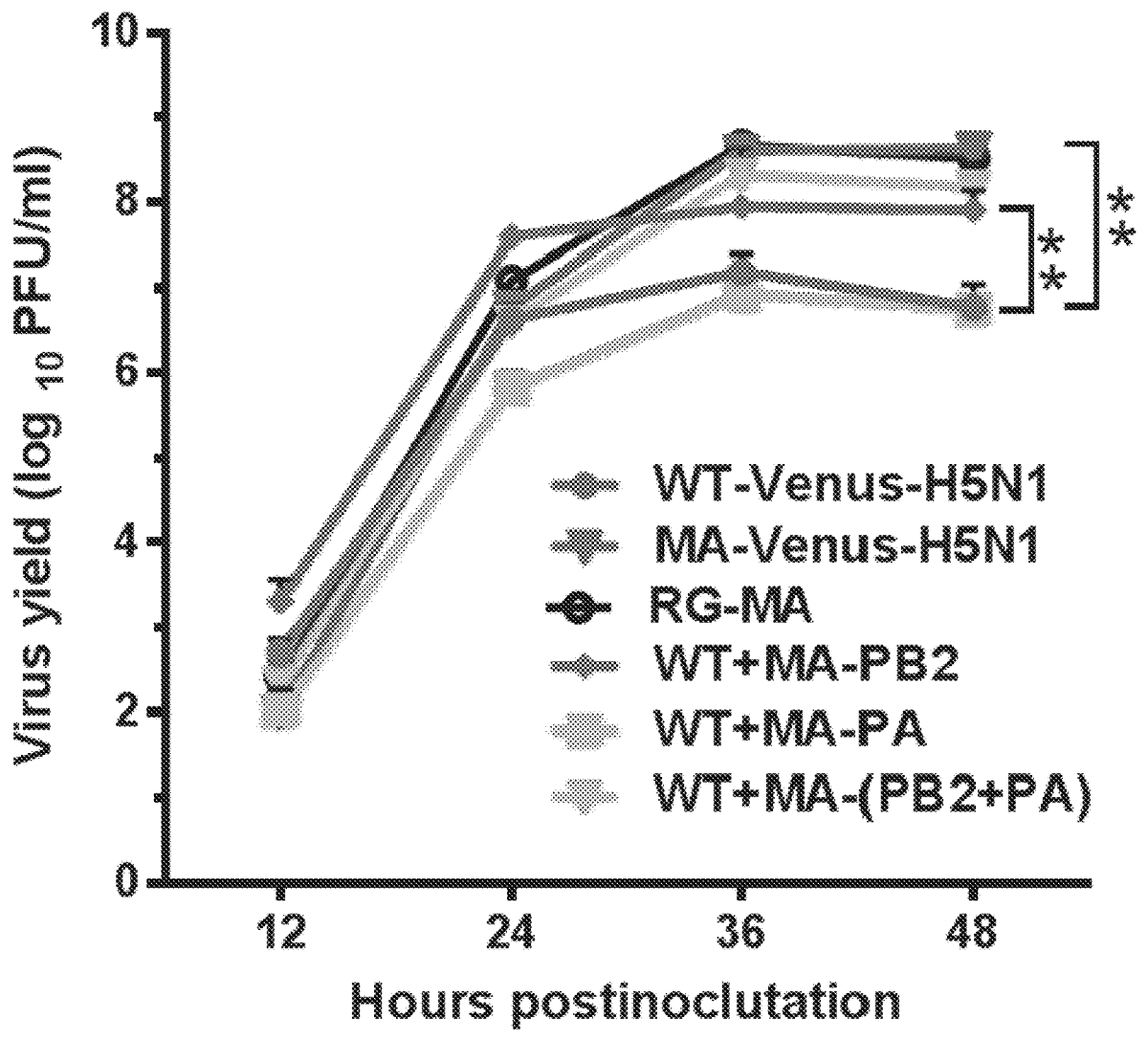

The replicative ability of these viruses was further examined in MDCK cells and it was found that the MA-Venus-H5N1 virus had similar replicative capability with RG-MA virus and grew more efficiently than WT-Venus-H5N1 virus, and that the titers of MA-Venus-H5N1 virus were significantly higher than those of WT-Venus-H5N1 virus at 36 and 48 hpi (FIG. 10). The contribution of the PB2 and PA gene segments to the replication of the two viruses was then investigated. Significantly higher titers of WT+MA-PB2 and WT+MA-(PB2+PA) were observed compared with those of WT-Venus-H5N1 virus at several time points post-infection, yet the replication efficiency of WT+MA-PA was comparable to that of WT-Venus-H5N1 virus (FIG. 10). The titers of WT+MA-(PB2+PA) were higher than those of WT+MA-PB2 at 36 and 48 hpi although the difference was not statistically significant (FIG. 10). These results indicate that the MA-PB2 gene enhances the replication of Venus-H5N1 virus in MDCK cells, and that this increase can be further enhanced by the presence of MA-PA, although MA-PA alone does not alter virus replication in MDCK cells.

The Mutations in the Polymerase Genes after Mouse Adaptation Decrease Viral Polymerase Activity in Mammalian Cells.

Figure 11:
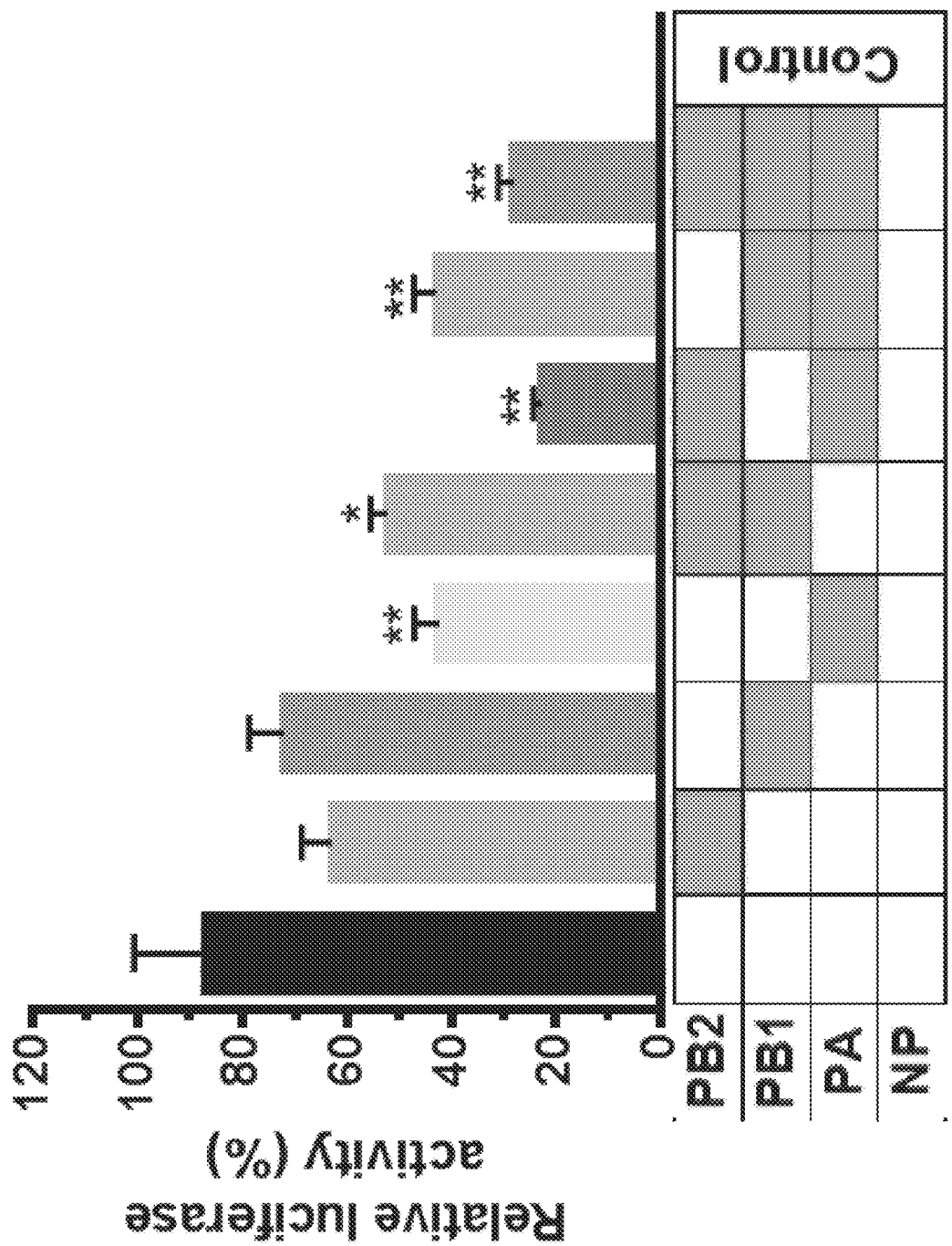
FIG. 11. Polymerase activity of different RNP combinations derived from the WT-Venus-H5N1 and MA-Venus-H5N1 viruses. 293 cells were transfected in triplicate with a luciferase reporter plasmid and an internal control plasmid, together with plasmids expressing PB1, PB2, PA, and NP from either WT-Venus-H5N1 or MA-Venus-H5N1 virus. Segments derived from WT-Venus-H5N1 virus are shown in white, whereas those derived from MA-Venus-H5N1 virus are in green. Cells were incubated at 37° C. for 24 hours, and cell lysates were analyzed to measure firefly and Renilla luciferase activities. The values shown are means±SD of the three independent experiments and are standardized to the activity of WT-Venus-H5N1 (100%). *, P<0.05 compared with that of WT-Venus-H5N1 virus. **, P<0.01 compared with that of WT-Venus-H5N1 virus.

The polymerase activity of the viral ribonucleoprotein (RNP) complex has been correlated with viral replication and virulence (Gabriel et al., 2005; Leung et al., 2010; Li et al., 2008; Salomen et al., 2006). The activity of the eight RNP combinations of PB1, PB2, and PA from either WT-Venus-H5N1 or MA-Venus-H5N1 virus was determined by measuring luciferase activity. The polymerase activity of the mouse-adapted virus was near 4-fold less than that of WT-Venus-H5N1 virus (FIG. 11). The substitution of any MA gene decreased the activity of the polymerase complex of WT-Venus-H5N1 virus, but the polymerase activity of complexes containing the double substitution of MA-PB2 and MA-PA was significantly decreased compared with that of WT-Venus-H5N1 virus and was similar with that of MA-Venus-H5N1 virus. These results indicate that the polymerase activity of RNP complexes was notably decreased after mouse adaptation, which is not in agreement with the enhanced replication and virulence.

Molecular Determinants of Venus Stability in Venus-H5N1 Virus In Vitro and In Vivo.

To assess Venus stability in the WT-Venus-H5N1 and RG-MA viruses in vitro, the two viruses were passaged five times in MDCK cells. During these passages Venus-negative plaques were picked up from WT-Venus-H5N1 virus, but not from RG-MA virus, suggesting that the Venus gene is more stable after mouse adaptation (Table 5). To identify the molecular determinants of this Venus stability, various reassortants were passaged five times in MDCK cells. Venus-negative plaques were acquired from reassortants with the MA-PB1, MA-NA, or MA-M gene, but we did not obtain any Venus-negative plaques from the fifth passages of Venus-H5N1 virus with the MA-PB2, MA-PA, MA-(PB2+PA), or MA-NS gene (Table 5). These data suggest that the MA-PB2, -PA, and -NS genes may play roles in Venus stability.

TABLE 5

Venus stability in Venus-H5N1 reassortants in MDCK cells[a].

| Virus | No. of passages in MDCK cells | No. of plaques checked | No. of Venus-negative plaques picked | No. of Venus-negative plaques after recheck |
|---|---|---|---|---|
| WT-Venus-H5N1 | 2 | 73 | 5 | 4 |
|  | 3 | 111 | 5 | 1 |
|  | 4 | 79 | 5 | 0 |
|  | 5 | 61 | 12 | 2 |
| RG-MA | 2 | 66 | 1 | 0 |
|  | 3 | 144 | 8 | 0 |
|  | 4 | 73 | 1 | 0 |
|  | 5 | 75 | 2 | 0 |
| WT + MA-PB2 | 5 | 84 | 2 | 0 |
| WT + MA-PB1 | 5 | 126 | 4 | 1 |
| WT + MA-PA | 5 | 104 | 16 | 0 |
| WT + MA-(PB2 + PA) | 5 | 123 | 6 | 0 |
| WT + MA-NS | 5 | 199 | 11 | 0 |

TABLE 5-continued

Venus stability in Venus-H5N1 reassortants in MDCK cells[a].

| Virus | No. of passages in MDCK cells | No. of plaques checked | No. of Venus-negative plaques picked | No. of Venus-negative plaques after recheck |
|---|---|---|---|---|
| WT + MA-NA | 5 | 73 | 16 | 1 |
| WT + MA-M [b] | 5 | 69 | 10 | 10 |

[a]Each virus was passaged five times in MDCK cells as describe in the Materials and Methods. Venus expression of different passage stocks was detected in MDCK cells by using fluorescence microscopy. Venus-negative plaques were picked up and amplified in MDCK cells. Amplified Venus-negative plaques were rechecked for Venus expression to exclude false-negative plaques.

[b] 69 plaques of the fifth passage stock of WT + MA-M were checked by using fluorescence microscopy, all of which were "Venus-negative". Ten of these plaques were picked up to further confirm the lack of Venus expression, all of which were confirmed to be Venus-negative.

Figure 12A:
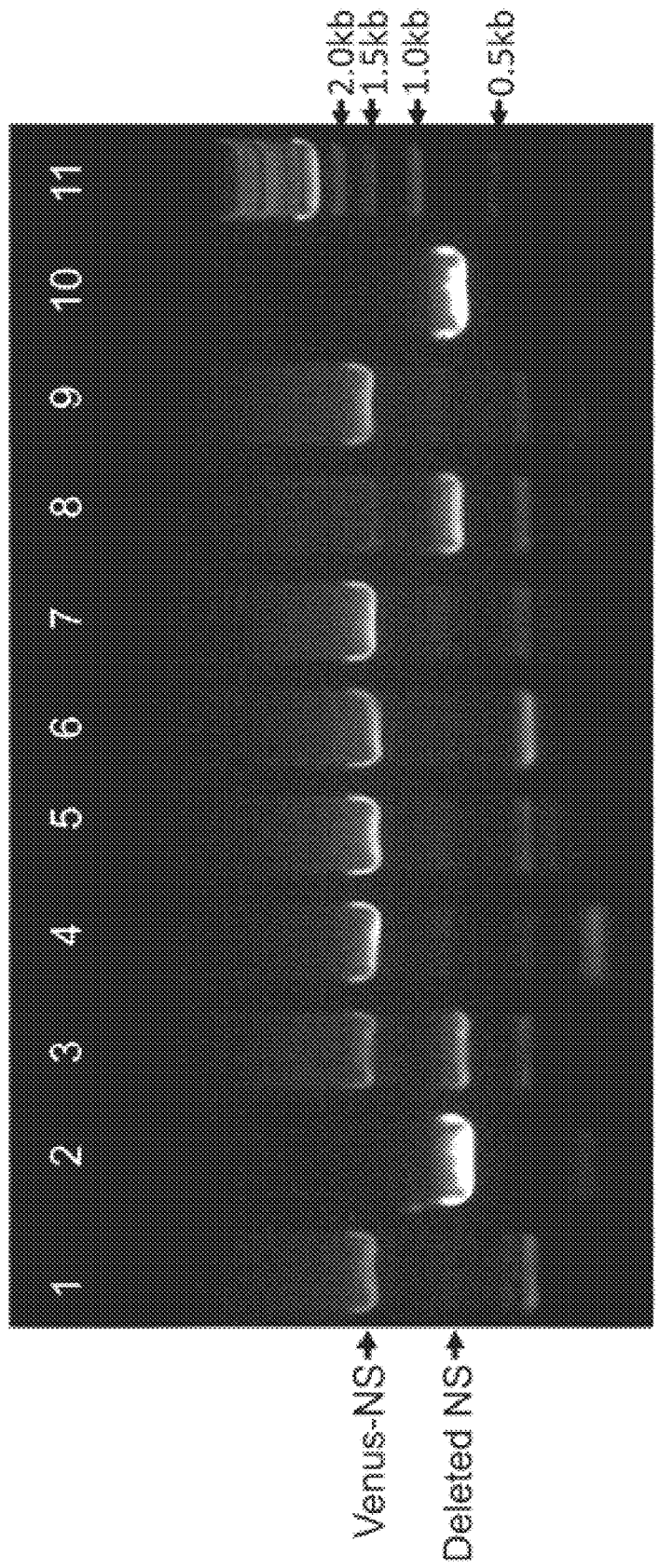
FIG. 12A. Venus-NS and deleted NS segments of Venus-H5N1-related reassortants. Viruses were passaged five times in MDCK cells and the vRNAs from the fifth passages were extracted by using a QIAamp® Viral RNA Mini Kit (QIAGEN). The respective NS segments were then amplified by using PCR with NS-specific primers and run on an agarose gel. Lane 1, WT+MA-NS; lane 2, WT+MA-M; lane 3, WT+MA-NA; lane 4, WT+MA-PA; lane 5, WT+MA-PB1; lane 6, WT+MA-PB2; lane 7, WT+MA-(PB2+PA); lane 8, WT-Venus-H5N1; lane 9, RG-MA; lane 10, PR8; and lane 11, 1-kb DNA marker.
Figure 12B:
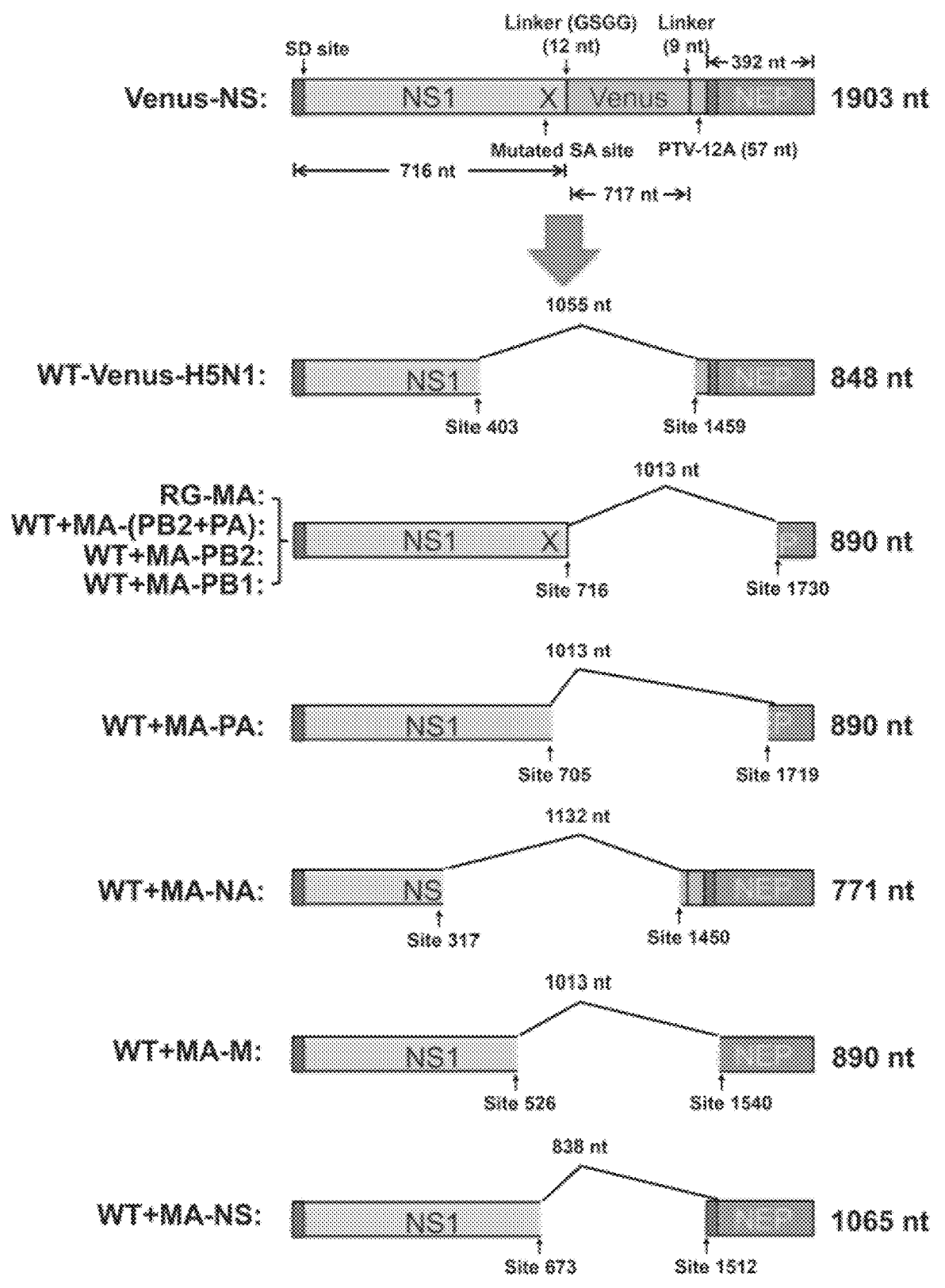
Figure 13:
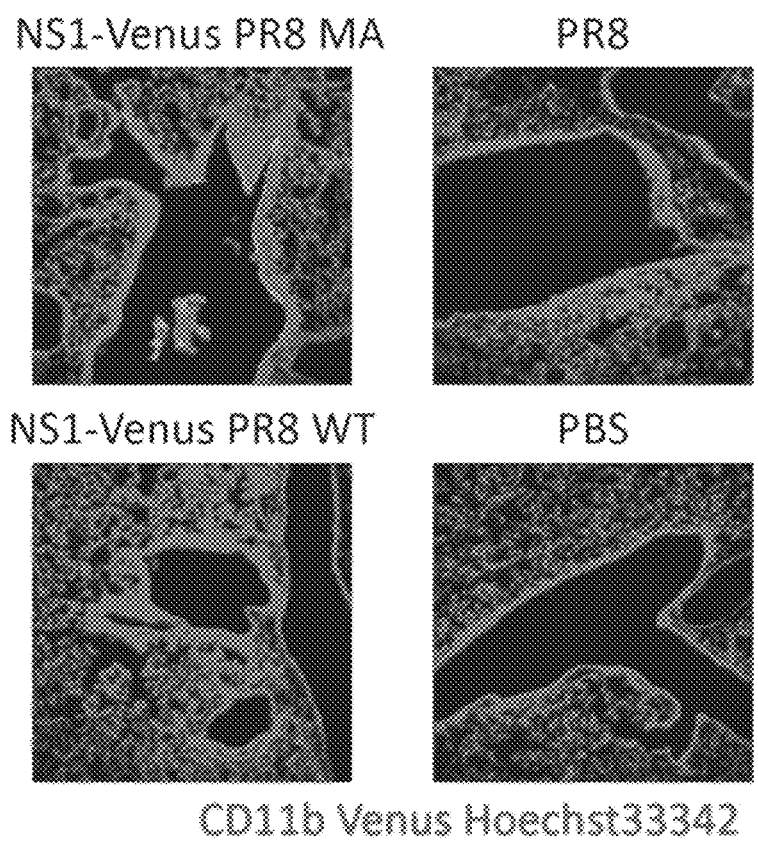
FIG. 13. High expression of Venus reassortants in mouse lung.

To further evaluate the roles of these different genes on Venus stability, the NS segments of the fifth-passage stocks from different reassortants were amplified by using PCR and NS-specific primers. Except for the Venus-NS segment (1.9 kb), the deleted NS segments were detectable, at a level similar to that for the NS segment of PR8, at less than 1 kb. The deleted NS segments of WT-Venus-H5N1 and of the reassortants with the MA-NA and MA-M genes were much brighter than those of the other reassortants (FIG. 12), further implying that the MA-NA and MA-M genes do not contribute to Venus stability in vitro. Although RG-MA virus and the reassortants with MA-NS, MA-PA, or MA-PB2 were more stable, the deleted Venus-NS segments were still amplified by using PCR albeit to a lesser degree (FIG. 12). The deleted NS segments from the various reassortants were extracted and sequenced, and the different deletion forms were identified from the different reassortants (FIG. 13).

In addition, to examine Venus stability in vivo, B6 mice were inoculated with $10^5$ PFU of WT-Venus-H5N1 virus, RG-MA virus, or WT+MA-(PB2+PA) virus. Lungs were collected on day 4 p.i., before the mice died, and were homogenized in PBS. The supernatants were inoculated into MDCK cells, and at 48 hpi Venus-negative plaques were picked up and amplified in MDCK cells. It should be noted that sometimes the Venus signal of the plaque correlates with the condition of the cultured cells and the detection time. Therefore the Venus expression of amplified Venus-negative plaques was rechecked in MDCK cells to exclude false negatives. More than 95 plaques were detected from each lung, and only one plaque without Venus expression was acquired from one of three mice infected with RG-MA virus, twelve Venus-negative plaques from three mice infected with WT+MA-(PB2+PA), and more than 15 Venus-negative plaques from each mouse infected with WT-Venus-H5N1 virus (Table 6). These results indicate that WT-Venus-H5N1 virus is the most unstable of these viruses in vivo, and that the PB2 and PA genes from MA-Venus-H5N1 virus enhance Venus stability, albeit to a lesser extent than occurs in MA-Venus-H5N1 virus. The mutations on PB1, PB2, PA, and NS may therefore synergistically contribute to Venus stability in MA-Venus-H5N1 virus in vivo.

TABLE 6

Venus stability in Venus-H5N1 viruses in mice[a].

| Virus | Mouse No. | No. of plaques checked | No. of Venus-negative plaques picked | No. of Venus-negative plaques after recheck |
|---|---|---|---|---|
| RG-MA | 1# | 105 | 4 | 1 |
|  | 2# | 109 | 6 | 0 |
|  | 3# | 127 | 5 | 0 |
| WT + MA-(PB2 + PA) | 4# | 116 | 12 | 6 |
|  | 5# | 111 | 8 | 3 |
|  | 6# | 115 | 14 | 3 |
| WT-Venus-H5N1 | 7# | 145 | 31 | 22 |
|  | 8# | 120 | 27 | 18 |
|  | 9# | 95 | 19 | 15 |

[a]Six-week-old SPF C57/BL6 mice were infected intranasally with $10^5$ PFU of each virus in a 50-µl volume. Three mice from each group were euthanized on day 4 p.i. and their lung tissues were collected and homogenized in PBS. The supernatants of the lung samples were inoculated into MDCK cells to check for Venus expression, and Venus-negative plaques were picked up and amplified in MDCK cells. Amplified Venus-negative plaques were rechecked for Venus expression to exclude false-negative plaques.

Discussion

Previously, a visualizable H5N1 virus expressing a Venus reporter gene that became more lethal to mice and more stable after mouse adaptation was constructed (Example I). In this study, the whole genome of this virus (MA-Venus-H5N1) was sequenced, and seven amino acids that differed from the WT-Venus-H5N1 virus sequence were identified. To explore the molecular determinants for the differences in virulence and Venus expression in mice between these two viruses, a series of reassortants of both viruses was generated using reverse genetics. The double mutation of PB2 (V25A) and PA (R443K) was found to dramatically enhance the pathogenicity of WT-Venus-H5N1 in mice. V25A of PB2 also significantly increased Venus expression and viral replication in MDCK cells and in mice, and that R443K of PA further enhanced these effects. The stability of different reassortants was examined in vitro, the reassortants with MA-PB2, MA-PA, or MA-NS were found to be more stable. These results suggest that the PB2 and PA proteins play important roles in the pathogenicity and Venus stability of Venus-expressing H5N1 viruses in mammalian hosts.

The pathogenicity of highly pathogenic H5N1 avian influenza viruses in mammals is determined by multiple viral genes. For example, the HA protein plays crucial roles in the systemic replication and lethal infection of H5 subtype viruses in chickens (Kawaoka and Webster, 1988) and mammals (Hatta et al., 2001; Suguitan et al., 2012). The HA and NS genes of H5N1 virus also contribute to high virulence in ferrets (Imai et al., 2010). The NS1 protein helps to subvert the antiviral immune response of the host and is essential for the pathogenicity of H5N1 viruses in mice (Jiao et al., 2005). Mutations in the M1 protein also affect the virulence of H5N1 viruses in mice (Fan et al., 2009). The amino acids at position 627 and 701 of PB2 are key determinants of the high virulence of H5N1 influenza viruses in mammals (Hatta et al., 2001; Li et al., 2005). Lastly, the PA protein is reported to contribute to the virulence of H5N1 avian influenza viruses in domestic ducks (Song et al., 2011) and in mice (Hu et al., 2013). Here, it was found that V25A of PB2 and R443K of PA synergistically contribute the pathogenicity of H5N1 virus in mice.

Based on all of the influenza virus sequences (23514 PB2 proteins and 24240 PA proteins) available in the public database (www.fludb.org), it was found that 25V in PB2 and 443R in PA are extremely conserved, whereas 25A in PB2 is present in only two viruses [A/Mallard/ON/499/2005

(H5N1), accession number EF392844; and A/Zhejiang/92/2009(H1N1), accession number CY095997] and 443K in PA is present in only one strain, isolated from a quail [A/Quail/Shantou/1425/2001 (H9N2), accession number EF154846]. Although the virulence of these viruses in mice is unknown, the present study is the first to suggest that the combination of 25A in PB2 and 443K in PA contributes to the increased virulence of a virus in mice and is a unique feature of MA-Venus-H5N1 virus.

The RNA polymerase of influenza A virus consists of the PB1, PB2, and PA subunits, and is implicated in numerous essential processes in the viral life cycle (Naffakh et al., 2005). PB1 performs polymerase and endonuclease activities, PB2 is responsible for capped-RNA recognition, and PA is involved in RNA replication and proteolytic activity (Obayasjo et al., 2005). The interfaces of these polymerase subunits are essential for transcription initiation (He et al., 2008; Sugiyama et al., 2009). Residues 1-37 at the N-terminus of the PB2 protein play a vital role in binding to the PB1 protein and affect the RNA polymerase activity, and these residues are highly conserved among all subtypes of influenza virus (Sugiyama et al., 2009). The amino acid at position 25 of PB2 is located within the third α-helix (amino acids 25 to 32) of its PB1-binding domain (Sugiyama et al., 2009). In this study, the amino acid at position 25 in PB2 was found to be changeable, and V25A in PB2 was found to increase viral replication in mammalian cells and in mice, resulting in higher pathogenicity of the H5N1 virus in mice. The R443 residue of the PA protein also plays an important role in replication activity (Obayashi et al., 2008; Regan et al., 2006), and the mutation R443A in PA prevents the production of infectious virus (Regan et al., 2006). In this study, reassortants with R443K in their PA protein were rescued, and demonstrated that R443K in PA enhances viral replication in mouse lungs, reinforcing it was the virulence of H5N1 virus in mice. The present data thus further emphasize the important role of the amino acid at position 443 of the PA protein for influenza virus.

Earlier reports have shown that the polymerase activity of the viral RNP complex closely correlates with viral replication and virulence (Gabriel et al., 2005; Leung et al., 2010; Li et al., 2008; Salomon et al., 2006). Viruses with higher polymerase activity in mammalian cells generally show higher virulence in mice (Zhang et al., 2014) and ferrets (Salomen et al., 2006). However, viruses with high polymerase activity are not always lethal to mice, which suggests that high pathogenicity of a virus in its host requires an optimal, appropriate level of polymerase activity (Gabriel et al., 2005). In this study, it was found that MA-Venus-H5N1 virus was more lethal to mice than was its wild-type counterpart, yet it had much lower polymerase activity, and any RNP combination with a polymerase gene from MA-Venus-H5N1 also had lower activity. These results may imply that the polymerase activity of the vRNP complex closely correlates with the viral genome, and that the lower level of polymerase activity is more compatible with the reconstructed genome of Venus-H5N1, which benefits its high pathogenicity in mice.

With the development of living imaging in vivo, the ability to visualize influenza viruses carrying fluorescent reporter genes will be of great benefit influenza virus-related research (Heaton et al, 2013; Helft et al., 2012; Manicassamy et al., 2010; Pan et al., 2013; Example I). An effective virus for this purpose should have good replicative ability and show considerable pathogenicity in its host. Moreover, it should both highly and stably express its fluorescent reporter protein. Many attempts to construct influenza A viruses carrying the GFP reporter gene have been reported (Kittel et al., 2004; Manicassamy et al., 2010); however, some of these viruses showed low replication or poor pathogenicity in mice (Kittle et al., 2004), while some produced relatively low fluorescent signals or did not stably express GFP during virus replication in vitro and in vivo (Manicassamy et al., 2010). The present data demonstrate that not only is MA-Venus-H5N1 virus highly pathogenic to mice, but it also highly and stably expresses Venus fluorescent protein in vitro and in vivo. In the present analysis of the molecular determinants of Venus expression and Venus stability, it was found that V25A in PB2 played an important role in determining Venus expression, which was further enhanced by the presence of R443K in PA. The analysis of Venus stability revealed that the single gene of MA-PB1, -PB2, -PA, or -NS determines Venus stability in vitro, but in vivo the situation is more complex and mutations in PB1, PB2, PA, and NS may synergistically codetermine Venus stability in MA-Venus-H5N1 virus.

In summary, molecular determinants in a mouse-adapted Venus-H5N1 virus were identified that play a crucial role in the pathogenicity of the virus in mice, and in its Venus expression and Venus stability in vitro and in vivo. These molecular markers will benefit future research on anti-influenza virus drug and vaccine development.

Example III

Materials and Methods

Cells and Viruses.

Madin-Darby canine kidney (MDCK) cells were maintained in minimum essential medium (MEM) containing 5% of newborn calf serum (NCS). Human embryonic kidney 293T (HEK293T) and HEK293 cells were maintained in Dulbecco's modified Eagle medium supplemented with 10% fetal calf serum (FCS). A/Puerto Rico/8/34 (H1N1; PR8) (Horimoto et al., 2007) and each NS1-Venus PR8 virus were generated by using reverse genetics and were propagated in MDCK cells at 37° C. for 48 hours in MEM containing L-(tosylamido-2-phenyl) ethyl chloromethyl ketone (TPCK)-treated trypsin (0.8 µg/mL) and 0.3% bovine serum albumin (BSA) (Sigma Aldrich).

Adaptation of NS1-Venus PR8 Virus in Mice.

Six- to eight-week-old female C57BL/6 mice (Japan SLC) were intranasally infected with 50 µL of $2.3 \times 10^6$ plaque-forming units (PFU) of NS1-Venus PR8 virus. Lungs were harvested 3-6 days post-infection (dpi) and homogenized in 1 mL of phosphate-buffered saline (PBS). To obtain a clone with high proliferative ability and Venus expression, plaque purification of the lung homogenate using MDCK cells was performed. A large, highly Venus-expressing plaque was picked and the cloned virus was propagated in MDCK cells at 37° C. for 48 hours, then 50 µL of the supernatant was used as an inoculum for the next passage. These procedures were repeated six times.

Sequence Analysis.

Sequence analysis of viral RNA was performed as described previously (Sakabe et al., 2011). Briefly, viral RNAs were extracted by using a QIAamp Viral RNA mini kit (QIAGEN) and Superscript III™ reverse transcriptase (Invitrogen) and an oligonucleotide complementary to the 12-nucleotide sequence at the 3' end of the viral RNA (Katz et al., 1990) were used for reverse transcription of viral RNAs. Each segment was amplified by using PCR with Phusion High Fidelity DNA polymerase (Finnzymes) and primers specific for each segment of the PR8 virus. The PCR products were purified and their sequences determined by using ABI 3130xl (Applied Biosystems).

Plasmid Construction and Reverse Genetics.

Plasmids containing the cloned cDNAs of PR8 genes between the human RNA polymerase I promoter and the mouse RNA polymerase I terminator (referred to as PolI plasmid) were used for reverse genetics and as templates for mutagenesis. The mutations found in NS1-Venus PR8 virus after passage were introduced into the plasmid constructs of PR8 by using site-directed mutagenesis (referred to as pPolIR-PR8-PB2-E712D and pPolIR-PR8-HA-T380A, respectively). Reverse genetics was performed as described previously (Neumann et al., 1999). The eight PolI plasmids were cotransfected into HEK293T cells together with eukaryotic protein expressing plasmids for PB2, PB1, PA, and NP derived from PR8 by using the TransIT-293 transfection reagent (Mirus). Forty-eight hours after transfection, the supernatant was harvested and propagated once in MDCK cells at 37° C. for 48 hours in MEM containing TPCK-treated trypsin (0.8 [g/mL) and 0.3% BSA. Cell debris was removed by centrifugation at 2,100×g for 20 minutes at 4° C., and the supernatants were stored at −80° C. until use. The virus titers were determined by means of a plaque assay using MDCK cells.

Polykaryon Formation Assay.

Polykaryon formation assay was performed as described previously (Imai et al., 2012) with modifications. HEK293 cells propagated in 24-well plates were infected with wild-type PR8 or PR8 possessing the hemagglutinin (HA) mutation found in NS1-Venus PR8 MA virus in DMEM containing 10% FCS at a multiplicity of infection (MOI) of 10. At 18 hours post-infection, cells were washed with MEM containing 0.3% BSA and treated with TPCK-treated trypsin (1 μg/mL) in MEM containing 0.3% BSA for 15 minutes at 37° C. to cleave the HA on the cell surface into HA1 and HA2. Trypsin was inactivated by washing the cells with DMEM containing 10% FCS. To initiate polykaryon formation, cells were exposed to low-pH buffer (145 mM NaCl, 20 mM sodium citrate (pH 6.0-5.4)) for 2 minutes at 37° C. Then the low-pH buffer was replaced with DMEM containing 10% FCS and the cells were incubated for 2 hours at 37° C. The cells were then fixed with methanol and stained with Giemsa's solution. A microscope mounted with a digital camera (Nikon) was used to obtain photographic images.

Western Blotting.

MDCK cells were infected with each virus at an MOI of 1 without trypsin. The cells were lysed with Novex® Tris-Glycine SDS sample buffer (Invitrogen) 12 hours after infection and subjected to SDS-polyacrylamide gel electrophoresis. Then, the proteins were transferred to a PVDF membrane in transfer buffer (100 mM Tris, 190 mM glycine). After membrane blocking, the membranes were incubated with a rabbit anti-GFP polyclonal antibody (MBL) or rabbit antiserum to A/WSN/33(H1N1)(R309), which was available in our laboratory. This antiserum reacts with influenza viral proteins including HA, NP, and matrix protein (M1). After incubation with the primary antibodies followed by washing with PBS containing 0.05% Tween-20 (PBS-T), the membranes were incubated with ECL™ anti-rabbit IgG HRP-linked whole antibody (GE Healthcare). Finally, specific proteins were detected by using the ECL Plus Western Blotting Detection System (GE Healthcare). The VersaDoc Imaging System (Bio-Rad) was used to obtain photographic images.

Pathogenicity and Replication of Viruses in Mice.

Six-week-old female C57BL/6 mice were intranasally infected with 50 μL of $10^3$, $10^4$ or $10^5$ PFU of each virus. Four mice per group were monitored for survival and body weight changes for 14 days after infection. Three mice per group were infected with $10^3$ PFU of each virus and euthanized on the indicated days. Their lungs were collected to determine viral titers by means of plaque assay on MDCK cells.

Immunofluorescence Assay.

Six-week-old female C57BL/6 mice were intranasally infected with 50 μL of $10^4$ PFU of each virus. Three mice per group were euthanized on the indicated days. To fix the lungs, they were intratracheally injected with 800 μL of 4% paraformaldehyde (PFA) phosphate buffer solution and then removed. After incubation with 10 mL of 4% PFA at 4° C. for 4 hours, the buffer was replaced with 10%, 20%, and 30% sucrose in PBS in a stepwise fashion. Then lungs were embedded in Optimum Cutting Temperature (OCT) Compound (Tissue-Tek) and frozen in liquid nitrogen. Frozen sections (6 μm in thickness) were permeabilized in 0.2% Triton X-100 in PBS and incubated with primary antibodies at 4° C. for 12 hours. Primary antibodies were goat anti-Clara cell 10 kDa protein (CC10) (Santa Cruz, sc-9772), rabbit anti-surfactant protein C (SP-C) (Santa Cruz, sc-13979), golden Syrian hamster anti-podoplanin (eBioscience, eBio8.1.1), and rabbit anti-calcitonin gene-related peptide (CGRP) (Sigma-Aldrich, C8198). After being washed with PBS, the sections were incubated with species-specific fluorescence dye-conjugated secondary antibodies at room temperature for 30 minutes. Nuclei were stained with Hoechst33342 (Invitrogen). A Nikon A1 confocal microscope (Nikon) was used to observe the sections.

Preparation of Transparent Samples.

Transparent samples were prepared by using SCA-LEVIEW A2 (Olympus) in accordance with a previous report (Hama et al., 2012). Six-week-old female C57BL/6 mice were intranasally infected with 50 μL of $10^5$ PFU of each virus. Intracardial perfusion was performed on the indicated days and lungs were fixed with 4% PFA in PBS for 4 hours at 4° C. Lungs were incubated with 10%, 20%, and 30% sucrose in PBS as described above, embedded in OCT compound, and frozen in liquid nitrogen. After the samples were thawed and rinsed in PBS, they were fixed again with 4% PFA in PBS for 30 minutes at room temperature. Then the lungs were transferred to SCALEVIEW A2 and incubated at 4° C. for at least 2 weeks. SCALEVIEW A2 was exchanged every 2-3 days. Transparent samples were observed by using a stereo fluorescence microscope (Leica M205FA) mounted with a digital camera (DFC365FX) and filter GFP 3 (480/40 LP510).

Flow Cytometry.

To prepare single-cell suspensions, lungs were minced with scissors and digested with 20 mg of collagenase D (Roche) and 200 units of DNase (Worthington) for 30 minutes at 37° C. Samples were then passed through 100-μm cell strainers and red blood cells were lysed by red blood cell lysis buffer (Sigma Aldrich). Single-cell suspensions were stained with a combination of the following antibodies: allophycocyanine-conjugated anti-F4/80 (eBioscience, BM8), allophycocyanine-cyanine 7-conjugated anti-CD11b (BioLegend, M1/70), phycoerythrin-cyanine 7-conjugated anti-CD11c (BD PharMingen, HL3), and eFluor 450-conjugated CD45 (eBioscince, 30-F11). Dead cells were stained with via-probe (Becton Dickinson). Stained samples were analyzed with FACSAria II (Becton Dickinson and Company) and FlowJo software (TreeStar).

RNA Isolation and Integrity.

Venus-positive and -negative cells from three pooled lungs were collected in TRIzol Reagent (Invitrogen). Total RNA was extracted by isopropanol precipitation with glycogen as a carrier. Isolated total RNA integrity was assessed by determining UV 260/280 absorbance ratios and by examining 28S/18S ribosomal RNA bands with an Agilent 2100 bioanalyzer (Agilent Technologies) according to the manufacturer's instructions.

Microarray Analysis.

Forty nanograms of total RNAs was amplified by using the Arcturus® Riboamp® Plus RNA Amplification Kit (Life technologies). Cy3-labeled complementary RNA probe synthesis was initiated with 100 ng of total RNA by using the Agilent Low Input Quick Amp Labeling kit, one color (Agilent Technologies) according to the manufacturer's instructions. The Agilent SurePrint G3 Gene Mouse GE 8×60 K microarray was also used. Slides were scanned with an Agilent's High-Resolution Microarray Scanner, and image data were processed by using Agilent Feature Extraction software ver. 10.7.3.1. All data were subsequently uploaded into GeneSpring GX ver 12.5 for data analysis. For the data analysis, each gene expression array data set was normalized to the in silico pool for samples from mice inoculated with PBS. Statistically significant differences in gene expression between the Venus-positive cells and -negative cells were determined by using one-way analysis of variance (ANOVA) followed by the Turkey HSD post-hoc test (P<0.05) and the Benjamin-Hochberg false discovery rate correction. Differentially expressed genes were further filtered to include genes whose expression changed 2.0-fold relatively to the level in the PBS group. Genes that passed the statistical analysis were further assigned to a gene ontology (GO) grouping.

Results

Establishment of a Mouse-Adapted NS1-Venus PR8 Virus.

Although NS1-Venus PR8 WT virus was successfully rescued by reverse genetics, this virus was avirulent in mice ($MLD_{50}$:>$10^5$ PFU), and the expression of Venus was very weak in MDCK cells and in the lung sections of mice infected with this virus. To increase the virulence and Venus expression of NS1-Venus PR8 WT virus, the virus was serially passed in mice via intranasal infection with plaque-purified high Venus-expressing clones (see Examples I and II). After six serial passages, the virulence of the virus appeared to have increased; therefore, I sequenced this mouse-adapted NS1-Venus PR8 WT virus to look for mutations.

The sequence analysis revealed that two amino acid substitutions had occurred after passaging (Table 7).

TABLE 7

Amino acid substitutions in NS1-Venus PR8 MA virus.

| Protein | amino acid position | amino acid encoded | |
|---|---|---|---|
| | | PR8 | NS1-Venus PR8 MA |
| PB2 | 712 | E | D |
| HA | 380 | T | A |

One of the mutations was in PB2 (a glutamine acid-to-asparagine acid substitution at position of 721), and the other was in HA (a threonine-to-alanine substitution at position of 380). To confirm their contribution to pathogenicity in mice, these mutations were introduced into a correspondent poll plasmid, and used reverse genetics to generate NS1-Venus PR8, which possessed the two mutations (referred to as NS1-Venus PR8 MA virus). The pathogenicity of NS1-Venus PR8 MA virus was higher than that of NS1-Venus PR8 WT virus ($MLD_{50}$: $2.1 \times 10^4$ PFU). Furthermore, the Venus signal in the lungs from mice infected with NS1-Venus PR8 MA virus was strong, whereas in the lung infected with NS1-Venus PR8 WT and that infected with PR8, no Venus signal was detected (data not shown). NS1-Venus PR8 MA, therefore, showed promise as a useful reporter virus.

Comparison of Mutant Virus Replication in MDCK Cells.

Figures 14, 15:
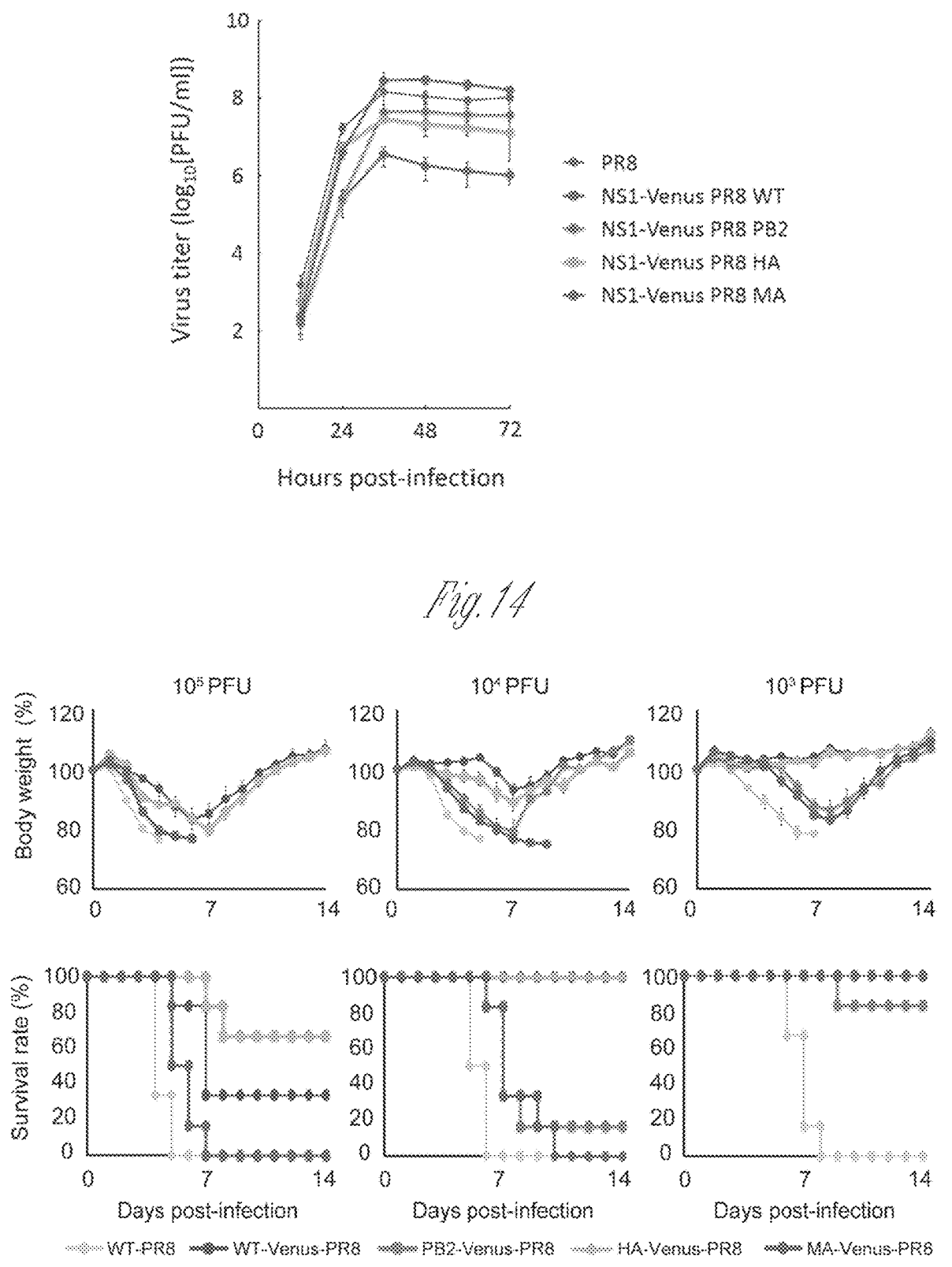

To compare the growth of these viruses in a cell line, two single-gene reassortants were generated that possessed the PB2 or HA gene of NS1-Venus PR8 MA virus and the remaining genes from NS-Venus PR8 WT virus for use in experiments with the NS1-Venus PR8 WT and NS1-Venus PR8 MA viruses. MDCK cells were infected with these viruses at an MOI of 0.001 and viral titers in supernatants were determined every 12 hours by means of a plaque assay (FIG. 14). Although NS1-Venus PR8 WT virus grew to $10^{6.5}$ PFU/mL, NS1-Venus PR8 MA virus grew to more than $10^8$ PFU/mL, comparable to wild-type PR8 virus. While the viral titers of NS1-Venus PR8 PB2 virus and NS1-Venus PR8 HA virus reached approximately $10^{7.5}$ PFU/mL, these were lower than that of NS1-Venus PR8 MA virus. Therefore, the growth capability of NS1-Venus PR8 MA virus was remarkably improved in MDCK cells, and the mutations in the PB2 and HA genes acted in an additive manner.

Comparison of the Pathogenicity and Relocation in Mice of the Mutant Viruses.

Figure 16A:
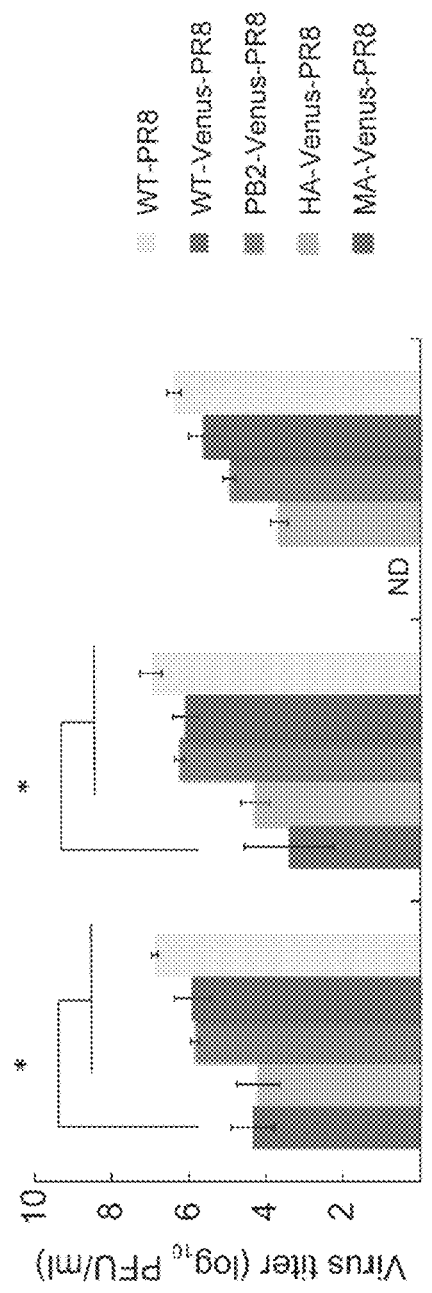
FIGS. 16A-B. Virus titers in mouse lung. Nine mice per group were intranasally infected with $10^3$ PFU of PR8 (A) or the respective NS1-Venus PR8 virus (B). Three mice per group were euthanized on days 3, 5, and 7 after infection and their lungs collected to determine virus titers. Virus titers were determined by means of plaque assays. Results are expressed as the mean of the titer ($\log_{10}$ PFU/g)±standard deviation. Statistical significance was calculated by using the Tukey-Kramer method. Asterisks indicate significant differences from titers from mice infected with PR8 or NS1-Venus WT virus ($P<0.05$). ND: Not detected (detection limit, 5 PFU/lung).
Figure 16B:
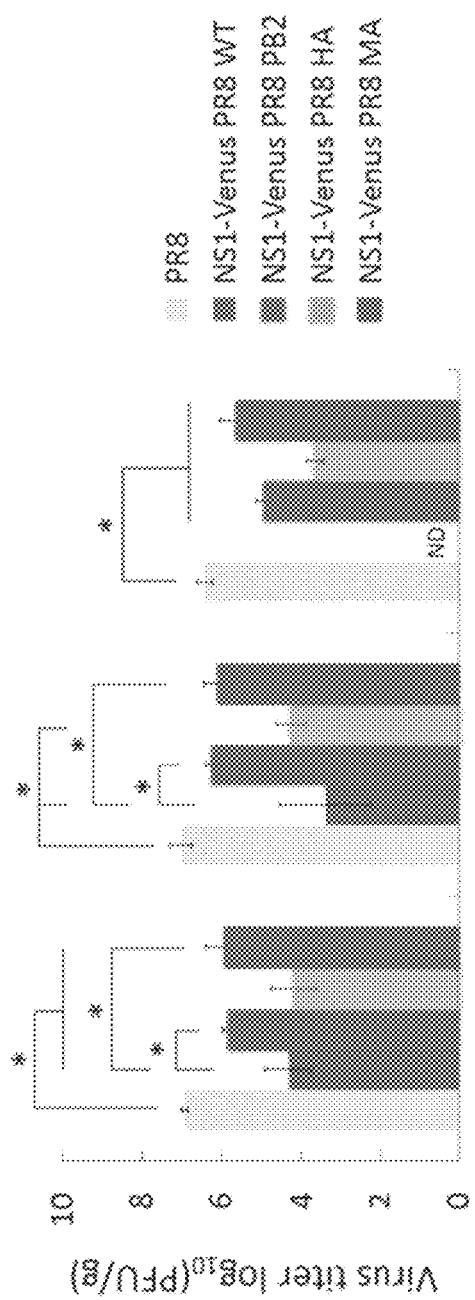

Next, to assess their pathogenicities, C57BL/6 mice were infected with $10^5$, $10^4$ or $10^3$ PFU of these viruses and monitored their body weights and survival (FIG. 15). The body weights of the mice infected with $10^5$ PFU of these viruses dramatically decreased and 1 out of 4 mice infected with NS1-Venus PR8 WT virus and all of the mice infected with NS1-Venus PR8 PB2 and NS1-Venus PR8 MA virus had to be euthanized during the observation period. In addition, mice infected with $10^4$ PFU of NS1-Venus PR8 PB2 and NS1-Venus PR8 MA virus showed pronounced body weight loss, and 1 out of 4 mice infected with NS1-Venus MA virus and 2 out of 4 mice infected with NS1-Venus PR8 PB2 virus succumbed to their infection. On the other hand, although the body weights of the mice infected with $10^4$ PFU of NS1-Venus PR8 HA and NS1-Venus PR8 WT virus decreased slightly, all of the mice survived. In the case of infection with $10^3$ PFU, while the body weights of the mice infected with NS1-Venus PR8 PB2 and NS1-Venus PR8 MA decreased slightly, all of these mice also survived. Mice infected with $10^3$ PFU of NS1-Venus PR8 WT and NS1-Venus PR8 HA showed little body weight loss, and all of the mice survived. The viral titers of these viruses were determined in mouse lung (FIG. 16). Mice were infected with $10^3$ PFU of the viruses and lungs were collected on days 3, 5, and 7 after infection. The maximum virus lung titer from mice infected with NS1-Venus PR8 PB2 virus was >$10^6$ PFU/g, which was similar to that from mice infected with NS1-Venus PR8 MA virus. In contrast, virus titers in lungs from mice infected with NS1-Venus PR8 WT and NS1-Venus PR8 HA virus were significantly lower than those in lungs from mice infected with NS1-Venus PR8 PB2 and NS1-Venus PR8 MA virus at all time points. Finally, viruses were not detected in lungs from mice infected with NS1-Venus PR8 WT at 7 days after infection. Taken together, these results demonstrate that only the PB2 mutation affected the pathogenicity and replication of NS1-Venus PR8 MA virus in mice.

The Stability of Venus Expression by NS1-Venus PR8 MA Virus During Replication In Vitro and In Vivo.

Figure 17:
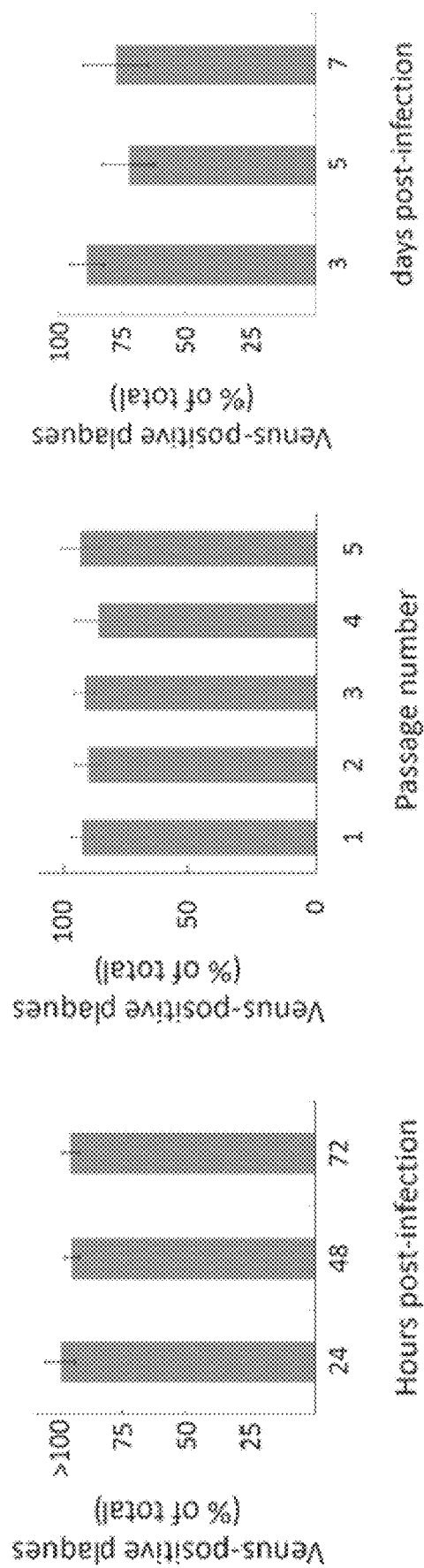
FIG. 17. The stability of Venus expression by NS1-Venus PR8 MA virus in vitro and in vivo. The positive rate of Venus expression was examined in MDCK cells (A, B) and in mouse lung (C). (A) MDCK cells were infected with NS1-Venus PR8 MA virus at an MOI of 0.001, and supernatants were collected every 24 hours. The positive rate of Venus expression was estimated by dividing the number of plaques that expressed Venus by the total number of plaques. (B) NS1-Venus PR8 MA virus was serially passaged in MDCK cells five times and the positive rates of Venus expression were estimated. (C) Nine mice were infected with $10^3$ PFU of NS1-Venus PR8 MA virus. Three mice were euthanized at each time point and plaque assays were performed using lung homogenates. The positive rates of Venus expression were estimated as described above.

In the Manicassamy study (Manicassamy et al., 2010), the proportion of GFP-negative virus increased over time. This is one of the obstacles to utilizing this virus for live imaging studies. The stability of Venus expression by NS1-Venus PR8 MA virus was assessed during replication in MDCK cells (FIG. 17A). More than 90% of plaques were Venus-positive even 72 hours after infection. The positive rate of Venus expression was monitored during repeated passages of the virus in cell culture (FIG. 17B). Approximately 90% of plaques expressed Venus even after 5 passages, suggesting that Venus expression by NS1-Venus PR8 MA virus was stable in cell culture. Finally, Venus expression was confirmed to be stable during virus replication in vivo (FIG. 17C). A plaque assay was performed using lung homogenates and estimated the positive rate of Venus expression essentially as described above. Although the percentage of Venus-positive plaques was more than 85% at 3 days after infection, that of Venus-positive plaques was approximately 75% at 7 days after infection. Taken together, these results indicate that Venus expression by NS1-Venus PR8 MA virus is stable during replication in vitro, and the percentage of Venus-positive plaques in mouse lung was similar to that reported previously (Manicassamy et al., 2010).

The PB2-E712D Substitution is Responsible for High Venus Expression.

Figure 18A:
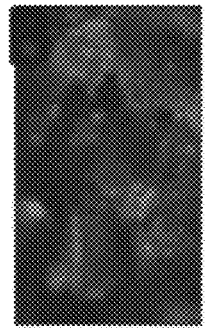
Figure 18B:
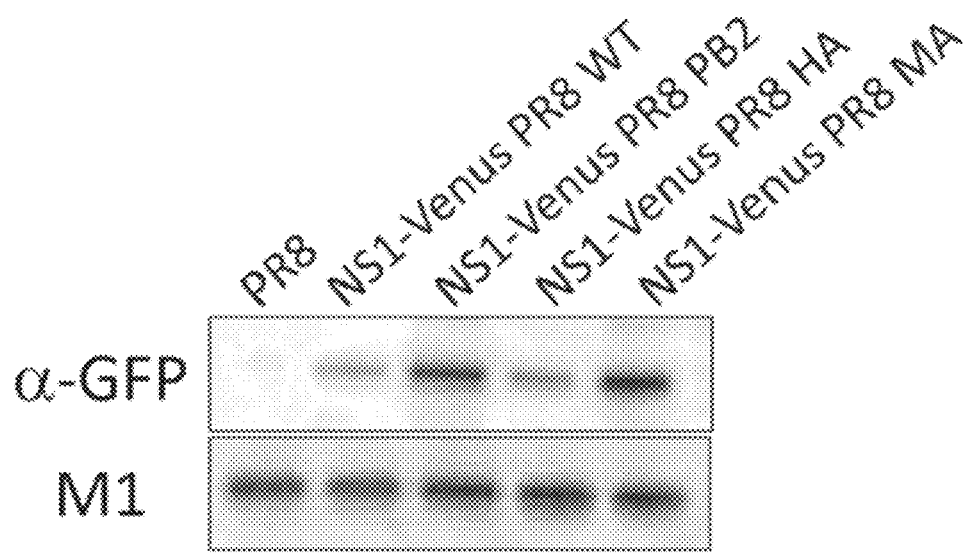

The Venus expression level of NS1-Venus PR8 MA virus was substantially higher than that of NS1-Venus PR8 WT virus. Since PB2 is one of the subunit of the influenza virus polymerase, it was hypothesized that the PB2-E712D substitution was important for the augmentation of Venus expression. To compare the Venus protein expression, western blots of the viral protein and Venus in infected cells were performed (FIG. 18A). Twelve hours post-infection, although the amount of M1 protein was similar for all of the viruses, the amount of Venus protein was higher in cells infected with NS1-Venus PR8 PB2 and NS1-Venus PR8 MA virus compared with the other two viruses that possessed the parental PB2 gene. Venus expression in infected cells was also observed by using a confocal laser microscope (FIG. 18B). As expected, the Venus signals in the cells infected with NS1-Venus PR8 PB2 and NS1-Venus PR8 MA virus were stronger than in the cells infected with the two viruses that possessed parental PB2 gene. Taken together, these results demonstrate that the PB2-E712D substitution was responsible for the high Venus expression.

Figure 18C:
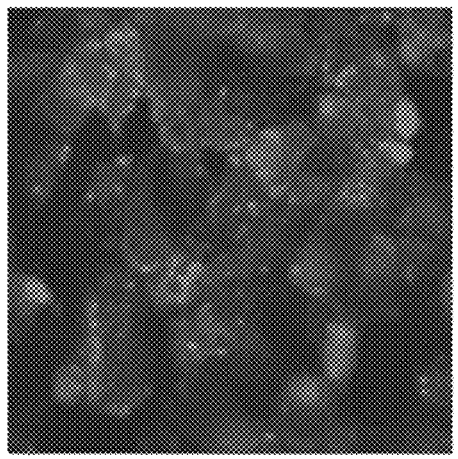

To demonstrate that the PB2-E712D mutation increased the Venus expression levels, MDCK cells were infected with the indicated viruses at an MOI of 1 and performed confocal microscopy 12 hours later (FIG. 18C). As expected, the levels of the NS1-Venus fusion protein were higher in cells infected with MA-Venus-PR8 or PB2-Venus-PR8 than in those infected with WT-Venus-PR8 or HA-Venus-PR8 (FIG. 18C).

Figure 18D:
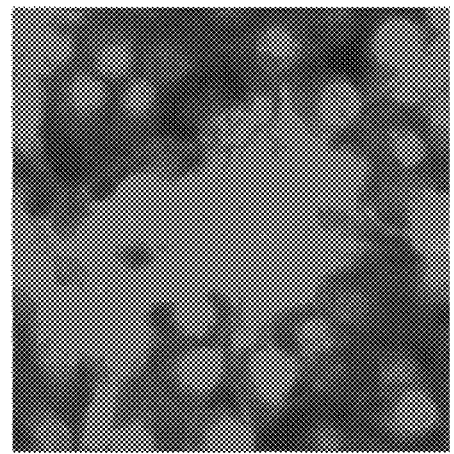
Figure 18E:
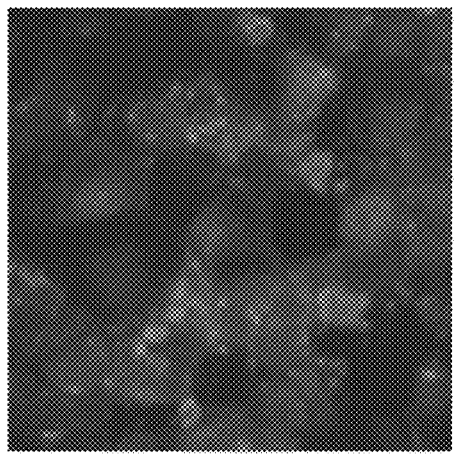
Figure 18F:
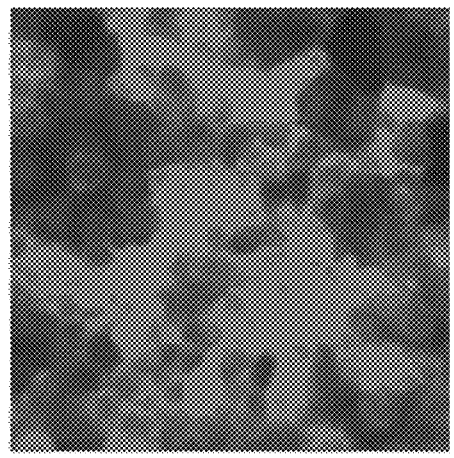
Figure 18C:
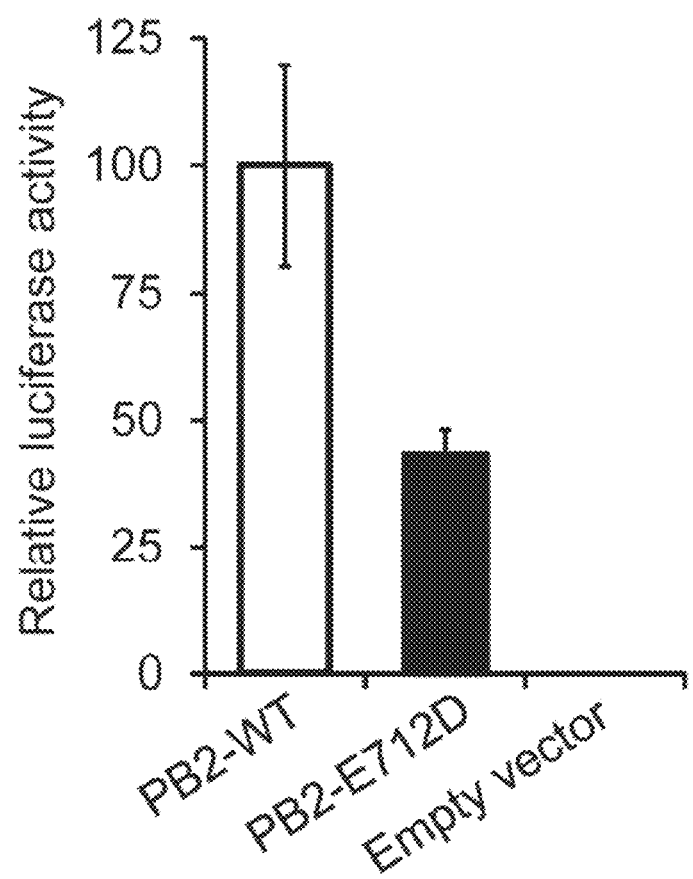

Collectively, the data indicate that the PB2-E712D substitution is primarily responsible for the increased replicative ability, Venus expression, and virulence in mice of MA-Venus-PR8 virus. To assess whether the PB2-E712D mutation directly affects the viral polymerase activity in a minireplicon assay, HEK293 cells were transfected with viral protein expression plasmids for NP, PA, PB1, and PB2 or PB2-E712D, together with a plasmid expressing a vRNA encoding the firefly luciferase gene; the pRL-null luciferase protein expression plasmid (Promega) served as a transfection control. Luciferase activities were measured by using a Dual-Glo luciferase assay system (Promega) at 48 hours post-transfection (Ozawa et al., 2007). Unexpectedly, the polymerase activity of PB2-E712D was lower than that of the parental PB2 (FIG. 18D). Similar results were obtained with canine MDCK cells (data not shown). In the context of a minireplicon that measures viral replication and transcription, the PB2-E712D mutation is thus attenuating; in contrast, this mutation enhances viral growth in the context of replicating virus. These findings indicate that the PB2 protein functions not only in viral replication/transcription, but performs additional roles in the viral life cycle.

The HA-T380A Substitution Raises the Threshold for Membrane Fusion.

Figure 19:
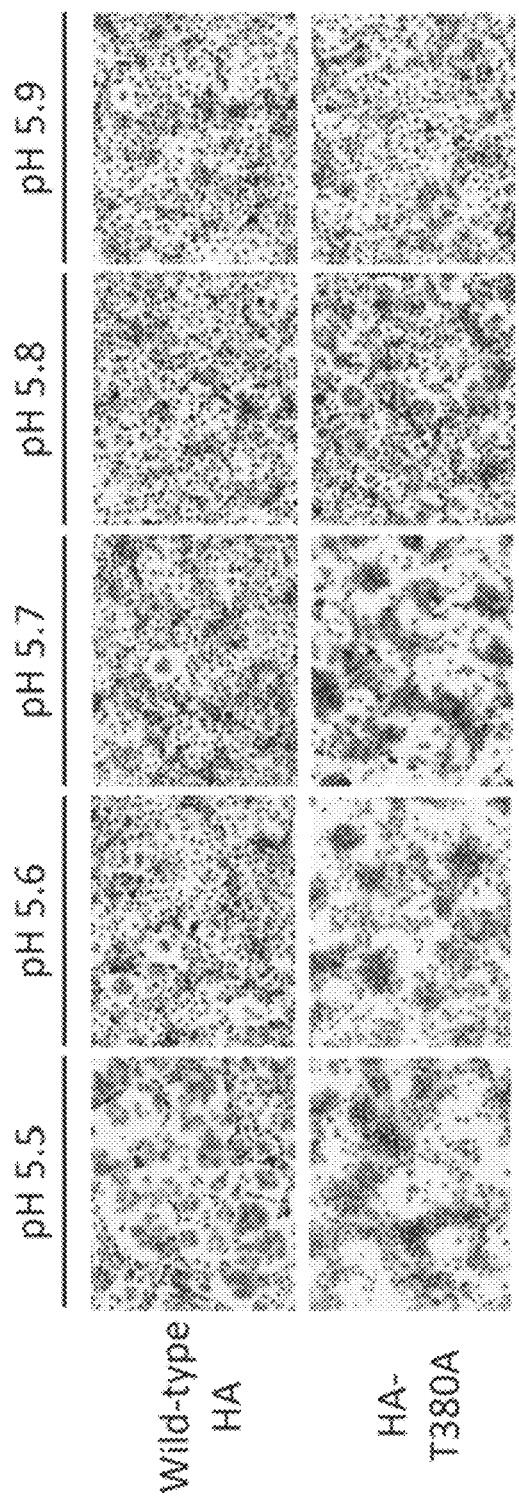
FIG. 19. Polykaryon formation by HEK293 cells infected with wild-type PR8 or PR8 that possesses the HA-T380A mutation after exposure to low pH buffer. The threshold for membrane fusion was examined at a pH range of 5.5-5.9. HEK293 cells were infected with PR8 or PR8 that possesses the HA-T380A substitution. Eighteen hours after infection, HA on the cell surface was digested with TPCK-trypsin, and exposure to the indicated pH buffer. After fixation with methanol, the cells were stained with Giemsa's solution. Representative pictures are shown.

The HA vRNA of MA-Venus-PR8 did not significantly increase the virulence of WT-Venus-PR8 in mice; however, HA-Venus-PR8 virus grew more efficiently in MDCK cells than WT-Venus-PR8 (FIG. 14), suggesting a contribution of the HA-T380A mutation to, at least, virus replication in cultured cells. Because the HA-T380A substitution is located on an a-helix in the HA2 subunit (Gamblin et al., 2004), its effect on HA membrane-fusion activity was evaluated by using a polykaryon formation assay (Imai et al., 2012). Briefly, HEK293 cells were infected with WT-PR8 or a mutant PR8 virus encoding HA-T380A at an MOI of 10. Eighteen hours later, cells were treated with TPCK-treated trypsin (1 µg/mL) for 15 minutes at 37° C., exposed to low-pH buffer (145 mM NaCl, 20 mM sodium citrate (pH 6.0-5.4)) for 2 minutes, incubated for 2 hours in maintenance medium at 37° C., fixed with methanol, and stained with Giemsa's solution. The wild-type HA had a threshold for membrane fusion of pH 5.5, whereas the threshold for HA-T380A was pH 5.8 (FIG. 19), leading to the conformational change in HA at an earlier stage of endosome maturation during influenza virus entry (Lozach et al., 2011). Changes in the pH threshold for membrane fusion may affect HA thermostability (Ruigrok et al., 1986), an effect that we did not observe at 50° C. (data not shown).

Time-Course Observation of Virus Propagation in Whole Mouse Lung.

Figure 20:
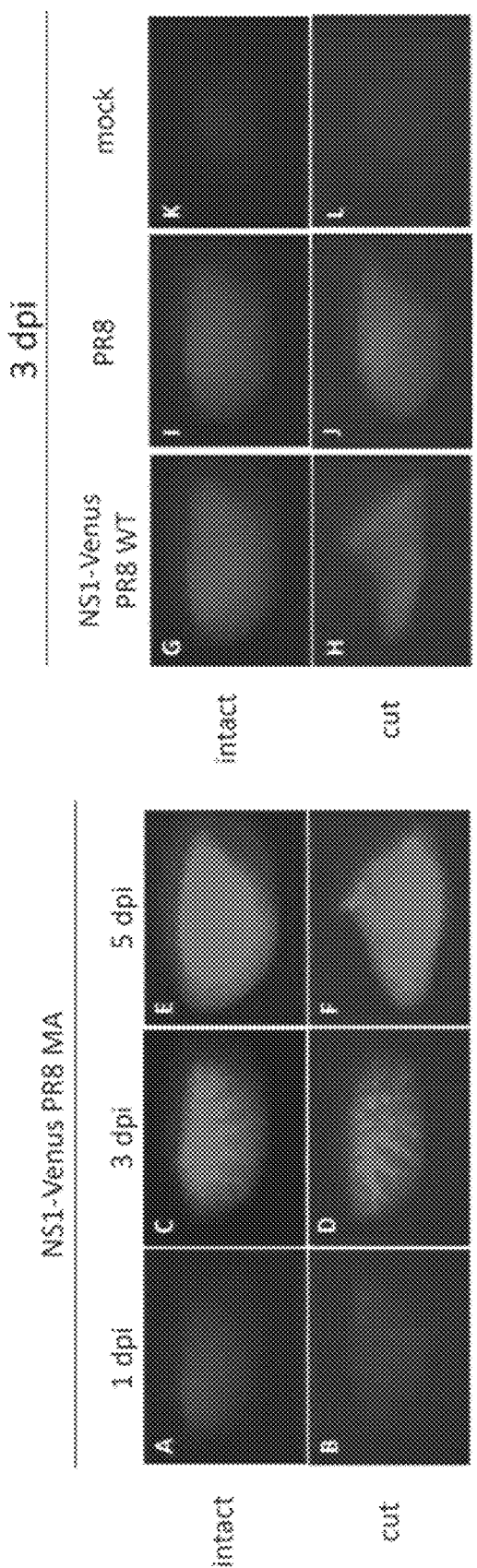
FIG. 20. Time-course observation of Venus-expressing cells in transparent lungs. Venus-expressing cells in whole lung lobe were observed. Three mice per group were intranasally infected with NS1-Venus PR8 MA (A-F), NS1-Venus PR8 WT (G, H) or PR8 (I, J) virus and lungs were collected on the indicated days. Mock-treated lungs served as a negative control (K, L). To image Venus-expressing cells deeper, lung samples were treated with SCALEVIEW A2, which make samples transparent, and were separated into each lobe and observed by using a stereo fluorescence microscope. After imaging the whole lung lobe (intact), samples were dissected to expose the bronchi (cut). Samples from mice infected with PR8 or NS1-Venus PR8 WT virus were prepared on day 3 post-infection to compare with NS1-Venus PR8 MA virus-infected lungs in which the Venus signal was the brightest during infection. Representative images are shown.

NS1-Venus PR8 MA virus allows the observation of virus-infected cells without immunostaining because the Venus expression by this virus is sufficiently high to permit the visualization of infected cells with a microscope. To observe how influenza virus propagates in the lung, transparent lungs are treated with SCALEVIEW A2, a reagent that make samples optically transparent without decreasing fluorescence intensity were used (FIG. 20). Mice were intranasally infected with $10^5$ PFU of PR8, NS1-Venus PR8 WT, and NS1-Venus PR8 MA virus, and lungs were collected on days 1, 3, and 5 after infection. After treatment with SCALEVIEW A2, the samples were observed using a stereo fluorescence microscope. Venus signals that were directly observed were ambiguous because of insufficient transparency. Therefore, the transparent samples were dissected in the direction of the long axis to expose the bronchi (FIG. 20, lower panel, "cut"). Venus expression was not observed in the transparent samples from mice infected with NS1-Venus PR8 WT virus at any time point (FIGS. 20G and H). Samples collected at 3 days post-infection are shown. In the case of NS1-Venus PR8 MA virus-infected lungs, although Venus signals were not observed at 1 day post-infection (FIGS. 20A and B), Venus expression was clearly observed in a large portion of the epithelial cells of the bronchi at 3 days post-infection (FIGS. 20C and D). Venus expression was also occasionally observed in alveolar epithelial cells around the bronchus. At 5 days post-infection, most of the Venus-positive cells found in the bronchial epithelium had disappeared and the number of Venus-positive cells in the bronchiole and alveoli had increased (FIGS. 20E and F). On the basis of these observations, it may be that the Venus-positive cells found in the bronchi at 3 days post-infection died and the influenza virus spread from the bronchi to the bronchioles and alveoli over time. No obvious Venus signals were observed in the transparent lungs from the mice inoculated with PR8 or PBS (FIGS. 20I-L). These results demonstrate that NS1-Venus PR8 MA virus and transparent reagent SCALEVIEW A2 permit the visualization of the dynamics of influenza virus infection in whole lung lobes.

Identification of the Target Cells of NS1-Venus PR8 MA Virus in Mouse Lung.

Figure 21:
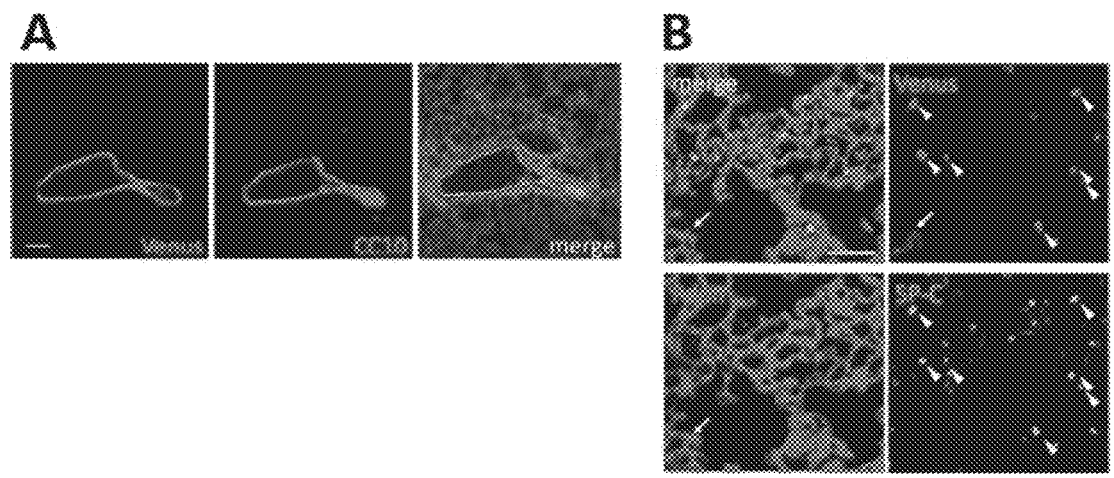
FIG. 21. Analysis of Venus expression in CC10$^+$ cells and SP-C$^+$ cells in lungs. Lung sections from mice infected with NS1-Venus PR8 MA virus were stained with several antibodies specific for the epithelial cells in the lung. Mice were infected with $10^4$ PFU of NS1-Venus PR8 MA virus and lungs were collected at 3 and 5 days post-infection. (A) Lung section of mice infected with NS1-Venus PR8 MA virus were prepared at 3 days post-infection and stained with an anti-CC10 polyclonal antibody (red). Scale bar: 100 µm. (B) Lung section of mice infected with NS1-Venus PR8 MA virus were prepared at 5 days post-infection and stained with an anti-SP-C polyclonal antibody (cyan) and an anti-podoplanin (Pdpn) polyclonal antibody (red). Venus-positive cells in the alveolar region comprised SP-C-positive cells (white arrowhead) and podoplanin-positive cells (white arrow). Scale bar: 50 µm.

Transparent lungs infected with NS1-Venus PR8 MA virus revealed that influenza virus first infected the bronchial epithelium and subsequently invaded the alveoli over time. Next, to identify the target cells of NS1-Venus PR8 MA virus, an immunofluorescence assay of frozen sections was performed using several antibodies specific for lung cells (FIG. 21). The epithelial cells of the bronchi and bronchioles include Clara cells, ciliated cells, goblet cells, and a small number of neuroendocrine cells, whereas alveoli comprise type I and type II alveolar epithelial cells. Of these cell types, I focused on Clara cells and type II alveolar epithelial cells because Clara cells constitute the bulk of the lumen of bronchi and bronchioles (Rawlins et al., 2006), and type II alveolar epithelial cells have previously been reported to be a target of influenza virus (Baskin et al., 2009). At 3 days post-infection, a large proportion of the bronchiole cells were Venus-positive and almost all of these cells were CC10-positive (FIG. 21A). In addition, cuboidal Venus signals in the alveolar regions were merged with SP-C positive cells (FIG. 21B, white arrowheads). Although rare, Venus-positive type I alveolar epithelial cells were observed at 5 days post-infection (FIG. 21B, white arrow). However, Venus expression in neuroendocrine cells was never detected (data not shown).

Figure 22:
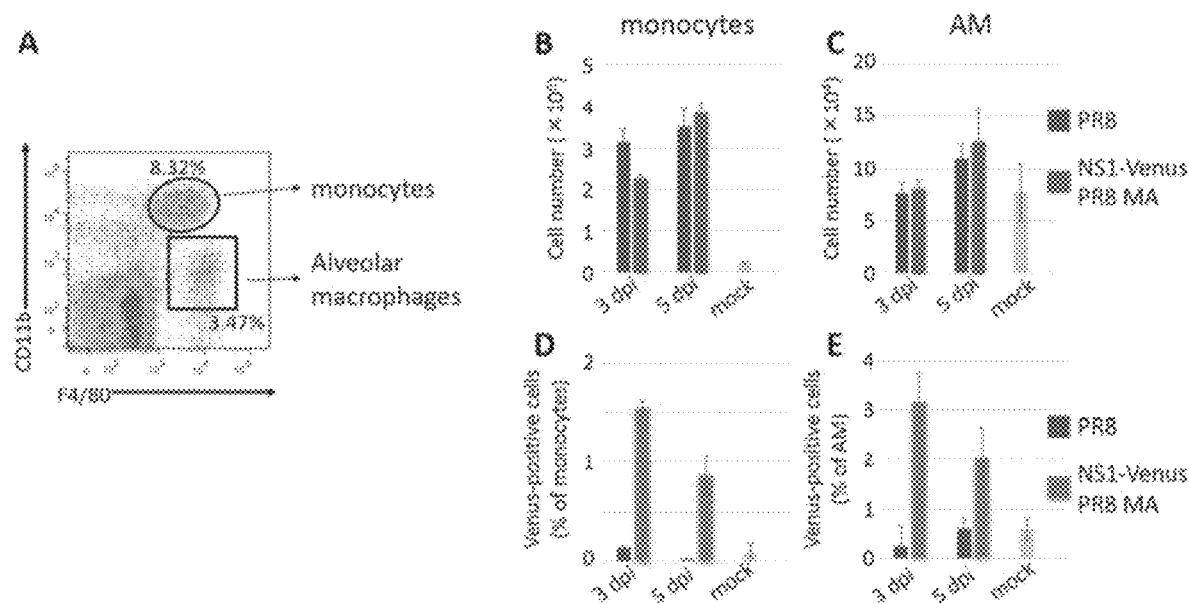
FIG. 22. Flow cytometric analysis of Venus-positive cells in specific cell types of the lung. Venus-positive cells in the indicated cell types were analyzed by using flow cytometry. Mice were infected with $10^5$ PFU of PR8 or NS1-Venus PR8 MA virus and lungs were collected at 3 and 5 days post-infection. Single cell suspensions were stained with antibodies. (A) Representative dot plot for CD45$^+$ live cells from the lung of mice inoculated with PBS are shown. (B, C) Total numbers of each specific cell species at the indicated time points are shown. Results are expressed as the mean cell numbers per lung±standard deviation. CD45$^+$ and via-probe$^-$ cells were analyzed for monocytes and alveolar macrophages. (D, E) The numbers of Venus-positive cells in cells defined in A and B at the indicated time points are shown. Results are expressed as the mean cell numbers±standard deviation. AM: alveolar macrophage.

Flow cytometry was performed to determine whether alveolar macrophages and monocytes were infected with NS1-Venus PR8 MA virus, because these immune cells are present in lung and function as the first line of defense against inhaled microbes and particulates. Alveolar macrophages were distinguished monocytes on the basis of the CD11b expression level in the F4/80$^+$ population (FIG. 22A). Mice were infected with $10^5$ PFU of PR8 or NS1-Venus PR8 MA virus and the total number of these cells were compared. After influenza virus infection, although the number of alveolar macrophages was rarely different from that of the control group, the number of monocyte dramatically increased because monocytes infiltrated sites of infection from blood vessels (FIGS. 22B and C). As to the proportion of Venus-positive cells, 3.16%±0.59% of the alveolar macrophages were Venus-positive cells and 1.55%±0.07% of the monocytes were Venus-positive at 3 days post-infection (FIGS. 22D and E). Further, the number of Venus-positive cells decreased slightly between 3 days and 5 days after NS1-Venus PR8 MA virus infection. For the PR8 infection, the number of Venus-positive cells was comparable to that in mock-treated mice. Taken together, these results demonstrate that the Clara cells in the bronchus and bronchiolus, type II alveolar epithelial cells, monocytes, and alveolar macrophages in the alveolar regions of the lung are target cells of influenza virus.

Differential Gene Expressions Between Venus-Positive and -Negative Cells in the F4/80$^+$ Cell Population.

Figure 23:
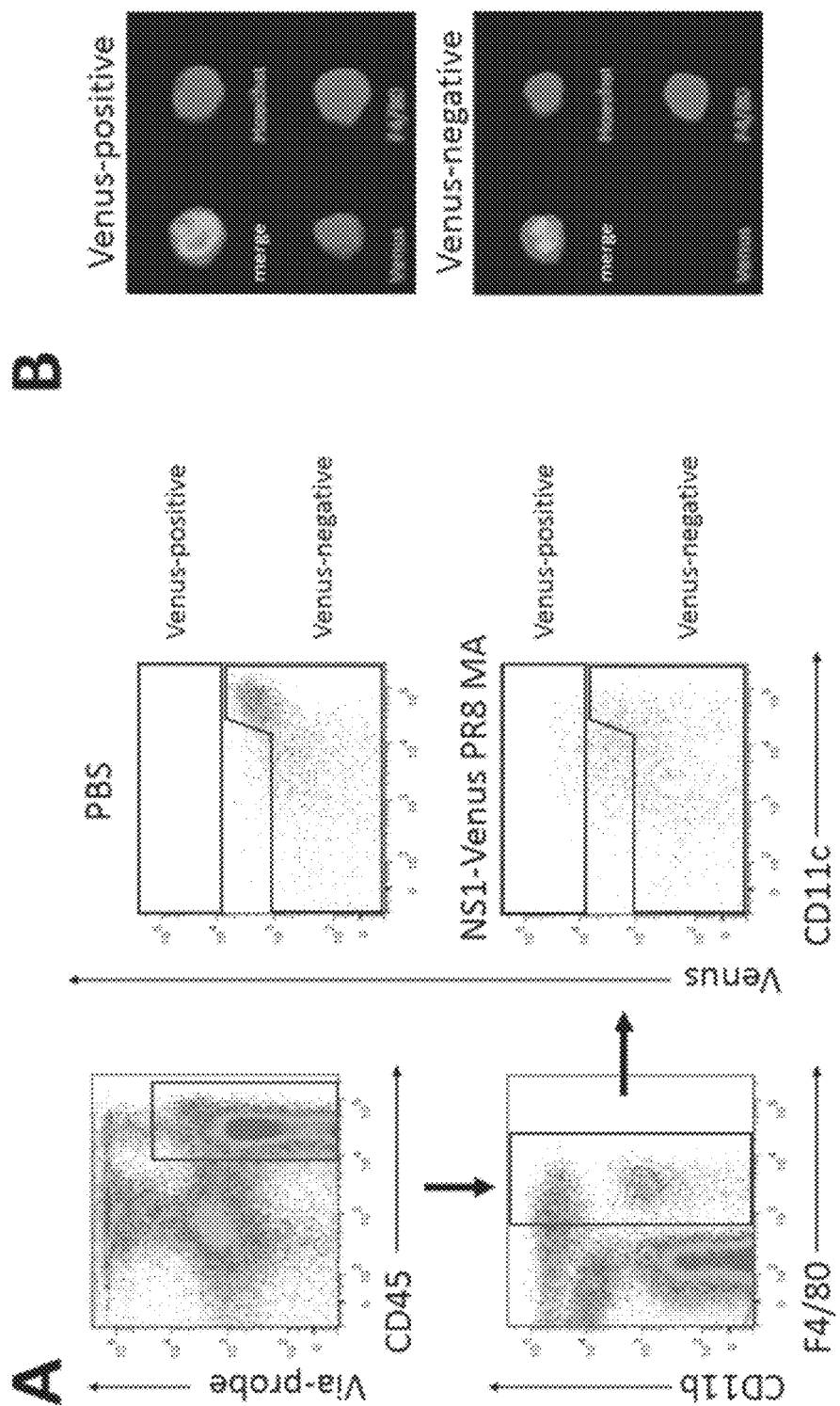
FIG. 23. Sorting strategy to collect Venus-positive and Venus-negative cells in the F4/80$^+$ population. Mice were infected with $10^5$ PFU of NS1-Venus PR8 MA virus and lungs were collected at 3 days post-infection. Single cell suspensions were stained with a set of antibodies. Lungs from mice inoculated with PBS were similarly stained to confirm the autofluorescence of alveolar macrophages. (A) Representative dot plots showing the gating strategy to collect Venus-positive and -negative cells in a population of $CD45^+$, via-probe$^-$ F4/80$^+$ cells. The Venus-positive gate was shown not to include alveolar macrophages. (B) Venus-positive and -negative cells collected from the lungs of mice infected with NS1-Venus PR8 MA virus were observed by using an immunofluorescence assay.
Figure 24:
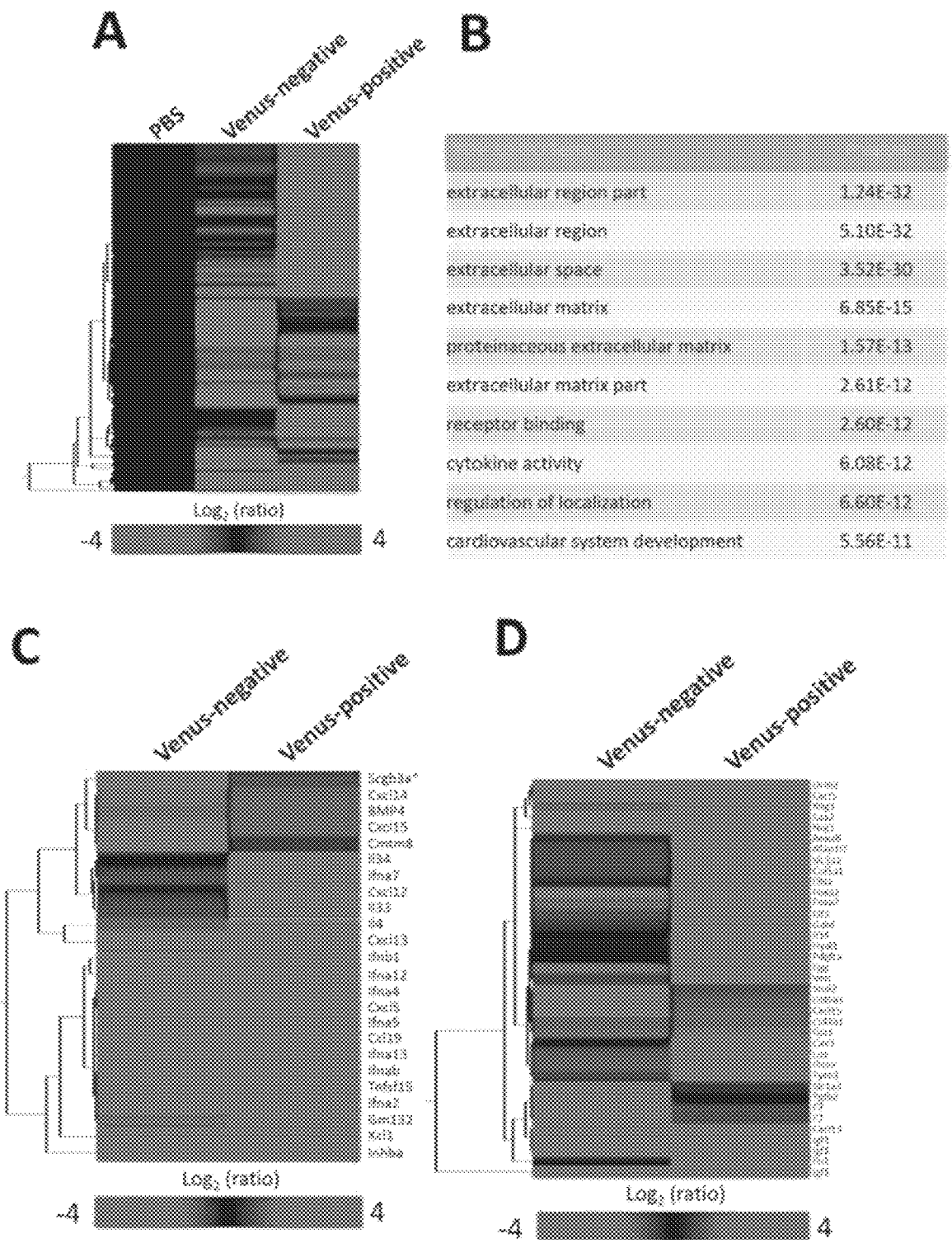
FIG. 24. Genes differentially expressed between Venus-positive and -negative F4/80$^+$ cells. Mice were infected with $10^5$ PFU of NS1-Venus PR8 MA virus and lungs were collected at 3 days post-infection. Single cell suspensions were stained in the same manner as described in FIG. 10. Venus-positive and -negative cells were separately harvested by using FACSAria II and subjected to microarray analysis. F4/80$^+$ cells isolated from the lungs of mice inoculated with PBS were used as a control. (A) A total of 633 genes were selected by student's T test ($P<0.05$) and by filtering the genes whose expression changed at least 4.0-fold between the Venus-positive and -negative groups from the genes whose expression changed at least 2.0-fold from the level of the PBS group. (B) These selected genes were functionally annotated by using Gene Ontology (GO) grouping. Statistical significance were determined by using Fisher's exact test ($P<0.01$). (C) Hierarchical analysis of genes annotated in "cytokine activity" enriched by genes that were significantly differentially expressed between Venus-positive and -negative F4/80$^+$ cells. (D) Hierarchical analysis of genes annotated in "response to wounding" enriched by genes that were significantly differentially expressed between Venus-positive and -negative F4/80$^+$ cells.

Because alveolar macrophages and monocytes act as the first line of defense against inhaled microbes, it is possible that infection of these cells with influenza virus might influence their ability to prevent the spread of infection. To assess this, the gene expression profiles between the Venus-positive and -negative cells among the alveolar macrophage and monocyte populations were compared by means of microarray analysis. Because the number of Venus-positive alveolar macrophages and monocytes that could be collected from one mouse by using flow cytometry was too small to perform a microarray analysis, these cells were analyzed together as F4/80$^+$ cells and pooled from three mice. Live mononuclear cells were gated as CD45$^+$ and via-probe cells. As shown in FIG. 22A, the cells were confirmed as alveolar macrophages and monocytes on the basis of CD11b expression levels in the F4/80$^+$ population. Venus-positive and -negative F4/80 cells were sorted from a fraction of the live mononuclear cells by FACSAria II. Since CD11c$^{high}$ alveolar macrophages possess high autofluorescence, the possibility existed for overlap with the Venus signal. Therefore, CD11c$^{high}$ alveolar macrophages with intermediate expression of Venus were excluded from the Venus-positive fraction (FIG. 23A). From confocal microscopic observation of the sorted cells, these cells could be collected properly based on Venus expression (FIG. 23B). In addition, given that Venus expression was observable throughout the cell, these cells would have been infected with virus, but did not engulf the infected cells. The microarray analysis revealed thousands of genes whose expression statistically changed at least 2.0-fold relative to the level of F4/80$^+$ cells from mice inoculated with PBS (data not shown). Among these genes, 633 genes whose expression statistically differed by at least 4.0-fold between Venus-positive and -negative F4/80$^+$ cells were identified (FIG. 24A). Gene Ontology analysis revealed that these genes were involved in extracellular activity (FIG. 24B). For genes annotated in "cytokine activity," a total of 24 genes had changed expression levels, including several cytokines, such as type I interferon (IFN), and chemokines (FIG. 24C). All of these genes except for the genes for interleukin (IL)-4 and Cxcl13 [chemokine (C-X-C motif) ligand 13] were up-regulated in Venus-positive cells relative to Venus-negative cells. Moreover, when I focused on the genes annotated in "response to wounding", most genes including those for collagen type 1α1 (Col1a1), collagen type 3α1 (Col3a1), collagen type 5a1 (Col5a1), hyaluronoglucosamidase 1 (Hyal1), and fibrinogen γ chain (Fgg) were up-regulated in Venus-positive F4/80$^+$ cells (FIG. 24D). Taken together, these results demonstrate that a small number of cells relative to the total number of F4/80$^+$ cells was infected with influenza virus and that the gene expression levels of several cytokines and chemokines were enhanced in the virus-infected cells at the site of infection. Furthermore, F4/80$^+$ cells infected with NS1-Venus PR8 MA virus enhanced the expression of genes involved in the response to wounding which would be caused by infection and inflammation.

REFERENCES

Arilor et al., *J. Virol.*, 86:1433 (2010).
Avilov et al., *Vaccine*, 34:741 (2012).
Basler et al., *Proc. Natl. Acad. Sci. USA*, 8:2746 (2001).
Chen et al., *The Lancet*, 383:714 (2014).
Dias et al., *Nature*, 458:914 (2009).
Diebold et al., *Science*, 303:1529 (2004).
Dos Santos Afonso et al., *Virology*, 341:34 (2015).
Edgar, *Nucl Acids Res.*, 32:1792 (2004).
Fan et al., *Virology*, 384:28 (2009).
Fujii et al., *J. Virol.*, 79:3766 (2005)

Fukuyama & Kawaoka, Curr. Opin. Immunol., 23:481 (2011).
Gabriel et al., Proc. Natl. Acad. Sci. USA, 102:18590 (2005).
Gambotto et al., Lancet, 371:1464 (2008).
Garcia-Sastre, Virus Res., 162:12 (2011).
Ghaznavi et al., Annu. Rev. Pathol., 8:331 (2013).
Go et al., BMC genomics, 13:627 (2012).
Hatta et al., PLoS Pathog., 3:1374 (2007).
Hatta et al., Science, 293: 1840 (2001).
He et al., Nature, 454:1123 (2008).
Heaton et al., J. Virol., 87:8272 (2013).
Helft et al., J. Clin. Invest., 122:4037 (2012).
Herold et al., J. Ex. Med., 205:3065 (2008).
Honda & Taniguchi, Nat. Rev. Immunol., 6:644 (2006).
Hu et al., J. Virol., 87:2660 (2013).
Imai et al., PLoS Pathog., 6:e1001106 (2010).
Isakova-Sivak et al., Clin. Vaccine Immunol., PMID: 24648485, epub Mar. 19 (2014).
Itoh et al., Nature, 460:1021 (2009).
Jiao et al., J. Virol., 82:1146 (2008).
Jobsis, Science, 198:1264 (1977).
Kaimal et al., Nucleic Acids Res., 38:W96 (2010).
Kawaoka and Webster, Proc. Natl. Acad. Sci. USA, 85:324 (1988).
Kawaoka et al., J. Virol., 63:4603 (1989).
Kittel et al., Virology, 324:67 (2004).
Larkin et al., Bioinform., 23:2947 (2007).
Leung et al., Virology, 401:96 (2010).
Li et al., J. Virol., 79:12058 (2005).
Li et al., J. Virol., 80:11115 (2006).
Li et al., J. Virol., 82:11880 (2008).
Li et al., J. Virol., 84:8389 (2010).
Li et al., N. Eng. J. Med., 370:520 (2013).
Liu et al., Zhonghna si Yan, 26:70 (2012).
Manicassamy et al., Proc. Natl. Acad. Sci. USA, 107:11531 (2010).
Murakami et al., J. Virol., 82:1605 (2008).
Naffakh et al., Annu. Rev. Microbiol., 62:403 (2008)
Nagai et al., Nat. Biotechnol., 20:87 (2002).
Neumann et al., Cell Res., 20:51 (2010).
Neumann et al., Proc. Natl. Acad. Sci. USA, 96:9345 (1999).
Obayashi et al., Nature, 454:1127 (2008).
Ozawa et al., J. Virol., 81:30 (2007).
Pan et al., Nature Commun., 4:2369 (2013).
Patterson et al., J. Cell Sci., 114:837 (2001).
Perez et al., J. Virol., 78:3083 (2004).
Perrone et al., PLoS Pathog., 4:e1000115 (2008).
Pichlmair et al., Science, 314:997 (2006).
Reed and Muench, Am. J. Hyg., 27:493 (1938).
Regan et al., J. Virol., 80:252 (2006).
Salomon et al., J. Ex. Med., 203:689 (2006).
Scholtissek et al., Virology, 87:13 (1978).
Shaner et al., Nat. Biotechnol., 22:1567 (2004).
Shieh et al., Am. J. Pathol., 177:166 (2010).
Shinya et al., J. Virol., 78:3083 (2004).
Smith et al., Nature, 459:1122 (2009).
Smyth, Stat. Appl. Genet. Mol. Biol., 3:3 (2004).
Song et al., J. Virol., 85:2180 (2011).
Sugiyama et al., EMBO J., 28:1803 (2009).
Suguitan et al., J. Virol., 86:2706 (2012).
Wang et al., PLoS One, 7:e52488 (2010).
Watanabe et al., J. Virol., 77:10575 (2003).
Watanabe et al., Nature, 501:551 (2013).
Wei et al., Vaccine, 29:7163 (2011).
Weissleder, Nature Biotech., 19:316 (2001).
Wright and Kawaoka, Fields Virology 6th edition, (Philadelphia, Pa., 2013).
Yamayoshi et al., J. Virol., 88:3127 (2013).
Yu et al., J. Virol., 85:6844 (2011).
Zhang et al., J. Gen. Virol., 95:779 (2014).
Zhang et al., Science, 341:410 (2013).
Zhao et al., Proteomics. 12:1970 (2012).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

---

What is claimed is:

1. A plurality of influenza A virus vectors for preparing a reassortant influenza virus comprising:

a) a vector for influenza A virus vRNA production comprising a promoter operably linked to an influenza A virus PA DNA linked to a transcription termination sequence, a vector for influenza A virus vRNA production comprising a promoter operably linked to an influenza A virus PB1 DNA linked to a transcription termination sequence, a vector for influenza A virus vRNA production comprising a promoter operably linked to an influenza A virus PB2 DNA linked to a transcription termination sequence, a vector for influenza A virus vRNA production comprising a promoter operably linked to an influenza A virus HA DNA linked to a transcription termination sequence, a vector for influenza A virus vRNA production comprising a promoter operably linked to an influenza A virus NP DNA linked to a transcription termination sequence, a vector for influenza A virus vRNA production comprising a promoter operably linked to an influenza A virus NA DNA linked to a transcription termination sequence, a vector for influenza A virus vRNA production comprising a promoter operably linked to an influenza A virus M DNA linked to a transcription termination sequence, and a vector for influenza A virus vRNA production comprising a promoter operably linked to an influenza A virus NS cDNA linked to a transcription termination sequence, wherein the PB1, PB2, PA, NP, NS, and M DNAs in the vectors for vRNA production encode at least one of: PA with a residue at position 443 that is not arginine, PB1 with a residue at position 737 that is not lysine, PB2 with a residue at position 25 that is not valine or a residue at position 712 that is not glutamic acid, NS1 with a residue at position 167 that is not proline, or HA with a residue at position 380 that is not threonine, wherein the position 443 in the PA corresponds to position 443 in a PA encoded by SEQ ID NO:1, wherein the position 737 in the PB1 corresponds to position 737 in a PB1 encoded by SEQ ID NO:2, wherein the position 25 or 712 in the PB2 corresponds to position 25 or 712 in a PB2 encoded by SEQ ID NO:3, or wherein the position 167 in the NS1 corresponds to position 167 in a NS1 encoded by SEQ ID NO:6, and wherein the HA DNA and NA DNA are from a different influenza A virus isolate relative to a virus having SEQ ID Nos. 1-6; and optionally b) a vector for mRNA production comprising a promoter operably linked to a DNA segment encoding influenza A virus PA, a vector for mRNA production comprising a promoter operably linked to a DNA segment encoding influenza A virus PB1, a vector for mRNA production comprising a promoter operably linked to a DNA segment encoding influenza A virus PB2, and a vector for mRNA production comprising a promoter operably linked to a DNA segment encoding influenza A virus NP, and optionally a vector for mRNA production comprising a promoter operably linked to a DNA segment encoding influenza A virus HA, a vector for mRNA production comprising a promoter operably linked to a DNA segment encoding influenza A virus NA, a vector for mRNA production comprising a promoter operably linked to a DNA segment encoding influenza virus M1, a vector for mRNA production comprising a promoter operably linked to a DNA segment encoding influenza virus M2, or a vector for mRNA production comprising a promoter operably linked to a DNA segment encoding influenza virus NS2.

2. The vectors of claim 1 wherein the wherein the PB1, PB2, PA, NP, NS, and M DNAs in the vectors for vRNA production have a sequence corresponding to one that encodes a polypeptide having at least 95% amino acid sequence identity to a corresponding polypeptide encoded by SEQ ID NOs:1-6 or 10-15.

3. The vectors of claim 1 wherein the residue at position 443 of PA is K or H, the residue at position 737 of PB1 is H or R, the residue at position 25 of PB2 is A, L, T, I, or G, the residue at position 712 of PB2 is D, the residue at position 167 of NS1 is S, C, M, A, L, I, G or T, or any combination thereof.

4. The vectors of claim 1 wherein at least one of the vectors for vRNA production includes a heterologous gene sequence encoding a gene product.

5. The vectors of claim 1 which comprise a further vector which provides for vRNA production comprising a heterologous gene sequence encoding a gene product.

6. The vectors of claim 1 wherein the heterologous sequence is in the NS vRNA, M vRNA, NP vRNA, PA vRNA, PB1 vRNA, or the PB2 vRNA.

7. The vectors of claim 1 wherein the heterologous sequence is 5' or 3' to the PA coding sequence in the PA vRNA, or 5' or 3' to the PB1 coding sequence in the PB1 vRNA.

8. The vectors of claim 1 wherein the heterologous sequence is 5' or 3' to the PB2 coding sequence in the PB2 vRNA.

9. The vectors of claim 1 wherein the heterologous sequence is 5' or 3' to the NS1 coding sequence in the NS vRNA.

10. The vectors of claim 5 wherein the further vector is for vRNA production of a NS vRNA, a M vRNA, a NP vRNA, a PA vRNA, a PB1 vRNA or a PB2 vRNA.

\* \* \* \* \*